US006828475B1

(12) United States Patent
Metz et al.

(10) Patent No.: US 6,828,475 B1
(45) Date of Patent: Dec. 7, 2004

(54) NUCLEIC ACID SEQUENCES ENCODING A PLANT CYTOPLASMIC PROTEIN INVOLVED IN FATTY ACYL-COA METABOLISM

(75) Inventors: James George Metz, Davis, CA (US); Kathryn Dennis Lardizabal, Woodland, CA (US); Michael W. Lassner, Davis, CA (US)

(73) Assignee: Calgene LLC, Davis, CA (US)

( * ) Notice: Subject to any disclaimer, the term of this patent is extended or adjusted under 35 U.S.C. 154(b) by 0 days.

(21) Appl. No.: 08/657,749

(22) Filed: May 30, 1996

Related U.S. Application Data

(63) Continuation-in-part of application No. PCT/US94/13686, filed on Nov. 30, 1994, which is a continuation-in-part of application No. 08/265,047, filed on Jun. 23, 1994, now Pat. No. 5,679,881.

(51) Int. Cl.[7] .......................... A01H 5/10; C12N 15/29; C12N 15/52; C12N 15/82; C12P 7/64

(52) U.S. Cl. ....................... 800/281; 800/278; 800/287; 800/298

(58) Field of Search ................................ 800/278, 281, 800/287, 298, 205, 250; 435/69.1, 69.2, 419; 530/350, 370; 536/23.2, 23.6, 24.5

(56) References Cited

U.S. PATENT DOCUMENTS

| 5,231,020 A | 7/1993 | Jorgensen et al. |
| 5,420,034 A | 5/1995 | Kridl et al. |
| 5,445,947 A | 8/1995 | Metz et al. |
| 5,475,099 A | 12/1995 | Knauf et al. |
| 5,510,255 A | 4/1996 | Knauf et al. |
| 5,679,881 A * | 10/1997 | Metz .......................... 800/205 |

FOREIGN PATENT DOCUMENTS

| WO | WO 93 10241 | 5/1993 |
| WO | WO 95/ 15387 | 6/1995 |

OTHER PUBLICATIONS

Broun P. et al. Science vol. 282; Nov. 13, 1998, pp. 1315–1317.*
Lassner M. et al. The Plant Cell, Feb. 1996; vol. 8; pp. 281–292.*
Millar A. et al. Plant Journal. 1997; vol. 12; No. 1; pp. 121–131.*
Akada et al. "Glycine Max Chalcone Synthase (CHS6) Gene, Complete CDS." *Database Embl Sequence Release 33 Accession No. L03352.5* Oct. 1992.
Batschauer, A. "Mustard Chalcone Synthase Gene (E. C. 2.3.1.74)" *Database Embl Sequence Release 22; Accession No. X16437.1* Dec. 1989.
Murphy, et al. "Elongases synthesizing very long chain monounsaturated fatty acids in developing oilseeds and their solubilization" *Z. Naturforschung*, vol. 44C, No. 7/8, 629–634 Jul. 1989.
Newman, T. "*392 Arabidopsis Thaliana cDNA clone 38D4T7*" *Database Embl Sequence Release 36. Accession No. T04345.30* Aug., 1993.
Quigley "A thaliana transcribed sequence; clone GBG3e129b" Database Embl Sequence Release 36; Accession No. Z26005.8 Sep. 1993.
Kunst et al. "Fatty acid elongation in developing seeds of Arabidopsis thaliana", *Plant Physiol. Biochem.* vol. 30, 425–434, 1992.
Taylor et al. "Biosynthesis of Acyl Lipids Containing Very–Long Chain Fatty Acids in Microspore–Derived and Zygotic Embryos of Brassica napus L. cv reston 1" *Plant Physiology*, vol. 99, 1609–1618, 1992.
Whitfield et al. "Sub–Cellular Localization of Fatty Acids Elongase in Developing Seeds of Lunaria annua and Brassica napus" *Phytochemistry*, vol. 32, No. 2, 255–258, 1933.
Fehling et al. "Solubilization and partial purification of constituents of acyl–CoA elonges from Lunaria annua" *Biochimica Biophysica Acta* vol. 1126 88–94, 1992.
Schopker, H., et al. "Charakterisierung und Isolierung von Fettsaure–Elongasen im Hinblick auf die Entwicklung von erucasaurereichem Industrieraps" see Abstracts and *48th Annual Meeting of the German Society for Fat Science*, Sep. 7–10, 1992.
Bessoule et al., "Partial Purification of the Acyl–CoA Elongase of *Allium porrum* Leaves", *Archives of Biochemistry and Biophysics*, 268(2):475–484 (1989).
Fehling et al., "Solubilization and Partial Purification of Constituents of acyl–CoA Elongase from *Lunaria annua*", *Biochimica et Biophysica Acta*, 1126:88–94 (1992).
Garver et al., "A High–Performance Liquid Chromatography–Based Radiometric Assay for Acyl–CoA:Alcohol Transacylase from Jojoba", *Analytical Biochemistry*, 207(2):335–340 (1992).
Harwood, J.L., "Fatty Acid Metabolism", *Annual Review of Plant Physiology and Plant Molecular Biology*, 39:101–138 (1988).

(List continued on next page.)

*Primary Examiner*—David T. Fox
*Assistant Examiner*—Russell Kallis
(74) *Attorney, Agent, or Firm*—Gary M. Bond; Arnold & Porter LLP

(57) ABSTRACT

By this invention, a plant β-ketoacyl-CoA synthase condensing enzyme is provided free from intact cells of said plant and capable of catalyzing the production of very long chain fatty acid molecules. Also contemplated are constructs comprising the nucleic acid sequence and a heterologous DNA sequence not naturally associated with the condensing enzyme encoding sequences, and which provide for at least transcription of a plant condensing enzyme encoding sequence in a host cell. In this fashion very long chain fatty acid molecules may be produced in a plant cell. Included are methods of modifying the composition of very long chain fatty acid molecules in a plant cell.

16 Claims, 59 Drawing Sheets

OTHER PUBLICATIONS

Lessire et al., "Involvement of a β–ketoacyl–CoA Intermediate in acyl–CoA Elongation by an acyl–CoA Elongase Purified from Leek Epidermal Cells", *Biochima et Biophysica Acta*, 1006:35–40 (1989).

Ohlrogge et al., "The Genetics of Plant Lipids", *International Journal of Biochemistry and Biophysics Lipids and Lipid Metabolism*, 1082:1–26 (1991).

Pollard et al., "Studies on Biosynthesis of Waxes by Developing Jojoba Seed II. The Demonstration of Wax Biosynthesis by Cell–Free Homogenates", *Lipids*, 14(7):651–662 (1979).

Pushnik et al., "Characterization of the Biosynthetic Pathway for Formation of Liquid Wax in Jojoba", *The Southwest Consortium Fourth Annual Meeting*, (Feb. 9, 1989).

Stumpf et al.,"Pathways of Fatty Acid Biosynthesis in Higher Plants with Particular Reference to Developing Rapeseed", *High and Low Erucic Acid Rapeseed Oils*, Academic Press, Canada, pp. 131–141 (1983).

van de Loo et al., "Unusual Fatty Acids", *Lipid Metabolism in Plants*, CRC Press, pp. 91–126 (1993).

von Wettstein–Knowles, P.M., "Waxes, Cutin and Suberin", *Lipid Metabolism in Plants*, CRC Press, pp. 127–166 (1993).

Wildner et al., "Wax Ester Biosynthesis in *Euglena gracilis*", *the Southwest Consortium Fifth Annual Meeting*, (Apr. 22–24, 1990).

Wu et al., "Studies of Biosynthesis of Waxes by Developing Jojoba Seed: III Biosynthesis of Wax Esters from Acyl–CoA and Long Chain Alcohols", *Lipids* 16(12): 897–902 (1981).

* cited by examiner

```
AAATCCTCCA CTCATACACT CCACTTCTCT CTCTCTCT CTCTCTCTGA AACAATTTGA    60

GTAGCAAACT TAAAAGAAA ATG GAG GAA ATG GGA AGC ATT TTA GAG TTT CTT  112
                     Met Glu Glu Met Gly Ser Ile Leu Glu Phe Leu
                      1               5                      10

GAT AAC AAA GCC ATT TTG GTC ACT GGT GCT ACT GGC TCC TTA GCA AAA  160
Asp Asn Lys Ala Ile Leu Val Thr Gly Ala Thr Gly Ser Leu Ala Lys
             15                  20                  25

ATT TTT GTG GAG AAG GTA CTG AGG AGT CAA CCG AAT GTG AAG AAA CTC  208
Ile Phe Val Glu Lys Val Leu Arg Ser Gln Pro Asn Val Lys Lys Leu
         30                  35                  40

TAT CTT CTT TTG AGA GCA ACC GAT GAC GAG ACA GCT GCT CTA CGC TTG  256
Tyr Leu Leu Leu Arg Ala Thr Asp Asp Glu Thr Ala Ala Leu Arg Leu
     45                  50                  55

CAA AAT GAG GTT TTT GGA AAA GAG TTG TTC AAA GTT CTG AAA CAA AAT  304
Gln Asn Glu Val Phe Gly Lys Glu Leu Phe Lys Val Leu Lys Gln Asn
 60                  65                  70                  75

FIG. 1A
```

| | | | | | | | | | | | | | | | | |
|---|---|---|---|---|---|---|---|---|---|---|---|---|---|---|---|---|
| TTA | GGT | GCA | AAT | TTC | TAT | TCC | TTT | GTA | TCA | GAA | AAA | GTG | ACT | GTA | GTA | 352 |
| Leu | Gly | Ala | Asn | Phe | Tyr | Ser | Phe | Val | Ser | Glu | Lys | Val | Thr | Val | Val | |
| | | 80 | | | | | 85 | | | | | 90 | | | | |
| CCC | GGT | GAT | ATT | ACT | GGT | GAA | GAC | TTG | TGT | CTC | AAA | GAC | GTC | AAT | TTG | 400 |
| Pro | Gly | Asp | Ile | Thr | Gly | Glu | Asp | Leu | Cys | Leu | Lys | Asp | Val | Asn | Leu | |
| | | | 95 | | | | | 100 | | | | | 105 | | | |
| AAG | GAA | GAA | ATG | TGG | AGG | GAA | ATC | GAT | GTT | GTT | GTC | AAT | CTA | GCT | GCT | 448 |
| Lys | Glu | Glu | Met | Trp | Arg | Glu | Ile | Asp | Val | Val | Val | Asn | Leu | Ala | Ala | |
| | | 110 | | | | | 115 | | | | | 120 | | | | |
| ACA | ATC | AAC | TTC | ATT | GAA | AGG | TAC | GAC | GTG | TCT | CTG | CTT | ATC | AAC | ACA | 496 |
| Thr | Ile | Asn | Phe | Ile | Glu | Arg | Tyr | Asp | Val | Ser | Leu | Leu | Ile | Asn | Thr | |
| | 125 | | | | | 130 | | | | | 135 | | | | | |
| TAT | GGA | GCC | AAG | TAT | GTT | TTG | GAC | TTC | GCG | AAG | AAG | TGC | AAC | AAA | TTA | 544 |
| Tyr | Gly | Ala | Lys | Tyr | Val | Leu | Asp | Phe | Ala | Lys | Lys | Cys | Asn | Lys | Leu | |
| 140 | | | | | 145 | | | | | 150 | | | | | 155 | |
| AAG | ATA | TTT | GTT | CAT | GTA | TCT | ACT | GCT | TAT | GTA | TCT | GGA | GAG | AAA | AAT | 592 |
| Lys | Ile | Phe | Val | His | Val | Ser | Thr | Ala | Tyr | Val | Ser | Gly | Glu | Lys | Asn | |
| | | | 160 | | | | | 165 | | | | | 170 | | | |

FIG. 1B

```
GGG TTA ATA CTG GAG AAG CCT TAT ATG GGC GAG TCA CTT AAT GGA    640
Gly Leu Ile Leu Glu Lys Pro Tyr Met Gly Glu Ser Leu Asn Gly
        175                 180                 185

AGA TTA GGT CTG GAC ATT AAT GTA GAG AAG AAA CTT GTG GAG GCA AAA    688
Arg Leu Gly Leu Asp Ile Asn Val Glu Lys Lys Leu Val Glu Ala Lys
        190                 195                 200

ATC AAT GAA CTT CAA GCA GGG GCA ACG GAA AAG TCC ATT AAA TCG    736
Ile Asn Glu Leu Gln Ala Gly Ala Thr Glu Lys Ser Ile Lys Ser
        205                 210                 215

ACA ATG AAG GAC ATG GGC ATC GAG AGG GCA AGA CAC TGG GGA TGG CCA    784
Thr Met Lys Asp Met Gly Ile Glu Arg Ala Arg His Trp Gly Trp Pro
        220                 225                 230                 235

AAT GTG TAT GTA TTC ACC AAG GCA TTA GGG GAG ATG CTT TTG ATG CAA    832
Asn Val Tyr Val Phe Thr Lys Ala Leu Gly Glu Met Leu Leu Met Gln
        240                 245                 250

TAC AAA GGG GAC ATT CCG CTT ACT ATT ATT CGT CCC ACC ATC ATC ACC    880
Tyr Lys Gly Asp Ile Pro Leu Thr Ile Ile Arg Pro Thr Ile Ile Thr
        255                 260                 265
```

FIG. 1C

```
AGC ACT TTT AAA GAG CCC TTT CCT GGT TGG GTT GAA GGT GTC AGG ACC    928
Ser Thr Phe Lys Glu Pro Phe Pro Gly Trp Val Glu Gly Val Arg Thr
            270                 275                 280

ATC GAT AAT GTA CCT GTA TAT TAT GGT AAA GGG AGA TTG AGG TGT ATG    976
Ile Asp Asn Val Pro Val Tyr Tyr Gly Lys Gly Arg Leu Arg Cys Met
        285                 290                 295

CTT TGC GGA CCC AGC ACA ATA ATT GAC CTG ATA CCG GCA GAT ATG GTC   1024
Leu Cys Gly Pro Ser Thr Ile Ile Asp Leu Ile Pro Ala Asp Met Val
300                 305                 310                 315

GTG AAT GCA ACG ATA GTA GCC ATG GTG ACA TAC CAT GTG GGA TCT TCA   1072
Val Asn Ala Thr Ile Val Ala Met Val Thr Tyr His Val Gly Ser Ser
            320                 325                 330

GCG GCG CAC GCA AAC CAA AGA TAC
Ala Ala His Ala Asn Gln Arg Tyr

GTA GAG CCG GTG ACA TAC CAT GTG GGA TCT TCA GCG GCG AAT CCA ATG   1120
Val Glu Pro Val Thr Tyr His Val Gly Ser Ser Ala Ala Asn Pro Met
        335                 340                 345

AAA CTG AGT GCA TTA CCA GAG ATG GCA CAC CGT TAC TTC ACC AAG AAT   1168
Lys Leu Ser Ala Leu Pro Glu Met Ala His Arg Tyr Phe Thr Lys Asn
350                 355                 360
```

FIG. 1D

| CCA | TGG | ATC | AAC | CCG | GAT | CGC | AAC | CCA | GTA | CAT | GTG | GGT | CGG | GCT | ATG | 1216 |
|---|---|---|---|---|---|---|---|---|---|---|---|---|---|---|---|---|
| Pro | Trp | Ile | Asn | Pro | Asp | Arg | Asn | Pro | Val | His | Val | Gly | Arg | Ala | Met | |
| 365 | | | | | 370 | | | | | 375 | | | | | | |

| GTC | TTC | TCC | TTC | TCC | ACC | TTC | CAC | CTT | TAT | CTC | ACC | CTT | AAT | TTC | 1264 |
|---|---|---|---|---|---|---|---|---|---|---|---|---|---|---|---|
| Val | Phe | Ser | Phe | Ser | Thr | Phe | His | Leu | Tyr | Leu | Thr | Leu | Asn | Phe | |
| 380 | | | | 385 | | | | | 390 | | | | | 395 | |

| CTC | CTT | CCT | TTG | AAG | GTA | CTG | GAG | ATA | GCA | AAT | ACA | ATA | TTC | TGC | CAA | 1312 |
|---|---|---|---|---|---|---|---|---|---|---|---|---|---|---|---|---|
| Leu | Leu | Pro | Leu | Lys | Val | Leu | Glu | Ile | Ala | Asn | Thr | Ile | Phe | Cys | Gln | |
| | | | 400 | | | | | 405 | | | | | | 410 | | |

| TGG | TTC | AAG | GGT | AAG | TAC | ATG | GAT | CTT | AAA | AGG | AAG | ACG | AGG | TTG | TTG | 1360 |
|---|---|---|---|---|---|---|---|---|---|---|---|---|---|---|---|---|
| Trp | Phe | Lys | Gly | Lys | Tyr | Met | Asp | Leu | Lys | Arg | Lys | Thr | Arg | Leu | Leu | |
| | | 415 | | | | | 420 | | | | | 425 | | | | |

| TTG | CGT | TTA | GTA | GAC | ATT | TAT | AAA | CCC | TAC | CTC | TTC | TTC | CAA | GGC | ATC | 1408 |
|---|---|---|---|---|---|---|---|---|---|---|---|---|---|---|---|---|
| Leu | Arg | Leu | Val | Asp | Ile | Tyr | Lys | Pro | Tyr | Leu | Phe | Phe | Gln | Gly | Ile | |
| 430 | | | | | 435 | | | | | 440 | | | | | | |

| TTT | GAT | GAC | ATG | AAC | ACT | GAG | AAG | TTG | CGG | ATT | GCT | GCA | AAA | GAA | AGC | 1456 |
|---|---|---|---|---|---|---|---|---|---|---|---|---|---|---|---|---|
| Phe | Asp | Asp | Met | Asn | Thr | Glu | Lys | Leu | Arg | Ile | Ala | Ala | Lys | Glu | Ser | |
| 445 | | | | | 450 | | | | | 455 | | | | | | |

FIG. 1E

```
ATA GTT GAA GCT GAT ATG TTT TAC TTT GAT CCC AGG GCA ATT AAC TGG    1504
Ile Val Glu Ala Asp Met Phe Tyr Phe Asp Pro Arg Ala Ile Asn Trp
460                 465                 470                 475

GAA GAT TAC TTC TTG AAA ACT CAT TTC CCA GGN GTC GTA GAG CAC GTT    1552
Glu Asp Tyr Phe Leu Lys Thr His Phe Pro Gly Val Val Glu His Val
        480                 485                 490

CTT AAC TAAAAGTTAC GGTACGAAAA TGAGAAGATT GGAATGCATG CACCGAAAGN    1608
Leu Asn

NCAACATAAA AGACGTGGTT AAAGTCATGG TCAAAAAAGA AATAAAATGC AGTTAGGTTT   1668

GTGTTGCAGT TTTGATTCCT TGTATTGTTA CTTGTACTTT TGATCTTTTT CTTTTTTAAT   1728

GAAATTCTC TCTTTGTTTT GTGAAAAAAA AAAAAAAAAA GAGCTCCTGC AGAAGCTT     1786
```

FIG. 1F

```
GGAACTCCAT CCCTTCCTCC CTCACTCCTC TCTCTACA ATG AAG GCC AAA ACA ATC          56
                                         Met Lys Ala Lys Thr Ile
                                           1               5

ACA AAC CCG GAG ATC CAA GTC TCC ACG ACC ATG ACC ACC ACG ACC ACG           104
Thr Asn Pro Glu Ile Gln Val Ser Thr Thr Met Thr Thr Thr Thr Thr
         10                  15                  20

ACT ATG ACC GCC ACT CTC CCC AAC TTC AAG TCC ATC AAC TTA CAC               152
Thr Met Thr Ala Thr Leu Pro Asn Phe Lys Ser Ile Asn Leu His
     25                  30                  35

CAC GTC AAG CTC GGC TAC CAC TAC TTA ATC TCC AAT GCC CTC TTC CTC           200
His Val Lys Leu Gly Tyr His Tyr Leu Ile Ser Asn Ala Leu Phe Leu
         40                  45                  50

GTA TTC ATC CCC CTT TTG GGC CTC GCT TCG GCC CAT CTC TCC TCC TTC           248
Val Phe Ile Pro Leu Leu Gly Leu Ala Ser Ala His Leu Ser Ser Phe
     55                  60                  65                  70

TCG GCC CAT GAC TTG TCC CTG CTC CTT CGC AAC CTC                           296
Ser Ala His Asp Leu Ser Leu Leu Arg Asn Leu
         75                  80                  85
```

FIG. 2A

CTC CCT GTT GTC GTT TGT TCT TTC CTC TTC GTT TTA TTA GCA ACC CTA 344
Leu Pro Val Val Val Cys Ser Phe Leu Phe Val Leu Leu Ala Thr Leu
                90                  95                 100

CAT TTC TTG ACC CGG CCC AGG AAT GTC TAC TTG GAC TTT GGA TGC 392
His Phe Leu Thr Arg Pro Arg Asn Val Tyr Leu Val Asp Phe Gly Cys
           105                 110                 115

TAT AAG CCT CAA CCG AAC CTG ATG ACA TCC CAC GAG ATG TTC ATG GAC 440
Tyr Lys Pro Gln Pro Asn Leu Met Thr Ser His Glu Met Phe Met Asp
    120                 125                 130

CGG ACC TCC CGG GCC GGG TCG TTT TCT AAG GAG AAT ATT GAG TTT CAG 488
Arg Thr Ser Arg Ala Gly Ser Phe Ser Lys Glu Asn Ile Glu Phe Gln
        135                 140                 145                 150

AGG AAG ATC TTG GAG AGG GCC GGT ATG GGT CGG GAA ACC TAT GTC CCC 536
Arg Lys Ile Leu Glu Arg Ala Gly Met Gly Arg Glu Thr Tyr Val Pro
            155                 160                 165

GAA TCC GTC ACT AAG GTG CCC GCC GAG CCG AGC ATA GCA GCC AGG 584
Glu Ser Val Thr Lys Val Pro Ala Glu Pro Ser Ile Ala Ala Arg
        170                 175                 180

FIG. 2B

```
GCC GAG GCG GAG GAG GTG ATG TAC GGG GCG ATC GAC GAG GTG TTG GAG    632
Ala Glu Ala Glu Glu Val Met Tyr Gly Ala Ile Asp Glu Val Leu Glu
        185                 190                 195

AAG ACG GGG GTG AAG CCG AAG CAG ATA GGA ATA CTG GTG GTG ANC TGC    680
Lys Thr Gly Val Lys Pro Lys Gln Ile Gly Ile Leu Val Val Xxx Cys
        200                 205                 210

AGC TTG TTT AAC CCA ACG CCG TCG TCA TCC ATG ATA GTT AAC CAT        728
Ser Leu Phe Asn Pro Thr Pro Ser Leu Ser Ser Met Ile Val Asn His
        215                 220                 225         230

TAC AAG CTN AGG GGT AAT ATA CTT AGC TAT AAT CTT GGT GGC ATG GGT    776
Tyr Lys Leu Arg Gly Asn Ile Leu Ser Tyr Asn Leu Gly Gly Met Gly
        235                 240                 245

TGC AGT GCT GGG CTC ATT GAT CTT GCC AAG GAC CTC CTA CAG            824
Cys Ser Ala Gly Leu Ile Asp Leu Ala Lys Asp Leu Leu Gln
        250                 255                 260

GTT TAC CGT AAA AAC ACA TAT GTG TTA GTA GTG AGC ACG GAA AAC ATG    872
Val Tyr Arg Lys Asn Thr Tyr Val Leu Val Val Ser Thr Glu Asn Met
        265                 270                 275
```

FIG. 2C

```
ACC CTT AAT TGG TAC TGG GGC AAT GAC CGC TCC ATG CTT ATC ACC AAC     920
Thr Leu Asn Trp Tyr Trp Gly Asn Asp Arg Ser Met Leu Ile Thr Asn
280                 285                 290

TGC CTA TTT CGC ATG GGT GCC ATC ATC CTC TCA AAC CGC TGG             968
Cys Leu Phe Arg Met Gly Ala Ile Ile Leu Ser Asn Arg Trp
295                 300                 305                 310

CGT GAT CGT CGC CGA TCC AAG TAC CAA CTC CTT CAT ACA GTA CGC ACC    1016
Arg Asp Arg Arg Arg Ser Lys Tyr Gln Leu Leu His Thr Val Arg Thr
            315                 320                 325

CAC AAG GGC GCT GAC AAG GAC AAG TCC TAT AGA TGC GTC TTA CAA GAA    1064
His Lys Gly Ala Asp Lys Asp Lys Ser Tyr Arg Cys Val Leu Gln Glu
330                 335                 340

GAT GAA AAT AAC AAG GTA GGT GTT GCC TTA TCC AAG GAT CTG ATG GCA    1112
Asp Glu Asn Asn Lys Val Gly Val Ala Leu Ser Lys Asp Leu Met Ala
345                 350                 355

GTT GCC GGT GAA GCT CTA AAG GCC AAC ATC ACG ACC CTT GGT CCC CTC    1160
Val Ala Gly Glu Ala Leu Lys Ala Asn Ile Thr Thr Leu Gly Pro Leu
360                 365                 370

GTG CTC CCC ATG TCA GAA CAA CTC CTC TTC TTT GCC ACC TTA GTG GCA    1208
Val Leu Pro Met Ser Glu Gln Leu Leu Phe Phe Ala Thr Leu Val Ala
375                 380                 385                 390
```

FIG. 2D

```
CGT AAG GTC TTC AAG ATG ACG AAC GTG AAG CCA TAC ATC CCA GAT TTC      1256
Arg Lys Val Phe Lys Met Thr Asn Val Lys Pro Tyr Ile Pro Asp Phe
            395                 400                 405

AAG TTG GCA GCG AAC GAC TTC TGC ATC CAT GCA GGA GGC AAA GCA GTG      1304
Lys Leu Ala Ala Asn Asp Phe Cys Ile His Ala Gly Gly Lys Ala Val
            410                 415                 420

TTG GAT GAG CTC GAG AAG CTG AAC TTG GAG TTG ACG CCA TGG CAC CTT GAA  1352
Leu Asp Glu Leu Glu Lys Leu Asn Leu Glu Leu Thr Pro Trp His Leu Glu
            425                 430                 435

CCC TCG AGG ATG ACA CTG TAT AGG TTT GGG AAC ACA TCG AGT AGC TCA      1400
Pro Ser Arg Met Thr Leu Tyr Arg Phe Gly Asn Thr Ser Ser Ser
            440                 445                 450

TTA TGG TAC GAG TTG GCA TAC GCT GAA GCA AAA GGG AGG ATC CGT AAG      1448
Leu Trp Tyr Glu Leu Ala Tyr Ala Glu Ala Lys Gly Arg Ile Arg Lys
            455                 460                 465                 470

GGT GAT CGA ACT TGG ATG ATT GGA TTT GGT TCA GGT TTC AAG TGT AAC      1496
Gly Asp Arg Thr Trp Met Ile Gly Phe Gly Ser Gly Phe Lys Cys Asn
            475                 480                 485
```

FIG. 2E

```
AGT GTT GTG TGG AGG GCT TTG AGG AGT GTC AAT CCG GCT AGA GAG AAG    1544
Ser Val Val Trp Arg Ala Leu Arg Ser Val Asn Pro Ala Arg Glu Lys
            490                 495                 500

AAT CCT TGG ATG GAT GAA ATT GAG AAG TTC CCT GTC CAT GTG CCT AAA    1592
Asn Pro Trp Met Asp Glu Ile Glu Lys Phe Pro Val His Val Pro Lys
            505                 510                 515

ATC GCA CCT ATC GCT TCG TAGAACTGCT AGGATGTGAT TAGTAATGAA           1640
Ile Ala Pro Ile Ala Ser
            520

AAATGTGTAT TATGTTAGTG ATGTAGAAAA AGAAACTTTA GTTGATGGGT GAGAACATGT  1700

CTCATTGAGA ATAACGTGTG CATCGTTGTG TTG                               1733
```

FIG. 2F

```
GTCGACACA ATG AAG GCC AAA ACA ATC ACA AAC CCG GAG ATC CAA GTC TCC        51
          Met Lys Ala Lys Thr Ile Thr Asn Pro Glu Ile Gln Val Ser
           1                   5                  10

ACG ACC ATG ACC ACG ACC ACG GCC ACT CTC CCC AAC TTC AAG                  99
Thr Thr Met Thr Thr Thr Thr Ala Thr Leu Pro Asn Phe Lys
 15                  20                  25          30

TCC TCC ATC AAC TTA CAC CAC GTC AAG CTC GGC TAC CAC TAC TTA ATC         147
Ser Ser Ile Asn Leu His His Val Lys Leu Gly Tyr His Tyr Leu Ile
             35                  40                  45

TCC AAT GCC CTC TTC CTC GTA TTC ATC CCC CTT TTG GGC CTC GCT TCG         195
Ser Asn Ala Leu Phe Leu Val Phe Ile Pro Leu Leu Gly Leu Ala Ser
         50                  55                  60

GCC CAC CTC TCC TTC TCG GCC CAT GAC TTG TCC CTG CTC TTC GAC             243
Ala His Leu Ser Phe Ser Ala His Asp Leu Ser Leu Leu Phe Asp
     65                  70                  75

CTC CTT CGC CGC AAC CTC CTC CCC GTT GTC GTT TGT TCT TTC CTC TTC         291
Leu Leu Arg Arg Asn Leu Leu Pro Val Val Val Cys Ser Phe Leu Phe
 80                  85                  90
```

FIG. 3A

```
GTT TTA TTA GCA ACC CTA CAT TTC TTG ACC CGG CCT AGG AAT GTC TAC    339
Val Leu Leu Ala Thr Leu His Phe Leu Thr Arg Pro Arg Asn Val Tyr
 95                 100                 105                 110

TTG GTG GAC TTT GCC TGC TAT AAG CCT CAC CCG AAC CTG ATA ACA TCC    387
Leu Val Asp Phe Ala Cys Tyr Lys Pro His Pro Asn Leu Ile Thr Ser
                    115                 120                 125

CAC GAG ATG TTC ATG GAC CGG ACC TCC CGG GCC GGG TCG TTT TCT AAG    435
His Glu Met Phe Met Asp Arg Thr Ser Arg Ala Gly Ser Phe Ser Lys
                130                 135                 140

GAG AAT ATT GAG TTT CAG AGG AAG ATC TTG GAG AGG GCC GGT ATG GGC    483
Glu Asn Ile Glu Phe Gln Arg Lys Ile Leu Glu Arg Ala Gly Met Gly
            145                 150                 155

CGG GAA ACC TAC GTC CCC GAA TCC GTC ACT AAG GTG CCG CCC GAG CCG    531
Arg Glu Thr Tyr Val Pro Glu Ser Val Thr Lys Val Pro Pro Glu Pro
        160                 165                 170

AGC ATA GCA GCC AGG GCC GAG GCG GAG GAG GTG ATG TAC GGG GCG        579
Ser Ile Ala Ala Arg Ala Glu Ala Glu Glu Val Met Tyr Gly Ala
175                 180                 185                 190
```

FIG. 3B

```
ATC GAG GTG TTG GAG AAG ACG GGG GTG AAG CCG AAG CAG ATA GGA    627
Ile Asp Glu Val Leu Glu Lys Thr Gly Val Lys Pro Lys Gln Ile Gly
195                 200                 205

ATA CTG GTG GTG AAC TGC AGC TTG TTT AAC CCA ACG CCG TCG CTG TCA    675
Ile Leu Val Val Asn Cys Ser Leu Phe Asn Pro Thr Pro Ser Leu Ser
            210                 215                 220

TCC ATG ATA GTT AAC CAT TAC AAG CTT AGG GGT AAT ATA CTT AGC TAT    723
Ser Met Ile Val Asn His Tyr Lys Leu Arg Gly Asn Ile Leu Ser Tyr
225                 230                 235

AAT CTT GGT GGC ATG GGT TGC AGT GCT GGG CTC ATT TCC ATT GAT CTT    771
Asn Leu Gly Gly Met Gly Cys Ser Ala Gly Leu Ile Ser Ile Asp Leu
        240                 245                 250

GCC AAG GAC CTC CTA CAG GTT TAC CGT AAC ACA TAT GTG TTA GTA GTG    819
Ala Lys Asp Leu Leu Gln Val Tyr Arg Asn Thr Tyr Val Leu Val Val
            255                 260                 265                 270

AGC ACA GAA AAC ATG ACC CTT AAT TGG TAC TGG GGC AAT GAC CGC TCC    867
Ser Thr Glu Asn Met Thr Leu Asn Trp Tyr Trp Gly Asn Asp Arg Ser
                275                 280                 285
```

FIG. 3C

```
ATG CTT ATC ACC AAC TGC CTA TTT CGC ATG GGT GGC GCT GCC ATC ATC      915
Met Leu Ile Thr Asn Cys Leu Phe Arg Met Gly Gly Ala Ala Ile Ile
            290                     295                 300

CTC TCA AAC CGC TGG CGT GAT CGT CGC CGA TCC AAG TAC CAA CTC CTT      963
Leu Ser Asn Arg Trp Arg Asp Arg Arg Arg Ser Lys Tyr Gln Leu Leu
            305                     310                 315

CAC ACA GTA CGC ACC CAC AAG GGC GCT GAC GAC AAG TCC TAT AGA TGC     1011
His Thr Val Arg Thr His Lys Gly Ala Asp Asp Lys Ser Tyr Arg Cys
            320                     325                 330

GTC TTA CAA CAA GAA GAT GAA AAT AAC AAG GTA GGT GTT GCC TTA TCC     1059
Val Leu Gln Gln Glu Asp Glu Asn Asn Lys Val Gly Val Ala Leu Ser
            335                     340             345         350

AAG GAT CTG ATG GCA GTT GCC GGT GAA GCC CTA AAG GCC AAC ATC ACG     1107
Lys Asp Leu Met Ala Val Ala Gly Glu Ala Leu Lys Ala Asn Ile Thr
            355                     360                 365

ACC CTT GGT CCC CTC GTG CTC CCC ATG TCA GAA CAA CTC CTC TTC TTT     1155
Thr Leu Gly Pro Leu Val Leu Pro Met Ser Glu Gln Leu Leu Phe Phe
            370                     375                 380
```

FIG. 3D

```
GCC ACC TTA GTG GCA CGT AAG GTC TTC AAG ATG ACG AAC GTG AAG CCA    1203
Ala Thr Leu Val Ala Arg Lys Val Phe Lys Met Thr Asn Val Lys Pro
            385                 390                 395

TAC ATC CCA GAT TTC AAG TTG GCA GCG AAG CAC TTC TGC ATC CAT GCA    1251
Tyr Ile Pro Asp Phe Lys Leu Ala Ala Lys His Phe Cys Ile His Ala
        400                 405                 410

GGA GGC AAA GCA GTG TTG GAT GAG CTC GAG ACG AAC TTG GAG TTG ACG    1299
Gly Gly Lys Ala Val Leu Asp Glu Leu Glu Thr Asn Leu Glu Leu Thr
    415                 420                 425                 430

CCA TGG CAC CTT GAA CCC TCG AGG ATG ACA CTG TAT AGG TTT GGG AAC    1347
Pro Trp His Leu Glu Pro Ser Arg Met Thr Leu Tyr Arg Phe Gly Asn
                435                 440                 445

ACA TCG AGT AGC TCA TTA TGG TAC GAG TTG GCA TAC GCT GAA GCA AAA    1395
Thr Ser Ser Ser Ser Leu Trp Tyr Glu Leu Ala Tyr Ala Glu Ala Lys
            450                 455                 460

GGG AGG ATC CGT AAG GGT GAT CGA ACT TGG ATG ATT GGA TTT GGT TCA    1443
Gly Arg Ile Arg Lys Gly Asp Arg Thr Trp Met Ile Gly Phe Gly Ser
        465                 470                 475
```

FIG. 3E

```
GGT TTC AAG TGT AAC AGT GTT GTG TGG AGG GCT TTG AGG AGT GTC AAT    1491
Gly Phe Lys Cys Asn Ser Val Val Trp Arg Ala Leu Arg Ser Val Asn
480                 485                 490

CCG GCT AGA GAG AAG AAT CCT TGG ATG GAT GAA ATT GAG AAT TTC CCT    1539
Pro Ala Arg Glu Lys Asn Pro Trp Met Asp Glu Ile Glu Asn Phe Pro
495                 500                 505                 510

GTC CAT GTG CCT AAA ATC GCA CCT ATC GCT TCG TAGAACTGCT AGGATGTGAT  1592
Val His Val Pro Lys Ile Ala Pro Ile Ala Ser
              515                 520

TAGTAATGAA AAATGTGTAT TATGTTAGTG ATGTAGAAAA AGAAACTTTA GTTGATGGGT  1652

GAGAACATGT CTCATTGAGA ATAACGTGTG CATCGTTGTG TTGAATTTGA ATTTGAGTAT  1712

TGGTGAAATT CTGTTAGAAT TGACGCATGA GTCATATATA TACAAATTTA AGTAAGATTT  1772

TACGCTTTCT T                                                      1783
```

FIG. 3F

```
GGCGGCGCCGG TACCTCTAGA CCTGGGCGATT CAACGTGGTC GGATCATGAC GCTTCCAGAA    60

AACATCGAGC AAGCTCTCAA AGCTGACCTC TTTCGGATCG TACTGAACCC GAACAATCTC   120

GTTATGTCCC GTCGTCTCCG AACAGACATC CTCGTAGCTC GGATTATCGA CGAATCCATG   180

GCTATACCCA ACCTCCGTCT TCGTCACGCC TGGAACCCTC TGGTACGCCA ATTCCGCTCC   240

CCAGAAGCAA CCGGCGCCGA ATTGCGCGAA TTGCTGACCT GGAGACGGAA CATCGTCGTC   300

GGGTCCCTTGC GCGATTGCGG CGGAAGCCGG GTCGGGTTGG GGACGAGACC CGAATCCGAG   360

CCTGGTGAAG AGGTTGTTCA TCGGAGATTT ATAGACGGAG ATGGATCGAG CGGTTTTGGG   420

GAAAGGGGAA GTGGGTTTGG CTCTTTTGGA TAGAGAGAGT GCAGCTTTGG AGAGAGACTG   480

GAGAGGTTTA GAGAGAGACG CGGCGGATAT TACCGGAGGA GAGGCGACGA GAGATAGCAT   540

TATCGAAGGG GAGGGAGAAA GAGTGACGTG GAGAAATAAG AAACCGTTAA GAGTCGGATA   600
```

FIG. 4A

```
TTTATCATAT TAAAAGCCCA ATGGGCCTGA ACCCATTTAA ACAAGACAGA TAAATGGGCC    660

GTGTGTTAAG TTAACAGAGT GTTAACGTTC GGTTTCAAAT GCCAACGCCA TAGGAACAAA    720

ACAAACGTGT CCTCAAGTAA ACCCCTGCCG TTTACACCTC AATGGCTGCA TGGTGAAGCC    780

ATTAACACGT GGCGTAGGAT GCATGACGAC GCCATTGACA CCTGACTCTC TTCCCTTCTC    840

TTCATATATC TCTAATCAAT TCAACTACTC ATTGTCATAG CTATTCGGAA AATACATACA    900

CATCCTTTTC TCTTCGATCT CTCTCAATTC ACAAGAAGCA AAGTCGACGG ATCCCTGCAG    960

TAAATTACGC CATGACTATT TTCATAGTCC AATAAGGCTG ATGTCGGGAG TCCAGTTTAT   1020

GAGCAATAAG GTGTTTAGAA TTTGATCAAT GTTTATAATA AAAGGGGGAA GATGATATCA   1080

CAGTCTTTTG TTCTTTTTGG CTTTTGTTAA ATTTGTGTGT TTCTATTTGT AAACCTCCTG   1140

TATATGTTGT ACTTCTTTCC CTTTTTAAGT GGTATCGTCT ATATGGTAAA ACGTTATGTT   1200
```

FIG. 4B

```
TGGTCTTTCC TTTTCTCTGT TTAGGATAAA AAGACTGCAT GTTTATCTT TAGTTATATT    1260

ATGTTGAGTA AATGAACTTT CATAGATCTG GTTCCGTAGA GTAGACTAGC AGCCGAGCTG    1320

AGCTGAACTG AACAGCTGGC AATGTGAACA CTGGATGCAA GATCAGATGT GAAGATCTCT    1380

AATATGGTGG TGGGATTGAA CATATCGTGT CTATATTTTT GTTGGCATTA AGCTCTTAAC    1440

ATAGATATAA CTGATGCAGT CATTGGTTCA TACACATATA TAGTAAGGAA TTACAATGGC    1500

AACCCAAACT TCAAAAACAG TAGGCCACCT GAATTGCCTT ATCGAATAAG AGTTTGTTTC    1560

CCCCCACTTC ATGGGATGTA ATACATGGGA TTTGGGAGTT TGAATGAACG TTGAGACATG    1620

GCAGAACCTC TAGAGGTACC GGCGCGC                                        1647
```

FIG. 4C

```
GAA ATG AGT AGG TCT AGC GAA CAA GAT CTA CTC TCT ACC GAG ATT GTT    48
Met Ser Arg Ser Ser Glu Gln Asp Leu Leu Ser Thr Glu Ile Val

AAC CGT GGG ATC GAA CCT TCC GGT CCA AAC GCC GGT TCA CCA ACG TTC    96
Asn Arg Gly Ile Glu Pro Ser Gly Pro Asn Ala Gly Ser Pro Thr Phe

TCG GTC AGA GTC CGG AGA CGT TTA CCG GAT TTT CTT CAA TCC GTA AAC   144
Ser Val Arg Val Arg Arg Arg Leu Pro Asp Phe Leu Gln Ser Val Asn

TTG AAG TAC GTG AAA CTT GGT TAT CAC TAC CTC ATA AAC CAT GCG GTT   192
Leu Lys Tyr Val Lys Leu Gly Tyr His Tyr Leu Ile Asn His Ala Val

TAC TTG GCG ACG ATA CCG GTT CTT GTG CTT GTG TTT AGT GCC GAA GTT   240
Tyr Leu Ala Thr Ile Pro Val Leu Val Leu Val Phe Ser Ala Glu Val

GGG AGT TTA AGC GGA GAA GAG ATT TGG AAG AAG CTT TGG GAC TAT GAT   288
Gly Ser Leu Ser Gly Glu Glu Ile Trp Lys Lys Leu Trp Asp Tyr Asp

ATC GCA ACC GTC ATC GGA TTC TTC GGT GTC TTT GTC TTG ACC GTT TGC   336
Ile Ala Thr Val Ile Gly Phe Phe Gly Val Phe Val Leu Thr Val Cys
```

FIG. 5A

```
GTC TAC TTC ATG TCT CGT CCA CGA TCT GTT TAT CTC ATT GAC TTC GCT    384
Val Tyr Phe Met Ser Arg Pro Arg Ser Val Tyr Leu Ile Asp Phe Ala

TGT TTC AAG CCT TCC GAT GAA CTT AAG GTG ACA AGA GAA GAG TTC ATA    432
Cys Phe Lys Pro Ser Asp Glu Leu Lys Val Thr Arg Glu Glu Phe Ile

GAT CTA GCT AGA AAA TCA GGC AAG TTC GAC GAA GAG ATC CTC GGA TTC    480
Asp Leu Ala Arg Lys Ser Gly Lys Phe Asp Glu Glu Ile Leu Gly Phe

AAG AGG ATC CTT CAA GCC TCA GGA ATA GGC GAT GAA ACG TAC GTC        528
Lys Arg Ile Leu Gln Ala Ser Gly Ile Gly Asp Glu Thr Tyr Val

CCA AGA TCA ATC TCT TCG GAA AAC ACA ACG ATG AAA GAA GGT GGT        576
Pro Arg Ser Ile Ser Ser Glu Asn Thr Thr Met Lys Glu Gly Gly

CGT GAA GAA GCC TCG ATG ATG ATA TTC GGC GCA CTC GAC GAA CTC TTC    624
Arg Glu Glu Ala Ser Met Met Ile Phe Gly Ala Leu Asp Glu Leu Phe

GAG AAG ACA CGT GTC AAA CCG AAA GAC GTA GGT GTC CTC GTT AAC        672
Glu Lys Thr Arg Val Lys Pro Lys Asp Val Gly Val Leu Val Asn

TGC AGT ATC TTT AAC CCG ACT CCG TCA CTC TCC GCG ATG GTG ATT AAC    720
Cys Ser Ile Phe Asn Pro Thr Pro Ser Leu Ser Ala Met Val Ile Asn
```

FIG. 5B

```
CAC TAC AAG ATG AGA GGG AAC ATA CTT AGC TAC AAC CTA GGA GGG ATG    768
His Tyr Lys Met Arg Gly Asn Ile Leu Ser Tyr Asn Leu Gly Gly Met

GGT TGC TCA GCA GGA ATC ATA GCC GTT GAT CTT GCT CGT GAC ATG CTT    816
Gly Cys Ser Ala Gly Ile Ile Ala Val Asp Leu Ala Arg Asp Met Leu

CAG TCT AAC CCG AAT AGT TAC GCG GTG GTT GTG AGT ACC GAG ATG GTT    864
Gln Ser Asn Pro Asn Ser Tyr Ala Val Val Val Ser Thr Glu Met Val

GGG TAT AAT TGG TAC GTG GGA CGT GAC AAG TCA ATG GTT ATA CCT AAC    912
Gly Tyr Asn Trp Tyr Val Gly Arg Asp Lys Ser Met Val Ile Pro Asn

TGC TTC TTT AGG ATG GGT TGC TCC GCC GTT ATG CTG TCT AAC CGC CGC    960
Cys Phe Phe Arg Met Gly Cys Ser Ala Val Met Leu Ser Asn Arg Arg

CGT GAC TTC CGC CAT GCT AAG TAC CGC CTT GAG CAC ATT GTC CGG ACT   1008
Arg Asp Phe Arg His Ala Lys Tyr Arg Leu Glu His Ile Val Arg Thr

CAC AAG GCT GCC GAC CGT AGC TTC AGG AGT GTG TAC CAG GAA GAA       1056
His Lys Ala Ala Asp Arg Ser Phe Arg Ser Val Tyr Gln Glu Glu

GAT GAA CAA GGA TTC AAG GGA TTA AAA ATA AGC AGA GAC CTA ATG GAA   1104
Asp Glu Gln Gly Phe Lys Gly Leu Lys Ile Ser Arg Asp Leu Met Glu
```

FIG. 5C

| | | | | | | | | | | |
|---|---|---|---|---|---|---|---|---|---|---|
| GTT | GGA | GGT | GAA | GCT | CTC | AAG | ACC | AAC | ATC | ACC | ACC | TTA | GGC | CCT | CTC | 1152 |
| Val | Gly | Gly | Glu | Ala | Leu | Lys | Thr | Asn | Ile | Thr | Thr | Leu | Gly | Pro | Leu | |

GTC CTT CCT TTC TCC GAG CAG CTT CTC TTC TTT GCC GCT TTG ATC CGT  1200
Val Leu Pro Phe Ser Glu Gln Leu Leu Phe Phe Ala Ala Leu Ile Arg

AGA ACT TTC TCA CCC GCC AAA ACT ACC ACC ACC TCC TCC TCA GCC  1248
Arg Thr Phe Ser Pro Ala Lys Thr Thr Thr Thr Ser Ser Ser Ala

ACT GCG AAA ATC AAC GGA GCC AAG TCG TCA TCC TCC TCT GAT CTA TCC  1296
Thr Ala Lys Ile Asn Gly Ala Lys Ser Ser Ser Ser Ser Asp Leu Ser

AAG CCG TAC ATC CCG GAC TAC AAG CTT GCC TTC GAG CAT TTC TGC TTC  1344
Lys Pro Tyr Ile Pro Asp Tyr Lys Leu Ala Phe Glu His Phe Cys Phe

CAC GCG GCA AGC AAA GCG GTG CTT GAG GAG CTT CAG AAG AAT CTA GGC  1392
His Ala Ala Ser Lys Ala Val Leu Glu Glu Leu Gln Lys Asn Leu Gly

TTG AGT GAT GAG AAC ATG GAG GCT TCT AAG ATG ACT TTA CAC AGG TTT  1440
Leu Ser Asp Glu Asn Met Glu Ala Ser Lys Met Thr Leu His Arg Phe

GGA AAC ACT TCC AGC AGT GGA ATC TGG TAC GAG CTT GCT TAC ATG GAG  1488
Gly Asn Thr Ser Ser Ser Gly Ile Trp Tyr Glu Leu Ala Tyr Met Glu

FIG. 5D

```
GCC AAG GAG AGT GTT CGT AGA GGC GAT AGG GTT TGG CAG ATT GCT TTT    1536
Ala Lys Glu Ser Val Arg Arg Gly Asp Arg Val Trp Gln Ile Ala Phe

GGG TCA GGT TTT AAG TGT AAC AGT GTG GTT TGG AAG GCA ATG AGG AAG    1584
Gly Ser Gly Phe Lys Cys Asn Ser Val Val Trp Lys Ala Met Arg Lys

GTG AAG AAG CCG GCA AGG AAC AAT CCT TGG GTT GAT TGC ATT AAC CGT    1632
Val Lys Lys Pro Ala Arg Asn Asn Pro Trp Val Asp Cys Ile Asn Arg

TAC CCT GTC GCT CTC TGATCATTTA TTTTTAAAAT TATTATTTCT TCTTAATTAA    1687
Tyr Pro Val Ala Leu

ATCATCTATG ATCTCTCTTC CTTGTGTTG GATGATAGAC GTTGTTTGC TGGTCATTCG    1747

TATCTTAAGA CTTCTATAAG AATGGATGGT TCAAGTCCAA AAAAAAAAA AAAAAAAAA    1807

AAA                                                                1810
```

FIG. 5E

```
GTCGACAAA ATG ACG TCC ATT AAC GTA AAG CTC CTT TAC CAT TAC GTC ATA    51
          Met Thr Ser Ile Asn Val Lys Leu Leu Tyr His Tyr Val Ile

ACC AAC CTT TTC AAC CTT TGT TTC TTT CCA TTA ACG GCG ATC GTC GCC      99
Thr Asn Leu Phe Asn Leu Cys Phe Phe Pro Leu Thr Ala Ile Val Ala

GGA AAA GCC TAT CGG CTT ACC ATA GAC GAT CTT CAC TTA TAC TAT         147
Gly Lys Ala Tyr Arg Leu Thr Ile Asp Asp Leu His Leu Tyr Tyr

TCC TAT CTC CAA CAC AAC CTC ATA ACC ATT GCT CCA CTC TTT GCC TTC     195
Ser Tyr Leu Gln His Asn Leu Ile Thr Ile Ala Pro Leu Phe Ala Phe

ACC GTT TTC GGT TCG GTT CTC TAC ATC GCA ACC CGG CCC AAA CCG GTT     243
Thr Val Phe Gly Ser Val Leu Tyr Ile Ala Thr Arg Pro Lys Pro Val

TAC CTC GTT GAG TAC TCA TGC TAC CTT CCA CCA ACG CAT TGT AGA TCA     291
Tyr Leu Val Glu Tyr Ser Cys Tyr Leu Pro Pro Thr His Cys Arg Ser

AGT ATC TCC AAG GTC ATG GAT ATC TTT TAC CAA GTA AGA AAA GCT GAT     339
Ser Ile Ser Lys Val Met Asp Ile Phe Tyr Gln Val Arg Lys Ala Asp
```

FIG. 6A

```
CCT TCT CGG AAC GGC ACG TGC GAT GAC TCG TCC TGG CTT GAC TTC TTG    387
Pro Ser Arg Asn Gly Thr Cys Asp Asp Ser Ser Trp Leu Asp Phe Leu

AGG AAG ATT CAA GAA CGT TCA GGT CTA GGC GAT GAA ACC CAC GGG CCC    435
Arg Lys Ile Gln Glu Arg Ser Gly Leu Gly Asp Glu Thr His Gly Pro

GAG GGG CTG CTT CAG GTC CCT CCC CGG AAG ACT TTT GCG GCG GCG CGT    483
Glu Gly Leu Leu Gln Val Pro Pro Arg Lys Thr Phe Ala Ala Ala Arg

GAA GAG ACG GAG CAA GTT ATC ATT GGT GCG CTA GAA AAT CTA TTC AAG    531
Glu Glu Thr Glu Gln Val Ile Ile Gly Ala Leu Glu Asn Leu Phe Lys

AAC ACC AAT GTT AAC CCT AAA GAT ATA GGT ATA CTT GTG GTC AAC TCA    579
Asn Thr Asn Val Asn Pro Lys Asp Ile Gly Ile Leu Val Val Asn Ser

AGC ATG TTT AAT CCA ACT CCT TCG CTC TCC GCG ATG GTC GTT AAC ACT    627
Ser Met Phe Asn Pro Thr Pro Ser Leu Ser Ala Met Val Val Asn Thr

TTC AAG CTC CGA AGC AAC GTA AGA AGC TTT AAC CTT GGT GGC ATG GGT    675
Phe Lys Leu Arg Ser Asn Val Arg Ser Phe Asn Leu Gly Gly Met Gly

TGT AGT GCC GGC GTT ATA GCC ATT GAT CTA GCA AAG GAC TTG TTG CAT    723
Cys Ser Ala Gly Val Ile Ala Ile Asp Leu Ala Lys Asp Leu Leu His
```

FIG. 6B

```
GTC CAT AAA AAT ACG TAT GCT CTT GTG GTG AGC ACA GAG AAC ATC ACT   771
Val His Lys Asn Thr Tyr Ala Leu Val Val Ser Thr Glu Asn Ile Thr

TAT AAC ATT TAC GCT GGT GAT AAT AGG TCC ATG ATG GTT TCA AAT TGC   819
Tyr Asn Ile Tyr Ala Gly Asp Asn Arg Ser Met Met Val Ser Asn Cys

TTG TTC CGT GTT GGG GCC GCT ATT TTG CTC TCC AAC AAG CCT AGA       867
Leu Phe Arg Val Gly Ala Ala Ile Leu Leu Ser Asn Lys Pro Arg

GAT CGT AGA CGG TCC AAG TAC GAG CTA GTT CAC ACG GTT CGA ACG CAT   915
Asp Arg Arg Arg Ser Lys Tyr Glu Leu Val His Thr Val Arg Thr His

ACC GGA GCT GAC GAC AAG TCT TTT CGT TGC GTG CAA CAA GGA GAC GTT  963
Thr Gly Ala Asp Asp Lys Ser Phe Arg Cys Val Gln Gln Gly Asp Val

GAG AAC GGC AAA ACC GGA GTG AGT TTG TCC AAG GAC ATA ACC GAT GTT  1011
Glu Asn Gly Lys Thr Gly Val Ser Leu Ser Lys Asp Ile Thr Asp Val

GCT GGT CGA ACG GTT AAG AAA ACA GCA AAC ATA GCA ACG CTG GGT CCG TTG ATT  1059
Ala Gly Arg Thr Val Lys Lys Thr Ala Asn Ile Ala Thr Leu Gly Pro Leu Ile

CTT CCG TTA AGC GAG AAA CTT CTT TTT GTT ACC TTC ATG GGC AAG      1107
Leu Pro Leu Ser Glu Lys Leu Leu Phe Val Thr Phe Met Gly Lys
```

FIG. 6C

```
AAA CTT TTC AAA GAC AAA ATC AAA CAT TAT TAC GTC CCG GAC TTC AAG     1155
Lys Leu Phe Lys Asp Lys Ile Lys His Tyr Tyr Val Pro Asp Phe Lys

CTT GCT ATC GAC CAT TTT TGT ATA CAT GCC GGA GGC AAA GCC GTG ATT     1203
Leu Ala Ile Asp His Phe Cys Ile His Ala Gly Gly Lys Ala Val Ile

GAT GTG CTA GAG AAG AAC CTA GGC CTA GCA CCG ATC GAT GTA GAG GCA     1251
Asp Val Leu Glu Lys Asn Leu Gly Leu Ala Pro Ile Asp Val Glu Ala

TCA AGA TCA ACG TTA CAT AGA TTT GGA AAC ACT TCA TCT AGC TCA ATA     1299
Ser Arg Ser Thr Leu His Arg Phe Gly Asn Thr Ser Ser Ser Ser Ile

TGG TAT GAG TTG GCA TAC ATA GAA GCA AAA GGA AGG ATG AAG AAA GGT     1347
Trp Tyr Glu Leu Ala Tyr Ile Glu Ala Lys Gly Arg Met Lys Lys Gly

AAT AAA GTT TGG CAG ATT GCT TTA GGG TCA GGC TTT AAG TGT AAC AGT     1395
Asn Lys Val Trp Gln Ile Ala Leu Gly Ser Gly Phe Lys Cys Asn Ser

GCA GTT TGG GTG GCT CTA AAC AAT GTC AAA GCT TCC AAA TAGGATCC        1442
Ala Val Trp Val Ala Leu Asn Asn Val Lys Ala Ser Lys
```

FIG. 6D

```
GTCGACAAA ATG ACG TCC ATT AAC GTA AAG CTC CTT TAC CAT TAC GTC ATA   51
          Met Thr Ser Ile Asn Val Lys Leu Leu Tyr His Tyr Val Ile

ACC AAC CTT TTC AAC CTT TGC TTC TTT CCG TTA ACG GCG ATC GTC GCC     99
Thr Asn Leu Phe Asn Leu Cys Phe Phe Pro Leu Thr Ala Ile Val Ala

GGA AAA GCC TAT CGG CTT ACC ATA GAC GAT CTT CAC CAC TTA TAC TAT    147
Gly Lys Ala Tyr Arg Leu Thr Ile Asp Asp Leu His His Leu Tyr Tyr

TCC TAT CTC CAA CAC AAC CTC ATA ACC ATC GCT CCA CTC TTT GCC TTC    195
Ser Tyr Leu Gln His Asn Leu Ile Thr Ile Ala Pro Leu Phe Ala Phe

ACC GTT TTC GGT TCG GTT CTC TAC ATC GCA ACC CGG CCC AAA CCG GTT    243
Thr Val Phe Gly Ser Val Leu Tyr Ile Ala Thr Arg Pro Lys Pro Val

TAC CTC GTT GAG TAC TCA TGC TAC CTT CCA ACG CAT TGT AGA TCA        291
Tyr Leu Val Glu Tyr Ser Cys Tyr Leu Pro Thr His Cys Arg Ser

AGT ATC TCC AAG GTC ATG GAT ATC TTT TAT CAA GTA AGA AAA GCT GAT    339
Ser Ile Ser Lys Val Met Asp Ile Phe Tyr Gln Val Arg Lys Ala Asp
```

FIG. 7A

```
CCT TCT CGG AAC GGC ACG TGC GAT GAC TCG TGG CTT GAC TTC TTG    387
Pro Ser Arg Asn Gly Thr Cys Asp Asp Ser Trp Leu Asp Phe Leu

AGG AAG ATT CAA GAA CGT TCA GGT CTA GGC GAT GAA ACT CAC GGG CCC   435
Arg Lys Ile Gln Glu Arg Ser Gly Leu Gly Asp Glu Thr His Gly Pro

GAG GGG CTG CTT CAG GTC CCT CCC CGG AAG ACT TTT GCG GCG CGT   483
Glu Gly Leu Leu Gln Val Pro Pro Arg Lys Thr Phe Ala Ala Arg

GAA GAG ACG GAG CAA GTT ATC ATT GGT GCG CTA GAA AAT CTA TTC AAG   531
Glu Glu Thr Glu Gln Val Ile Ile Gly Ala Leu Glu Asn Leu Phe Lys

AAC ACC AAC GTT AAC CCT AAA GAT ATA GGT ATA CTT GTG GTG AAC TCA   579
Asn Thr Asn Val Asn Pro Lys Asp Ile Gly Ile Leu Val Val Asn Ser

AGC ATG TTT AAT CCA ACT CCA TCG CTC TCC GCG ATG GTC GTT AAC ACT   627
Ser Met Phe Asn Pro Thr Pro Ser Leu Ser Ala Met Val Val Asn Thr

TTC AAG CTC CGA AGC AAC GTA AGA AGC TTT AAC CTT GGT GGC ATG GGT   675
Phe Lys Leu Arg Ser Asn Val Arg Ser Phe Asn Leu Gly Gly Met Gly

TGT AGT GCC GGC GTT ATA GCC ATT GAT CTA GCA AAG GAC TTG TTG CAT   723
Cys Ser Ala Gly Val Ile Ala Ile Asp Leu Ala Lys Asp Leu Leu His
```

FIG. 7B

```
GTC CAT AAA AAT ACG TAT GCT CTT GTG GTG AGC ACA GAG AAC ATC ACT    771
Val His Lys Asn Thr Tyr Ala Leu Val Val Ser Thr Glu Asn Ile Thr

TAT AAC ATT TAC GCT GGT GAT AAT AGG TCC ATG ATG GTT TCA AAT TGC    819
Tyr Asn Ile Tyr Ala Gly Asp Asn Arg Ser Met Met Val Ser Asn Cys

TTG TTC CGT GTT GGT GGG GCC GCT ATT TTG CTC TCC AAC AAG CCT GGA    867
Leu Phe Arg Val Gly Gly Ala Ala Ile Leu Leu Ser Asn Lys Pro Gly

GAT CGT AGA CGG TCC AAG TAC GAG CTA GTT CAC ACG GTT CGA ACG CAT    915
Asp Arg Arg Arg Ser Lys Tyr Glu Leu Val His Thr Val Arg Thr His

ACC GGA GCT GAC GAC AAG TCT TTT CGT TGC GTG CAA CAA GGA GAC GAT    963
Thr Gly Ala Asp Asp Lys Ser Phe Arg Cys Val Gln Gln Gly Asp Asp

GAG AAC GGC AAA ATC GGA GTG AGT TTG TCC AAG GAC ATA ACC GAT GTT   1011
Glu Asn Gly Lys Ile Gly Val Ser Leu Ser Lys Asp Ile Thr Asp Val

GCT GGT CGA ACG GTT AAG AAA AAC ATA GCA ACG TTG GGT CCG TTG ATT   1059
Ala Gly Arg Thr Val Lys Lys Asn Ile Ala Thr Leu Gly Pro Leu Ile

CTT CCG TTA AGC GAG AAA CTT CTT TTC GTT ACC TTC ATG GGC AAG       1107
Leu Pro Leu Ser Glu Lys Leu Leu Phe Val Thr Phe Met Gly Lys
```

FIG. 7C

```
AAA CTT TTC AAA GAT AAA ATC AAA CAT TAC TAC GTC CCG GAT TTC AAA    1155
Lys Leu Phe Lys Asp Lys Ile Lys His Tyr Tyr Val Pro Asp Phe Lys

CTT GCT ATT GAC CAT TTT TGT ATA CAT GCC GGA GGC AGA GCC GTG ATT    1203
Leu Ala Ile Asp His Phe Cys Ile His Ala Gly Gly Arg Ala Val Ile

GAT GTG CTA GAG AAG AAC CTA GCA CCG ATC GAT GTA GAG GCA            1251
Asp Val Leu Glu Lys Asn Leu Ala Pro Ile Asp Val Glu Ala

TCA AGA TCA ACG TTA CAT AGA TTT GGA AAC ACT TCA TCT AGC TCA ATA    1299
Ser Arg Ser Thr Leu His Arg Phe Gly Asn Thr Ser Ser Ser Ser Ile

TGG TAT GAG TTG GCA TAC ATA GAA GCA AAA GGA AGG ATG AAG AAA GGT    1347
Trp Tyr Glu Leu Ala Tyr Ile Glu Ala Lys Gly Arg Met Lys Lys Gly

AAT AAA GTT TGG CAG ATT GCT TTA GGG TCA GGC TTT AAG TGT AAC AGT    1395
Asn Lys Val Trp Gln Ile Ala Leu Gly Ser Gly Phe Lys Cys Asn Ser

GCA GTT TGG GTG GCT CTA AAC AAT GTC AAA GCT TCC AAA TAGGATCC       1442
Ala Val Trp Val Ala Leu Asn Asn Val Lys Ala Ser Lys
```

FIG. 7D

| | | | | | | | | | | | | | | | | |
|---|---|---|---|---|---|---|---|---|---|---|---|---|---|---|---|---|
| AAG | CTT | AAA | CTA | GTG | TAT | CAT | TAC | CTA | ATC | TCC | AAC | GCT | CTC | TAC | ATC | 48 |
| Lys | Leu | Lys | Leu | Val | Tyr | His | Tyr | Leu | Ile | Ser | Asn | Ala | Leu | Tyr | Ile | |
| CTC | CTC | CTT | CCT | CTC | GCC | GCA | ACA | ATC | GCT | AAC | CTC | TCT | TCT | TTC | | 96 |
| Leu | Leu | Leu | Pro | Leu | Ala | Ala | Thr | Ile | Ala | Asn | Leu | Ser | Ser | Phe | | |
| ACC | ATC | AAC | GAC | CTC | CTC | CTC | TAC | AAC | ACA | CTC | CGT | TTC | CAT | TTC | | 144 |
| Thr | Ile | Asn | Asp | Leu | Leu | Leu | Tyr | Asn | Thr | Leu | Arg | Phe | His | Phe | | |
| CTC | TCC | GCC | ACA | CTC | GCC | GCA | CTC | TTG | ATC | TCT | CTC | TCC | ACC | GCT | | 192 |
| Leu | Ser | Ala | Thr | Leu | Ala | Ala | Leu | Leu | Ile | Ser | Leu | Ser | Thr | Ala | | |
| TAC | TTC | ACC | ACC | CGT | CCT | CGC | CGT | GTC | TTC | CTC | CTC | GAC | TTC | TCG | TGT | 240 |
| Tyr | Phe | Thr | Thr | Arg | Pro | Arg | Arg | Val | Phe | Leu | Leu | Asp | Phe | Ser | Cys | |
| TAC | AAA | CCA | GAC | CCT | TCA | CTG | ATC | TGC | ACT | CGT | GAA | ACA | TTC | ATG | GAC | 288 |
| Tyr | Lys | Pro | Asp | Pro | Ser | Leu | Ile | Cys | Thr | Arg | Glu | Thr | Phe | Met | Asp | |
| AGA | TCT | CAA | CGT | GTA | GGC | ATC | TTC | ACA | GAA | GAC | AAC | TTA | GCT | TTC | CAA | 336 |
| Arg | Ser | Gln | Arg | Val | Gly | Ile | Phe | Thr | Glu | Asp | Asn | Leu | Ala | Phe | Gln | |

FIG. 8A

| | | | | | | | | |
|---|---|---|---|---|---|---|---|---|
| CAA | AAG | ATC | CTC | GAA | AGA | TCC | GGT | CTA | GGT | CAG | AAA | ACT | TAC | TTC | CCT | 384 |
| Gln | Lys | Ile | Leu | Glu | Arg | Ser | Gly | Leu | Gly | Gln | Lys | Thr | Tyr | Phe | Pro | |
| GAA | GCT | CTT | CGT | GTT | CCT | CCT | AAT | CCT | TGT | ATG | GAA | GAA | GCG | AGA | 432 |
| Glu | Ala | Leu | Arg | Val | Pro | Pro | Asn | Pro | Cys | Met | Glu | Glu | Ala | Arg | |
| AAA | GAG | GCA | GAA | ACA | GTT | ATG | TTC | GGA | GCT | ATT | GAC | GCG | GTT | CTT | GAG | 480 |
| Lys | Glu | Ala | Glu | Thr | Val | Met | Phe | Gly | Ala | Ile | Asp | Ala | Val | Leu | Glu | |
| AAG | ACC | GGT | GTG | AAA | CCT | AAA | GAT | ATT | GGA | ATC | CTT | GTG | GTG | AAT | TGT | 528 |
| Lys | Thr | Gly | Val | Lys | Pro | Lys | Asp | Ile | Gly | Ile | Leu | Val | Val | Asn | Cys | |
| AGC | TTG | TTT | AAT | CCA | ACA | CCG | TCA | CTT | TCT | GCT | ATG | ATT | GTG | AAT | AAG | 576 |
| Ser | Leu | Phe | Asn | Pro | Thr | Pro | Ser | Leu | Ser | Ala | Met | Ile | Val | Asn | Lys | |
| TAT | AAG | CTT | AGA | GGC | AAC | ATT | TTG | AGC | TAT | AAT | TTC | GGC | GGG | ATG | GG | 623 |
| Tyr | Lys | Leu | Arg | Gly | Asn | Ile | Leu | Ser | Tyr | Asn | Phe | Gly | Gly | Met | Gly | |

FIG. 8B.

```
AAG CTT AAG TTA GGC TAC CAC TAT CTG ATC ACT CAC TTT TTT AAA CTC    48
Lys Leu Lys Leu Gly Tyr His Tyr Leu Ile Thr His Phe Phe Lys Leu

ATG TTC CTC CCT CTA ATG GCT GTT TTG TTC ATG AAT GTC TCA TTG TTA    96
Met Phe Leu Pro Leu Met Ala Val Leu Phe Met Asn Val Ser Leu Leu

AGC CTA AAC CAT CTT CAG CTC TAT TAC AAT TCC ACC GGA TTC ATC TTC   144
Ser Leu Asn His Leu Gln Leu Tyr Tyr Asn Ser Thr Gly Phe Ile Phe

GTC ATC ACT CTC GCC ATT GTC GGA TCC ATT GTC TTC TTC ATG TCT CGA   192
Val Ile Thr Leu Ala Ile Val Gly Ser Ile Val Phe Phe Met Ser Arg

CCT AGA TCC ATC TAC CTT CTA GAT TAC TCT TGC TAC CTC CCG CCT TCG   240
Pro Arg Ser Ile Tyr Leu Leu Asp Tyr Ser Cys Tyr Leu Pro Pro Ser

AGT CAA AAA GTT AGC GAA TAC CAG AAA TTC ATG AAC AAC TCT AGT TTG ATT   288
Ser Gln Lys Val Ser Glu Tyr Gln Lys Phe Met Asn Asn Ser Ser Leu Ile

CAA GAT TTC AGC GAA ACT TCT CTT GAG TTC CAG AGG AAG ATC TTG ATT   336
Gln Asp Phe Ser Glu Thr Ser Leu Glu Phe Gln Arg Lys Ile Leu Ile

CGC TCT GGT CTC GGT GAA GAG ACT TAT TTA CCG GAT TCT ATT CAC TCT   384
Arg Ser Gly Leu Gly Glu Glu Thr Tyr Leu Pro Asp Ser Ile His Ser

FIG. 9A
```

```
ATC CCT CCG CGT CCT ACT ATG GCT GCA GCG CGT GAA GAA GCG GAG CAG    432
Ile Pro Pro Arg Pro Thr Met Ala Ala Ala Arg Glu Glu Ala Glu Gln

GTA ATC TTC GGT GCA CTC GAC AAT CTT TTC GAG AAT ACA AAA ATC AAT    480
Val Ile Phe Gly Ala Leu Asp Asn Leu Phe Glu Asn Thr Lys Ile Asn

CCT AGG GAG ATT GGT GTT CTT GTT GTG AAT TGT AGT TTG TTT AAC CCC    528
Pro Arg Glu Ile Gly Val Leu Val Val Asn Cys Ser Leu Phe Asn Pro

ACG CCT TCT TTA TCC GCC ATG ATT GTT AAC AAG TAT AAG CTT AGA GGA    576
Thr Pro Ser Leu Ser Ala Met Ile Val Asn Lys Tyr Lys Leu Arg Gly

AAC ATT AAG AGC TTT AAT CTC GGC GGC ATG G                          607
Asn Ile Lys Ser Phe Asn Leu Gly Gly Met
```

FIG. 9B

```
AAG CTT AAA CTG GGG TAC CAC TAC CTC ATT ACT CAT CTC TTC AAG CTC     48
Lys Leu Lys Leu Gly Tyr His Tyr Leu Ile Thr His Leu Phe Lys Leu

TGT TTG GTT CCA TTA ATG GCG GTT TTA GTC ACA GAG ATC TCC CGA TTA     96
Cys Leu Val Pro Leu Met Ala Val Leu Val Thr Glu Ile Ser Arg Leu

ACA ACA GAC GAT CTT TAC CAG ATT TGC CTT CAT CTC CAA TAC AAT CTC    144
Thr Thr Asp Asp Leu Tyr Gln Ile Cys Leu His Leu Gln Tyr Asn Leu

GTT GCT TTC ATC TTT CTC TCT GCT TTA GCT ATC TTT GGC TCC ACC GTT    192
Val Ala Phe Ile Phe Leu Ser Ala Leu Ala Ile Phe Gly Ser Thr Val

TAC ATC ATG AGT CGT CCC AGA TCT GTT TAT CTC GTT GAT TAC TCT TGT    240
Tyr Ile Met Ser Arg Pro Arg Ser Val Tyr Leu Val Asp Tyr Ser Cys

TAT CTT CCT CCG GAG AGT CTT CAG GTT CAG TAT CAG AAG TAT TTT ATG GAT    288
Tyr Leu Pro Pro Glu Ser Leu Gln Val Gln Tyr Gln Lys Tyr Phe Met Asp

CAT TCT AAG TTG ATT GAA GAT TTC AAT GAG TCA TCT TTA GAG TTT CAG    336
His Ser Lys Leu Ile Glu Asp Phe Asn Glu Ser Ser Leu Glu Phe Gln
```

FIG. 10A

```
AGG AAG ATT CTT GAA CGT TCT GGT TTA GGA GAA GAG ACT TAT CTC CCT    384
Arg Lys Ile Leu Glu Arg Ser Gly Leu Gly Glu Glu Thr Tyr Leu Pro

GAA GCT TTA CAT TGT ATC CCT CCG AGG CCT ACG ATG ATG GCG GCT CGT    432
Glu Ala Leu His Cys Ile Pro Pro Arg Pro Thr Met Met Ala Ala Arg

GAG GAA GCT GAG CAG GTA ATG TTT GGT GCT CTT GAT AAG CTT TTC GAG    480
Glu Glu Ala Glu Gln Val Met Phe Gly Ala Leu Asp Lys Leu Phe Glu

AAT ACC AAG ATT AAC CCT AGG GAT ATT GGT GTG TTG GTT GTG AAT TGT    528
Asn Thr Lys Ile Asn Pro Arg Asp Ile Gly Val Leu Val Val Asn Cys

AGC TTG TTT AAT CCT ACA CCT TCG TTG TCA GCT ATG ATT GTT AAC AAG    576
Ser Leu Phe Asn Pro Thr Pro Ser Leu Ser Ala Met Ile Val Asn Lys

TAT AAG CTT AGA GGG AAT GTT AAG AGT TTT AAC CTG GGG GGC ATT G      622
Tyr Lys Leu Arg Gly Asn Val Lys Ser Phe Asn Leu Gly Gly Ile
```

FIG. 10B

```
AAG CTT AAG TTA TGG TAT CAC TAC CTG ATT TCT CAC CTT TTT AAG CTC    48
Lys Leu Lys Leu Trp Tyr His Tyr Leu Ile Ser His Leu Phe Lys Leu

TTG TTG GTT CCT TTA ATG GCG GTT CTG TTC ACG AAT GTC TCC CGG TTA    96
Leu Leu Val Pro Leu Met Ala Val Leu Phe Thr Asn Val Ser Arg Leu

AGC CTA AAC CAG CTC TGT CTC GAT CTC TCT CTC CAG CTC CAG TTC AAT   144
Ser Leu Asn Gln Leu Cys Leu Asp Leu Ser Leu Gln Leu Gln Phe Asn

CTC GTC GGA TTC ATC TTC TTC ATT ACC GTC TCC ATT TTC GGA TTC ACA   192
Leu Val Gly Phe Ile Phe Phe Ile Thr Val Ser Ile Phe Gly Phe Thr

GTT ATC TTC ATG TCC CGA CCT AGA TCC GTT TAC CTC GAC TAC TCA       240
Val Ile Phe Met Ser Arg Pro Arg Ser Val Tyr Leu Asp Tyr Ser

TGT TAC CTC CCG CCG TCG AAT CTC AAA GTT AGC TAC CAG ACA TTC ATG   288
Cys Tyr Leu Pro Pro Ser Asn Leu Lys Val Ser Tyr Gln Thr Phe Met

AAT CAT TCT AAA CTG ATT GAA GAT TTC GAC GAG TCG CTT GAG TTC       336
Asn His Ser Lys Leu Ile Glu Asp Phe Asp Glu Ser Leu Glu Phe
```

FIG. 11A

```
CAG CGG AAG ATC CTG AAG CGA TCC GGT CTC GGC GAA GAG ACT TAC CTC    384
Gln Arg Lys Ile Leu Lys Arg Ser Gly Leu Gly Glu Glu Thr Tyr Leu

CCG GAA TCT ATC CAC TGC ATC CCG CCG CGT CCG ACT ATG GCG GCG GCG    432
Pro Glu Ser Ile His Cys Ile Pro Pro Arg Pro Thr Met Ala Ala Ala

CGT GAG GAA TCG GAG CAG GTA ATC TTC GGT GCA CTC GAC AAT CTC TTC    480
Arg Glu Glu Ser Glu Gln Val Ile Phe Gly Ala Leu Asp Asn Leu Phe

GAG AAT ACC AAA ATC GAC CCT AGG GAG ATT GGT GTT GTG GTG AAC        528
Glu Asn Thr Lys Ile Asp Pro Arg Glu Ile Gly Val Val Val Asn

TGC AGC TTG TTT AAC CCG ACG CCT TCT TTA TCC GCC ATG ATT GTG AAC    576
Cys Ser Leu Phe Asn Pro Thr Pro Ser Leu Ser Ala Met Ile Val Asn

AAG TAT AAG CTT AGA GGA AAC GTG AAG AGC TTT AAT CTC GGT GGC ATG G  625
Lys Tyr Lys Leu Arg Gly Asn Val Lys Ser Phe Asn Leu Gly Gly Met>
```

FIG. 11B

```
GTTCATTGAT TTGTTTGAGA CTCTGTTGCA GAAATCTCCA C ATG GAT GAT GAA TCC    56
                                              Met Asp Asp Glu Ser

GTT AAT GGA GGA TCC GTA CAG ATC CGG ACC CGA AAG TAC GTC AAG CTG     104
Val Asn Gly Gly Ser Val Gln Ile Arg Thr Arg Lys Tyr Val Lys Leu

GGT TAT CAC TAC CTG ATT TCT CAC CTT TTT AAG CTC TTG TTG GTT CCT     152
Gly Tyr His Tyr Leu Ile Ser His Leu Phe Lys Leu Leu Leu Val Pro

TTA ATG GCG GTT CTG TTC ACG AAT GTC TCC CGG TTA AGC CTA AAC CAG     200
Leu Met Ala Val Leu Phe Thr Asn Val Ser Arg Leu Ser Leu Asn Gln

CTC TGT CTC GAT CTC TCT CTC CAG CTC CAG TTC AAT CTC GTC GGA TTC     248
Leu Cys Leu Asp Leu Ser Leu Gln Leu Gln Phe Asn Leu Val Gly Phe

ATC TTC TTC ATT ACC GCC TCC ATT TTC GGA TTC ACA GTT ATC TTC ATG     296
Ile Phe Phe Ile Thr Ala Ser Ile Phe Gly Phe Thr Val Ile Phe Met

TCC CGA CCT AGA TCC GTT TAC CTC CTC GAC TAC TCA TGT TAC CTC CCG     344
Ser Arg Pro Arg Ser Val Tyr Leu Leu Asp Tyr Ser Cys Tyr Leu Pro
```

FIG. 12A

```
NCG GCG AAT CTC AAA GTT AGC TAC CAG ACA TTC ATG AAT CAT TCT AAA       392
Xxx Ala Asn Leu Lys Val Ser Tyr Gln Thr Phe Met Asn His Ser Lys

CTG ATT GAA GAT TTC GAC GAG TCG CTT GAG TCG CTT GAG TTC CAG CGG AAG ATC   440
Leu Ile Glu Asp Phe Asp Glu Ser Leu Glu Ser Phe Gln Arg Lys Ile

CTG AAG CGA TCC GGT CTC GGC GAA GAG ACT TAC CTC CCG GAA TCT ATC       488
Leu Lys Arg Ser Gly Leu Gly Glu Glu Thr Tyr Leu Pro Glu Ser Ile

CAC TGC ATC CCG CGT CCG ACT ATG GCG GCG GCG CGT GAG GAA TCG           536
His Cys Ile Pro Arg Pro Thr Met Ala Ala Ala Arg Glu Glu Ser

GAG CAG GTA ATC TTC GGT GCA CTC GAC AAT CTC TTC GAG AAT ACC AAA       584
Glu Gln Val Ile Phe Gly Ala Leu Asp Asn Leu Phe Glu Asn Thr Lys

ATC GAC CCT AGG GAG ATT GGT GTT GTG GTG AAC TGC AGC TTG TTT           632
Ile Asp Pro Arg Glu Ile Gly Val Val Val Asn Cys Ser Leu Phe

AAC CCG ACG CCT TCT TTA TCC GCC ATG ATT GTG AAC AAG TAT AAG CTT       680
Asn Pro Thr Pro Ser Leu Ser Ala Met Ile Val Asn Lys Tyr Lys Leu
```

FIG. 12B

| | | | | | | | | | | | | | | | | |
|---|---|---|---|---|---|---|---|---|---|---|---|---|---|---|---|---|
| AGA | GGA | AAC | GTG | AAG | AGC | TTT | AAC | CTC | GGA | GGA | ATG | GGA | TGT | AGG | GCT | 728 |
| Arg | Gly | Asn | Val | Lys | Ser | Phe | Asn | Leu | Gly | Gly | Met | Gly | Cys | Arg | Ala | |
| GGT | GTC | ATC | GCC | GTT | GAT | CTC | GCT | AAT | GAC | ATT | TTA | CAG | CTC | CAT | AGA | 776 |
| Gly | Val | Ile | Ala | Val | Asp | Leu | Ala | Asn | Asp | Ile | Leu | Gln | Leu | His | Arg | |
| AAC | ACA | TTA | GCT | CTT | GTG | GTT | AGC | ACA | GAG | AAC | ATC | ACT | CAG | AAT | TGG | 824 |
| Asn | Thr | Leu | Ala | Leu | Val | Val | Ser | Thr | Glu | Asn | Ile | Thr | Gln | Asn | Trp | |
| TAC | TTT | GGT | AAC | AAC | AAA | GCA | ATG | TTG | ATT | CCT | AAT | TGC | TTG | TTT | AGG | 872 |
| Tyr | Phe | Gly | Asn | Asn | Lys | Ala | Met | Leu | Ile | Pro | Asn | Cys | Leu | Phe | Arg | |
| GTT | GGA | TCC | GCG | GTT | CTG | CTT | TCG | AAC | AAG | CCT | CGT | GAT | CGA | AAA | | 920 |
| Val | Gly | Ser | Ala | Val | Leu | Leu | Ser | Asn | Lys | Pro | Arg | Asp | Arg | Lys | | |
| CGA | TCC | AAG | TAT | AAA | CTT | GTT | CAC | ACG | GTA | CGG | ACT | CAT | AAA | GGA | TCT | 968 |
| Arg | Ser | Lys | Tyr | Lys | Leu | Val | His | Thr | Val | Arg | Thr | His | Lys | Gly | Ser | |
| GAT | GAG | AAA | GCA | TTC | AAC | TGT | GTG | TAC | CAA | GAA | CAA | GAC | GAG | GAC | TTG | 1016 |
| Asp | Glu | Lys | Ala | Phe | Asn | Cys | Val | Tyr | Gln | Glu | Gln | Asp | Glu | Asp | Leu | |

FIG. 12C

```
AAA ACC GGA GTT TCT TTG TCT AAA GAC CTA ATG TCT ATA GCT GGA GAA    1064
Lys Thr Gly Val Ser Leu Ser Lys Asp Leu Met Ser Ile Ala Gly Glu

GCT CTA AAG ACA AAT ATC ACC ACT TTG GGT CCT CTG GTT CTT CCA ATA    1112
Ala Leu Lys Thr Asn Ile Thr Thr Leu Gly Pro Leu Val Leu Pro Ile

AGC GAG CAG ATT CTG TTC ATT GCG ACT TTT GTT GCA AAG AGA TTG TTC    1160
Ser Glu Gln Ile Leu Phe Ile Ala Thr Phe Val Ala Lys Arg Leu Phe

AGT GCC AAG AAG AAG AAG CCT TAC ATA CCG GAT TTC AAG CTT            1208
Ser Ala Lys Lys Lys Lys Pro Tyr Ile Pro Asp Phe Lys Leu

GCC TTT GAT CAT TTC TGT ATT CAC GCA GGA GGT AGA GCC GTG ATC GAT    1256
Ala Phe Asp His Phe Cys Ile His Ala Gly Gly Arg Ala Val Ile Asp

GAA CTA GAG AAG AGT TTA AAG CTA TTG CCA AAA CAT GTG GAG GCT TCT    1304
Glu Leu Glu Lys Ser Leu Lys Leu Leu Pro Lys His Val Glu Ala Ser

AGA ATG ACA TTG CAT AGA TTT GGA AAC ACT TCA TCG AGC TCT ATT TGG    1352
Arg Met Thr Leu His Arg Phe Gly Asn Thr Ser Ser Ser Ser Ile Trp
```

FIG. 12D

```
TAT GAA TTA GCT TAC ACA GAA GCT AAA GGA AGA ATG AGA AAA GGG AAT    1400
Tyr Glu Leu Ala Tyr Thr Glu Ala Lys Gly Arg Met Arg Lys Gly Asn

CGA GTT TGG CAG ATT GCT TTT GGA AGC GGC TTT AAG TGT AAC AGC GCG    1448
Arg Val Trp Gln Ile Ala Phe Gly Ser Gly Phe Lys Cys Asn Ser Ala

GTT TGG GTG GCT CTT CGT GAT GTC GAG CCC TCG GTT AAC AAT CCT TGG    1496
Val Trp Val Ala Leu Arg Asp Val Glu Pro Ser Val Asn Asn Pro Trp

GAA CAT TGC ATC CAT AGA TAT CCG GTT AAG ATC GAT CTC TGATTTCAGC     1545
Glu His Cys Ile His Arg Tyr Pro Val Lys Ile Asp Leu

TTAACCGGTA AAATTGGTCT GTACATATAT TTACCACTGA GTAAAGACAT CAGTTAATGA  1605

TTTGTTGTTA CTCAATTGGG CTAAGTGTAT TATTATATGT GTTGTATATA ATAAAGGTAG  1665

AACGTAAATT TACTAAGAAA AAAAAAAAAA AAAAAAAA                          1704
```

FIG. 12E

```
CA ATG ACG TCT GTG AAC GTA AAA CTC CTT TAC CAT TAC GTC ATA ACC   47
   Met Thr Ser Val Asn Val Lys Leu Leu Tyr His Tyr Val Ile Thr

AAC TTT TTC AAC CTC TGT TTC CCA CTG ACG GGG ATC CTC GCC GGA      95
Asn Phe Phe Asn Leu Cys Phe Pro Leu Thr Gly Ile Leu Ala Gly

AAA GGC TCT CGT CTT ACC ACA AAC GAT CTC CAC CAC TTC TAT TCA TAT 143
Lys Gly Ser Arg Leu Thr Thr Asn Asp Leu His His Phe Tyr Ser Tyr

CTC CAA CAC AAN CTT ATA ACC TTA ACC CTA CTC TTT GGC TTC ACC GTT 191
Leu Gln His Xxx Leu Ile Thr Leu Thr Leu Leu Phe Gly Phe Thr Val

TTT GGT TCG GTT CTC TAC TTC GTA ANC CGA CCC AAA CCG GTT TAC CTC 239
Phe Gly Ser Val Leu Tyr Phe Val Xxx Arg Pro Lys Pro Val Tyr Leu

GTT GAC TAC TCC TGC TAC CTT CCA CCA CAA CAT CTT AGC GCT GGT ATC 287
Val Asp Tyr Ser Cys Tyr Leu Pro Pro Gln His Leu Ser Ala Gly Ile

TCT AAG ACC ATG GAA ATC TTT TAT CAA ATA AGA AAA TCT GAT CCT TTA 335
Ser Lys Thr Met Glu Ile Phe Tyr Gln Ile Arg Lys Ser Asp Pro Leu
```

FIG. 13A

```
CGA AAC GTG GCA TTA GAT GAT TCG TCT TCT CTT GAT TTC TTG AGA AAG       383
Arg Asn Val Ala Leu Asp Asp Ser Ser Ser Leu Asp Phe Leu Arg Lys

ATT CAA GAG CGT TCA GGT CTA GGC GAT GAA ACC TAC GGC CCC GAG GGA       431
Ile Gln Glu Arg Ser Gly Leu Gly Asp Glu Thr Tyr Gly Pro Glu Gly

CTG TTT GAG ATT CCT CCG AGG AAG AAT TTA GCG TCG GCG CGT GAA GAG       479
Leu Phe Glu Ile Pro Pro Arg Lys Asn Leu Ala Ser Ala Arg Glu Glu

ACG GAG CAA GTA ATC AAC GGT GCG CTA AAA AAT CTA TTC GAG AAC AAC       527
Thr Glu Gln Val Ile Asn Gly Ala Leu Lys Asn Leu Phe Glu Asn Asn

AAA GTT AAC CCT AAA GAG ATT GGT ATA CTT GTG GTG AAC TCA AGC ATG       575
Lys Val Asn Pro Lys Glu Ile Gly Ile Leu Val Val Asn Ser Ser Met

TTT AAT CCG ACT CCT TCG TTA TCC GCG ATG GTA GTT AAT ACT TCC AAG       623
Phe Asn Pro Thr Pro Ser Leu Ser Ala Met Val Val Asn Thr Ser Lys

CTC CGA AGC AAC ATC AAA AGC TTT AAT CTT GGA ATG GGT TGC AGT           671
Leu Arg Ser Asn Ile Lys Ser Phe Asn Leu Gly Met Gly Cys Ser
```

FIG. 13B

```
GCT GGT GTT ATC GCC ATT GAT CTA GCT AAA GAC TTG TTG CAT GTT CAT    719
Ala Gly Val Ile Ala Ile Asp Leu Ala Lys Asp Leu Leu His Val His

AAA AAC ACA TAT GCT CTT GTG GTG AGC ACA GAG AAC ATC ACT CAA AAC    767
Lys Asn Thr Tyr Ala Leu Val Val Ser Thr Glu Asn Ile Thr Gln Asn

ATT TAT ACC GGT GAT AAC AGA TCC ATG ATG GTT TCG AAT TGC TTG TTC    815
Ile Tyr Thr Gly Asp Asn Arg Ser Met Met Val Ser Asn Cys Leu Phe

CGT GTC GGG GCA GCG ATT CTG CTC TCC AAC AAG CCG GGG GAT CGA        863
Arg Val Gly Ala Ala Ile Leu Leu Ser Asn Lys Pro Gly Asp Arg

AGA CGG TCC AAG TAC AAG CTA GCT CAC ACG GTT CGA ACG CAT ACC GGA    911
Arg Arg Ser Lys Tyr Lys Leu Ala His Thr Val Arg Thr His Thr Gly

GCT GAC GAC AAG TCT TTT GGA TGT GTG CGG CAA GAA GAT GAT AGC        949
Ala Asp Asp Lys Ser Phe Gly Cys Val Arg Gln Glu Asp Asp Ser

GGT AAA ACC GGA GTT AGT TTG TCA AAA GAC ATA ACC GTT GTT GCC GGG    1007
Gly Lys Thr Gly Val Ser Leu Ser Lys Asp Ile Thr Val Val Ala Gly
```

FIG. 13C

```
ATA ACG GTT CAG AAA AAC ATA ACA TTG GGT CCG TTG GTT CTT CCT    1055
Ile Thr Val Gln Lys Asn Ile Thr Leu Gly Pro Leu Val Leu Pro

CTG AGC GAA AAA ATC CTT TTT GTC GTT ACA TTC GTA GCC AAG AAA CTA  1103
Leu Ser Glu Lys Ile Leu Phe Val Val Thr Phe Val Ala Lys Lys Leu

TTA AAA GAT AAG ATC AAA CAC TAT TAC GTG CCG GAT TTC AAA CTT GCA  1151
Leu Lys Asp Lys Ile Lys His Tyr Tyr Val Pro Asp Phe Lys Leu Ala

GTA GAT CAT TTC TGT ATT CAT GCG GGA GGT AGA GCC GTG ATA GAT GTG  1199
Val Asp His Phe Cys Ile His Ala Gly Gly Arg Ala Val Ile Asp Val

TTA GAG AAG AAC TTA GGG CTA TCG CCG ATA GAT GTG GAG GCA TCA AGA  1247
Leu Glu Lys Asn Leu Gly Leu Ser Pro Ile Asp Val Glu Ala Ser Arg

TCA ACA TTA CAT AGA TTT GGG AAT ACA TCG TCT AGT TCA ATT TGG TAT  1295
Ser Thr Leu His Arg Phe Gly Asn Thr Ser Ser Ser Ile Trp Tyr

GAA TTA GCA TAC ATA GAG CCA AAA GGA AGG ATG AAG AAA GGT AAT AAA  1343
Glu Leu Ala Tyr Ile Glu Pro Lys Gly Arg Met Lys Lys Gly Asn Lys
```

FIG. 13D

```
GCT TGC CAA ATA GCT GGT GGG TCA GGT TTT AAG TGT AAT AGT GCG GTT    1391
Ala Cys Gln Ile Ala Gly Gly Ser Gly Phe Lys Cys Asn Ser Ala Val

TGG GTC GCT TTA CGC AAT GTC GAG GCT TCA GCT AAT AGT CCT TGG GAA    1439
Trp Val Ala Leu Arg Asn Val Glu Ala Ser Ala Asn Ser Pro Trp Glu

CAT TGC ATT CAC AAA TAT CCG GTT CAA ATG TAT TCT GGT TCA TCA AAG    1487
His Cys Ile His Lys Tyr Pro Val Gln Met Tyr Ser Gly Ser Ser Lys

TCA GAG ACT CCT GTC CAA AAC GGT CGG TCC TAATTTATGT ATCTCAAATG      1537
Ser Glu Thr Pro Val Gln Asn Gly Arg Ser

ATGTGTCCA CTTTCTCTTT TTTTTTTCT TTTTTAGTT ATAATTAAT GGTTACGATG      1597

TTTGTCTAG GTCGTTATAA ATAAAGAATA CATGGGTGTT ACTAGTATAA AAAAAAAAAA   1657

AAAAAAA                                                             1664
```

FIG. 13E

```
CTTTCTTCTT CCCCAACA ATG ACC CAT AAC CAA CCT CAC CGG GCA                    51
                    Met Thr His Asn Gln Pro His Arg Ala

GTT CCG GTT CAC GTT ACA AAC TCC GAT CAA AAC CAA AAC CAA                    99
Val Pro Val His Val Thr Asn Ser Asp Gln Asn Gln Asn Gln

AAC AAT CTC CCA AAT TTT CTC TTA TCT GTT CGG CTC AAA TAT GTA AAA          147
Asn Asn Leu Pro Asn Phe Leu Leu Ser Val Arg Leu Lys Tyr Val Lys

CTT GGG TAC CAT TAC CTA ATC TCC AAC GGT CTC TAC ATC CTC CTC CTC          195
Leu Gly Tyr His Tyr Leu Ile Ser Asn Gly Leu Tyr Ile Leu Leu Leu

CCT CTC CTC GGC ACA ATC GTA AAA CTC CTC TCT TCC TTC ACA CTC AAC          243
Pro Leu Leu Gly Thr Ile Val Lys Leu Leu Ser Ser Phe Thr Leu Asn

GAA CTC TCT CTC CTC TAC AAC CAC CTC CGT TTT CAT TTC CTC TCC GCC          291
Glu Leu Ser Leu Leu Tyr Asn His Leu Arg Phe His Phe Leu Ser Ala

ACA CTC GCT ACC GGA CTC TTA ATC TCT CTC ATC TCC ACC GCC TAC TTC ACC      339
Thr Leu Ala Thr Gly Leu Leu Ile Ser Leu Ile Ser Thr Ala Tyr Phe Thr
```

FIG. 14A

```
ACC CGT CCT CGT CAT GTC TTC CTC GAC TTC TCA TGC TAC AAA CCT   387
Thr Arg Pro Arg His Val Phe Leu Asp Phe Ser Cys Tyr Lys Pro

GAC CCT TCC TTA ATA TGC ACT CGT GAA ACA TTC ATG GAC CGA TCT CAA   435
Asp Pro Ser Leu Ile Cys Thr Arg Glu Thr Phe Met Asp Arg Ser Gln

CGT GTA GGT ATC TTC ACA GAA GAC AAC CTC GCT TTT CAA CAA AAG ATC   483
Arg Val Gly Ile Phe Thr Glu Asp Asn Leu Ala Phe Gln Gln Lys Ile

CTC GAA AGA TCC GGT CTT GGG CAG AAA ACT TAC TTC CCT GAA GCT CTT   531
Leu Glu Arg Ser Gly Leu Gly Gln Lys Thr Tyr Phe Pro Glu Ala Leu

CTT CGT GTT CCT CCC AAT CCT TGT ATG GAA GAA GCG AGA AAA GAA GCA   579
Leu Arg Val Pro Pro Asn Pro Cys Met Glu Glu Ala Arg Lys Glu Ala

GAG ACT GTT ATG TTC GGA GCT ATA GAC TCT GTT CTT GAG AAA ACC GGT   627
Glu Thr Val Met Phe Gly Ala Ile Asp Ser Val Leu Glu Lys Thr Gly

GTG AAA CCT AAA GAT ATC GGA ATC CTT GTC GTG AAT TGT AGT TTG TTT   675
Val Lys Pro Lys Asp Ile Gly Ile Leu Val Val Asn Cys Ser Leu Phe

AAT CCG ACG CCG TCA CTT TCC GCC ATG ATT GTG AAT AAG TAT AAG CTT   723
Asn Pro Thr Pro Ser Leu Ser Ala Met Ile Val Asn Lys Tyr Lys Leu
```

FIG. 14B

```
AGA GGA AAC ATT TTG AGC TAT AAT CTC GGT GGA ATG GGT TGT AGT GCT    771
Arg Gly Asn Ile Leu Ser Tyr Asn Leu Gly Gly Met Gly Cys Ser Ala

GGA CTT ATC TCC ATT GAT CTC GCT AAA CAG CTT CAG GTC CAA CCA        819
Gly Leu Ile Ser Ile Asp Leu Ala Lys Gln Leu Gln Val Gln Pro

AAC TCA TAC GCA CTA GTG GTG AGC ACA GAG AAC ATA ACC TTA AAC TGG    867
Asn Ser Tyr Ala Leu Val Val Ser Thr Glu Asn Ile Thr Leu Asn Trp

TAC TTA GGC AAC GAC CGA TCA ATG CTT CTC TCT AAC TGC ATC TTC CGT    915
Tyr Leu Gly Asn Asp Arg Ser Met Leu Leu Ser Asn Cys Ile Phe Arg

ATG GGA GGA GCC GCC GTA CTT CTC TCA AAC CGT ACC TCC GAT CGC ACC    963
Met Gly Gly Ala Ala Val Leu Leu Ser Asn Arg Thr Ser Asp Arg Thr

CGT TCA AAA TAT CAG CTC ATC CAC CCC GTC CGT ACC CAC AAA GGA GCC    1011
Arg Ser Lys Tyr Gln Leu Ile His Pro Val Arg Thr His Lys Gly Ala

AAC GAC AAC GCA TTT GGC TGC GTT TAC CAA CGA GAA GAC AAC AAC GAA    1059
Asn Asp Asn Ala Phe Gly Cys Val Tyr Gln Arg Glu Asp Asn Asn Glu
```

FIG. 14C

```
GAA GAA ACC GCC AAA ATC GGA GTC TCA CTC TCT AAA AAC CTA ATG GCA      1107
Glu Glu Thr Ala Lys Ile Gly Val Ser Leu Ser Lys Asn Leu Met Ala

ATA GCC GGA GAA GCT CTC AAG ACA AAC ATA ACA ACA CTC GGA CCA CTA      1155
Ile Ala Gly Glu Ala Leu Lys Thr Asn Ile Thr Thr Leu Gly Pro Leu

GTC TTA CCA ATG TCC GAA CAG ATT CTG TTT TTC CCA ACA CTC GTG GCT      1203
Val Leu Pro Met Ser Glu Gln Ile Leu Phe Phe Pro Thr Leu Val Ala

CGA AAA ATC TTC AAA GTC AAG AAA ATA AAG CCT TAC ATA CCC GAT TTC      1251
Arg Lys Ile Phe Lys Val Lys Lys Ile Lys Pro Tyr Ile Pro Asp Phe

AAG CTA GCT TTC GAG CAT TTC TGC ATC CAT GCG GGA GGT AGA GCA GTG      1299
Lys Leu Ala Phe Glu His Phe Cys Ile His Ala Gly Gly Arg Ala Val

CTT GAT GAG ATA GAG AAG AAT TTG GAT TTA TCA GAG TGG CAT ATG GAA      1347
Leu Asp Glu Ile Glu Lys Asn Leu Asp Leu Ser Glu Trp His Met Glu

CCA TCG AGG ATG ACT TTA AAC CGG TTT GGT AAT ACT TCG AGT AGC TCA      1395
Pro Ser Arg Met Thr Leu Asn Arg Phe Gly Asn Thr Ser Ser Ser Ser
```

FIG. 14D

```
CTT TGG TAT GAA CTT GCG TAT AGT GAA GCT AAA GGG AGG ATT AAG AGA    1443
Leu Trp Tyr Glu Leu Ala Tyr Ser Glu Ala Lys Gly Arg Ile Lys Arg

GGA GAT AGG ACT TGC CAA ATT GCG TTT GGA TCG GGA TTT AAG TGT AAT    1491
Gly Asp Arg Thr Cys Gln Ile Ala Phe Gly Ser Gly Phe Lys Cys Asn

AGT GCG GTT TGG AAA GCT TTG AGA ACC ATT GAT CCT ATT GAT GAG AAG    1539
Ser Ala Val Trp Lys Ala Leu Arg Thr Ile Asp Pro Ile Asp Glu Lys

AAG AAT CCA TGG AGT GAT GAG ATT CAT GAG TTT CCA GTT TCT GTT CCT    1587
Lys Asn Pro Trp Ser Asp Glu Ile His Glu Phe Pro Val Ser Val Pro

AGG ATC ACT CCA GTT ACT TCT AAC TAGTGTTTTT TTTTGGGTC CAACTAGGA     1641
Arg Ile Thr Pro Val Thr Ser Asn

TAATATTTGT TATGGTTTTG TTCTTACGTA CGTACTTTAA GTGATTTAGT CTAAAAATAA  1701

ATTGGTTTCA TAAAAAAAAA AAAAAAAAA A                                  1732
```

FIG. 14E

```
AAG CTT AAA CTA GTA TAC CAT TAC TTG ATC TCC AAC GCC ATG TAT TTG    48
Lys Leu Lys Leu Val Tyr His Tyr Leu Ile Ser Asn Ala Met Tyr Leu

TTA ATG GTG CCG CTT CTA GCA GTA GCC TTT GCT CAT CTC TCC ACG TTG    96
Leu Met Val Pro Leu Leu Ala Val Ala Phe Ala His Leu Ser Thr Leu

ACG ATT CAA GAT CTG GTT CAT CTT TGG GAA CAG CTT AAG TTC AAT TTA   144
Thr Ile Gln Asp Leu Val His Leu Trp Glu Gln Leu Lys Phe Asn Leu

CTG TCA GTA ACT CTC TGC TCG AGC CTT ATG GTG TTT TTA GGG ACT CTG   192
Leu Ser Val Thr Leu Cys Ser Ser Leu Met Val Phe Leu Gly Thr Leu

TAT TTC ATG AGC CGA CCG ACG AAG ATT TAC TTG GTG GAT TTC TCT TGT   240
Tyr Phe Met Ser Arg Pro Thr Lys Ile Tyr Leu Val Asp Phe Ser Cys

TAC AAG CCG GAA AAA GAG CGT ATA TGC ACG AGA GAG ATT TTC TAT GAG   288
Tyr Lys Pro Glu Lys Glu Arg Ile Cys Thr Arg Glu Ile Phe Tyr Glu

AGA TCG AAA CTA ACT GGG AAT TTT ACC GAT GAT AAT TTA ACT TTC CAA   336
Arg Ser Lys Leu Thr Gly Asn Phe Thr Asp Asp Asn Leu Thr Phe Gln
```

FIG. 15A

```
AAG AAA ATT ATC GAA AGA TCT GGA TTA GGT CAG AAC ACG TAC TTA CCT   384
Lys Lys Ile Ile Glu Arg Ser Gly Leu Gly Gln Asn Thr Tyr Leu Pro

GAG GCC GTT CTA CGG GTT CCG CCC AAT CCG TGT ATG GCG GAG GCT AGA   432
Glu Ala Val Leu Arg Val Pro Pro Asn Pro Cys Met Ala Glu Ala Arg

AAG GAG GCT GAG ATG GTT ATG TTC GGT GCG ATC GAT GAA TTG TTG GAG   480
Lys Glu Ala Glu Met Val Met Phe Gly Ala Ile Asp Glu Leu Leu Glu

AAA ACC GGG GTT AAA CCT AAG GAT ATC GGT ATT CTT GTG GTG AAT TGC   528
Lys Thr Gly Val Lys Pro Lys Asp Ile Gly Ile Leu Val Val Asn Cys

AGC TTG TTC AAT CCG ACG CCG TCT CTG TCC GCA ATG GTG GTT AAT CGG   576
Ser Leu Phe Asn Pro Thr Pro Ser Leu Ser Ala Met Val Val Asn Arg

TAC AAG CTT AGA GGG AAT ATC ATA AGT TAT AAC CTT GGC GGG ATG G     622
Tyr Lys Leu Arg Gly Asn Ile Ile Ser Tyr Asn Leu Gly Gly Met
```

FIG. 15B

NUCLEIC ACID SEQUENCES ENCODING A PLANT CYTOPLASMIC PROTEIN INVOLVED IN FATTY ACYL-COA METABOLISM

This application is a continuation-in-part of PCT/US94/13686, filed Nov. 30, 1994, which is a continuation-in-part of U.S. patent application Ser. No. 08/265,047, filed Jun. 23, 1994, now issued U.S. Pat. No. 5,679,881.

TECHNICAL FIELD

The present invention is directed to enzymes, methods to purify, and obtain such enzymes, amino acid and nucleic acid sequences related thereto, and methods of use for such compositions in genetic engineering applications.

INTRODUCTION

Background

Through the development of plant genetic engineering techniques, it is possible to transform and regenerate a variety of plant species to provide plants which have novel and desirable characteristics. One area of interest for such plant genetic engineering techniques is the production of valuable products in plant tissues. Such applications require the use of various DNA constructs and nucleic acid sequences for use in transformation events to generate plants which produce the desired product. For example, plant functional promoters are required for appropriate expression of gene sequences, such expression being either in the whole plant or in selected plant tissues. In addition, selective marker sequences are often used to identify the transformed plant material. Such plant promoters and selectable markers provide valuable tools which are useful in obtaining the novel plants.

One desirable goal, which involves such genetic engineering techniques, is the ability to provide crop plants having a convenient source of wax esters. Wax esters are required in a variety of industrial applications, including pharmaceuticals, cosmetics, detergents, plastics, and lubricants. Such products, especially long chain wax esters, have previously been available from the sperm whale, an endangered species, or more recently, from the desert shrub, jojoba. Neither of these sources provides a convenient supply of wax esters.

Jojoba is also a plant which synthesizes very long chain fatty acids (VLCFA) in its seed oil. VLCFA are fatty acids having chain lengths longer than 18 carbons. VLCFA are found in the cuticular "waxes" of many plant species as well as in the seed oil of several plant species. Wild type *Brassica* plants contain VLCFA in their seed oil. Canola is rapeseed that has been bred to eliminate VLCFA from its seed oil. Enzymes involved in the elongation of fatty acids to VLCFA ("elongase" enzymes) have been difficult to characterize at a biochemical level because they are membrane associated (Harwood, J L, "Fatty acid metabolism", *Annual rev. of Plant Physiol, and Plant Mal. Biol.* (1988) 39:101–38); (von Wettstein-Knowles, P M, "Waxes, cutin, and suberin" in ed. Moore, T S, *Lipid Metabolism in Plants* (1993), CRC Press, Ann Arbor, pp. 127–166). Although several groups have claimed to partially purify some of these elongase enzymes, to date no one has claimed complete purification of one of these enzymes or cloning of the corresponding genes. von Wettstein-Knowles, P M, (1993) supra; van de Loo, F J, Fox, H G, and Somerville C. "Unusual fatty acids" in ed. Moore, T S, *Lipid Metabolism in Plants*, (1993) CRC Press Ann Arbor, pp. 91–126.

A possible mechanism for fatty acid elongation by the cytoplasmic elongase enzyme system is through a series similar to that found for chloroplast fatty acid synthesis, i.e. via a 4 step reaction (Stumpf and Pollard (1983) supra; van de Loo et al (1993) supra). The first step would be a condensation reaction between malonyl CoA and oleyl CoA by β-ketoacyl-CoA synthase. Then β-ketoacyl-CoA reductase, β-hydroxyacyl-CoA dehydratase, and enoyl-CoA reductase enzymes would act sequentially to generate an acyl-CoA molecule elongated by two carbon atoms.

In order to obtain a reliable source of very long chain fatty acid molecules, such as wax esters or VLCFA, transformation of crop plants, which are easily manipulated in terms of growth, harvest and extraction of products, is desirable. In order to obtain such transformed plants, however, the genes responsible for the biosynthesis of the desired VLCFA or wax ester products must first be obtained.

Wax ester production results from the action of at least two enzymatic activities of fatty acyl CoA metabolism; fatty acyl reductase and fatty acyl;fatty alcohol acyltransferase, or wax synthase. Preliminary studies with such enzymes and extensive analysis and purification of a fatty acyl reductase, indicate that these proteins are associated with membranes, however the enzyme responsible for the fatty acyl:fatty alcohol ligation reaction in wax biosynthesis has not been well characterized. Thus, further study and ultimately, purification of this enzyme is needed so that the gene sequences which encode the enzymatic activity may be obtained.

It is desirable, therefore, to devise a purification protocol whereby the wax synthase protein may be obtained and the amino acid sequence determined and/or antibodies specific for the wax synthase obtained. In this manner, library screening, polymerase chain reaction (PCR) or immunological techniques may be used to identify clones expressing a wax synthase protein. Clones obtained in this manner can be analyzed so that the nucleic acid sequences corresponding to wax synthase activity are identified. The wax synthase nucleic acid sequences may then be utilized in conjunction with fatty acyl reductase proteins, either native to the transgenic host cells or supplied by recombinant techniques, for production of wax esters in host cells.

It would also be desirable to have a gene to an enzyme involved in the formation of very long chain fatty acids. Such a gene could be used to increase the chain length of fatty acids in oilseeds by overexpression of the gene in transgenic plants of virtually any species. The gene could also be used as a probe in low stringency hybridization to isolate homologous clones from other species as a means to clone the gene from other taxa, such as *Brassica*, *Arabidopsis*, Crambe, Nasturtium, and Limnanthes, that produce VLCFA. These derived genes could then be used in antisense experiments to reduce the level of VLCFA in the species from which they were isolated, or overexpressed to increase the quantity of VLCFA in transgenic plants of virtually any species. Additionally, the DNA from the homologous *Brassica* gene encoding this enzyme could be used as a plant breeding tool to develop molecular markers to aid in breeding high erucic acid rapeseed (HEAR) and canola and other oilseed crops. Such techniques would include using the gene itself as a molecular probe or using the DNA sequence to design PCR primers to use PCR based screening techniques in plant breeding programs. Finally, overexpression of the gene in plant epidermal cells could increase cuticle accumulation thereby increasing drought and stress tolerance of transgenic plants over control plants.

Relevant Literature

Cell-free homogenates from developing jojoba embryos were reported to have acyl-CoA fatty alcohol acyl transferase activity. The activity was associated with a floating wax pad which formed upon differential centrifugation (Pollard et al. (1979) supra; Wu et al. (1981) supra).

Solubilization of a multienzyme complex from *Euglena gracilis* having fatty acyl-SCoA transacylase activity is reported by Wildner and Hallick (Abstract from *The Southwest Consortium Fifth Annual Meeting*, April 22–24, 1990, Las Cruces, N.Mex.).

Ten-fold purification of jojoba acyl-CoA: alcohol transacylase protein is reported by Pushnik et al. (Abstract from *The Southwest Consortium Fourth Annual Meeting*, Feb. 7, 1989, Riverside, Calif.).

An assay for jojoba acyl-CoA: alcohol transacylase activity was reported by Garver et al. (*Analytical Biochemistry* (1992) 207:335–340).

Extracts of developing seeds from HEAR and canola plants were found to differ in their ability to elongate oleyl CoA into VLCFA, with HEAR extracts capable of catalyzing elongation, while canola extracts were not. Stumpf, P K and Pollard M R, "Pathways of fatty acid biosynthesis in higher plants with particular reference to developing rapeseed", in *High and Low Erucic Acid Rapeseed Oils* (1983) Academic Press Canada, pp. 131–141.

BRIEF DESCRIPTION OF THE DRAWINGS

FIG. 1. The nucleic acid sequence (SEQ ID NO: 1) and translated amino acid sequence (SEQ ID NO: 2) of a jojoba fatty acyl reductase, as determined from the cDNA sequence, is provided in FIG. 1.

FIG. 2. Preliminary nucleic acid sequence (SEQ ID NO: 3) and translated amino acid sequence (SEQ ID NO: 4) of a jojoba plant cytoplasmic protein involved in fatty acyl-CoA metabolism cDNA clone are provided.

FIG. 3. Nucleic acid (SEQ ID NO: 5) and translated amino acid (SEQ ID NO: 6) sequences of second class of the jojoba clones, as represented by the sequence of pCGN7614, is provided.

FIG. 4. Nucleic acid sequence (SEQ ID NO: 7) of an oleosin expression cassette is provided.

FIG. 5. Nucleic acid sequence (SEQ ID NOS 8 and 9) of a *Brassica* condensing enzyme clone, CE15, is provided from a LEAR variety (212).

FIG. 6. Nucleic acid sequence (SEQ ID NOS 10 and 11) of a CE20 from the 212 *Brassica* variety.

FIG. 7. Nucleic acid sequence (SEQ ID NOS 12 and 13) of a *Brassica* Reston variety (HEAR) clone, of the CE20 class, is provided.

FIG. 8. Nucleic acid sequence (SEQ ID NOS 14 and 15) of an Arabadopsis condensing enzyme clone, CE15.

FIG. 9. Nucleic acid sequence (SEQ ID NOS 16 and 17) of an Arabadopsis condensing enzyme clone, CE17.

FIG. 10. Nucleic acid sequence (SEQ ID NOS 18 and 19) of an Arabadopsis condensing enzyme clone, CE19.

FIG. 11. Partial nucleic acid sequence (SEQ ID NOS 20 and 21) of Lunaria condensing enzyme clone designated LUN CE8.

FIG. 12. Nucleic acid sequence (SEQ ID NOS 22 and 23) of a Lunaria condensing enzyme clone, Lunaria 1, obtained by probing with LUN CE8.

FIG. 13. Nucleic acid sequence (SEQ ID NOS 24 and 25) of a second Lunaria condensing enzyme clone obtained from LUN CE8, Lunaria 5.

FIG. 14. Nucleic acid sequence (SEQ ID NOS 26 and 27) of third Lunaria condensing enzyme clone from LUN CE8, Lunaria 27.

FIG. 15. Nucleic acid sequence (SEQ ID NOS 28 and 29) to a Nasturtium condensing enzyme clone obtained by PCR.

SUMMARY OF THE INVENTION

By this invention, a DNA sequence encoding a plant cytoplasmic protein involved in fatty acyl-CoA metabolism is provided. Such a sequence is desirable for use in methods aimed at altering the composition of very long chain wax fatty acid related products, such as wax esters and very long chain fatty acids in host cells.

In one aspect, the protein of this invention may demonstrate fatty acyl-CoA: fatty alcohol O-acyltransferase activity, such activity being referred to herein as "wax synthase".

In a second aspect, this protein may be required for elongation reactions involved in the formation of very long chain fatty acids. Thus, for example, the protein provides for elongation of C18 fatty acyl CoA molecules to form C20 fatty acids, and also for elongation of C20 fatty acids to form even longer chain fatty acids. It is likely that the elongase activity is the result of β-ketoacyl-CoA synthase activity of this protein, although the possibility exists that the protein provided herein has a regulatory function required for the expression of a β-ketoacyl-CoA synthase or provides one of the other activities known to be involved in acyl-CoA elongation, such as β-ketoacyl-CoA reductase, β-hydroxyacyl-CoA dehydratase, or enoyl-CoA reductase activities. In any event, the fatty acyl CoA elongation aspect of this protein is referred to herein as "elongase" activity.

The DNA sequence of this invention is exemplified by sequences obtained from a jojoba embryo cDNA library. Several related jojoba sequences have been discovered and are provided in FIGS. 2 and 3 herein.

In a different aspect of this invention, nucleic acid sequences associated with other proteins related to the exemplified plant cytoplasmic protein involved in fatty acyl-CoA metabolism are considered. Methods are described whereby such sequences may be identified and obtained from the amino acid sequences and nucleic acid sequences of this invention. Uses of the structural gene sequences for isolation of sequences encoding similar cytoplasmic proteins involved in fatty acyl-CoA metabolism from other plant species, as well as in recombinant constructs for transcription and/or expression in host cells of the protein encoded by such sequences are described. Uses of other nucleic acid sequences associated with the protein encoding sequences are also considered, such as the use of 5' and 3' noncoding regions.

In yet a different aspect of this invention, cells containing recombinant constructs coding for sense and antisense sequences for plant cytoplasmic protein involved in fatty acyl-CoA metabolism are considered. In particular, cells which contain the preferred long chain acyl-CoA substrates of the jojoba protein, such as those cells in embryos of *Brassica* plants, are considered.

In addition, a method of producing a plant cytoplasmic protein involved in fatty acyl-CoA metabolism in a host cell is provided. Accordingly, a plant cytoplasmic protein involved in fatty acyl-CoA metabolism that ie recovered as the result of such expression in a host cell is also considered in this invention.

Further, it may be recognized that the sequences of this invention may find application in the production of wax esters in such host cells which contain fatty acyl and fatty alcohol substrates of the wax synthase. Such host cells may exist in nature or be obtained by transformation with nucleic acid constructs which encode a fatty acyl reductase. Fatty acyl reductase, or "reductase", is active in catalyzing the reduction of a fatty acyl group to the corresponding alcohol. Co-pending U.S. patent application Ser. No. 07/659,975 (filed Feb. 22, 1991), Ser. No. 07/767,251 (filed Sep. 27, 1991) and Ser. No. 07/920,430 (filed Jul. 31, 1992), which are hereby incorporated by reference, are directed to such reductase proteins. This information is also provided in published PCT patent application WO 92/14816. In addition, other sources of wax synthase proteins are described herein which are also desirable sources of reductase proteins. In this regard, plant cells which contain the preferred alcohol substrates of the jojoba wax synthase activity described herein may be prepared by transformation with recombinant nucleic acid constructs which encode a fatty acyl reductase nucleic acid sequence.

A further method considered herein involves the production of very long chain fatty acids, or modification of the amounts of such fatty acids, in host cells. Increased production of very long chain fatty acids may be obtained by expression of DNA sequences described herein. On the other hand, antisense constructs containing such sequences may be used to reduce the content of the very long chain fatty acids in a target host organism. In particular, such sense and antisense methods are directed to the modification of fatty acid profiles in plant seed oils and may result in novel plant seed oils having desirable fatty acid compositions.

DETAILED DESCRIPTION OF THE INVENTION

The nucleic acid sequences of this invention encode a plant cytoplasmic protein involved in fatty acyl-CoA metabolism. Such as a protein includes any sequence of amino acids, such as protein, polypeptide or peptide fragment, which provides the "elongase" activity responsible for production of very long chain fatty acids and for the "wax synthase" activity which provides for esterification of a fatty alcohol by a fatty acyl group to produce a wax ester.

The plant cytoplasmic protein involved in fatty acyl-CoA metabolism of this invention may demonstrate activity towards a variety of acyl substrates, such as fatty acyl-CoA fatty alcohol and fatty acyl-ACP molecules. In addition, both the acyl and alcohol substrates acted upon by the wax synthase may have varying carbon chain lengths and degrees of saturation, although the plant cytoplasmic protein involved in fatty acyl-CoA metabolism may demonstrate preferential activity towards certain molecules.

Many different organisms contain products derived from very long chain fatty acyl-CoA molecules and are desirable sources of a plant cytoplasmic protein involved in fatty acyl-CoA metabolism of this invention. For example, plants produce epidermal, or cuticular wax (Kolattukudy (1980) in *The Biochemistry of Plants* (Stumpf, P. K. and Conn, E. E., eds.) Vol.4, p. 571–645), and the desert shrub, jojoba, produces a seed storage wax (Ohlrogge et al. (*Lipids* (1978) 13:203–210). Such waxes are the result of a wax synthase catalyzed combination of a long chain or very long chain acyl-CoA molecule with a fatty alcohol molecule. Wax synthesis has also been observed in various species of bacteria, such as Acinetobacter (Fixter et al. (1986) *J. Gen. Microbiol.* 132:3147–3157) and Micrococcus (Lloyd (1987) *Microbios* 52:29–37), and by the unicellular organism, *Euglena* (Khan and Kolattukudy (1975) *Arch. Biochem. Biophys.* 170:400–408). In addition, wax production and wax synthase activity have been reported in microsomal preparations from bovine meibomian glands (Kolattukudy et al. (1986) *J. Lipid Res.* 27:404–411), avian uropygial glands, and various insect and marine organisms. Consequently, many different wax esters which will have various properties may be produced by wax synthase activity of plant cytoplasmic protein involved in fatty acyl-CoA metabolism of this invention, and the type of wax ester produced may depend upon the available substrate or the substrate specificity of the particular protein of interest.

Thus, nucleic acid sequences associated with the plant cytoplasmic protein involved in fatty acyl-CoA metabolism may be cloned into host cells for the production of the enzyme and further studies of the activity. For example, one may clone the nucleic acid encoding sequence into vectors for expression in *E. coli* cells to provide a ready source of the protein. The protein so produced may also be used to raise antibodies for use in identification and purification of related proteins from various sources, especially from plants. In addition, further study of the protein may lead to site-specific mutagenesis reactions to further characterize and improve its catalytic properties or to alter its fatty alcohol or fatty acyl substrate specificity. A plant cytoplasmic protein involved in fatty acyl-CoA metabolism having such altered substrate specificity may find application in conjunction with other FAS enzymes.

Prior to the instant invention, amino acid sequences of wax synthase proteins were not known. Thus, in order to obtain the nucleic acid sequences associated with wax synthase, it was necessary to first purify the protein from an available source and determine at least partial amino acid sequence so that appropriate probes useful for isolation of wax synthase nucleic acid sequences could be prepared.

The desert shrub, *Simmondsia chinensis* (jojoba) is the source of the encoding sequences exemplified herein. However, related proteins may be identified from other source organisms and the corresponding encoding sequences obtained.

For example, *Euglena gracilis* produces waxes through the enzymatic actions of a fatty acyl-CoA reductase and a fatty acyl-CoA alcohol transacylase, or wax synthase. Typically, waxes having carbon chain lengths ranging from 24–32 are detected in this organism. The *Euglena* wax synthase enzyme may be solubilized using a CHAPS/NaCl solution, and a partially purified wax synthase preparation is obtained by Blue A chromatography. In this manner, a 41 kD peptide band associated with wax synthase activity is identified.

Acinetobacter species are also known to produce wax ester compositions, although the mechanism is not well defined. As described herein a fatty acyl-CoA alcohol transacylase, or wax synthase activity is detected in Acinetobacter species. The wax synthase activity is solubilized in CHAPS/NaCl, enriched by Blue A column chromatography and may be further purified using such techniques as size exclusion chromatography. By these methods, an approximately 45 kD peptide band associated with wax synthase activity is obtained in a partially purified preparation.

In addition, a plant cytoplasmic protein involved in fatty acyl-CoA metabolism which is required for production of very long chain fatty acids may also be found in various sources, especially plan sources. In plants, fatty acids up to 18 carbons in chain length are synthesized in the chloroplasts by fatty acid synthase (FAS), a system of several enzymes that elongate fatty acid thioesters of acyl carrier protein (ACP) in 2 carbon increments. After reaching the chain length of 18, the thioester linkage is cleaved by a thioesterase, and the fatty acid is transported to the cytoplasm where it is utilized as a coenzyme A (CoA) thioester as acyl-CoA. Further elongation, when it occurs, is catalyzed by an endoplasmic reticulum membrane associated set of elongation enzymes. Very long chain fatty acids (those fatty acids longer than 18 carbons) are found in the cuticular "waxes" of many plant species, and are found in the seed oil of several plant species. The enzymes involved in elongation of fatty acids to VLCFA are membrane associated (Harwood 1988, von Wettstein-Knowles 1993).

Plants which contain desirable "elongase" activities include *Arabidopsis*, Crambe, Nasturtium and Limnanthes. Thus, the proteins responsible for such elongase activity may be purified and the corresponding encoding sequences identified. Alternatively, such sequences may be obtained by hybridization to the jojoba encoding sequences provided herein.

Although the hydrophobic nature of the proteins of this invention may present challenges to purification, recovery of substantially purified protein can be accomplished using a variety of methods. See, for example, published PCT application WO 93/10241 where purification of jojoba wax synthase protein is described.

Thus, the nucleic acid sequences which encode a plant cytoplasmic protein involved in fatty acyl-CoA metabolism of this invention may be used to provide for transcription of the sequences and/or expression of the protein in host cells, either prokaryotic or eukaryotic.

Ultimately, stable plant expression in a plant which produces substrates recognized by this enzyme is desired. If a plant targeted for transformation with wax synthase sequences does not naturally contain the fatty alcohol and/or fatty acyl ester substrates of this enzyme, a plant extract may be prepared and assayed for activity by adding substrates to the extract. Constructs and methods for transformation of plant hosts are discussed in more detail below.

As discussed in more detail in the following examples, expression of the nucleic acid sequences provided herein in an initial experiment resulted in increased wax synthase activity. This result, however, was not observed in further *E. coli* expression experiments. In plants, expression of the exemplified sequences (construct pCGN7626, described in Example 8) resulted in production of very long chain fatty acids in a canola type *Brassica*, and modification of the very long chain fatty acid profile in transformed *Arabidopsis* plants (Example 11).

The nucleic acids of this invention may be genomic or cDNA and may be isolated from cDNA or genomic libraries or directly from isolated plant DNA. Methods of obtaining gene sequences once a protein is purified and/or amino acid sequence of the protein is obtained are known to those skilled in the art.

For example, antibodies may be raised to the isolated protein and used to screen expression libraries, thus identifying clones which are producing the plant cytoplasmic protein involved in fatty acyl-CoA metabolism synthase protein or an antigenic fragment thereof. Alternatively, oligonucleotides may be synthesized from the amino acid sequences and used in isolation of nucleic acid sequences. The oligonucleotides may be useful in PCR to generate a nucleic acid fragment, which may then be used to screen cDNA or genomic libraries. In a different approach, the oligonucleotides may be used directly to analyze Northern or Southern blots in order to identify useful probes and hybridization conditions under which these oligonucleotides may be used to screen cDNA or genomic libraries.

Nucleic acid sequences of this invention include those corresponding to the jojoba plant cytoplasmic protein involved in fatty acyl-CoA metabolism, as well as sequences obtainable from the jojoba protein or nucleic acid sequences. By "corresponding" is meant nucleic acid sequences, either DNA or RNA, including those which encode the jojoba plant cytoplasmic protein involved in fatty acyl-CoA metabolism protein or a portion thereof, regulatory sequences found 5' or 3' to said encoding sequences which direct the transcription or transcription, and translation (expression) of the protein in jojoba embryos, intron sequences not present in the cDNA, as well as sequences encoding any leader or signal peptide of a precursor protein that may be required for insertion into the endoplasmic reticulum membrane, but is not found in the mature plant cytoplasmic protein involved in fatty acyl-CoA metabolism.

By sequences "obtainable" from the jojoba sequence or protein, is intended any nucleic acid sequences associated with a desired plant cytoplasmic protein involved in fatty acyl-CoA metabolism protein that may be synthesized from the jojoba amino acid sequence, or alternatively identified in a different organism, and isolated using as probes the provided jojoba nucleic acid sequences or antibodies prepared against the jojoba plant cytoplasmic protein involved in fatty acyl-CoA metabolism. In this manner, it can be seen that sequences of these other plant cytoplasmic protein involved in fatty acyl-CoA metabolism may similarly be used to isolate nucleic acid sequences associated with such proteins from additional sources.

For isolation of nucleic acid sequences, cDNA or genomic libraries may be prepared using plasmid or viral vectors and techniques well known to those skilled in the art. Useful nucleic acid hybridization and immunological methods that may be used to screen for the desired sequences are also well known to those in the art and are provided, for example in Maniatis, et al. (*Molecular Cloning: A Laboratory Manual, Second Edition* (1989) Cold Spring Harbor Laboratory, Cold Spring Harbor, N.Y.).

Typically, a sequence obtainable from the use of nucleic acid probes will show 60–70% sequence identity between the target sequence and the given sequence encoding a wax synthase enzyme of interest. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding a wax synthase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest.

Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (*1983*) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba protein can be prepared by injecting rabbits or mice (or other appropriate small mammals) with the purified protein. Methods of preparing antibodies are well known to those in the art, and companies which specialize in antibody production are also available. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba plant cytoplasmic protein involved in fatty acyl-CoA metabolism. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some of the available systems have been described by Oberfelder (*Focus* (1989) BRL/Life Technologies, Inc. 11:1–5). If initial experiments fail to detect a related protein, other detection systems and blocking agents may be utilized. When cross-reactivity is observed, genes encoding the related proteins can be isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related protein. Other plant cytoplasmic protein involved in fatty acyl-CoA metabolism may be obtained through the use of the "new" sequences in the same manner as the jojoba sequence was used.

It will be recognized by one of ordinary skill in the art that nucleic acid sequences of this invention may be modified using standard techniques of site specific mutation or PCR, or modification of the sequence may be accomplished in producing a synthetic nucleic acid sequence. Such modified sequences are also considered in this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the protein) may be synthesized using codons preferred by a selected host. Host-preferred codons may be determined, for example, from the codons used most frequently in the proteins expressed in a desired host species.

The nucleic acid sequences associated with plant cytoplasmic protein involved in fatty acyl-CoA metabolism will find many uses. For example, recombinant constructs can be prepared which can be used as probes or will provide for expression of the protein in host cells. Depending upon the intended use, the constructs may contain the sequence which encodes the entire protein, or a portion thereof. For example, critical regions of the protein, such as an active site may be identified. Further constructs containing only a portion of the sequence which encodes the amino acids necessary for a desired activity may thus be prepared. In addition, antisense constructs for inhibition of expression may be used in which and a portion of the cDNA sequence is transcribed.

Useful systems for expression of the sequences of this invention include prokaryotic cells, such as *E. coli*, yeast cells, and plant cells, both vascular and nonvascular plant cells being desired hosts. In this manner, the plant cytoplasmic protein involved in fatty acyl-CoA metabolism may be produced to allow further studies, such as site-specific mutagenesis of encoding sequences to analyze the effects of specific mutations on reactive properties of the protein.

The DNA sequence encoding a plant cytoplasmic protein involved in fatty acyl-CoA metabolism of this invention may be combined with foreign DNA sequences in a variety of ways. By "foreign" DNA sequences is meant any DNA sequence which is not naturally found joined to the plant cytoplasmic protein involved in fatty acyl-CoA metabolism sequence, including DNA sequences from the same organism which are not naturally found joined to the plant cytoplasmic protein involved in fatty acyl-CoA metabolism sequences. Both sense and antisense constructs utilizing encoding sequences are considered, wherein sense sequence may be used for expression of a plant cytoplasmic protein involved in fatty acyl-CoA metabolism in a host cell, and antisense sequences may be used to decrease the endogenous levels of a protein naturally produced by a target organism. In addition, the gene sequences of this invention may be employed in a foreign host in conjunction with all or part of the sequences normally associated with the plant cytoplasmic protein involved in fatty acyl-CoA metabolism such as regulatory or membrane targeting sequences.

In its component parts, a DNA sequence encoding a plant cytoplasmic protein involved in fatty acyl-CoA metabolism is combined in a recombinant construct having, in the 5' to 3' direction of transcription, a transcription initiation control region capable of promoting transcription and translation in a host cell, the protein encoding sequence and a transcription termination region. Depending upon the host, the regulatory regions will vary, and may include regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as E. coli, B. subtilis, Sacchromyces cerevisiae, including genes such as beta-galactosidase, T7 polymerase, tryptophan E and the like.

For the most part, the recombinant constructs will involve regulatory regions functional in plants which provide for transcription of the plant cytoplasmic protein involved in fatty acyl-CoA metabolism gene either in the sense or antisense orientation, to produce a functional protein or a complementary RNA respectively. For protein expression, the open reading frame, coding for the plant protein or a functional fragment thereof will be joined at its 5' end to a transcription initiation regulatory region such as the wild-type sequence naturally found 5' upstream to the exemplified jojoba. Numerous other promoter regions from native plant genes are available which provide for a wide variety of constitutive or regulatable, e.g., inducible, expression of structural gene sequences.

In addition to sequences from native plant genes, other sequences can provide for constitutive gene expression in plants, such as regulatory regions associated with Agrobacterium genes, including regions associated with nopaline synthase (Nos), mannopine synthase (Mas), or octopine synthase (Ocs) genes. Also useful are regions which control expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the plant cytoplasmic protein involved in fatty acyl-CoA metabolism is desired in a plant host, the use of all or part of the complete plant gene may be desired, namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source or enhanced promoters, such as double 35S CaMV promoters, the sequences may be joined together using standard techniques. Additionally, 5' untranslated regions from highly expressed plant genes may be useful to provide for increased expression of the proteins described herein.

The DNA constructs which provide for expression in plants may be employed with a wide variety of plant life, particularly, plants which produce the fatty acyl-CoA substrates of the plant cytoplasmic protein involved in fatty acyl-CoA metabolism, such as Brassica. Other plants of interest produce desirable fatty acyl substrates, such as medium or long chain fatty acyl molecules, and include but are not limited to rapeseed (Canola varieties), sunflower, safflower, cotton, Cuphea, soybean, peanut, coconut and oil palms, and corn.

As to the fatty alcohol substrate for the ester production, other than jojoba, seed plants are not known to produce large quantities of fatty alcohols, although small amounts of this substrate may be available to the wax synthase enzyme. Therefore, in conjunction with the constructs of this invention, it is desirable to provide the target host cell with the capability to produce fatty alcohols from the fatty acyl molecules present in the host cells. For example, a plant fatty acyl reductase and methods to provide for expression of the reductase enzymes in plant cells are described in co-pending application U.S. Ser. No. 07/767,251. The nucleic acid sequence and translated amino acid sequence of the jojoba reductase is provided in FIG. 1. Thus, by providing both the wax synthase and reductase activities to the host plant cell, wax esters may be produced from the fatty alcohol and fatty acyl substrates.

In addition to the jojoba reductase, reductase enzymes from other organisms may be useful in conjunction with the wax synthases of this invention. Other potential sources of reductase enzymes include Euglena, Acinetobacter, Micrococus, certain insects and marine organisms, and specialized mammalian or avian tissues which are known to contain wax esters, such as bovine meibomian glands or avian uropygial glands. Other potential sources of reductase proteins may be identified by their ability to produce fatty alcohols or, if wax synthase is also present, wax esters.

The sequences encoding wax synthase activity and reductase sequences may be provided during the same transformation event, or alternatively, two different transgenic plant lines, one having wax synthase constructs and the other having reductase constructs may be produced by transformation with the various constructs. These plant lines may then be crossed using known plant breeding techniques to provide wax synthase and reductase containing plants for production of wax ester products.

For applications leading to wax ester production, 5' upstream non-coding regions obtained from genes regulated during seed maturation are desired, especially those preferentially expressed in plant embryo tissue, such as regions derived from ACP, oleosin (Lee and Huang (1991) Plant Physiol. 96:1395–1397) and napin regulatory regions. Transcription initiation regions which provide for preferential expression in seed tissue, i.e., which are undetectable in other plant parts, are considered desirable for wax ester production in order to minimize any disruptive or adverse effects of the gene product in other plant parts. Further, the seeds of such plants may be harvested and the lipid reserves of these seeds recovered to provide a ready source of wax esters. Thus, a novel seed product may be produced in oilseed plants which, absent transformation with wax synthase constructs as described herein, are not known to produce wax esters as a component of their seed lipid reserves.

Similarly, seed promoters are desirable where VLCFA production or inhibition of VLCFA are desired. In this manner, levels of VLCFA may be modulated in various plant species. Such "seed-specific promoters" may be obtained and used in accordance with the teachings of U.S. Ser. No. 07/147,781, filed Jan. 25, 1988 (now U.S. Ser. No. 07/742,834, filed Aug. 8, 1981), and U.S. Ser. No. 07/494,722 filed on Mar. 16, 1990 having a title "Novel Sequences Preferentially Expressed In Early Seed Development and Methods Related Thereto", all of which co-pending applications are incorporated herein by reference. In addition, where plant genes, such as the jojoba protein is expressed, it may be desirable to use the entire plant gene, including 5' and 3' regulatory regions and any introns that are present in the encoding sequence, for expression of the jojoba genes in a transformed plant species, such as Arabidopsis or Brassica.

Regulatory transcription termination regions may be provided in recombinant constructs of this invention as well. Transcription termination regions may be provided by the DNA sequence encoding the plant cytoplasmic protein involved in fatty acyl-CoA metabolism or a convenient transcription termination region derived from a different gene source, especially the transcription termination region which is naturally associated with the transcription initiation region. The transcript termination region will contain at least about 0.5 kb, preferably about 1–3 kb of sequence 3' to the structural gene from which the termination region is derived.

Additional plant gene regions may be used to optimize expression in plant tissues. For example, 5' untranslated regions of highly expressed genes, such as that of the small subunit (SSU) of RuBP-carboxylase, inserted 5' to DNA encoding sequences may provide for enhanced translation efficiency. Portions of the SSU leader protein encoding region (such as that encoding the first 6 amino acids) may also be used in such constructs. In addition, for applications where targeting to plant plastid organelles is desirable, transit peptide encoding sequences from SSU or other nuclear-encoded chloroplast proteins may be used in conjunction with wax synthase and reductase sequences.

Depending on the method for introducing the DNA expression constructs into the host cell, other DNA sequences may be required. Importantly, this invention is applicable to dicotyledon and monocotyledon species alike and will be readily applicable to new and/or improved transformation and regeneration techniques.

In developing the recombinant construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the number of different host species the expression construct or components thereof are introduced, one or more markers may be employed, where different conditions for selection are used for the different hosts.

In addition to the sequences providing for transcription of sequences encoding the plant cytoplasmic protein involved in fatty acyl-CoA metabolism of this invention, the DNA constructs of this invention may also provide for expression of an additional gene or genes, whose protein product may act in conjunction with the protein described herein to produce a valuable end product. For example, as discussed above, DNA constructs which provide for expression of wax synthase activity and a fatty acyl reductase so that wax esters may produced in transformed hosts, are considered in this invention. Furthermore, production of different wax esters having varying carbon chain lengths and degrees of saturation is desired and may be provided by transforming host plants having fatty alcohol or fatty acyl substrates of varying chain lengths. Such plants may be provided, for example, by methods described in the published international patent application number PCT WO 91/16421, which describes various thioesterase genes and methods of using such genes to produce fatty acyl substrates having varying chain lengths in transformed plant hosts.

Furthermore, to optimize the production of wax esters in oilseed plant hosts, one may wish to decrease the production of the triacylglyceride oils that are normally produced in the seeds of such plants. One method to accomplish this is to antisense a gene critical to this process, but not necessary for the production of wax esters. Such gene targets include diacylglycerol acyltransferase, and other enzymes which catalyze the synthesis of triacylglycerol. Additionally, it may be desirable to provide the oilseed plants with enzymes which may be used to degrade wax esters as a nutrient source, such as may be isolated from jojoba or various other wax producing organisms. In this manner, maximal production of wax esters in seed plant hosts may be achieved.

Wax esters produced in the methods described herein may be harvested using techniques for wax extraction from jojoba or by various production methods used to obtain oil products from various oilseed crops. The waxes thus obtained will find application in many industries, including pharmaceuticals, cosmetics, detergents, plastics, and lubricants. Applications will vary depending on the chain length and degree of saturation of the wax ester components. For example, long chain waxes having a double band in each of the carbon chains are liquid at room temperature, whereas waxes having saturated carbon chain components, may be solid at room temperature, especially if the saturated carbon chains are longer carbon chains.

In applications related to elongase activity, the jojoba gene can be used to increase the chain length of fatty acids in oilseeds by overexpression of the gene in transgenic plants of virtually any species; the gene can also be used as a probe in low stringency hybridization to isolate homologous clones from other species that produce VLCFA. These derived genes can then be used in antisense experiments to reduce the level of VLCFA in the species from which they were isolated, or in other plant species where sufficient gene homology is present. Alternatively, these genes could be overexpressed to increase the quantity of VLCFA in transgenic plants.

Additionally, the DNA from the homologous *Brassica* gene encoding this enzyme could be used as a plant breeding tool to develop molecular markers to aid in breeding NEAR and canola and other oilseed crops. Such techniques would include using the gene itself as a molecular probe or using the DNA sequence to design PCR pruners to use PCR based screening techniques in plant breeding programs.

Furthermore, overexpression of the gene in plant epidermal cells could increase cuticle accumulation thereby increasing drought and stress tolerance of transgenic plants over control plants.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

When Agrobacterium is utilized for plant transformation, it may be desirable to have the desired nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri-containing the T-DNA for recombination may be armed (capable of causing gall formation), or disarmed (incapable of causing gall formation), the latter being permissible so long as a functional complement of the vir genes, which encode trans-acting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region (s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host Agrobacterium vir regions can supply trans-acting factors required for transfer of the T-DNA bordered sequences to plant host cells. For transformation of *Brassica* cells, Agrobacterium transformation methods may be used, One such method is described, for example, by Radke et al. (*Theor. Appl. Genet.* (1988) 75:685–694).

The invention now being generally described, it will be more readily understood by reference to the following examples, which are included for purposes of illustration only and are not intended to limit the invention unless so stated.

EXAMPLES

Example 1

Wax Synthase Assays

Methods to assay for wax synthase activity in microsomal membrane preparations or solubilized protein preparations are described.

A. Radiolabeled Material

The substrate generally used in the wax synthase assays, [1-$^{14}$C] palmitoyl-CoA, is purchased from Amersham (Arlington Heights, Ill.). Other chain length substrates were synthesized in order to perform chain length specification studies. Long chain [1-$^{14}$C] fatty acids (specific activity 51–56 Ci/mole), namely 11-cis-eicosenoic acid, 13-cis-docosenoic acid and 15-cis-tetracosenoic acid are prepared by the reaction of potassium [$^{14}$C] cyanide with the corresponding alcohol mesylate, followed by the base hydrolysis of the alcohol nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] free fatty acids by the method of Young and Lynen (*J. Bio. Chem.* (1969) 244:377), to a specific activity of 10 Ci/mole. [1-$^{14}$C] hexadecanal is prepared by the dichromate oxidation of [1-$^{14}$C] hexadecan-1-ol, according to a micro-scale modification of the method of Pletcher and Tate (*Tet. Lett.* (1978) 1601–1602). The product is purified by preparative silica TLC, and stored as a hexane solution at −70° C. until use.

B. Assay for Wax Synthase Activity in a Microsomal Membrane

Preparation

Wax synthase activity in a microsomal membrane preparation is measured by incubation of 40 μM [1-$^{14}$C] acyl-CoA (usually palmitoyl-CoA, sp. act. 5.1–5.6 mCi/mmol) and 200 μM oleyl alcohol with the sample to be assayed in a total volume of 0.25 ml. The incubation mixture also contains 20% w/v glycerol, 1 mM DTT, 0.5M NaCl and is buffered with 25 mM HEPES (4-[2-hydroxyethyl]-1-piperazineethane-sulfonic acid). HEPES, here and as referred to hereafter is added from a 1M stock solution adjusted to pH 7.5.

A substrate mixture is prepared in a glass vial, with oleyl alcohol being added immediately before use, and is added to samples. Incubation is carried out at 30° C. for one hour. The assay is terminated by placing the assay tube on ice and immediately adding 0.25 ml isopropanol:acetic acid (4:1 v/v). Unlabeled wax esters (0.1 mg) and oleyl alcohol (0.1 mg) are added as carriers. The [$^{14}$C] lipids are extracted by the scaled-down protocol of Hara and Radin (*Anal. Biochem.* (1978) 90:420). Four ml of hexane/isopropanol (3:2, v/v) is added to the terminated assay. The sample is vortexed, 2 ml of aqueous sodium sulphate solution (6.6% w/v) is added, and the sample is again vortexed.

C. Assay for Solubilized Wax Synthase Activity

For assaying solubilized wax synthase activity, reconstitution of the protein is required. Reconstitution is achieved by the addition of phospholipids (Sigam P-3644, ~40% L-phosphatidyl choline) to the 0.75% CHAPS-solubilized sample at a concentration of 2.5 mg/ml, followed by dilution of the detergent to 0.3%, below the CMC. Reconstitution of activity is presumed to be based on the incorporation of wax synthase into the phospholipid vesicles. It is recognized that the amount of wax synthase activity detected after their reconstitution can be influenced by many factors (e.g., the phospholipid to protein ratio and the physical state of the wax synthase protein (e.g. aggregate or dispersed).

D. Analysis of Assay Products

For analyzing the products of either the microsomal membrane preparation wax synthase assay or the solubilized wax synthase assay, two protocols have been developed. One protocol, described below as "extensive assay" is more time-consuming, but yields more highly quantitative results. The other protocol, described below as "quick assay" also provides a measure of wax synthase activity, but is faster, more convenient and less quantitative.

1. Extensive Analysis: Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of hexane, and an aliquot is assayed for radioactivity by liquid scintillation counting. The remainder of the sample can be used for TLC analysis of the labeled wax classes and thereby give a measure of total wax produced.

For lipid class analysis the sample is applied to a silica TLC plate, and the plate is developed in hexane/diethyl ether/acetic acid (80:20:1 v/v/v). The distribution of radioactivity between the lipid classes, largely wax esters, free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis. Reversed-phase TLC systems using C18 plates developed in methanol have also been used for the analysis.

2. Quick Analysis: Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in hexane and spotted on TLC plates and developed and scanned as described for the detailed assay. In this manner the percentage of the total counts which are incorporated into wax is determined.

Example 2

Radiolabeling Wax Synthase Protein

Radiolabeled [1-$^{14}$C] palmitoyl-CoA (Amersham) is added to a wax synthase preparation, either solubilized or a microsomal membrane fraction, in the ratio of 5 $\mu$l of label to 40 $\mu$l protein sample. The sample is incubated at room temperature for at least 15 minutes prior to further treatment. For SDS-PAGE analysis the sample is treated directly with SDS sample buffer and loaded onto gels for electrophoresis.

Example 3

Further Studies to Characterize Wax Synthase Activity

A. Seed Development and Wax Synthase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Wax synthase activity was measured in developing embryos as described in Example 1. As the jojoba seed coats were determined to be the source of an inhibiting factor(s), the seed coats were removed prior to freezing the embryos in liquid nitrogen for storage at −70° C.

Development profiles for wax synthase activities as measured in either a cell free homogenate or a membrane fraction, indicate a large induction in activity which peaks at approximately 110–115 days after anthesis. Embryos for enzymology studies were thus harvested between about 90 to 110 days postanthesis, a period when the wax synthase activity is high, lipid deposition has not reached maximum levels, and the seed coat is easily removed. The highest rate of increase of wax synthase activity is seen between days 80 and 90 postanthesis. Embryos for cDNA library construction were thus harvested between about 80 to 90 days postanthesis when presumably the rate of synthase of wax synthase protein would be maximal. Correspondingly, the level of mRNA encoding wax synthase would be presumed to be maximal at this stage.

B. Substrate Specificity

Acyl-CoA and alcohol substrates having varying carbon chain lengths and degrees of unsaturation were added to a microsomal membrane fraction having wax synthase activity to determine the range of substrates recognized by the jojoba wax synthase. Wax synthase activity was measured as described in Example 1, with acyl specificity measured using 80 $\mu$M of acyl-CoA substrate and 100 $\mu$M of radiolabeled oleyl alcohol. Alcohol specificity was measured using 100 $\mu$M of alcohol substrate and 40 $\mu$M of radiolabeled eicosenoyl-CoA. Results of these experiments are presented in Table 1 below.

TABLE 1

Acyl and Alcohol Substrate Specificity of Jojoba Wax Synthase

| Substrate Structure | Wax synthase Activity (pmoles/min) | |
|---|---|---|
| | Acyl Group | Alcohol Group |
| 12:0 | 12 | 100 |
| 14:0 | 95 | 145 |
| 16:0 | 81 | 107 |
| 18:0 | 51 | 56 |
| 20:0 | 49 | 21 |
| 22:0 | 46 | 17 |
| 18:1 | 22 | 110 |
| 18:2 | 7 | 123 |
| 20:1 | 122 | 72 |
| 22:1 | 39 | 41 |
| 24:1 | 35 | 24 |

The above results demonstrate that the jojoba wax synthase utilizes a broad range of fatty acyl-CoA and fatty alcohol substrates.

In addition, wax synthase activity towards various acyl-thioester substrates was similarly tested using palmitoyl-CoA, palmitoyl-ACP and N-acetyl-S-palmitoyl cysteamine as acyl substrates. The greatest activity was observed with the acyl-CoA substrate. Significant activity (~10% of that with acyl-CoA) was observed with acyl-ACP, but no activity was detectable with the N-acetyl-S-palmitoyl cysteamine substrate.

C. Effectors of Activity

Various sulphydryl agents were screened for their effect on wax synthase activity. Organomercurial compounds were shown to strongly inhibit activity. Iodoacetamide and N-ethylmaleamide were much less effective. Inhibition by para-hydroxymercuribenzoate was observed, but this inhibition could be reversed by subsequent addition of DTT. These results demonstrate that inhibition by para-hydroxymercuribenzoate involves blocking of an essential sulphydryl group.

D. Size Exclusion Chromatography

A column (1.5 cm×46 cm) is packed with Sephacryl-200 (Pharmacia), sizing range: 5,000–250,000 daltons) and equilibrated with column buffer (25 mM HEPES, 20% glycerol, 0.75% CHAPS, 1 mM EDTA) containing 0.5M NaCl. Approximately 2 ml of a pooled concentrate from a single 1.5 M NaCl elution from a Blue A column (see Ex. 4C) is loaded and the column run at 0.5 ml/min. The eluted fractions are assayed for wax synthase activity according to the reconstitution protocol described in Example 1. Wax synthase activity appears as a broad peak beginning at the void fraction and decreasing throughout the remainder of the run. A portion of the fractions having wax synthase activity are treated with 1-$^{14}$C 16:0-CoA (0.0178 uM) for 15 minutes at room temperature. SDS is added to 2% and the samples are loaded on an SDS-PAGE gel. Following electrophoresis, the gel is blotted to Problott (Applied Biosystems; Foster City, Calif.) and the dried blot membrane analyzed by autoradiography. Alternatively, the blot may be scanned for radioactivity using an automated scanning system (AMBIS; San Diego, Calif.). In this manner, it is observed that the 57 kD radiolabeled band tracks with wax synthase activity in the analyzed fractions.

Protein associated with wax synthase activity is further characterized by chromatography on a second size exclusion matrix. A fraction (100 ul) of a 10× concentrated 1.5M NaCl elution from a Blue A column (following a 1.0M NaCl elution step) which contains wax synthase activity is chromatographed on a Superose 12 HR10/30 column (Pharmacia; Piscataway, N.J.) and analyzed by Fast Protein Liquid Chromatography (FPLC) on a column calibrated with molecular weight standards (MW GF-70 and MW GF-1000; Sigma). Activity assays are performed on the eluted fractions. Most 53% of the recovered wax synthase activity is found in the void fractions, but an easily detectable activity is found to elute at ~55 kd according to the calibration curve. These data indicate the minimum size of an active native wax synthase protein is very similar to the 57 kD size of the labeled band, thus providing evidence that wax synthase activity is provided by a single polypeptide. The fraction of wax synthase activity observed in the void fractions is presumably an aggregated form of the enzyme.

E. Palmitoyl-CoA Agarose Chromatography

A column (1.0×3 cm) is packed with 16:0-CoA agarose (Sigma P-5297) and equilibrated with column buffer (See, Example 1, D.) containing 0.2M NaCl. Approximately 4 ml of a pooled concentrate from the 1.5M NaCl wash of the Blue A column is thawed and the salt concentration reduced by passage of the concentrate over a PD-10 (Pharmacia) desalting column equilibrated in 0.2M NaCl column buffer. The reduced salt sample (5 ml) is loaded onto the 16:0 CoA agarose column at a flow rate of 0.15 ml/min. The column is washed with 0.5M NaCl column buffer and then with 1.5M NaCl column buffer. Although some wax synthase activity flows through the column or is removed by the 0.5M NaCl wash, the majority of the recovered activity (21% of the loaded activity) is recovered in the 1.5M NaCl eluted peak.

Portions of the fractions which demonstrate wax synthase activity are radiolabeled with [$^{14}$C] palmitoyl-CoA as described in Example 2 and analyzed by SDS polyacrylamide gel electrophoresis (Laemmli, *Nature* (1970) 227:680–685). Again the approximate 57 kD radio labelled protein band is observed to track with wax synthase activity.

Example 4

Purification of Jojoba Wax Synthase

Methods are described which may be used for isolation of a jojoba membrane preparation having wax synthase activity, solubilization of wax synthase activity and further purification of the wax synthase protein.

A. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3M NaCl, 0.3M sucrose, 100 mM HEPES, 2 mM DTT, and the protease inhibitors, 1 mM EDTA, 0.7 μg/ml leupeptin, 0.5 g/ml pepstatin and 17 μg/ml PMSF. A cell free homogenate (CFH) is formed by dispersing the powdered embryos in the buffer with a tissue homogenizer (Kinematica, Switzerland; model PT10/35) for approximately 30 sec. and then filtering through three layers of Miracloth (CalBioChem, Lajolla, Calif.). The filtrate is centrifuged at 100,000×g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 0.5M EDTA. The dialyzate is centrifuged at 200,000×g for 1½ hour to yield a pellet, DP2. The pellet is suspended in 25 mM HEPES and 10% glycerol, at ⅟₂₀ of the original CFH volume, to yield the microsomal membrane preparation.

Activity is assayed as described in Example 1. Recovery of wax synthase activity is estimated at 34% of the original activity in the cell free homogenate. Wax synthase activity in this preparation is stable when stored at −70° C.

B. Solubilization of Wax Synthase Protein

CHAPS (3-[(3-cholamidopropyl)-dimethyl-ammonio]-1-propanesulfonate) and NaCl are added to the microsomal membrane preparation to yield final concentrations of 2% and 0.5M, respectively. The samples are incubated on ice for approximately one hour and then diluted with 25 mM HEPES, 20% glycerol, 0.5M NaCl to lower the CHAPS concentration to 0.75%. The sample is then centrifuged at 200,000×g for one hour and the supernatant recovered and assayed for wax synthase activity as described in Example 1.C. Typically, 11% of the wax synthase activity from the microsomal membrane preparation is recovered in the supernatant fraction. The solubilized wax synthase activity is stable when stored at −70° C.

C. Blue A Column Chromatography

A column (2.5×8 cm) with a bed volume of approximately 30 ml is prepared which contains Blue A (Cibacron Blue F3GA; Amicon Division, W.R. Grace & Co.), and the column is equilibrated with the column buffer (25 mM HEPES, 20% glycerol, 0.75% CHAPS, 1 mM EDTA) containing 0.4M NaCl. The solubilized wax synthase preparation is diluted to 0.4M NaCl by addition of column buffer (25 mM HEPES, 20% glycerol, 0.75% CHAPS, 1 mM EDTA) and loaded to the Blue A column.

The column is washed with column buffer containing 0.5M NaCl until no protein can be detected (as measured by absorbance at 280 nm) in the buffer flowing through the column. Greater than 94% of the wax synthase activity binds to the column, while greater than 83% of other protein passes through. Typically, approximately 20% of the loaded wax synthase activity is recovered by elution. A portion of the recovered activity (17%) elutes with a 1.0M NaCl column buffer wash, while approximately 75% of the recovered activity elutes as a broad peak in a 150 ml wash with 1.5M NaCl column buffer. Five ml fractions of the 1.5M wash are collected and assayed for wax synthase activity as described in Example 1. Fractions containing wax synthase activity are pooled and concentrated ten fold using an Amicon stirred cell unit and a YM30 membrane. The concentrated wax synthase preparation may be stored at −70° C.

D. Size Exclusion Column Chromatography

In fractions collected from chromatography on Blue A the acyl-transferase enzyme activity responsible for formation of wax esters from fatty alcohol and acyl-CoA co-elutes with the measurable activity of β-ketoacyl-CoA synthase. The β-ketoacyl-CoA synthase activity can be separated from this wax synthase activity through size exclusion chromatography using S 100 sepharose. The preferred column buffer for size exclusion chromatography comprises 1.0% CHAPS, as at 0.75% CHAPS the enzyme tends to aggregate, i.e., stick to itself and other proteins. Using a column buffer adjusted to 1.0% CHAPS allows clean separation of the activity of wax synthase on S 100, wax synthase being retained, from the β-ketoacyl-CoA synthase protein, the latter being voided. The majority of wax synthase activity elutes from the S 100 sizing column as a peak with a molecular mass ~ of 57 kDa. At 0.75% CHAPS only a small portion of total assayable wax synthase activity is found at 57 kDa, with the remainder distributed over void and retained fractions.

Wax synthase also has an estimated molecular mass of ~57 kDa based on SDS gels of radiolabelled protein, i.e., wax synthase protein which has been labeled by the procedure described above by incubation with 14C-palmitoyl-CoA. The labelled band tracks with wax synthase activity in fractions collected from a size exclusion column, while β-ketoacyl-CoA synthase activity is completely voided by the S 100 column.

As a predominant 57 kDa protein from the Blue A column fraction, the β-ketoacyl-CoA synthase can be amino acid sequenced from bands removed from SDS PAGE. Wax synthase activity can be isolated by SDS PAGE and cloned by a similar procedure from fractions retained on S 100.

E. SDS PAGE Analysis

Samples from the S 100 or active Blue A column fractions are diluted in SDS PAGE sample buffer (1× buffer=2% SDS, 30 mM DTT, 0.001% bromphenol blue) and analyzed by electrophoresis on 12% tris/glycine precast gels from NOVEX (San Diego, Calif.). Gels are run at 150V, constant voltage for approximately 1.5 hours. Protein is detected by silver staining (Blum et al., *Electrophoresis* (1987) 8:93–99). Careful examination of the gel reveals only a few polypeptides, including one of approximately 57 kD, whose staining intensity in the various fractions can be correlated with the amount of wax synthase activity detected in those fractions. Furthermore, if radiolabeled [1-$^{14}$C] palmitoyl-CoA is added to the protein preparation prior to SDS PAGE analysis, autoradiography of the gel reveals that the 57 kD labeled band tracks with wax synthase activity in these fractions. Other proteins are also present in the preparation, including the 56 and 54 kD reductase proteins described in co-pending application U.S. Ser. No. 07/767,251.

F. Continuous Phase Elution

Wax synthase protein is isolated for amino acid sequencing using an SDS-PAGE apparatus, Model 491 Prep Cell (Bio-Rad Laboratories, Inc., Richmond, Calif.), according to manufacturer's instructions. A portion (15 ml) of the wax synthase activity from the 1.5M NaCl elution of the Blue A column is concentrated 10 fold in a Centricon 30 (Amicon Division, W. R. Grace & Co.; Beverly, Mass.) and desalted with column buffer on a Pharmacia PD-10 desalting column. The sample is treated with 2% SDS and a small amount of bromphenol blue tracking dye and loaded onto a 5 ml, 4% acrylamide stacking gel over a 20 ml, 12% acrylamide running gel in the Prep Cell apparatus. The sample is electrophoresed at 10 W and protein is continuously collected by the Prep Cell as it elutes from the gel. The eluted protein is then collected in 7.5–10 ml fractions by a fraction collector. One milliliter of each fraction in the area of interest (based on the estimated 57 kD size of the wax synthase protein) is concentrated to 40 μl in a Centricon 30 and treated with 2% SDS. The samples are run on 12% acrylamide mini-gels (Novex) and stained with silver. Various modifications to the continuous phase elution process in order to optimize for wax synthase recovery may be useful. Such modifications include adjustments of acrylamide percentages in gels volume of the gels, and adjustments to the amount of wax synthase applied to the gels. For example, to isolate greater amounts of the wax synthase protein the Blue A column fractions may be applied to larger volume, 20–55 ml, acrylamide gels at a concentration of approximately 1 mg of protein per 20 ml of gel. The protein fractions eluted from such gels may then be applied 10–15% gradient acrylamide gels for increased band separation.

The protein content of each fraction is evaluated visually and fractions containing wax synthase protein are pooled and concentrated for amino acid sequencing. In order to maximize the amount of wax synthase enzyme collected, fractions which also contain the 56 kD reductase protein band are included in the pooled preparation. As the reductase protein sequence is known (see FIG. 1), further purification of wax synthase protein in the pooled preparation is not necessary prior to application of amino acid sequencing techniques (see Example 5).

G. Blotting Proteins to Membranes

Alternatively, wax synthase protein may be further isolated for amino acid sequencing by transfer to PVDF membranes following SDS-PAGE, either Immobilon-P (Millipore; Bedford, Mass.) or ProBlott (Applied Biosystems; Foster City, Calif.). Although transfer to nitrocellulose may also be useful, initial studies indicate poor transfer to nitrocellulose membranes, most likely due to the hydrophobic nature of this protein. PVDF membranes, such as ProBlott and Immobilon-P find preferential use in different methods, depending on the amino acid sequencing technique to be employed. For example, transfer to ProBlott is useful for N-terminal sequencing methods and for generation of peptides from cyanogen bromide digestion, Immobilon-P is preferred.

1. Blotting to Nitrocellulose: When protein is electroblotted to nitrocellulose, the blotting time is typically 1–5 hours in a buffer such as 25 mM Tris, 192 mM glycine in 5–20% methanol. Following electroblotting, membranes are stained in 0.1% (w/v) Ponceau S in 1% (v/v) acetic acid for 2 minutes and destained in 2–3 changes of 0.1% (v/v) acetic acid, 2 minutes for each change. These membranes are then stored wet in heat-sealed plastic bags at −20° C. If time permits, blots are not frozen but used immediately for digestion to create peptides for determination of amino acid sequence as described below.

2. Blotting to PVDF: When protein is electroblotted to Immobilon P PVDF, the blotting time is generally about 1–2 hours in a buffer such as 25 mM Tris/192 mM glycine in 20% (v/v) methanol. Following electroblotting to PVDF, membranes are stained in 0.1% (w/v) Coomassie Blue in 50% (v/v) methanol/10% (v/v) acetic acid for 5 minutes and destained in 2–3 changes of 50% (v/v) methanol/10% (v/v) acetic acid, 2 minutes for each change. PVDF membranes are then allowed to air dry for 30 minutes and are then stored dry in heat-sealed plastic bags at −20° C. Protein blotted to PVDF membranes such as Pro Blott, may be used directly to determine N-terminal sequence of the intact protein. A protocol for electroblotting proteins to ProBlott is described below in Example 5A.

Example 5

Determination of Amino Acid Sequence

In this example, methods for determination of amino acid sequences of plant proteins associated with wax synthase activity are described.

A. Cyanogen Bromide Cleavage of Protein and Separation of Peptides

Cyanogen bromide cleavage is performed on the protein of interest using the methodology described in the Probe-Design Peptide Separation System Technical Manual from Promega, Inc. (Madison, Wis.). The wax synthase protein, if not available in a purified liquid sample, is blotted to a PVDF membrane as described above. Purified wax synthase protein or wax synthase bands from the PVDF blot, are placed in a solution of cyanogen bromide in 70% (v/v) formic acid, and incubated overnight at room temperature. Following this incubation the cyanogen bromide solutions are removed, pooled and dried under a continuous nitrogen stream using a Reacti-Vap Evaporator (Pierce, Rockford, Ill.). Additional elution of cyanogen bromide peptides from PVDF may be conducted to ensure complete removal, using a peptide elution solvent such as 70% (v/v) isopropanol, 0.2% (v/v) trifluoroacetic acid, 0.1 mM lysine, and 0.1 mM thioglycolic acid. The elution solvents are then removed and added to the tube containing the dried cyanogen bromide solution, and dried as described above. The elution procedure may be repeated with fresh elution solvent. 50 µl of HPLC grade water is then added to the dried peptides and the water removed by evaporation in a Speed-Vac (Savant, Inc., Farmingdale, N.Y.).

Peptides generated by cyanogen bromide cleavage are separated using a Tris/Tricine SDS-PAGE system similar to that described by Schagger and von Jagow (*Anal. Biochem.* (1987) 166:368–379). Gels are run at a constant voltage of 125–150 volts for approximately 1 hour or until the tracking dye has begun to run off the bottom edge of the gel. Gels are soaked in transfer buffer (125 mM Tris, 50 mM glycine, 10% (v/v) methanol) for 15–30 minutes prior to transfer. Gels are blotted to ProBlott sequencing membranes (Applied Biosystems, Foster City, Calif.) for 2 hours at a constant voltage of 50 volts. The membranes are stained with Coomassie blue (0.1% in 50% (v/v) methanol/10% (v/v) acetic acid) and destained for 3×2 min. in 50% (v/v) methanol/10% (v/v) acetic acid. Membranes are air-dried for 30–45 minutes before storing dry at −20° C.

Peptides blotted on to ProBlott can be directly loaded to the sequencer cartridge of the protein sequencer without the addition of a Polybrene-coated glass fiber filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

B. Protease Digestion and Separation of Peptides

Purified wax synthase protein provided in a liquid solution or wax synthase proteins blotted to nitrocellulose may be subjected to digestion with proteases in order to obtain peptides for sequencing. The method used is that of Aebersold, et al. (*PNAS* (1987) 84:6970).

For protein provided on nitrocellulose, bands of the wax synthase proteins, and also an equal amount of blank nitrocellulose to be used as a control, are cut out of the nitrocellulose membrane and washed several times with HPLC grade water in order to remove the Ponceau S. Following this wash, 1.0 ml of 0.5% polyvinylpyrrolidone (PVP-40, Aldrich, Milwaukee, Wis.) in 0.5% acetic acid is added to the membrane pieces and this mixture is incubated for 30 minutes at 37° C. In order to remove the PVP-40 completely, nitrocellulose pieces are washed with many volumes of HPLC grade water (8×5 ml), checking the absorbance of the washes at 214 nm on a spectrophotometer. Also, PVP-40 is more easily removed if bands are not cut into small pieces until after PVP-40 treatment and washing.

The proteins, in solution or on nitrocellulose pieces, are then suspended in an appropriate digest buffer, for example trypsin digest buffer, 100 mM sodium bicarbonate pH 8.2, or endoproteinase gluC buffer, 25 mM ammonium carbonate/1 mM EDTA, pH 7.8. Acetonitrile is added to the digest mixture to a concentration of 5–10% (v/v). Proteases are diluted in digest buffer and added to the digest mixture, typically at a ratio of 1:10 (w/w) protease to protein. Digests are incubated 18–24 hours. For example, trypsin digests are incubated at 37° C. and endoproteinase gluC digests are incubated at room temperature. Similarly, other proteases may be used to digest the wax synthase proteins, including lysC and aspN. While the individual digest buffer conditions may be different, the protocols for digestion, peptide separation, purification and sequencing are substantially the same as those described for digestion with trypsin and gluC.

Following overnight incubation, digest reactions are stopped by the addition of 10 µl 10% (v/v) trifluoroacetic acid (TFA) or 1 µl 100% TFA. When the protein is provided on nitrocellulose, the nitrocellulose pieces are washed with 1–5 100 µl volumes of digest buffer with 5–10% acetonitrile, and these volumes are concentrated to a volume of less than 100 µl in a Speed-Vac.

The peptides resulting from digestion are separated on a Vydac reverse phase C18 column (2.1 mm×100 mm) installed in an Applied Biosystems (Foster City, Calif.) Model 130 High Performance Liquid Chromatograph (HPLC). Mobile phases used to elute peptides are: Buffer A: 0.1 mM sodium phosphate, pH2.2; Buffer B: 70% acetonitrile in 0.1 mM sodium phosphate, pH2.2. A 3-step gradient of 10–55% buffer B over two hours, 55–75% buffer B over 5 minutes, and 75% buffer B isocratic for 15 minutes at a flow rate of 50 µl/minute is used. Peptides are detected at 214 nm, collected by hand, and then stored at −20° C.

Due to the hydrophobic nature of the wax synthase proteins, addition of a detergent in enzyme digestions buffers may be useful. For example, fractions from the continuous phase elution procedure described above which contain the jojoba wax synthase are concentrated in a Centricon 30 in 100 mM NaHCO$_3$/1.0% CHAPS to a final volume of 110 µl. Two µg of trypsin in 5 µl of 100 mM Na HCO$_3$/1.0%

CHAPS is added to the protein solution and the mixture is incubated overnight at 37° C., and the digestion stopped by addition of trifluoroacetic acid (TFA). The sample is centrifuged lightly and the peptides separated on a Vydac C18 column and eluted as described above. In this procedure, the CHAPS elutes at ~40–53% Buffer B, and obscures the peptide peaks in this region.

Where the primary separation yields a complex peptide pattern, such as where excess protein is used or contaminants (such as the jojoba reductase protein) are present, peptide peaks may be further chromatographed using the same column, but a different gradient system. For the above jojoba wax synthase preparation, hydrophilic peaks were separated using a gradient of 0–40% Buffer B for 60 minutes, 40–75% B for 35 minutes and 75–100% B for 10 minutes. Hydrophobic peaks were separated using 0–40% Buffer B for 40 minutes, 40–80% B for 60 minutes and 80–100% B for 10 minutes. For these separations, Buffer A is 0.1% TFA and Buffer B is 0.1% TFA in acetonitrile.

C. N-terminal Sequencing of Proteins and Peptides

All sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored using an Applied BioSystems model 610A data analysis system for the Apple Macintosh and also on to a Digital Microvax using ACCESS*CHROM software from PE NELSON, Inc. (Cupertino, Calif.). Sequence data is read from a chart recorder, which receives input from the PTH Analyzer, and is confirmed using quantitative data obtained from the model 610A software. All sequence data is read independently by two operators with the aid of the data analysis system.

For peptide samples obtained as peaks off of an HPLC, the sample is loaded on to a Polybrene coated glass fiber filter (Applied Biosystems, Foster City, Calif.) which has been subjected to 3 pre-cycles in the sequencer. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, pre-cycled as above and the reaction cartridge is assembled according to manufacturer's specifications. For protein samples which have been electroblotted to ProBlott, the glass fiber filter is not required.

In order to obtain protein sequences from small amounts of sample (5–30 moles), the 477A conversion cycle and the 120A analyzer as described by Tempst and Riviere (Anal. Biochem. (1989) 183:290).

Amino acid sequence of jojoba peptides obtained by trypsin digestion as described above are presented in Table 2 below.

TABLE 2

Amino Acid Sequence of Jojoba 57 kDa protein Tryptic Peptides

| | | |
|---|---|---|
| SQ1114 | ETYVPESVTKK | (SEQ ID NO:30) |
| SQ1084 | VPXEPSIAAX | (SEQ ID NO:31) |
| SQ1083 | ETYVPEEvtk | (SEQ ID NO:32) |
| SQ1120 | DLMAVAGEAlk | (SEQ ID NO:33) |
| SQ1125 | MTNVKPYIPDF | (SEQ ID NO:34) |
| SQ1129 | FLPXXVAiTGe | (SEQ ID NO:35) |

TABLE 2-continued

Amino Acid Sequence of Jojoba 57 kDa protein Tryptic Peptides

| | | |
|---|---|---|
| SQ1131 | FGNTSSXXLyxelayak | (SEQ ID NO:36) |
| SQ1137 | AEAEEVMYGAIDEVLEK | (SEQ ID NO:37) |

The amino acid sequence is represented using the one letter code. "X" represents a position where the amino acid could not be identified, and amino acids represented by lower case letters represent residues which were identified with a lesser degree of confidence.

Example 6

Purification of Additional Wax Synthases and Reductases

A. Adaptation of jojoba wax synthase solubilization and purification methods to obtain partially purified preparations of wax synthase from other organisms are described.

Acinetobacter

Cells of *Acinetobacter calcoaceticus* strain BD413 (ATCC #33305) are grown on ECLB (*E. coli* luria broth), collected during the logarithmic growth phase and washed in a buffer containing; Hepes, pH 7.5, 0.1M NaCl, 1 mM DTT and protease inhibitors. Washed cells were resuspended in fresh buffer and ruptured by passage through a French pressure cell (two passes at ~16,000 p.s.i.). Unbroken cells are removed by centrifugation at 5000×g for 10 minutes, and membranes are collected by centrifugation at 100,000×g for 1 hour. The membrane pellet is homogenized in storage buffer (25 mM Hepes, pH 7.5, 10% (w/v) glycerol). Wax synthase activity is detected in these membranes using assay conditions described for the jojoba enzyme in Example 1B, using [1-$^{14}$C] palmitoyl-CoA and 18:1 alcohol as the substrates.

Wax synthase activity is solubilized by incubation of the membranes with 2% CHAPS in the presence of 0.5M NaCl, as described for the jojoba enzyme in Example 4B. Solubilization of the activity is demonstrated by the detection of wax synthase enzyme activity in the supernatant fraction after centrifugation at 200,000 g for 1 hour and by size exclusion chromatography (i.e. the activity elutes from the column in the retained fractions as a symmetrical peak). The activity of the solubilized enzyme is detected by simple dilution of the CHAPS concentration to ~0.3% (i.e. to below its CMC). Incorporation of the enzyme into phospholipid vesicles is not required to detect solubilized activity.

For purification, the solubilized Acinetobacter wax synthase activity is subjected to chromatographic purification procedures similar to those described for the jojoba acyl-CoA reductase. The soluble protein preparation is loaded to a Blue A agarose column under low salt conditions (150 mM NaCl in a column buffer containing 0.75% CHAPS, 10% glycerol, 25 mM Hepes, pH 7.5) and eluted from the column using 1.0M NaCl in the column buffer.

Size exclusion chromatography on Superose 12 (Pharmacia; Piscataway, N.J.) medium is used to obtain an estimate of the size of the native enzyme and to aid in identifying candidate polypeptides. Comparison to molecular mass standards chromatographed under identical conditions yields an estimate of ~46 kD for the native wax synthase activity. Three polypeptides bands,.with apparent molecular masses of 45 kD, 58 kD and 64 kD, were identified which tracked with wax synthase activity. N-terminal sequence of the 45 kD polypeptide, the strongest candidate for wax synthase, is determined as XDIAIIGSG-sAGLAQaxilkdag (SEQ ID NO: 38), where the one letter code for amino acids is used, "X" represents a position where the amino acid could not be identified, and amino acids represented by lower case letters represent residues which were identified with a lesser degree of confidence. In addition, sequence of a tryptic peptide of the Acinetobacter wax synthase protein is determined as QQFTVWXNASEPS (SEQ ID NO: 39).

Euglena

*Euglena gracilis*, strain Z (ATCC No. 12716) is grown heterotrophically in the dark (Tani et al. (1987) *Agric. Biol. Chem.* 51:225–230) at ~26° C. with moderate shaking. Cells are collected and washed in buffer containing 25 mM Bis-Tris-Propane, pH 7.0, 0.25M NaCl and 1 mM EDTA. Washed cells are resuspended in fresh buffer and ruptured by passage through a French pressure cell (two passes at ~16,000 p.s.i.). Unbroken cells, cell debris and nuclei are removed by centrifugation at 20,000×g for 20 minutes, and microsomal membranes are collected by centrifugation at 200,000×g for 1 hour. The membrane pellet is homogenized in storage buffer (25 mM Bis-Tris-Propane, pH 7.0, 0.25M NaCl, 10% (w/v) glycerol and 1 mM EDTA). Wax synthase activity is detected in these membranes using assay conditions as described for the jojoba enzyme. The radiolabelled substrate is the same as for the jojoba example (i.e. [1-$^{14}$C] palmitoyl-CoA), however, 16:0 rather than 18:1 is used as the alcohol acceptor, and Bis-Tris-Propane buffer at pH 7.0 is utilized.

The *Euglena* wax synthase activity is solubilized by incubation of the membranes with 2% CHAPS in the presence of 0.5M NaCl. Solubilization of the protein is demonstrated by the detection of enzyme activity in the supernatant fraction after centrifugation at 200,000×g for 1 hour. The activity of the solubilized enzyme is detected by dilution of the CHAPS concentration to ~0.3% (i.e. to below its CMC). It is not necessary to incorporate the enzyme into phospholipid vesicles as was the case for the solubilized jojoba wax synthase.

For partial purification, the solubilized *Euglena* wax synthase activity is subjected to chromatographic separation on Blue A agarose medium. The column is equilibrated with 0.1M NaCl in a column buffer containing; 25 mM Bis-Tris-Propane, pH 7.0, 20% (w/v) glycerol, 0.75% CHAPS and 1 mM EDTA. The sample containing solubilized wax synthase activity is diluted to 0.1M NaCl and loaded onto a 1×7 cm column (5.5 ml bed volume). The column is washed with equilibration buffer and subjected to a linear NaCl gradient (0.1M to 1.0M NaCl) in column buffer. Wax synthase activity is eluted as a broad peak in the last half of the salt gradient.

SDS-PAGE analysis of column fractions reveals that the polypeptide complexity of the activity eluted from the column is greatly reduced relative to the loaded material. A polypeptide with an apparent molecular mass of ~41 kD was observed to track with wax synthase activity in the column fractions. Further purification techniques, such as described for jojoba and Acinetobacter are conducted to verify the association of wax synthase activity with the ~41 kD peptide.

For further analysis of wax synthase activity in Euglena, size exclusion chromatography was conducted as follows. A microsomal membrane preparation was obtained from *Euglena* cells grown on liquid, heterotrophic, medium (Tani et al., supra) in the dark. Wax synthase activity was solubilized by treating the membranes with 2% (w/v) CHAPS and 500 mM NaCl in a buffered solution (25 mM Bis-Tris, pH 7.0, 1 mM EDTA and 10% (w/v) glycerol) for 1 hour on ice. After dilution of the CHAPS to 0.75% and the NaCl to 200 mM by addition of a dilution buffer, the sample was centrifuged at ~200,000×g for 1.5 hours. The supernatant fraction was loaded onto a Blue A dye column pre-equilibrated with Column Buffer (25 mM Bis-Tris pH 7.0, 1 mM EDTA, 10% glycerol, 0.75% CHAPS) which also contained 200 mM NaCl. The column was washed with Column Buffer containing 200 mM NaCl until the A280 of the effluent returned to the preload value. Wax synthase activity which had bound to the column was released by increasing the NaCl concentration in the Column Buffer to 1.5M. The fractions from the Blue A column containing wax synthase activity released by the 1.5M NaCl (~20 ml combined volume) were pooled and concentrated approximately 30-fold via ultrafiltration (Amicon pressure cell fitted with a YM 30 membrane). The concentrated material from the Blue A column was used as the sample for a separation via size exclusion chromatography on Superose 12 medium (Pharmacia).

Approximately 200 μl of the sample was loaded onto a Superose 12 column (HR 10/30), pre-equilibrated with Column Buffer containing 0.5M NaCl, and developed at a flow rate of 0.1 ml/min. The wax synthase activity eluted from the column as a smooth peak. Comparison of the elution volume of the wax synthase activity with the elution profiles of molecular mass standard proteins yielded an estimate of 166 kD for the apparent molecular mass of the enzyme. Fractions which contained wax synthase activity were analyzed via SDS-polyacrylamide gel electrophoresis followed by silver staining. A preliminary analysis of the polypeptide profiles of the various fractions did not reveal any proteins with molecular masses of 100 kD or greater whose staining intensity appeared to match the activity profile. The wax synthase polypeptide may be present as a minor component in the sample mixture that is not readily detectable on the silver-stained gel. Alternatively, the enzyme may be composed of subunits which are dissociated during SDS-PAGE.

B. In addition to jojoba reductase, such as that encoded by the sequence provided in FIG. 1, reductase proteins from other sources are also desirable for use in conjunction with the wax synthase proteins of this invention. Such proteins may be identified and obtained from organisms known to produce wax esters from alcohol and acyl substrates.

For example, an NADH-dependent fatty acyl-CoA reductase activity can be obtained from microsomal membranes isolated from *Euglena gracilis*. Methods which may be used to isolate microsomal membranes are described, for example in the published PCT patent application WO 92/14816 (application number PCT/US92/03164, filed Feb. 21, 1992). The reductase activity is solubilized from these membranes using the same approaches as used for jojoba reductase and wax synthase. Membranes are incubated on ice for one hour with various amounts of the detergent, CHAPS, in a buffering solution consisting of 25 mM BisTris, pH 6.9, 250 mM NaCl, 10% glycerol and 1 mM EDTA. The sample is then centrifuged at 200,000×g for one hour, and the supernatant and pellet fractions assayed for NADH-dependent reductase activity using radiolabeled palmitoyl-CoA and NADH as substrates. A convenient assay for reductase activity is described in PCT patent application WO 92/14816. Incubation of the membranes with 0.3, 0.5 or 0.7 % (w/v) CHAPS results in retention of reductase activity in the supernatant fractions, indicative of solubilization of the enzyme. If CHAPS is omitted during the incubation and centrifugation, all of the reductase activity is found in the pellet fraction. All of the samples are diluted ten-fold in this same buffer solution prior to assaying in order to dilute the CHAPS present during the incubation. The presence of CHAPS in the assay at levels above the CMC (approximately 0.5% (w/v) results in inhibition of enzyme activity. Stability of the reductase activity in up to 2% CHAPS may be improved by increasing the glycerol concentration in the buffering solution to 20%. Reductase activity is recovered by dilution of the CHAPS to below the CMC.

Example 7

Isolation of Nucleic Acid Sequences

Isolation of nucleic acid sequences from cDNA libraries or from genomic DNA is described.

A. Construction of Jojoba cDNA Libraries

RNA is isolated from jojoba embryos collected at 80–90 days post-anthesis using a polyribosome isolation method, initially described by Jackson and Larkins (*Plant Physiol.* (1976) 57:5–10), as modified by Goldberg et al. (*Developmental Biol.* (1981) 83:201–217). In this procedure all steps, unless specifically stated, are carried out at 4° C. 10 gm of tissue are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgCl2, 1% Triton X-100, 0.5% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000×g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000×g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgCl2, 1.8M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM $MgCl_2$, 5 mM β-mercaptoethanol) is added to each tube. The tubes are placed on ice for 10 minutes, after which the pellets are thoroughly resuspended and pooled. The supernatant is then centrifuged at 120×g for 10 minutes to remove insoluble material. One volume of self-digested 1 mg/ml proteinase K in 20 mM Tris pH 7.6, 200 mM EDTA, 2% N-laurylsarcosinate is added to the supernatant and the mixture incubated at room temperature for 30 minutes.

RNA is precipitated by adding 1/10 volume of sodium acetate and 2 volumes of ethanol. After several hours at −20° C. RNA is pelleted by centrifugation at 12,000×g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000×g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

Polyadenylated RNA is used to construct a cDNA library in the plasmid cloning vector pCGN1703, derived from the commercial cloning vector Bluescribe M13- (Stratagene Cloning Systems; San Diego, Calif.), and made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA wax synthase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3' C-tail end. Following ligation and repair the circular complexes are transformed into *E. coli* strain DH5α (BRL, Gaithersburg, Md.) to generate the cDNA library. The jojoba embryo cDNA bank contains between approximately $1.5 \times 10^6$ clones with an average cDNA insert size of approximately 500 base pairs.

Additionally, jojoba polyadenylated RNA is also used to construct a cDNA library in the cloning vector λZAPII/ EcoRI (Stratagene, San Diego, Calif.). The library is constructed using protocols, DNA and bacterial strains as supplied by the manufacturer. Clones are packaged using Gigapack Gold packaging extracts (Stratagene), also according to manufacturer's recommendations. The cDNA library constructed in this manner contains approximately $1 \times 10^6$ clones with an average cDNA insert size of approximately 400 base pairs.

B. Polymerase Chain Reaction

Using amino acid sequence information, nucleic acid sequences are obtained by polymerase chain reaction (PCR).

Synthetic oligonucleotides are synthesized which correspond to the amino acid sequence of selected peptide fragments. If the order of the fragments in the protein is known, such as when one of the peptides is from the N-terminus or the selected peptides are contained on one long peptide fragment, only one oligonucleotide primer is needed for each selected peptide. The oligonucleotide primer for the more N-terminal peptide, forward primer, contains the encoding sequence for the peptide. The oligonucleotide primer for the more C-terminal peptide, reverse primer, is complementary to the encoding sequence for the selected peptide. Alternatively, when the order of the selected peptides is not known, two oligonucleotide primers are required for each peptide, one encoding the selected amino acid sequence and one complementary to the selected amino acid sequence. Any sequenced peptides may be selected for construction of oligonucleotides, although more desirable peptides are those which contain amino acids which are encoded by the least number of codons, such as methionine, tryptophan, cysteine, and other amino acids encoded by fewer than four codons. Thus, when the oligonucleotides are mixtures of all possible sequences for a selected peptide, the number of degenerate oligonucleotides may be low.

PCR is conducted with these oligonucleotide primers using techniques that are well known to those skilled in the art. Jojoba nucleic acid sequences, such as reverse transcribed cDNA, DNA isolated from the cDNA libraries described above or genomic DNA, are used as template in these reactions. In this manner, segments of DNA are produced. Similarly, segments of Acinetobacter w DNA are obtained from PCR reactions using oligonucleotide primers to the N-terminal and tryptic digest peptides described in Example 6A. The PCR products are analyzed by gel electrophoresis techniques to select those reactions yielding a desirable wax synthase fragment.

C. Screening Libraries for Sequences

DNA fragments obtained by PCR are labeled and used as a probe to screen clones from the cDNA libraries described above. DNA library screening techniques are known to those in the art and described, for example in Maniatis et al. (*Molecular Cloning: A Laboratory Manual, Second Edition* (1989) Cold Spring Harbor Laboratory Press). In this manner, nucleic acid sequences are obtained which may be analyzed for nucleic acid sequence and used for expression of the plant cytoplasmic protein involved in fatty acyl-CoA metabolism in various hosts, both procaryotic and eucaryotic.

An approximately 1500 nucleotide jojoba cDNA clone is obtained in this manner. Comparison to the peptide fragments provided in Table 2 reveals the presence of each of these peptides in the translated sequence, with the exception of SQ1129. Northern analysis of jojoba embryo RNA indicates that the mRNA is approximately 2 kb in length. Additional nucleic acid sequence is obtained using further PCR techniques, such as 5' RACE (Frohman et al., *Proc. Nat. Acad. Sci.* (1988) 85:8998–9002). Alternatively, additional sequences may be obtained by rescreening cDNA libraries or from genomic DNA. Preliminary DNA sequence of a jojoba gene is presented in FIG. 2. Further DNA sequence analysis of additional clones indicates that there are at least two classes of cDNA's encoding this jojoba protein. A plasmid containing the entire coding region in pCGN1703 is constructed to contain a SalI site approximately 8 nucleotides 5' to the ATG start codon, and is designated pCGN7614. The complete DNA sequence of pCGN7614 is presented in FIG. 3. The major difference between the two classes of cDNAs as represented in the sequences in FIGS. 2 and 3 is the presence (FIG. 2) or absence (FIG. 3) of the 6 nucleotide coding sequence for amino acids 23 and 24 of FIG. 2.

D. Expression of Wax Synthase Activity in *E. coli*

The gene from pCGN7614 is placed under the control of the Tac promoter of *E. coli* expression vector pDR540 (Pharmacia) as follows. pCGN7614 DNA is digested at the SalI sites and the ends are partially filled in using the Klenow fragment of DNA polymerase I and the nucleotides TTP and dCTP. The pDR540 vector is prepared by digesting with BamHI and partially filling in the ends with dGTP and DATP. The 1.8 kb fragment from pCGN7614 and the digested pDR540 vector are gel purified using low melting temperature agarose and ligated together using T4 DNA ligase. A colony containing the encoding sequence in the sense orientation relative to the *E. coli* promoter was designated pCGN7620, and a colony containing the gene in the antisense orientation was designated pCGN7621.

To assay for wax synthase activity, 50 ml cultures of pCGN7620 and pCGN7621 are grown to log phase in liquid culture, and induced for 2 hours by the addition of IPTG to a concentration of 1 mM. The cells are harvested by centrifugation and subjected to the assay for wax synthase activity as described for jojoba extracts. TLC analysis indicates that the cell extract from pCGN7620 directs synthesis of wax ester, while the control extract from pCGN7621 does not direct the synthesis of wax ester. The wax synthase assay in these harvested cells was verified by a second assay, however, further attempts to produce wax synthase activity in *E. coli* cells transformed with reductase constructs have been unsuccessful.

Example 8

Constructs for Plant Expression

Constructs which provide for expression of the plant cytoplasmic protein involved in fatty acyl-CoA metabolism and reductase sequences in plant cells may be prepared as follows.

A. Expression Cassettes

Expression cassettes which contain 5' and 3' regulatory regions from genes expressed preferentially in seed tissues may be prepared from napin, Bce4 and ACP genes as described, for example in WO 92/03564.

For example, napin expression cassettes may be prepared as follows. A napin expression cassette, pCGN1808, which may be used for expression of wax synthase or reductase gene constructs is described in Kridl et al. (*Seed Science Research* (1991) 1:209–219), which is incorporated herein by reference.

Alternatively, pCGN1808 may be modified to contain flanking restriction sites to allow movement of only the expression sequences and not the antibiotic resistance marker to binary vectors such as pCGN1557 (McBride and Summerfelt, supra). Synthetic oligonucleotides containing KpnI, NotI and HindIII restriction sites are annealed and ligated at the unique HindIII site of pCGN1808, such that only one HindIII site is recovered. The reulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restriction sites as well as nucleotides 409–423 of the napin 5'-sequence (from the EcoRV site) and the reverse primer contains the complement to napin sequences 718–739 which include the unique SacI site in the 5'-promoter. The PCR was performed using a Perkin Elmer/Cetus thermocycler according to manufacturer's specifications. The PCR fragment is subcloned as a blunt-ended fragment into pUCB (Vieira and Messing (1982) *Gene* 19:259–268) and digested with HincII to give pCGN3217. Sequence of pCGN3217 across the napin insert verifies that no improper nucleotides were introduced by PCR. The napin 5'-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3' noncoding regions.

Similarly, a cassette for cloning of sequences for transcription regulation under the control of 5' and 3' regions from an oleosin gene may be prepared. Sequence of a *Brassica napes* oleosin gene was reported by Lee and Huang (*Plant Phys.* (1991) 96:1395–1397). Primers to the published sequence are used in PCR reactions to obtain the 5' and 3' regulatory regions of an oleosin gene from *Brassica napus* cv. Westar. Two PCR reactions were performed, one to amplify approximately 950 nucleotides upstream of the ATG start codon for the oleosin gene, and one to PCR amplify approximately 600 bp including and downstream of the TAA stop codon for the oleosin gene. The PCR products were cloned into plasmid vector pAMP1 (BRL) according to manufacturers protocols to yield plasmids pCGN7629 which contains the oleosin 5' flanking region and pCGN7630 which contains the 3' flanking region. The PCR primers included convenient restriction sites for cloning the 5' and 3' flanking regions together into an expression cassette. A PstI fragment containing the 5' flanking region from pCGN7629 was cloned into PstI digested pCGN7630 to yield plasmid pCGN7634. The BssHII (New England BioLabs) fragment from pCGN7634, which contains the entire oleosin expression cassette was cloned into BssHII digested pBCSK+ (Stratagene) to provide the oleosin cassette in a plasmid, pCGN7636. Sequence of the oleosin cassette in pCGN7636 is provided in FIG. 4. The oleosin cassette is flanked by BssHII, KpnI and XbaI restriction sites, and contains SalI, BamHI and PstI sites for insertion of wax synthase, reductase, or other DNA sequences of interest between the 5' and 3' oleosin regions.

The gene sequences are inserted into such cassettes to provide expression constructs for plant transformation methods. For example, such constructs may be inserted into binary vectors for Agrobacterium-mediated transformation as described below.

B. Constructs for Plant Transformation

The plasmid pCGN7614 is digested with AflIII, and ligated with adapters to add BclI sites to the AflIII sticky ends, followed by digestion with SalI and BclI. The fragment containing the plant cytoplasmic protein involved in fatty acyl-CoA metabolism gene is gel purified and cloned into SalI/BamHI digested pCGN3223, a napin expression cassette. The resulting plasmid which contains the plant cytoplasmic protein involved in fatty acyl-CoA metabolism gene in a sense orientation in the napin expression cassette is designated pCGN7624. DNA isolated from pCGN7624 is digested with Asp718 (a KpnI isoschizimer), and the napin/plant cytoplasmic protein involved in fatty acyl-CoA metabolism fusion gene is cloned into Asp718 digested binary vector pCGN1578 (McBride and Summerfelt, supra). The resultant binary vector, designated pCGN7626, is transformed into Agrobacterium strain EHA101 and used for transformation of *Arabidopsis* and rapeseed explants.

Additional binary vectors are prepared from pCGN1578, pCGN1559 and other vectors described by McBride et al. (supra) by substitution of the pCGN1578 and pCGN1559 linker regions with a linker region containing the following restriction digestion sites: Asp718/AscI/PacI/XbaI/BamHI/SwaI/Sse8387 (PstI)/HindIII. This results in pCGN1578PASS or pCGN1559PASS, and other modified vectors which are designated similarly. AscI, PacI, SwaI and Sse8387 have 8-base restriction recognition sites. These enzymes are available from New England BioLabs: AscI, PacI; Boehringer Manheim: SwaI and Takara (Japan): Sse8387.

C. Reductase Constructs for Plant Transformation Constructs for expression of reductase in plant cells using 5' and 3' regulatory regions from a napin gene, are prepared.

A reductase cDNA (in the pCGN1703 vector described above) designated pCGN7571, is digested with SphI (site in 3' untranslated sequence at bases 1594–1599) and a SalI linker is inserted at this site. The resulting plasmid is digested with BamHI and SalI and the fragment containing the reductase cDNA gel purified and cloned into BglII/XhoI digested pCGN3223, the napin cassette described above, resulting in pCGN7585.

A HindIII fragment of pCGN7585 containing the napin 5'/reductase/napin 3' construct is cloned into HindIII digested pCGN1578 (McBride and Summerfelt, supra), resulting in pCGN7586, a binary vector for plant transformation.

Plant transformation construct pCGN7589, also containing the jojoba reductase gene under expression of a napin promoter, is prepared as follows. pCGN7571 is in vitro mutagenized to introduce an NdeI site at the first ATG of the reductase coding sequence and a BglII site immediately upstream of the NdeI site. BamHI linkers are introduced into the SphI site downstream of the reductase coding region. The 1.5 kb BglII-BamHI fragment is gel purified and cloned into BglII-BamHI digested pCGN3686 (see below), resulting in pCGN7582.

pCGN3686 is a cloning vector derived from Bluescript KS+ (Stratagene Cloning Systems; San Diego, Calif.), but having a chloramphenicol resistance gene and a modified linker region. The source of the chloramphenicol resistance gene, pCGN565 is a cloning vector based on pUC12-cm (K. Buckley Ph.D. Thesis, Regulation and expression of the phi X174 lysis gene, University of California, San Diego, 1985), but containing pUC18 linkers (Yanisch-Perron, et al., *Gene* (1985) 53:103–119). pCGN565 is digested with HbaI and the fragment containing the chloramphenicol resistance gene is excised, blunted by use of mung bean nuclease, and inserted into the EcoRV site of Bluescript KS– (Stratagene: La Jolla, Calif.) to create pCGN2008. The chloramphenicol resistance gene of pCGN2008 is removed by EcoRI/HindIII digestion. After treatment with Klenow enzyme to blunt the ends, the fragment is ligated to DraI digested Bluescript KS+. A clone that has the DraI fragment containing ampicillin resistance replaced with the chloramphenicol resistance is chosen and named pCGN2015. The linker region of pCGN2015 is modified to provide pCGN3686, which contains the following restriction digestion sites, 5' to 3' in the lacZ linker region: PstI, BglII, XhoI, HincII, SalI, HindIII, EcoRV, EcoRI, PstI, SmaI, BamHI, SpeI, XbaI and SacI.

An XhoI linker is inserted at the XbaI site of pCGN7582. The BglII-XhoI fragment containing the reductase gene is isolated and cloned into BglII-XhoI digested pCGN3223. The resulting plasmid, which lacks the 5' untranslated leader sequence from the jojoba gene, is designated pCGN7802. The napin/reductase fragment from pCGN7802 is excised with HindIII and cloned into HindIII digested pCGN1578 to yield pCGN7589.

An additional napin/reductase construct is prepared as follows. The reductase cDNA pCGN7571 (FIG. 1) is mutagenized to insert SalI sites 5' to the ATG start codon (site is 8 base pairs 5' to ATG) and immediately 3' to the TAA translation stop codon, resulting in pCGN7631. pCGN7631 is digested with SalI and the approximately 1.5 kb fragment containing the reductase encoding sequence is cloned into SalI/XhoI digested napin cassette pCGN3223. A resulting plasmid containing the reductase sequence in the sense orientation is designated pCGN7640. pCGN7640 is digested with HindIII, and the fragment containing the oleosin/reductase construct is cloned into HindIII digested binary vector pCGN1559PASS, resulting in binary construct pCGN7642.

A construct for expression of reductase under control of oleosin regulatory regions is prepared as follows. The reductase encoding sequence is obtained by digestion of pCGN7631 with SalI, and ligated into SalI digested pCGN7636, the oleosin cassette. A resulting plasmid containing the reductase sequence in the sense orientation is designated pCGN7641. pCGN7641 is digested with XbaI, and the fragment containing the oleosin/reductase construct is cloned into XbaI digested binary vector pCGN1559PASS, resulting in binary construct pCGN7643.

Binary vector constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163.181–187) and used in plant transformation methods as described below.

Example 9

Plant Transformation Methods

A variety of methods have been developed to insert a DNA sequence of interest into the genome of a plant host to obtain the transcription or transcription and translation of the sequence to effect phenotypic changes.

*Brassica* Transformation

Seeds of high erucic acid, such as cultivar Reston, or Canola-type varieties of *Brassica* napus are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyriodoxine (50 $\mu$g/l), nicotinic acid (50 $\mu$g/l), glycine (200 $\mu$g/l), and 0.6% Phytagar (Gibco) pH 5.8. Seeds are germinated in a Percival chamber at 22° C. in a 16 h photoperiod with cool fluorescent and red light of intensity approximately 65$\mu$ Einsteins per square meter per second ($\mu EM^{-2}S^{-1}$).

Hypocotyls are excised from 5–7 day old seedlings, cut into pieces approximately 4 mm in length, and plated on feeder plates (Horsch et al., *Science* (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg $KH_2PO_4$ with 3% sucrose, 2,4-D (1.0 mg/l), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu Em^{-2}S^{-1}$ to 65 $\mu Em^{-2}S^{-1}$.

Single colonies of *A. tumefaciens* strain EHA101 containing a binary plasmid with the desired gene construct are transferred to 5 ml MG/L broth and grown overnight at 30° C. Hypocotyl explants are immersed in 7–12 ml MG/L broth with bacteria diluted to 1×10$^8$ bacteria/ml and after 10–25 min. are placed onto feeder plates. Per liter MG/L broth contains 5 g mannitol, 1 g L-Glutamic acid or 1.15 g sodium glutamate, 0.25 g $kH_2PO_4$, 0.10 g NaCl, 0.10 g $MGSO_4.7H_2O$, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/l.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 18 sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 18 sucrose, 2 mg/l indolebutyric acid, 50 mg/l kanamycin sulfate and 0.68 Phytagar). Green rooted shoots are tested for thioesterase activity.

Arabidposis Transformation

Transgenic *Arabidopsis thaliana* plants may be obtained by Agrobacterium-mediated transformation as described by vaiverkens et al., (*Prot. Nat. Acad. Sci.* (1988) 85:5536–5540). Constructs are transformed into Agrobacterium cells, such as of strain EHA101 (Hood et al., *J. Bacteriol* (1986) 168:1291–1301), by the method of Holsters et al. (*Mol. Can. Genet.* (1978) 163:181–187).

Peanut Transformation

DNA sequences of interest may be introduced as expression cassettes, comprising at least a promoter region, a gene of interest, and a termination region, into a plant genome via particle bombardment.

Briefly, tungsten or gold particles of a size ranging from 0.5 mM–3 mM are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers. The bombardment of the tissue with the DNA-coated particles is carried out using a Biolistics particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 mM to 300 mM.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15;473) (MS plus 2.0 mg/l 6-benzyladenine (BA) for the cotyledon segments) and incubated in the dark for 1 week at 25±2° C. and are subsequently transferred to continuous cool white fluorescent light (6.8 W/m$^2$). On the 10th day of culture, the plantlets are transferred to pots containing sterile soil, are kept in the shade for 3–5 days are and finally moved to greenhouse. The putative transgenic shoots are rooted. Integration of exogenous DNA into the plant genome may be confirmed by various methods know to those skilled in the art.

Example 10

Analysis of Transformed Plants for Wax Production

Seeds or other plant material from transformed plants may be analyzed for wax synthase activity using the wax synthase assay methods described in Example 1.

Plants which have both the reductase and wax synthase constructs are also assayed to measure wax production. Such plants may be prepared by Agrobacterium transformation methods as described above. Plants having both of the desired gene constructs may be prepared by co-transformation with reductase and wax synthase constructs or by combining the wax synthase and reductase constructs on a single plant transformation binary vector. In addition, re-transformation of either wax synthase expressing plants or reductase expressing plants with constructs encoding the other desired gene sequence may also be used to provide such reductase and wax synthase expressing plants. Alternatively, transgenic plants expressing reductase produced by methods described herein may be crossed with plants expressing wax synthase which have been similarly produced. In this manner, known methods of plant breeding are used to provide reductase and wax synthase expressing transgenic plants.

Such plants may be assayed for the presence of wax esters, for example by separation of TAG from wax esters as described by Tani et al. (supra). GC analysis methods may be used to further analyze the resulting waxes, for example as described by Pina et al. (Lipids (1987) 22(5):358–361.

The above results demonstrate the ability to obtain partially purified wax synthase proteins which are active in the formation of wax esters from fatty alcohol and fatty acyl substrates. Methods to obtain the wax synthase proteins and amino acid sequences thereof are provided. In addition wax synthase nucleic acid sequences obtained from the amino acid sequences are also provided. These nucleic acid sequences may be manipulated to provide for transcription of the sequences and/or expression of wax synthase proteins in host cells, which proteins may be used for a variety of applications. Such applications include the production of wax ester compounds when the wax synthase is used in host cells having a source of fatty alcohol substrates, which substrates may be native to the host cells or supplied by use of recombinant constructs encoding a fatty acyl reductase protein which is active in the formation of alcohols from fatty acyl substrates.

Example 11

Analysis of Transformed Plants for VLCFA Production

Seeds from transformed plants are analyzed by gas chromatography (GC) for fatty acid content. The following tables provide breakdowns of fatty acids on a percentage basis, demonstrating altered VLCFA production in plants transformed with binary vector pCGN7626 (Example 8).

TABLE 3

Seeds from canola plants, some transformed by pCGN7626, showing percentage of fatty acids of a given carbon chain length:saturation. Twenty seeds were pooled for each plant and fatty acids determined by gas chromatography.
Control canola plants (plants 1 and 2) of Table 3 contain less than 2% VLCFA in their seed oil. Plants 3 through 20 in Table 3 are transgenic. The majority (14/18) of the plants transformed with pCGN7626 have significantly higher levels of VLCFA. The VLCFA for the highly expresssing transgenics range from about 5% to about 22% of the total fatty acids.

| NO | % 18:0 | % 18:1 | % 18:2 | % 18:3 | % 20:0 | % 20:1 | % 20:2 | % 22:0 | % 22:1 | % 22:2 |
|---|---|---|---|---|---|---|---|---|---|---|
| 1 | 1.30 | 58.42 | 21.14 | 12.48 | 0.45 | 1.20 | 0.08 | 0.24 | 0.01 | 0.00 |
| 2 | 1.12 | 58.89 | 22.09 | 11.25 | 0.41 | 1.31 | 0.09 | 0.25 | 0.01 | 0.00 |
| 3 | 1.11 | 52.01 | 19.24 | 15.95 | 0.46 | 4.97 | 0.33 | 0.24 | 0.47 | 0.01 |
| 4 | 0.76 | 38.12 | 19.60 | 14.57 | 0.49 | 14.27 | 1.11 | 0.39 | 4.84 | 0.66 |
| 5 | 0.90 | 46.74 | 18.76 | 14.89 | 0.49 | 9.75 | 0.67 | 0.31 | 1.73 | 0.21 |
| 6 | 0.95 | 51.00 | 20.34 | 13.74 | 0.46 | 6.93 | 0.47 | 0.27 | 0.88 | 0.02 |
| 7 | 0.99 | 52.36 | 19.40 | 14.90 | 0.44 | 5.41 | 0.35 | 0.34 | 0.49 | 0.01 |
| 8 | 1.10 | 60.63 | 19.52 | 11.20 | 0.45 | 1.27 | 0.09 | 0.31 | 0.01 | 0.00 |
| 9 | 0.91 | 47.57 | 20.51 | 16.15 | 0.45 | 7.24 | 0.53 | 0.24 | 1.39 | 0.02 |
| 10 | 0.93 | 48.91 | 20.48 | 15.52 | 0.44 | 6.72 | 0.48 | 0.24 | 0.88 | 0.08 |
| 11 | 1.16 | 53.17 | 21.44 | 16.83 | 0.41 | 1.25 | 0.10 | 0.25 | 0.00 | 0.01 |
| 12 | 0.94 | 48.04 | 22.28 | 17.50 | 0.39 | 4.88 | 0.41 | 0.28 | 0.46 | 0.02 |
| 13 | 1.07 | 56.23 | 21.08 | 14.35 | 0.43 | 1.35 | 0.11 | 0.26 | 0.01 | 0.00 |

TABLE 3-continued

Seeds from canola plants, some transformed by pCGN7626, showing percentage of fatty acids of a given carbon chain length:saturation. Twenty seeds were pooled for each plant and fatty acids determined by gas chromatography.
Control canola plants (plants 1 and 2) of Table 3 contain less than 2% VLCFA in their seed oil. Plants 3 through 20 in Table 3 are transgenic. The majority (14/18) of the plants transformed with pCGN7626 have significantly higher levels of VLCFA. The VLCFA for the highly expresssing transgenics range from about 5% to about 22% of the total fatty acids.

| NO | % 18:0 | % 18:1 | % 18:2 | % 18:3 | % 20:0 | % 20:1 | % 20:2 | % 22:0 | % 22:1 | % 22:2 |
|---|---|---|---|---|---|---|---|---|---|---|
| 14 | 0.88 | 53.08 | 20.93 | 15.39 | 0.39 | 1.17 | 0.04 | 0.34 | 0.00 | 0.01 |
| 15 | 0.89 | 47.06 | 20.65 | 19.78 | 0.39 | 4.19 | 0.34 | 0.26 | 0.46 | 0.02 |
| 16 | 0.93 | 46.98 | 23.86 | 15.51 | 0.47 | 5.03 | 0.47 | 0.33 | 0.69 | 0.08 |
| 17 | 1.26 | 53.62 | 20.04 | 14.89 | 0.47 | 3.86 | 0.24 | 0.26 | 0.25 | 0.00 |
| 18 | 1.02 | 52.20 | 19.57 | 15.20 | 0.43 | 5.13 | 0.31 | 0.26 | 0.44 | 0.01 |
| 19 | 1.14 | 53.74 | 19.77 | 15.09 | 0.43 | 3.77 | 0.25 | 0.22 | 0.26 | 0.02 |
| 20 | 0.92 | 44.57 | 20.15 | 22.87 | 0.36 | 4.48 | 0.41 | 0.15 | 0.58 | 0.02 |

TABLE 4

Canola plants, some transformed by pCGN7626, showing percentage of fatty acids of a given carbon chain length:saturation.
Plants 1 and 2 in Table 4 are controls. Plant 3 is a repeat of plant 4 of Table 3.
Plants 4 through 13 are seed of plants grown out from the seed of a single canola plant transformed by pCGN7626, showing inheritance of the altered VLCFA phenotype. One plant, plant 11, did not inherit the altered phenotype. This plant also did not show inheritance of the transgene by a Kan germination assay.

| NO | % 18:0 | % 18:1 | % 18:2 | % 18:3 | % 20:0 | % 20:1 | % 20:2 | % 22:0 | % 22:1 | % 22:2 | % 24:0 | % 24:1 |
|---|---|---|---|---|---|---|---|---|---|---|---|---|
| 1 | 1.25 | 58.14 | 21.61 | 11.87 | 0.43 | 1.19 | 0.08 | 0.25 | 0.00 | 0.00 | 0.01 | 0.01 |
| 2 | 1.02 | 58.73 | 22.38 | 10.71 | 0.42 | 1.30 | 0.09 | 0.26 | 0.01 | 0.00 | 0.01 | 0.10 |
| 3 | 0.80 | 36.80 | 20.37 | 15.92 | 0.51 | 12.31 | 1.05 | 0.39 | 3.93 | 0.58 | 0.24 | 0.67 |
| 4 | 0.98 | 43.21 | 20.97 | 16.61 | 0.50 | 7.70 | 0.63 | 0.34 | 1.78 | 0.22 | 0.18 | 0.41 |
| 5 | 0.87 | 42.48 | 23.36 | 13.39 | 0.46 | 8.83 | 0.76 | 0.31 | 1.76 | 0.25 | 0.21 | 0.36 |
| 6 | 0.87 | 44.00 | 22.75 | 13.91 | 0.45 | 8.67 | 0.66 | 0.29 | 1.56 | 0.20 | 0.04 | 0.43 |
| 7 | 0.96 | 43.13 | 22.15 | 16.31 | 0.46 | 7.80 | 0.64 | 0.29 | 1.27 | 0.17 | 0.01 | 0.32 |
| 8 | 1.17 | 48.73 | 20.34 | 14.36 | 0.53 | 6.83 | 0.47 | 0.31 | 0.84 | 0.09 | 0.21 | 0.24 |
| 9 | 0.97 | 52.27 | 23.14 | 13.22 | 0.39 | 3.48 | 0.24 | 0.24 | 0.27 | 0.01 | 0.01 | 0.03 |
| 10 | 1.12 | 46.79 | 21.21 | 13.53 | 0.55 | 7.68 | 0.54 | 0.33 | 1.08 | 0.12 | 0.19 | 0.36 |
| 11 | 0.98 | 51.73 | 24.05 | 14.91 | 0.41 | 1.18 | 0.11 | 0.28 | 0.01 | 0.00 | 0.02 | 0.00 |
| 12 | 1.10 | 44.56 | 23.03 | 14.04 | 0.50 | 7.58 | 0.62 | 0.29 | 1.76 | 0.23 | 0.26 | 0.59 |
| 13 | 0.88 | 41.32 | 24.20 | 14.92 | 0.47 | 7.62 | 0.79 | 0.34 | 1.83 | 0.32 | 0.04 | 0.37 |

TABLE 5

The results of measurements of seeds of HEAR plants, controls and pCGN7626 transgenic, evaluated for VLCFA content. Pools of twenty seeds were analyzed by GC.
Plants 1 and 2 are control HEAR plants. The remaining plants are transgenic. Control HEAR (variety Reston) has 22:1 levels between 33 and 41 percent of its fatty acids with 24:1 comprising about 0.1 to 0.5%. The results show significant alteration of the VLCFA patterns. Plants 3, 4, 7, 12–14 and 16–19 particularly showed an increase in 24:1 content, with one transgenic plant showing a 24:1 level of 2.7% of the seed oil.

| NO | % 18:0 | % 18:1 | % 18:2 | % 18:3 | % 20:0 | % 20:1 | % 20:2 | % 22:0 | % 22:1 | % 22:2 | % 24:0 | % 24:1 |
|---|---|---|---|---|---|---|---|---|---|---|---|---|
| 1 | 0.90 | 13.69 | 18.07 | 12.32 | 0.46 | 6.00 | 0.75 | 0.48 | 40.57 | 0.78 | 0.03 | 0.12 |
| 2 | 1.03 | 19.90 | 18.49 | 9.74 | 0.46 | 8.36 | 0.68 | 0.28 | 33.57 | 0.45 | 0.01 | 0.66 |
| 3 | 1.06 | 12.94 | 17.45 | 12.68 | 0.45 | 5.22 | 0.80 | 0.81 | 38.32 | 1.72 | 0.06 | 2.69 |
| 4 | 0.96 | 13.39 | 19.74 | 11.29 | 0.48 | 6.60 | 0.90 | 0.54 | 37.84 | 1.16 | 0.05 | 1.21 |
| 5 | 1.05 | 13.85 | 19.55 | 12.77 | 0.42 | 6.32 | 0.95 | 0.53 | 37.16 | 1.22 | 0.06 | 0.13 |
| 6 | 1.04 | 14.56 | 19.29 | 11.26 | 0.44 | 6.49 | 0.93 | 0.47 | 38.29 | 1.27 | 0.05 | 0.14 |
| 7 | 1.03 | 15.03 | 18.35 | 11.73 | 0.48 | 6.68 | 0.80 | 0.44 | 37.38 | 0.95 | 0.02 | 1.41 |
| 8 | 1.02 | 16.14 | 18.67 | 10.60 | 0.44 | 7.51 | 0.86 | 0.41 | 37.02 | 0.62 | 0.00 | 0.09 |
| 9 | 1.17 | 17.00 | 18.99 | 11.03 | 0.56 | 6.05 | 0.70 | 0.61 | 36.48 | 0.96 | 0.04 | 0.13 |
| 10 | 1.01 | 18.78 | 18.22 | 10.25 | 0.51 | 8.48 | 0.72 | 0.06 | 34.55 | 0.59 | 0.02 | 0.10 |
| 11 | 0.92 | 14.36 | 20.64 | 12.52 | 0.35 | 5.85 | 0.84 | 0.37 | 35.82 | 0.73 | 0.03 | 0.75 |
| 12 | 0.99 | 17.10 | 18.19 | 10.10 | 0.46 | 7.23 | 0.68 | 0.47 | 36.34 | 0.92 | 0.03 | 1.43 |
| 13 | 0.95 | 17.99 | 19.65 | 10.01 | 0.47 | 6.97 | 0.78 | 0.49 | 33.93 | 0.72 | 0.02 | 1.39 |
| 14 | 0.87 | 16.02 | 18.67 | 10.92 | 0.41 | 7.39 | 0.87 | 0.43 | 35.69 | 1.16 | 0.05 | 1.58 |
| 15 | 1.01 | 45.08 | 22.48 | 16.95 | 0.35 | 5.88 | 0.54 | 0.17 | 0.78 | 0.02 | 0.01 | 0.03 |
| 16 | 0.94 | 14.92 | 16.48 | 10.86 | 0.45 | 6.30 | 0.78 | 0.77 | 39.10 | 1.56 | 0.03 | 2.53 |
| 17 | 0.93 | 15.40 | 19.23 | 10.79 | 0.51 | 6.10 | 0.79 | 0.60 | 36.76 | 1.12 | 0.02 | 1.46 |

TABLE 5-continued

The results of measurements of seeds of HEAR plants, controls and pCGN7626 transgenic, evaluated for VLCFA content. Pools of twenty seeds were analyzed by GC. Plants 1 and 2 are control HEAR plants. The remaining plants are transgenic. Control HEAR (variety Reston) has 22:1 levels between 33 and 41 percent of its fatty acids with 24:1 comprising about 0.1 to 0.5%. The results show significant alteration of the VLCFA patterns. Plants 3, 4, 7, 12–14 and 16–19 particularly showed an increase in 24:1 content, with one transgenic plant showing a 24:1 level of 2.7% of the seed oil.

| NO | % 18:0 | % 18:1 | % 18:2 | % 18:3 | % 20:0 | % 20:1 | % 20:2 | % 22:0 | % 22:1 | % 22:2 | % 24:0 | % 24:1 |
|---|---|---|---|---|---|---|---|---|---|---|---|---|
| 18 | 1.04 | 16.35 | 18.31 | 9.42 | 0.52 | 7.17 | 0.87 | 0.60 | 37.05 | 1.10 | 0.04 | 1.30 |
| 19 | 0.99 | 14.82 | 16.50 | 11.43 | 0.53 | 7.16 | 0.83 | 0.68 | 38.53 | 1.24 | 0.03 | 1.85 |

TABLE 6

*Arabidopsis thaliana* plants transformed with pCGN7626. *Arabidopsis thaliana* typically has seed oil with 21% 20:1 fatty acid, 2% 22:1 fatty acid, 0.02% 24:1 fatty acid (control plants 1–3). The oil composition of plants transformed with pCGN7626 (plants 4–12) is shifted towards the longer chain fatty acids at the expense of 20:1. The 20:1 in transgenic plants decreased to as low as 15.5% while the 22:1 percentage increased to as high as 7.5%. In one transgenic plant the 24:1 content increased to 1.6% of the total fatty acids in the seed oil. In Table 7 oil seed analysis results are given for T3 Brassica plants, (LEAR variety 212) transformed with pCGN7626.

| NO | % 18:0 | % 18:1 | % 18:2 | % 18:3 | % 20:0 | % 20:1 | % 20:2 | % 22:0 | % 22:1 | % 22:2 | % 24:0 | % 24:1 |
|---|---|---|---|---|---|---|---|---|---|---|---|---|
| 1 | 2.88 | 17.24 | 26.82 | 18.08 | 2.17 | 20.84 | 2.03 | 0.33 | 2.07 | 0.04 | 0.01 | 0.03 |
| 2 | 3.55 | 18.27 | 25.24 | 18.61 | 2.22 | 20.95 | 1.83 | 0.26 | 1.80 | 0.02 | 0.01 | 0.01 |
| 3 | 2.91 | 17.61 | 26.18 | 18.30 | 2.07 | 21.02 | 2.02 | 0.10 | 2.00 | 0.02 | 0.05 | 0.05 |
| 4 | 3.65 | 17.97 | 26.46 | 18.67 | 1.99 | 20.70 | 1.77 | 0.06 | 1.58 | 0.02 | 0.05 | 0.03 |
| 5 | 2.88 | 15.79 | 25.51 | 20.80 | 1.85 | 18.58 | 1.97 | 0.85 | 4.03 | 0.32 | 0.07 | 0.74 |
| 6 | 2.78 | 15.41 | 24.64 | 20.19 | 1.97 | 17.55 | 1.97 | 0.74 | 3.36 | 0.04 | 0.51 | 0.42 |
| 7 | 2.83 | 19.55 | 26.43 | 18.80 | 1.84 | 20.30 | 1.64 | 0.04 | 1.92 | 0.01 | 0.02 | 0.04 |
| 8 | 2.17 | 15.33 | 25.62 | 20.56 | 1.56 | 15.66 | 1.80 | 1.29 | 5.72 | 0.69 | 1.11 | 1.55 |
| 9 | 3.34 | 15.i1 | 25.89 | 19.48 | 2.05 | 19.58 | 2.03 | 0.44 | 2.60 | 0.12 | 0.03 | 0.04 |
| 10 | 2.69 | 14.90 | 26.10 | 20.51 | 1.83 | 18.17 | 2.01 | 0.90 | 3.98 | 0.40 | 0.84 | 0.67 |
| 11 | 1.86 | 16.65 | 25.91 | 18.45 | 1.55 | 15.69 | 1.84 | 1.49 | 7.47 | 0.73 | 0.09 | 1.40 |
| 12 | 1.94 | 17.82 | 24.95 | 19.91 | 1.42 | 15.52 | 1.44 | 1.34 | 6.40 | 0.43 | 1.06 | 1.60 |

TABLE 7

| NO | STRAIN ID | % 16:0 | % 16:1 | % 18:0 | % 18:1 | % 18:2 | % 18:3 | % 20:0 | % 20:1 | % 20:2 | % 22:0 | % 22:1 | % 22:2 | % 24:0 | % 24:1 | >18 |
|---|---|---|---|---|---|---|---|---|---|---|---|---|---|---|---|---|
| 1 | RESTON | 2.54 | 0.05 | 0.79 | 17.54 | 12.12 | 9.59 | 0.54 | 8.80 | 0.49 | 0.55 | 46.13 | 0.38 | 0.00 | 0.08 | 56.97 |
| 2 | RESTON | 2.68 | 0.12 | 0.78 | 19.96 | 11.79 | 8.80 | 0.52 | 9.98 | 0.45 | 0.46 | 42.84 | 0.05 | 0.03 | 0.92 | 55.25 |
| 3 | RESTON | 2.59 | 0.12 | 0.73 | 19.15 | 11.96 | 7.90 | 0.46 | 8.40 | 0.41 | 0.38 | 47.30 | 0.06 | 0.00 | 0.10 | 57.11 |
| 4 | RESTON | 2.49 | 0.09 | 0.83 | 16.37 | 11.98 | 10.22 | 0.50 | 8.49 | 0.52 | 0.52 | 46.23 | 0.48 | 0.06 | 0.86 | 57.66 |
| 5 | RESTON | 2.65 | 0.15 | 0.81 | 17.63 | 14.18 | 6.51 | 0.43 | 7.80 | 0.35 | 0.40 | 46.87 | 0.46 | 0.00 | 1.21 | 57.52 |
| 6 | RESTON | 2.52 | 0.10 | 0.79 | 17.50 | 11.61 | 10.35 | 0.49 | 8.50 | 0.52 | 0.67 | 45.07 | 0.34 | 0.12 | 1.02 | 56.73 |
| 7 | RESTON | 2.84 | 0.20 | 0.73 | 17.86 | 11.60 | 9.18 | 0.44 | 9.51 | 0.46 | 0.30 | 45.97 | 0.21 | 0.00 | 0.18 | 57.07 |
| 8 | RESTON | 2.71 | 0.14 | 0.81 | 17.64 | 12.09 | 11.15 | 0.50 | 8.56 | 0.54 | 0.60 | 43.46 | 0.39 | 0.10 | 0.81 | 54.96 |
| 9 | RESTON | 2.46 | 0.10 | 0.84 | 22.84 | 9.72 | 6.50 | 0.56 | 9.30 | 0.31 | 0.50 | 45.02 | 0.20 | 0.00 | 1.15 | 57.04 |
| 10 | RESTON | 2.57 | 0.13 | 0.78 | 23.40 | 9.80 | 6.41 | 0.53 | 8.83 | 0.36 | 0.38 | 45.28 | 0.15 | 0.00 | 0.86 | 56.39 |
| 11 | 7626-212-2-1 | 2.92 | 0.15 | 0.64 | 22.92 | 10.42 | 6.85 | 0.46 | 15.21 | 0.61 | 0.92 | 28.79 | 1.33 | 0.45 | 7.78 | 55.55 |
| 12 | 7626-212-2-1 | 3.05 | 0.28 | 0.74 | 29.57 | 11.37 | 6.94 | 0.56 | 17.72 | 0.65 | 0.77 | 22.67 | 0.77 | 0.11 | 4.43 | 47.68 |
| 13 | 7626-212-2-1 | 2.80 | 0.12 | 0.52 | 19.06 | 11.56 | 8.73 | 0.41 | 13.78 | 0.77 | 0.67 | 33.64 | 1.45 | 0.00 | 5.44 | 56.16 |
| 14 | 7626-212-2-1 | 2.88 | 0.25 | 0.76 | 20.92 | 11.12 | 5.38 | 0.58 | 11.50 | 0.48 | 1.19 | 34.51 | 1.26 | 0.65 | 7.79 | 57.96 |
| 15 | 7626-212-2-1 | 3.14 | 0.23 | 0.99 | 26.29 | 11.02 | 8.18 | 0.65 | 19.12 | 0.76 | 0.82 | 24.17 | 1.07 | 0.00 | 3.06 | 49.65 |
| 16 | 7626-212-2-1 | 2.83 | 0.23 | 0.77 | 28.54 | 10.55 | 7.50 | 0.67 | 18.72 | 0.62 | 0.93 | 23.40 | 0.98 | 0.31 | 3.48 | 49.11 |
| 17 | 7626-212-2-1 | 2.82 | 0.15 | 0.68 | 23.05 | 10.65 | 6.93 | 0.53 | 16.81 | 0.70 | 0.88 | 28.46 | 1.25 | 0.08 | 6.41 | 55.12 |
| 18 | 7626-212-2-1 | 2.59 | 0.17 | 0.69 | 22.36 | 11.75 | 9.63 | 0.56 | 15.58 | 0.82 | 0.97 | 29.52 | 1.26 | 0.19 | 3.48 | 52.38 |
| 19 | 7626-212-2-1 | 2.46 | 0.15 | 0.71 | 21.51 | 11.35 | 9.03 | 0.54 | 13.52 | 0.64 | 0.78 | 33.54 | 1.14 | 0.15 | 3.87 | 54.18 |
| 20 | 7626-212-2-1 | 3.07 | 0.18 | 0.69 | 28.80 | 13.12 | 9.24 | 0.40 | 17.80 | 0.78 | 0.45 | 20.33 | 0.88 | 0.00 | 3.39 | 44.03 |
| 21 | 7626-212-2-2 | 3.36 | 0.30 | 0.83 | 25.51 | 14.30 | 10.62 | 0.44 | 14.30 | 0.75 | 0.39 | 26.58 | 0.61 | 0.00 | 1.48 | 44.55 |
| 22 | 7626-212-2-2 | 3.23 | 0.15 | 0.92 | 25.00 | 12.47 | 8.23 | 0.59 | 16.69 | 0.69 | 0.43 | 28.65 | 0.59 | 0.01 | 1.82 | 49.47 |
| 23 | 7626-212-2-2 | 2.62 | 0.11 | 0.86 | 21.14 | 12.45 | 11.23 | 0.54 | 16.50 | 0.90 | 0.48 | 29.92 | 0.86 | 0.07 | 1.72 | 50.99 |
| 24 | 7626-212-2-2 | 3.35 | 0.24 | 0.81 | 24.25 | 12.09 | 10.84 | 0.53 | 15.83 | 0.76 | 0.38 | 27.79 | 0.66 | 0.07 | 1.99 | 48.01 |
| 25 | 7626-212-2-2 | 3.44 | 0.13 | 1.12 | 35.66 | 14.49 | 10.23 | 0.61 | 16.32 | 0.59 | 0.46 | 14.47 | 0.14 | 0.05 | 1.67 | 34.31 |
| 26 | 7626-212-2-2 | 2.90 | 0.22 | 0.79 | 20.44 | 13.05 | 11.06 | 0.43 | 12.54 | 0.68 | 0.00 | 35.58 | 0.09 | 0.02 | 1.60 | 50.94 |
| 27 | 7626-212-2-2 | 2.59 | 0.08 | 0.69 | 16.89 | 11.94 | 9.99 | 0.50 | 10.67 | 0.77 | 0.77 | 39.93 | 1.40 | 0.14 | 3.22 | 57.40 |
| 28 | 7626-212-2-2 | 2.80 | 0.12 | 0.82 | 21.71 | 12.94 | 9.73 | 0.61 | 14.96 | 0.90 | 0.72 | 30.39 | 1.04 | 0.00 | 2.82 | 51.44 |
| 29 | 7626-212-2-2 | 3.41 | 0.15 | 1.07 | 36.19 | 15.14 | 10.55 | 0.46 | 17.10 | 0.57 | 0.08 | 14.66 | 0.00 | 0.00 | 0.10 | 32.97 |
| 30 | 7626-212-2-2 | 2.97 | 0.11 | 0.96 | 24.24 | 13.21 | 9.58 | 0.58 | 15.50 | 0.84 | 0.56 | 26.59 | 3.09 | 0.00 | 1.60 | 48.76 |

TABLE 7-continued

| NO | STRAIN ID | % 16:0 | % 16:1 | % 18:0 | % 18:1 | % 18:2 | % 18:3 | % 20:0 | % 20:1 | % 20:2 | % 22:0 | % 22:1 | % 22:2 | % 24:0 | % 24:1 | >18 |
|---|---|---|---|---|---|---|---|---|---|---|---|---|---|---|---|---|
| 31 | 7626-212-2-3 | 2.71 | 0.12 | 0.87 | 24.30 | 11.93 | 9.40 | 0.53 | 10.45 | 0.46 | 0.58 | 35.32 | 0.50 | 0.06 | 2.09 | 49.99 |
| 32 | 7626-212-2-3 | 2.71 | 0.12 | 0.94 | 23.18 | 11.13 | 7.34 | 0.64 | 10.98 | 0.34 | 0.41 | 40.76 | 0.06 | 0.00 | 0.97 | 54.16 |
| 33 | 7626-212-2-3 | 3.83 | 0.18 | 2.28 | 23.96 | 11.50 | 8.17 | 0.49 | 8.80 | 0.53 | 0.57 | 36.37 | 0.41 | 0.07 | 1.96 | 49.20 |
| 34 | 7626-212-2-3 | 3.22 | 0.13 | 1.74 | 39.52 | 13.91 | 7.96 | 0.71 | 16.79 | 0.26 | 0.24 | 14.33 | 0.03 | 0.00 | 0.70 | 33.06 |
| 35 | 7626-212-2-3 | 2.79 | 0.00 | 1.74 | 26.41 | 11.98 | 4.23 | 1.15 | 11.37 | 0.47 | 0.84 | 36.39 | 0.08 | 0.00 | 1.68 | 51.98 |
| 36 | 7626-212-2-3 | 3.81 | 0.20 | 1.49 | 37.32 | 15.55 | 9.58 | 0.65 | 16.61 | 0.55 | 0.05 | 13.35 | 0.01 | 0.00 | 0.16 | 31.38 |
| 37 | 7626-212-2-3 | 2.88 | 0.16 | 1.37 | 25.49 | 12.95 | 8.90 | 0.69 | 14.10 | 0.58 | 0.35 | 30.54 | 0.11 | 0.02 | 1.25 | 47.64 |
| 38 | 7626-212-2-3 | 3.47 | 0.13 | 1.37 | 22.30 | 14.75 | 11.27 | 0.68 | 10.43 | 0.45 | 0.48 | 33.74 | 0.20 | 0.07 | 0.14 | 46.19 |
| 39 | 7626-212-2-3 | 3.61 | 0.18 | 1.98 | 29.46 | 11.76 | 5.03 | 1.17 | 13.56 | 0.36 | 0.74 | 29.88 | 0.18 | 0.00 | 1.42 | 47.31 |
| 40 | 7626-212-2-3 | 2.77 | 0.12 | 1.06 | 20.51 | 13.59 | 11.14 | 0.60 | 10.57 | 0.32 | 0.45 | 36.98 | 0.06 | 0.07 | 1.05 | 50.10 |
| 41 | 7626-212-2-4 | 2.71 | 0.15 | 0.74 | 16.79 | 14.51 | 10.60 | 0.51 | 9.40 | 0.89 | 0.67 | 37.72 | 1.22 | 0.06 | 3.36 | 53.83 |
| 42 | 7626-212-2-4 | 3.07 | 0.26 | 0.80 | 17.32 | 13.47 | 10.23 | 0.52 | 10.91 | 0.85 | 0.78 | 36.07 | 1.31 | 0.06 | 3.77 | 54.27 |
| 43 | 7626-212-2-4 | 3.00 | 0.09 | 0.94 | 23.10 | 15.70 | 9.32 | 0.52 | 16.33 | 0.92 | 0.47 | 25.53 | 0.73 | 0.07 | 2.62 | 47.19 |
| 44 | 7626-212-2-4 | 2.77 | 0.11 | 0.60 | 19.54 | 14.82 | 6.57 | 0.32 | 13.32 | 0.89 | 0.86 | 30.73 | 1.51 | 0.29 | 7.39 | 55.31 |
| 45 | 7626-212-2-4 | 2.87 | 0.14 | 0.96 | 17.40 | 14.75 | 9.39 | 0.66 | 7.58 | 0.72 | 0.83 | 41.22 | 0.72 | 0.10 | 2.00 | 53.83 |
| 46 | 7626-212-2-4 | 2.86 | 0.25 | 0.63 | 15.72 | 14.40 | 10.12 | 0.40 | 8.99 | 0.79 | 0.53 | 40.59 | 1.10 | 0.00 | 3.01 | 55.41 |
| 47 | 7626-212-2-4 | 3.30 | 0.18 | 0.96 | 18.64 | 14.78 | 14.88 | 0.36 | 13.37 | 0.76 | 0.08 | 31.24 | 0.18 | 0.00 | 0.00 | 45.99 |
| 48 | 7626-212-2-4 | 3.10 | 0.21 | 0.93 | 20.82 | 14.19 | 6.07 | 0.62 | 10.33 | 0.58 | 0.61 | 37.79 | 0.70 | 0.09 | 3.74 | 54.46 |
| 49 | 7626-212-2-4 | 3.70 | 0.10 | 0.91 | 16.43 | 15.05 | 13.39 | 0.52 | 10.59 | 1.07 | 0.56 | 33.09 | 1.26 | 0.06 | 2.38 | 49.53 |
| 50 | 7626-212-2-4 | 3.10 | 0.24 | 1.69 | 29.12 | 12.66 | 6.21 | 1.06 | 14.43 | 0.55 | 0.83 | 25.96 | 0.41 | 0.43 | 2.68 | 46.35 |

Analysis of T3 seed oil from LEAR plants transformed with the jojoba CE shows that up to 7.8% of the seed oil is 24:1. As is seen from the controls, the Reston plants, which are HEAR, typically have only about 1% or less 24:1.

These data clearly show that the plant cytoplasmic protein involved in fatty acyl-CoA metabolism encoded by pCGN7626 can markedly alter the fatty acid composition of seed oil from several plant species. In plants that do not accumulate VLCFA, pCGN7626 causes the accumulation of significant quantities of VLCFA. In plants that do accumulate VLCFA, pCGN7626 shifts the fatty acid composition towards longer VLCFA.

When searching protein data bases for the jojoba protein sequence disclosed herein, a large region of homology was found between the jojoba encoded protein and stilbene, reservatrol, and chalcone synthase. Stilbene, reservatrol and chalcone synthases are very similar to each other, catalyzing multiple condensing reactions between two CoA thioesters, with malonyl CoA as one subtrate. The condensing reactions are similar to the proposed condensing reaction for the cytoplasmic membrane bound elongase enzymes, in that in both cases an enzyme condenses two CoA thioester molecules to form two products: a β-ketoacyl-CoA thioester and a carbon dioxide. The region of homology between the jojoba gene and chalcone synthase includes the chalcone synthase active site (Lanz et al. "Site-directed mutagenesis of reservatrol and chalcone synthase, two key enzymes in different plant specific pathways" (1991) *J. Biol. Chem.*, 266:9971–6). This active site is postulated to be involved in forming an enzyme-fatty acid intermediate.

Homology was also detected between the jojoba protein and KASIII. KASIII is a soluble enzyme which catalyzes the condensation of a CoA thioester to an ACP thioester, resulting in a β-ketoacyl-ACP thioester. A carbon dioxide molecule is released in this reaction.

While not concusive, these noted homologies suggest that the jojoba enzyme may have β-ketoacyl-CoA synthase activity.

Example 12

Analysis of Plants by a β-Keto-acyl-CoA Synthase Assay

A. The activity of β-Keto-acyl-CoA synthase may be directly assayed in plants according to the following procedure.

Developing seeds are harvested after pollination and frozen at −70° C. For *Brassica napus*, the seeds are harvested 29 days after pollination. An appropriate number of seeds are thawed and homogenized in 1 ml 50 mM Hepes-NaOH, pH 7.5, 2 mM EDTA, 250 mM NaCl, 5 mM b-mercaptoethanol (twenty seeds per assay for *Brassica napus*). The homogenate is centrifuged at 15,000×g for 10 min, and the oil layer is discarded. The supernatant fraction is collected and centifuged again at 200,000×g for 1 hour.

The pellet is then resuspended in 1 ml of homogenization buffer and centrifuged a second time at 200,000×g for 1 hour. The pellet is resuspended in 50 μl of 100 mM Hepes-NaOH, pH 7.5, 4 mM EDTA, 10% (w/v) glycerol, 2 mM b-mercaptoethanol. 10 μl of the sample is added to 10 μl of a reaction mixture cocktail and incubated at 30° C. for 15 min. The final concentrations of components in the reaction mixture are: 100 mM Hepes-NaOH, pH 7.5, 1 mM b-mercaptoethanol, 100 mM oleyl CoA, 44 μM [2-$^{14}$C] malonyl CoA, 4 mM EDTA and 5% (w/v) glycerol.

The reaction is stopped and the β-ketoacyl product reduced to a diol by adding 400 μl of reducing agent solution comprised of 0.1 M K$_2$HPO4, 0.4 M KCl, 30% (v/v) tetrahydrofuran, and 5 mg/ml NaBH$_4$ (added to the solution just prior to use). The mixture is incubated at 37° C. for 30 min. Neutral lipids are extracted from the sample by addition of 400 μl of toluene. Radioactivity present in 100 μl of the organic phase is determined by liquid scintillation counting. The remaining toluene extract is collected and spotted onto a silica G TLC plate. The TLC plate is developed in diethyl ether:concentrated NH40H (100:1, v/v). The migration of the diol product of the reduction reaction is located by use of a cold diol standard.

B. Using this procedure plants can be assayed to determine the level of, or lack of, detectable β-ketoacyl synthase activity. For example, HEAR plants have high levels of β-ketoacyl synthase activity, while canola plants do not show appreciable enzyme activity. By this assay, plant species or varieties can be screened for β-ketoacyl synthase activity to determine candidates for transformation with the sequences of this invention to achieve altered VLCFA production, or to determine canditates for screening with probes for related enzymes.

The β-ketoacyl-CoA synthase enzyme assays demonstrate that developing embryos from high erucic acid rapeseed contain β-ketoacyl-CoA synthase activity, while LEAR embryos do not. Embryos from transgenic plants transformed with the jojoba cDNA exhibit restored β-ketoacyl-CoA synthase activity.

The jojoba cDNA encoding sequence thus appears to complement the mutation that differenitiates high and low erucic acid rapeseed cultivars. The phenotype of the transgenic plants transformed with the jojoba gene show that a single enzyme can catalyze the formation of 20, 22 and 24 carbon fatty acids. The seed oil from the primary LEAR transformants also contains higher levels of 22:1 than 20:1 fatty acids. This was also true for the majority of the individual T2 seed analyzed from the 7626-212/86-2 plant. Five T2 seeds that exhibited the highest VLCFA content also contain higher levels of 22:1 than 20:1. This suggests that the β-ketoacyl-CoA synthase is a rate limiting step in the formation of VLCFA's, and that as the enzyme activity increases in developing embryos, the fatty acid profile can be switched to the longer chain lengths. The increase in the amount of 24:1 fatty acid in the oil of transgenic HEAR plants and the increase in the amount of 22:1 in transgenic arabidopsis plants without a concomitant increase in the quantity of VLCFAs may be a result of a difference in substrate specificities of the jojoba, *Arabidopsis*, and *Brassica* enzymes rather than an increase in enzyme activity which is already abundant in HEAR and *Arabidopsis*.

Example 13

Other β-Keto-acyl-CoA Synthases

The active β-ketoacyl CoA synthase chromatographs on superose with a size consistant with the enzyme being composed of two 138 kDa subunits. This suggests that the enzyme is active as a multimer, although the enzyme may be a homodimer, a heterodimer, or a higher order multimer. The mass of one of the subunits is estimated to be 57 kDa by SDS gel electrophoresis and 59 kDA by calculation of the theoretical mass from translation of the cDNA sequence. The analogous soluble enzymes in plant and bacterial FAS, β-ketoacyl-ACP synthases, are active as dimers with ~50 kDa subunits. Chalcone and Stilbene synthases are also active as dimers.

The jojoba β-ketoacyl-CoA synthase subunit is a discrete 59 kDa protein. Thus, seed lipid FAE in jojobas is comprised of individual polypeptides with discrete enzyme activities similar to a type II FAS, rather than being catalyzed by the large multifunctional proteins found in type I FAS. Since the jojoba enzyme complements a *Brassica* mutation in FAE, it is possible that *Brassica* FAE is a type I system.

The DBEST data bank was searched with the jojoba β-ketoacyl-CoA synthase DNA sequence at the NCBI using BLAST software (Altschul et al., 1990). Two *Arabidopsis* clones (Genbank accession Z26005, Locus 39823; and genbank accession T04090, Locus315250) homologous to the jojoba CE cDNA were detected. The 39823 clone exhibited a high degree of homology with the jojoba β-ketoacyl-CoA synthase clone. PCR primers were designed to PCR amplify and clone this sequence from *Arabidopsis* genomic DNA. No mRNA was detected in either developing *Arabidopsis* or developing *Brassica* seeds that cross hybridized with this clone. The probe was also hybridized to RFLP blots designed to determine if homologous sequences segregate with the difference between HEAR and LEAR lines. At low hybridization stringency too many cross hybridizing bands are present to detect polymorphism between the HEAR and LEAR lines. At higher hybridization stringency, the bands did not cosegregate with the HEAR phenotype.

In order to isolate clones that encode related enzymes, the protein sequences of the jojoba β-ketoacyl-CoA synthase and the *Arabidopsis* locus 398293 were compared to find conserved domains. Several peptide sequences were identical in the jojoba β-ketoacyl-CoA synthase and the translation of the *Arabidopsis* homologue 398293. Two peptides: 1) NITTLG (SEQ ID NO: 40) (amino acids 389 to 394 of the jojoba β-ketoacyl-CoA synthase) and 2) SNCKFG (SEQ ID NO:41) (amino acids 525 to 532 of the jojoba β-ketoacyl-CoA synthase) were also present in the translation of 398293. Degenerate oligonucleote primers AAYATHACNACNYTNGG (SEQ ID NO: 42) and SWRTTRCAYTTRAANCC (SEQ ID NO: 43) encode the sense and antisense strands of the respective peptides.

The above primers PCR amplify an approximately 430 bp DNA fragment from both the jojoba β-ketoacyl-CoA synthase cDNA and the *Arabidopsis* 398293 sequence. These primers can be used to PCR amplify DNA sequences that encode related proteins from other tissues and other species that share nearly idendical amino acids at these conserved peptides. Using the degenerate oligonucleotides *Arabidopsis* green silique, HEAR, and LEAR RNA were subjected to RTPCR. Prominant bands of the expected size were amplified from all 3 RNAs. One clone was obtained from the reston PCR reaction, and 2 clones from the 212/86 reaction, which appear to form two classes of cDNA clones, designated CE15 and CE20. The 212/86 CE15 clone encoded the entire CE protein (FIG. 5). The protein sequences translated from these clones are >98% identical to one another. The clones are approximately 50% homologous to the jojoba β-ketoacyl-CoA synthase. The C-terminal portions of the proteins are more conserved, with the cDNAs sharing about 70% identity. Northern analysis of RNA isolated from *Brassica* leaf tissue and developing seed tissue showed that CE20 is highly expressed in developing seeds, and is expressed at very low levels in leaves. CE15 is expressed at high levels in leaves, and at a much lower level in developing seeds. The CE20 class is thus most likely to be the active condensing enzyme involved in fatty acid elongation in developing *Brassica* seeds.

The original 212/86 CE20 clone was short, and did not contain the initiator methionine. The HEAR *Brassica campestris* library screened with the CE15 and CE20 probes was of poor quality, and yielded only short clones. Thus, 5' RACE was used to clone the 5' end of the CE20 cDNA from 212/86 and from Reston. The sequence of the 5' race clones showed that coding region of CE 20 in both reston (HEAR) and 212/86 (LEAR) extended 3 amino acids past the 5' end of the 212/86 CE20 clone.

CE20 primers were then chosen to get full-length CE20 sequences. Consequently, CAUCAUCAUCAUGTCGACAAAATGACGTCCATTAACGTAAAG (SEQ ID NO: 44) and CUACUACUACUAGTCGACGGATCCTATTTGGAAGCTTTGACATTGTTTAG (SEQ ID NO: 45) were utilized. These are homologous to the 5' and 3' ends of the protein coding region of CE20, respectively. These primers were used to PCR the entire coding region of the CE20 cDNA (by RTPCR) from 212/86 (FIG. 6) and Reston (FIG. 7). Sequences were additionally designed for the ends of the primers which facilitated cloning of the PCR products in the CloneAmp vector (BRL), and restriction enzyme sites were introduced to allow introduction of the CE20 clones into the napin expression cassette for both sense and antisense expression of CE20 in transgenic *Brassica* plants.

The proteins deduced from *Brassica* clones CE15 and CE20 can be aligned with the protein sequence of the jojoba β-ketoacyl-CoA synthase and *Arabidopsis* loci 398293 and 315250, with several regions of conserved protein sequence detectable. Different pairs of sense and antisense primers can thus be used to PCR amplify and isolate DNA encoding related β-ketoacyl-CoA synthases from many different tissues, of both plant and animal species.

Three classes of cDNA clones were isolated, Lunaria 1, Lunaria 5, and Lunaria 27 (FIGS. 12, 13 and 14, respectively). Of total clones, 81% (26/32) of the clones isolated were of a class similar to Lunaria 5. Of the remainder, 16% (5/32) of the clones were similar to the PCR

TABLE 8

The CE15, and CE20 Brassica cDNA sequences shown in FIGS. 8, 9 and 10 and the condensing enzyme encoding sequence from jojoba (FIG. 3) were used in determining the following primers from conserved amino acids.

| | |
|---|---|
| SENSE PRIMER TO PEPTIDE KL(L/G)YHY | (SEQ ID NO:46) |
| 5381-CAUCAUCAUCAUGAATTCAAGCTTAARYTNBKNTAYCAYTA | (SEQ ID NO:47) |
| SENSE PRIMER TO PEPTIDE NLGGMGC | (SEQ ID NO:48) |
| 5384-CAUCAUCAUCAUGAATTCAAGCTTAAYYTNGGNGGNATGGG | (SEQ ID NO:49) |
| ANTISENSESENSE PRIMER TO PEPTIDE NLGGMGC | (SEQ ID NO:48) |
| 5382-CUACUACUACUAGGATCCGTCGACCCATNCCNCCNARRTT | (SEQ ID NO:50) |
| ANTISENSESENSE PRIMER TO PEPTIDE GFKCNS | (SEQ ID NO:51) |
| 5385-CUACUACUACUAGGATCCGTCGACSWRTTRCAYTTRAANCC | (SEQ ID NO:52) |
| ANTISENSESENSE PRIMER TO PEPTIDE GFKCNS | (SEQ ID NO:51) |
| 4872-CUACUACUACUASWRTTRCAYTTRAANCC | (SEQ ID NO:53) |

These primers from Table 8 were variously used to PCR (RTPCR) amplify fragments from RNA isolated from developing seeds of *Lunaria annua, Tropaoelu majus* (Nasturtium), and green siliques of *Arabidopsis thaliana*. The primers most successfully utilized were 5381-CAUCAUCAUCAUGAATTCAAGCTTAARYTNB-KNTAYCAYTA (SEQ ID NO: 47) (a sense primer to peptide KL(L/G)YHY) (SEQ ID NO: 46) and CUACUACUAC-UAGGATCCGTCGACCCATNCCNCCNARRTT (SEQ ID NO: 50) (an antisense primer to peptide NLGGMGC) (SEQ ID NO: 48). These primers were used to produce three clones encoding a portion of the elongase condensing enzyme from *Arabidopsis*, desingated ARAB CE15, ARAB CE17 and ARAB CE19 (FIGS. 8, 9 and 10, respectively).

From Lunaria a single clone was identified, LUN CE8 (FIG. 11). Since Lunaria produces high levels of 24:1 fatty acid in its seed oil (up to 30%), a cDNA library from RNA isolated from developing seeds of Lunaria was constructed, and LUN CE8 was used to screen this Lunaria cDNA library.

probe, LUN CE8, designated Lunaria 1. One clone, Lunaria 27, was unique.

As seen in Table 9, Lunaria 5 shares approximately 85% homology with the *Brassica* CE20 clones. The high degree of homology with the *Brassica* seed expressed cDNA, and the high abundance of the Lunaria 5 cDNA in developing seed tissue suggest that Lunaria 5 is the cDNA that is active in seed oil fatty acid elongation. table,

TABLE 9

Sequence pair distances based on the BIG ALIGN ™ program, using a Clustal method with PAM250 residue weight table.

Percent Similarity

| | 1 | 2 | 3 | 4 | 5 | 6 | 7 | | |
|---|---|---|---|---|---|---|---|---|---|
| 1 | | 55.6 | 55.4 | 53.0 | 51.2 | 59.0 | 67.9 | 1 | JOJOBA |
| 2 | 44.7 | | 99.1 | 85.1 | 41.0 | 61.7 | 52.3 | 2 | 212/86 CE20 |
| 3 | 43.5 | 0.7 | | 85.2 | 40.6 | 61.7 | 52.8 | 3 | RESTON CE20 |
| 4 | 44.7 | 16.1 | 16.2 | | 40.5 | 63.4 | 53.0 | 4 | LUNARIA 5 (PRELIMINARY) |
| 5 | 44.8 | 53.1 | 53.1 | 52.5 | | 49.1 | 49.1 | 5 | 212/86 CE15 |
| 6 | 40.6 | 37.9 | 38.9 | 36.4 | 43.7 | | 58.8 | 6 | LUNARIA 1 (PRELI |
| 7 | 33.0 | 45.6 | 46.0 | 45.0 | 46.3 | 39.2 | | 7 | LUNARIA 27 (PREL |
| | 1 | 2 | 3 | 4 | 5 | 6 | 7 | | |

(Percent Divergence shown on left)

Finally, a partial Nasturtium PCR clone was obtained using the same primers as were used to isolate LUN CE8. The sequence to the nasturtuim clone (NAST CE26) is provided in FIG. 15.

The use of β-ketoacyl-CoA synthases obtained in this manner from other tissues or other species that have different substrate specificities can be used to create modified seed oils with different chain length fatty acids. This could include enzymes isolated from plant taxa such as lunaria, which synthesizes significant quantities of 24:1 fatty acid in its seed tissue. This could also include enzymes involved in cuticular wax synthesis of any plant species which may be capable of synthesizing fatty acids of chain lengths greater than 24 carbons. For instance, Lunaria seeds contain up to 30% 24:1 in their seed oil. Condensing enzyme assay on crude extract from developing Lunaria seeds shows that the enzyme is active at elongating 18:1 to 20:1, 20:1 to 22:1 and 22:1 to 24:1. These data suggest that the Lunaria enzyme will be useful for producing 24:1 in transgenic plants. As it is, expression of the jojoba enzyme in transgenic *Brassica* has resulted in plants having up to 7.8% of the seed oil composed of 24:1. The source jojoba seeds only produce 4.1% of the oil in the seed as 24:1. The above respresents the first description of an approach for increasing the 24:1 content of transgenic oil.

The above Examples also demonstrate that the primers of Table 7 can be used to successfully isolate condensing enzyme clones from diverse plant species. These oligonucleotides may be especially useful for isolating the corresponding fatty acid synthase animal genes, which have not been previously cloned. Since the β-ketoacyl-CoA synthase expression is repressed in several demyelinating nervous system disorders of humans, for instance adrenoleukodystrophy, adrenomyeloneuropathy, and multiple svlrtodid (reviewed in Sargent and Coupland, 1994), the human genes may be useful in human gene therapy. Similarly, vegetable oils high in 22:1 or 24:1 may be useful dietary therapeutic agents for these diseases.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A method for the production of an increased level of very long chain fatty acid molecules in a plant seed cell, said method comprising the steps of:
   growing a plant under conditions wherein said plant produces long chain fatty acyl-CoA molecules in said plant seed cell,
   in the presence of an expression product of a jojoba β-ketoacyl-CoA synthase DNA sequence operably linked to regulatory elements for directing the expression of said DNA sequence such as to effect the contact between such long chain fatty acyl-CoA molecules and said expression product,
   and producing said very long chain fatty acid molecules in said plant seed cell at a level that is increased relative to the native level of said very long chain fatty acid molecules in said plant seed cell.

2. The method of claim 1 wherein said very long chain fatty acid molecules are produced in said plant seed cell to a level greater than 7% by weight.

3. The method of claim 1 wherein said regulatory elements direct preferential expression of said DNA sequence in plant seed embryo cells.

4. A plant seed containing very long chain fatty acid molecules produced in accordance with claim 1.

5. A plant seed produced in accordance with claim 1.

6. A method for altering the composition of fatty acids in a plant cell, said method comprising the steps of:
   growing a plant under conditions wherein said plant produces long chain fatty acyl-CoA molecules,
   in the presence of an expression product of a jojoba β-ketoacyl-CoA synthase DNA sequence operably linked to regulatory elements for directing the expression of said DNA sequence such as to effect the contact between such long chain fatty acyl-CoA molecules and said jojoba β-ketoacyl-CoA synthase, wherein
   (i) said jojoba β-ketoacyl-CoA synthase is capable of catalyzing the production of very long chain fatty acids from a long chain fatty acyl-CoA substrate and malonyl-CoA,
   (ii) said DNA sequence is heterologous to said plant, and
   (iii) very long chain fatty acids are produced in said plant such as to alter the overall fatty acid composition of said plant cell.

7. The method of claim 1, wherein said very long chain fatty acid molecules are produced in said plant seed cell to a level greater than 5% by weight.

8. The method of claim 1, wherein said very long chain fatty acid molecules are 24:1 very long chain fatty acid molecules.

9. The method of claim 1, wherein said very long chain fatty acid molecules are 22:1 very long chain fatty acid molecules.

10. The method of claim 1, wherein said very long chain fatty acid molecules are 20:1 very long chain fatty acid molecules.

11. The method of claim 6, wherein said plant cell is a plant seed cell.

12. The method of claim 11, wherein said very long chain fatty acids are produced in said plant seed cell to a level greater than 7% by weight.

13. The method of claim 11, wherein said very long chain fatty acids are produced in said plant seed cell to a level greater than 5% by weight.

14. The method of claim 6, wherein said very long chain fatty acids are 24:1 very long chain fatty acids.

15. The method of claim 6, wherein said very long chain fatty acids are 22:1 very long chain fatty acids.

16. The method of claim 6, wherein said very long chain fatty acids are 20:1 very long chain fatty acids.

* * * * *

SEQUENCE LISTING

```
<160> NUMBER OF SEQ ID NOS: 53

<210> SEQ ID NO 1
<211> LENGTH: 1786
<212> TYPE: DNA
<213> ORGANISM: Simmondsia chinensis
<220> FEATURE:
<221> NAME/KEY: CDS
<222> LOCATION: (80)..(1558)
<220> FEATURE:
<221> NAME/KEY: modified_base
<222> LOCATION: (1537)
<223> OTHER INFORMATION: a, c, t, or g
<220> FEATURE:
<221> NAME/KEY: modified_base
<222> LOCATION: (1608)..(1609)
<223> OTHER INFORMATION: a, c, t, or g

<400> SEQUENCE: 1
aaatcctcca ctcatacact ccacttctct ctctctctct ctctctctga aacaatttga      60
gtagcaaact taaagaaa atg gag gaa atg gga agc att tta gag ttt ctt       112
                    Met Glu Glu Met Gly Ser Ile Leu Glu Phe Leu
                     1               5                  10 gat aac aaa gcc att ttg gtc act ggt gct act ggc tcc tta gca aaa       160
Asp Asn Lys Ala Ile Leu Val Thr Gly Ala Thr Gly Ser Leu Ala Lys
             15                  20                  25 att ttt gtg gag aag gta ctg agg agt caa ccg aat gtg aag aaa ctc       208
Ile Phe Val Glu Lys Val Leu Arg Ser Gln Pro Asn Val Lys Lys Leu
         30                  35                  40 tat ctt ctt ttg aga gca acc gat gac gag aca gct gct cta cgc ttg       256
Tyr Leu Leu Leu Arg Ala Thr Asp Asp Glu Thr Ala Ala Leu Arg Leu
     45                  50                  55 caa aat gag gtt ttt gga aaa gag ttg ttc aaa gtt ctg aaa caa aat       304
Gln Asn Glu Val Phe Gly Lys Glu Leu Phe Lys Val Leu Lys Gln Asn
 60                  65                  70                  75 tta ggt gca aat ttc tat tcc ttt gta tca gaa aaa gtg act gta gta       352
Leu Gly Ala Asn Phe Tyr Ser Phe Val Ser Glu Lys Val Thr Val Val
                 80                  85                  90 ccc ggt gat att act ggt gaa gac ttg tgt ctc aaa gac gtc aat ttg       400
Pro Gly Asp Ile Thr Gly Glu Asp Leu Cys Leu Lys Asp Val Asn Leu
             95                 100                 105 aag gaa gaa atg tgg agg gaa atc gat gtt gtt gtc aat cta gct gct       448
Lys Glu Glu Met Trp Arg Glu Ile Asp Val Val Val Asn Leu Ala Ala
```

```
                  110                 115                 120
aca atc aac ttc att gaa agg tac gac gtg tct ctg ctt atc aac aca      496
Thr Ile Asn Phe Ile Glu Arg Tyr Asp Val Ser Leu Leu Ile Asn Thr
    125                 130                 135 tat gga gcc aag tat gtt ttg gac ttc gcg aag aag tgc aac aaa tta      544
Tyr Gly Ala Lys Tyr Val Leu Asp Phe Ala Lys Lys Cys Asn Lys Leu
140                 145                 150                 155 aag ata ttt gtt cat gta tct act gct tat gta tct gga gag aaa aat      592
Lys Ile Phe Val His Val Ser Thr Ala Tyr Val Ser Gly Glu Lys Asn
                160                 165                 170 ggg tta ata ctg gag aag cct tat tat atg ggc gag tca ctt aat gga      640
Gly Leu Ile Leu Glu Lys Pro Tyr Tyr Met Gly Glu Ser Leu Asn Gly
            175                 180                 185 aga tta ggt ctg gac att aat gta gag aag aaa ctt gtg gag gca aaa      688
Arg Leu Gly Leu Asp Ile Asn Val Glu Lys Lys Leu Val Glu Ala Lys
        190                 195                 200 atc aat gaa ctt caa gca gcg ggg gca acg gaa aag tcc att aaa tcg      736
Ile Asn Glu Leu Gln Ala Ala Gly Ala Thr Glu Lys Ser Ile Lys Ser
    205                 210                 215 aca atg aag gac atg ggc atc gag agg gca aga cac tgg gga tgg cca      784
Thr Met Lys Asp Met Gly Ile Glu Arg Ala Arg His Trp Gly Trp Pro
220                 225                 230                 235 aat gtg tat gta ttc acc aag gca tta ggg gag atg ctt ttg atg caa      832
Asn Val Tyr Val Phe Thr Lys Ala Leu Gly Glu Met Leu Leu Met Gln
                240                 245                 250 tac aaa ggg gac att ccg ctt act att att cgt ccc acc atc atc acc      880
Tyr Lys Gly Asp Ile Pro Leu Thr Ile Ile Arg Pro Thr Ile Ile Thr
            255                 260                 265 agc act ttt aaa gag ccc ttt cct ggt tgg gtt gaa ggt gtc agg acc      928
Ser Thr Phe Lys Glu Pro Phe Pro Gly Trp Val Glu Gly Val Arg Thr
        270                 275                 280 atc gat aat gta cct gta tat tat ggt aaa ggg aga ttg agg tgt atg      976
Ile Asp Asn Val Pro Val Tyr Tyr Gly Lys Gly Arg Leu Arg Cys Met
    285                 290                 295 ctt tgc gga ccc agc aca ata att gac ctg ata ccg gca gat atg gtc     1024
Leu Cys Gly Pro Ser Thr Ile Ile Asp Leu Ile Pro Ala Asp Met Val
300                 305                 310                 315 gtg aat gca acg ata gta gcc atg gtg gcg cac gca aac caa aga tac     1072
Val Asn Ala Thr Ile Val Ala Met Val Ala His Ala Asn Gln Arg Tyr
                320                 325                 330 gta gag ccg gtg aca tac cat gtg gga tct tca gcg gcg aat cca atg     1120
Val Glu Pro Val Thr Tyr His Val Gly Ser Ser Ala Ala Asn Pro Met
            335                 340                 345 aaa ctg agt gca tta cca gag atg gca cac cgt tac ttc acc aag aat     1168
Lys Leu Ser Ala Leu Pro Glu Met Ala His Arg Tyr Phe Thr Lys Asn
        350                 355                 360 cca tgg atc aac ccg gat cgc aac cca gta cat gtg ggt cgg gct atg     1216
Pro Trp Ile Asn Pro Asp Arg Asn Pro Val His Val Gly Arg Ala Met
    365                 370                 375 gtc ttc tcc tcc ttc tcc acc ttc cac ctt tat ctc acc ctt aat ttc     1264
Val Phe Ser Ser Phe Ser Thr Phe His Leu Tyr Leu Thr Leu Asn Phe
380                 385                 390                 395 ctc ctt cct ttg aag gta ctg gag ata gca aat aca ata ttc tgc caa     1312
Leu Leu Pro Leu Lys Val Leu Glu Ile Ala Asn Thr Ile Phe Cys Gln
                400                 405                 410 tgg ttc aag ggt aag tac atg gat ctt aaa agg aag acg agg ttg ttg     1360
Trp Phe Lys Gly Lys Tyr Met Asp Leu Lys Arg Lys Thr Arg Leu Leu
            415                 420                 425 ttg cgt tta gta gac att tat aaa ccc tac ctc ttc ttc caa ggc atc     1408
```

```
Leu Arg Leu Val Asp Ile Tyr Lys Pro Tyr Leu Phe Gln Gly Ile
        430                 435                 440 ttt gat gac atg aac act gag aag ttg cgg att gct gca aaa gaa agc       1456
Phe Asp Asp Met Asn Thr Glu Lys Leu Arg Ile Ala Ala Lys Glu Ser
445                 450                 455 ata gtt gaa gct gat atg ttt tac ttt gat ccc agg gca att aac tgg       1504
Ile Val Glu Ala Asp Met Phe Tyr Phe Asp Pro Arg Ala Ile Asn Trp
460                 465                 470                 475 gaa gat tac ttc ttg aaa act cat ttc cca ggn gtc gta gag cac gtt       1552
Glu Asp Tyr Phe Leu Lys Thr His Phe Pro Gly Val Val Glu His Val
            480                 485                 490 ctt aac taaaagttac ggtacgaaaa tgagaagatt ggaatgcatg caccgaaagn       1608
Leu Asn ncaacataaa agacgtggtt aaagtcatgg tcaaaaaga ataaaatgc agttaggttt       1668 gtgttgcagt tttgattcct tgtattgtta cttgtacttt tgatctttt ctttttaat       1728 gaaatttctc tctttgttt gtgaaaaaaa aaaaaaaaaa gagctcctgc agaagctt       1786

<210> SEQ ID NO 2
<211> LENGTH: 493
<212> TYPE: PRT
<213> ORGANISM: Simmondsia chinensis

<400> SEQUENCE: 2

Met Glu Glu Met Gly Ser Ile Leu Glu Phe Leu Asp Asn Lys Ala Ile
1               5                   10                  15

Leu Val Thr Gly Ala Thr Gly Ser Leu Ala Lys Ile Phe Val Glu Lys
                20                  25                  30

Val Leu Arg Ser Gln Pro Asn Val Lys Lys Leu Tyr Leu Leu Leu Arg
            35                  40                  45

Ala Thr Asp Asp Glu Thr Ala Ala Leu Arg Leu Gln Asn Glu Val Phe
        50                  55                  60

Gly Lys Glu Leu Phe Lys Val Leu Lys Gln Asn Leu Gly Ala Asn Phe
65                  70                  75                  80

Tyr Ser Phe Val Ser Glu Lys Val Thr Val Pro Gly Asp Ile Thr
                85                  90                  95

Gly Glu Asp Leu Cys Leu Lys Asp Val Asn Leu Lys Glu Met Trp
            100                 105                 110

Arg Glu Ile Asp Val Val Asn Leu Ala Ala Thr Ile Asn Phe Ile
        115                 120                 125

Glu Arg Tyr Asp Val Ser Leu Leu Ile Asn Thr Tyr Gly Ala Lys Tyr
        130                 135                 140

Val Leu Asp Phe Ala Lys Lys Cys Asn Lys Leu Lys Ile Phe Val His
145                 150                 155                 160

Val Ser Thr Ala Tyr Val Ser Gly Glu Lys Asn Gly Leu Ile Leu Glu
                165                 170                 175

Lys Pro Tyr Tyr Met Gly Glu Ser Leu Asn Gly Arg Leu Gly Leu Asp
            180                 185                 190

Ile Asn Val Glu Lys Lys Leu Val Glu Ala Lys Ile Asn Glu Leu Gln
        195                 200                 205

Ala Ala Gly Ala Thr Glu Lys Ser Ile Lys Ser Thr Met Lys Asp Met
    210                 215                 220

Gly Ile Glu Arg Ala Arg His Trp Gly Trp Pro Asn Val Tyr Val Phe
225                 230                 235                 240

Thr Lys Ala Leu Gly Glu Met Leu Leu Met Gln Tyr Lys Gly Asp Ile
                245                 250                 255
```

-continued

```
Pro Leu Thr Ile Ile Arg Pro Thr Ile Ile Thr Ser Thr Phe Lys Glu
            260                 265                 270
Pro Phe Pro Gly Trp Val Glu Gly Val Arg Thr Ile Asp Asn Val Pro
        275                 280                 285
Val Tyr Tyr Gly Lys Gly Arg Leu Arg Cys Met Leu Cys Gly Pro Ser
    290                 295                 300
Thr Ile Ile Asp Leu Ile Pro Ala Asp Met Val Val Asn Ala Thr Ile
305                 310                 315                 320
Val Ala Met Val Ala His Ala Asn Gln Arg Tyr Val Glu Pro Val Thr
                325                 330                 335
Tyr His Val Gly Ser Ser Ala Ala Asn Pro Met Lys Leu Ser Ala Leu
            340                 345                 350
Pro Glu Met Ala His Arg Tyr Phe Thr Lys Asn Pro Trp Ile Asn Pro
        355                 360                 365
Asp Arg Asn Pro Val His Val Gly Arg Ala Met Val Phe Ser Ser Phe
    370                 375                 380
Ser Thr Phe His Leu Tyr Leu Thr Leu Asn Phe Leu Leu Pro Leu Lys
385                 390                 395                 400
Val Leu Glu Ile Ala Asn Thr Ile Phe Cys Gln Trp Phe Lys Gly Lys
                405                 410                 415
Tyr Met Asp Leu Lys Arg Lys Thr Arg Leu Leu Leu Arg Leu Val Asp
            420                 425                 430
Ile Tyr Lys Pro Tyr Leu Phe Phe Gln Gly Ile Phe Asp Asp Met Asn
        435                 440                 445
Thr Glu Lys Leu Arg Ile Ala Ala Lys Glu Ser Ile Val Glu Ala Asp
    450                 455                 460
Met Phe Tyr Phe Asp Pro Arg Ala Ile Asn Trp Glu Asp Tyr Phe Leu
465                 470                 475                 480
Lys Thr His Phe Pro Gly Val Val Glu His Val Leu Asn
                485                 490
```

<210> SEQ ID NO 3
<211> LENGTH: 1733
<212> TYPE: DNA
<213> ORGANISM: Simmondsia chinensis
<220> FEATURE:
<221> NAME/KEY: CDS
<222> LOCATION: (39)..(1610)
<220> FEATURE:
<221> NAME/KEY: modified_base
<222> LOCATION: (676)
<223> OTHER INFORMATION: a, c, t, or g
<220> FEATURE:
<221> NAME/KEY: modified_base
<222> LOCATION: (737)
<223> OTHER INFORMATION: a, c, t, or g

<400> SEQUENCE: 3

```
ggaactccat cccttcctcc ctcactcctc tctctaca atg aag gcc aaa aca atc      56
                                         Met Lys Ala Lys Thr Ile
                                           1               5 aca aac ccg gag atc caa gtc tcc acg acc atg acc acc acg acc acg     104
Thr Asn Pro Glu Ile Gln Val Ser Thr Thr Met Thr Thr Thr Thr Thr
           10                  15                  20 act atg acc gcc act ctc ccc aac ttc aag tcc tcc atc aac tta cac     152
Thr Met Thr Ala Thr Leu Pro Asn Phe Lys Ser Ser Ile Asn Leu His
        25                  30                  35 cac gtc aag ctc ggc tac cac tac tta atc tcc aat gcc ctc ttc ctc     200
His Val Lys Leu Gly Tyr His Tyr Leu Ile Ser Asn Ala Leu Phe Leu
```

```
                   40                    45                     50
gta ttc atc ccc ctt ttg ggc ctc gct tcg gcc cat ctc tcc tcc ttc    248
Val Phe Ile Pro Leu Leu Gly Leu Ala Ser Ala His Leu Ser Ser Phe
 55                  60                     65                 70 tcg gcc cat gac ttg tcc ctg ctc ttc gac ctc ctt cgc cgc aac ctc    296
Ser Ala His Asp Leu Ser Leu Leu Phe Asp Leu Leu Arg Arg Asn Leu
                 75                     80                 85 ctc cct gtt gtc gtt tgt tct ttc ctc ttc gtt tta tta gca acc cta    344
Leu Pro Val Val Val Cys Ser Phe Leu Phe Val Leu Leu Ala Thr Leu
             90                     95                    100 cat ttc ttg acc cgg ccc agg aat gtc tac ttg gtg gac ttt gga tgc    392
His Phe Leu Thr Arg Pro Arg Asn Val Tyr Leu Val Asp Phe Gly Cys
            105                    110                    115 tat aag cct caa ccg aac ctg atg aca tcc cac gag atg ttc atg gac    440
Tyr Lys Pro Gln Pro Asn Leu Met Thr Ser His Glu Met Phe Met Asp
        120                    125                    130 cgg acc tcc cgg gcc ggg tcg ttt tct aag gag aat att gag ttt cag    488
Arg Thr Ser Arg Ala Gly Ser Phe Ser Lys Glu Asn Ile Glu Phe Gln
135                    140                    145                150 agg aag atc ttg gag agg gcc ggt atg ggt cgg gaa acc tat gtc ccc    536
Arg Lys Ile Leu Glu Arg Ala Gly Met Gly Arg Glu Thr Tyr Val Pro
                   155                    160                    165 gaa tcc gtc act aag gtg ccc gcc gag ccg agc ata gca gca gcc agg    584
Glu Ser Val Thr Lys Val Pro Ala Glu Pro Ser Ile Ala Ala Ala Arg
               170                    175                    180 gcc gag gcg gag gag gtg atg tac ggg gcg atc gac gag gtg ttg gag    632
Ala Glu Ala Glu Glu Val Met Tyr Gly Ala Ile Asp Glu Val Leu Glu
            185                    190                    195 aag acg ggg gtg aag ccg aag cag ata gga ata ctg gtg gtg anc tgc    680
Lys Thr Gly Val Lys Pro Lys Gln Ile Gly Ile Leu Val Val Xaa Cys
        200                    205                    210 agc ttg ttt aac cca acg ccg tcg ctg tca tcc atg ata gtt aac cat    728
Ser Leu Phe Asn Pro Thr Pro Ser Leu Ser Ser Met Ile Val Asn His
215                    220                    225                230 tac aag ctn agg ggt aat ata ctt agc tat aat ctt ggt ggc atg ggt    776
Tyr Lys Xaa Arg Gly Asn Ile Leu Ser Tyr Asn Leu Gly Gly Met Gly
                   235                    240                    245 tgc agt gct ggg ctc att tcc att gat ctt gcc aag gac ctc cta cag    824
Cys Ser Ala Gly Leu Ile Ser Ile Asp Leu Ala Lys Asp Leu Leu Gln
               250                    255                    260 gtt tac cgt aaa aac aca tat gtg tta gta gtg agc acg gaa aac atg    872
Val Tyr Arg Lys Asn Thr Tyr Val Leu Val Val Ser Thr Glu Asn Met
            265                    270                    275 acc ctt aat tgg tac tgg ggc aat gac cgc tcc atg ctt atc acc aac    920
Thr Leu Asn Trp Tyr Trp Gly Asn Asp Arg Ser Met Leu Ile Thr Asn
        280                    285                    290 tgc cta ttt cgc atg ggt ggc gct gcc atc atc ctc tca aac cgc tgg    968
Cys Leu Phe Arg Met Gly Gly Ala Ala Ile Ile Leu Ser Asn Arg Trp
295                    300                    305                310 cgt gat cgt cgc cga tcc aag tac caa ctc ctt cat aca gta cgc acc   1016
Arg Asp Arg Arg Arg Ser Lys Tyr Gln Leu Leu His Thr Val Arg Thr
                   315                    320                    325 cac aag ggc gct gac gac aag tcc tat aga tgc gtc tta caa caa gaa   1064
His Lys Gly Ala Asp Asp Lys Ser Tyr Arg Cys Val Leu Gln Gln Glu
               330                    335                    340 gat gaa aat aac aag gta ggt gtt gcc tta tcc aag gat ctg atg gca   1112
Asp Glu Asn Asn Lys Val Gly Val Ala Leu Ser Lys Asp Leu Met Ala
            345                    350                    355 gtt gcc ggt gaa gcc cta aag gcc aac atc acg acc ctt ggt ccc ctc   1160
```

```
              Val Ala Gly Glu Ala Leu Lys Ala Asn Ile Thr Thr Leu Gly Pro Leu
                  360                 365                 370 gtg ctc ccc atg tca gaa caa ctc ctc ttt gcc acc tta gtg gca           1208
Val Leu Pro Met Ser Glu Gln Leu Leu Phe Ala Thr Leu Val Ala
375                 380                 385                 390 cgt aag gtc ttc aag atg acg aac gtg aag cca tac atc cca gat ttc       1256
Arg Lys Val Phe Lys Met Thr Asn Val Lys Pro Tyr Ile Pro Asp Phe
                    395                 400                 405 aag ttg gca gcg aac gac ttc tgc atc cat gca gga ggc aaa gca gtg       1304
Lys Leu Ala Ala Asn Asp Phe Cys Ile His Ala Gly Gly Lys Ala Val
        410                 415                 420 ttg gat gag ctc gag aag aac ttg gag ttg acg cca tgg cac ctt gaa       1352
Leu Asp Glu Leu Glu Lys Asn Leu Glu Leu Thr Pro Trp His Leu Glu
            425                 430                 435 ccc tcg agg atg aca ctg tat agg ttt ggg aac aca tcg agt agc tca       1400
Pro Ser Arg Met Thr Leu Tyr Arg Phe Gly Asn Thr Ser Ser Ser Ser
                440                 445                 450 tta tgg tac gag ttg gca tac gct gaa gca aaa ggg agg atc cgt aag       1448
Leu Trp Tyr Glu Leu Ala Tyr Ala Glu Ala Lys Gly Arg Ile Arg Lys
455                 460                 465                 470 ggt gat cga act tgg atg att gga ttt ggt tca ggt ttc aag tgt aac       1496
Gly Asp Arg Thr Trp Met Ile Gly Phe Gly Ser Gly Phe Lys Cys Asn
                    475                 480                 485 agt gtt gtg tgg agg gct ttg agg agt gtc aat ccg gct aga gag aag       1544
Ser Val Val Trp Arg Ala Leu Arg Ser Val Asn Pro Ala Arg Glu Lys
        490                 495                 500 aat cct tgg atg gat gaa att gag aag ttc cct gtc cat gtg cct aaa       1592
Asn Pro Trp Met Asp Glu Ile Glu Lys Phe Pro Val His Val Pro Lys
            505                 510                 515 atc gca cct atc gct tcg tagaactgct aggatgtgat tagtaatgaa             1640
Ile Ala Pro Ile Ala Ser
                520 aaatgtgtat tatgttagtg atgtagaaaa agaaacttta gttgatgggt gagaacatgt    1700 ctcattgaga ataacgtgtg catcgttgtg ttg                                 1733

<210> SEQ ID NO 4
<211> LENGTH: 524
<212> TYPE: PRT
<213> ORGANISM: Simmondsia chinensis
<220> FEATURE:
<221> NAME/KEY: MOD_RES
<222> LOCATION: (213)
<223> OTHER INFORMATION: Variable amino acid
<220> FEATURE:
<221> NAME/KEY: MOD_RES
<222> LOCATION: (233)
<223> OTHER INFORMATION: Variable amino acid

<400> SEQUENCE: 4

Met Lys Ala Lys Thr Ile Thr Asn Pro Glu Ile Gln Val Ser Thr Thr
1               5                   10                  15

Met Thr Thr Thr Thr Thr Met Thr Ala Thr Leu Pro Asn Phe Lys
            20                  25                  30

Ser Ser Ile Asn Leu His His Val Lys Leu Gly Tyr His Tyr Leu Ile
        35                  40                  45

Ser Asn Ala Leu Phe Leu Val Phe Ile Pro Leu Leu Gly Leu Ala Ser
    50                  55                  60

Ala His Leu Ser Ser Phe Ser Ala His Asp Leu Ser Leu Leu Phe Asp
65                  70                  75                  80

Leu Leu Arg Arg Asn Leu Leu Pro Val Val Val Cys Ser Phe Leu Phe
```

-continued

```
                85                  90                  95
Val Leu Leu Ala Thr Leu His Phe Leu Thr Arg Pro Arg Asn Val Tyr
            100                 105                 110
Leu Val Asp Phe Gly Cys Tyr Lys Pro Gln Pro Asn Leu Met Thr Ser
            115                 120                 125
His Glu Met Phe Met Asp Arg Thr Ser Arg Ala Gly Ser Phe Ser Lys
            130                 135                 140
Glu Asn Ile Glu Phe Gln Arg Lys Ile Leu Glu Arg Ala Gly Met Gly
145                 150                 155                 160
Arg Glu Thr Tyr Val Pro Glu Ser Val Thr Lys Val Pro Ala Glu Pro
                165                 170                 175
Ser Ile Ala Ala Ala Arg Ala Glu Ala Glu Val Met Tyr Gly Ala
            180                 185                 190
Ile Asp Glu Val Leu Glu Lys Thr Gly Val Lys Pro Lys Gln Ile Gly
            195                 200                 205
Ile Leu Val Val Xaa Cys Ser Leu Phe Asn Pro Thr Pro Ser Leu Ser
            210                 215                 220
Ser Met Ile Val Asn His Tyr Lys Xaa Arg Gly Asn Ile Leu Ser Tyr
225                 230                 235                 240
Asn Leu Gly Gly Met Gly Cys Ser Ala Gly Leu Ile Ser Ile Asp Leu
                245                 250                 255
Ala Lys Asp Leu Leu Gln Val Tyr Arg Lys Asn Thr Tyr Val Leu Val
            260                 265                 270
Val Ser Thr Glu Asn Met Thr Leu Asn Trp Tyr Trp Gly Asn Asp Arg
            275                 280                 285
Ser Met Leu Ile Thr Asn Cys Leu Phe Arg Met Gly Gly Ala Ala Ile
290                 295                 300
Ile Leu Ser Asn Arg Trp Arg Asp Arg Arg Ser Lys Tyr Gln Leu
305                 310                 315                 320
Leu His Thr Val Arg Thr His Lys Gly Ala Asp Asp Lys Ser Tyr Arg
                325                 330                 335
Cys Val Leu Gln Gln Glu Asp Glu Asn Asn Lys Val Gly Val Ala Leu
            340                 345                 350
Ser Lys Asp Leu Met Ala Val Ala Gly Glu Ala Leu Lys Ala Asn Ile
            355                 360                 365
Thr Thr Leu Gly Pro Leu Val Leu Pro Met Ser Glu Gln Leu Leu Phe
            370                 375                 380
Phe Ala Thr Leu Val Ala Arg Lys Val Phe Lys Met Thr Asn Val Lys
385                 390                 395                 400
Pro Tyr Ile Pro Asp Phe Lys Leu Ala Ala Asn Asp Phe Cys Ile His
                405                 410                 415
Ala Gly Gly Lys Ala Val Leu Asp Glu Leu Glu Lys Asn Leu Glu Leu
            420                 425                 430
Thr Pro Trp His Leu Glu Pro Ser Arg Met Thr Leu Tyr Arg Phe Gly
            435                 440                 445
Asn Thr Ser Ser Ser Leu Trp Tyr Glu Leu Ala Tyr Ala Glu Ala
            450                 455                 460
Lys Gly Arg Ile Arg Lys Gly Asp Arg Thr Trp Met Ile Gly Phe Gly
465                 470                 475                 480
Ser Gly Phe Lys Cys Asn Ser Val Val Trp Arg Ala Leu Arg Ser Val
                485                 490                 495
Asn Pro Ala Arg Glu Lys Asn Pro Trp Met Asp Glu Ile Glu Lys Phe
            500                 505                 510
```

```
Pro Val His Val Pro Lys Ile Ala Pro Ile Ala Ser
        515                 520

<210> SEQ ID NO 5
<211> LENGTH: 1783
<212> TYPE: DNA
<213> ORGANISM: Simmondsia chinensis
<220> FEATURE:
<221> NAME/KEY: CDS
<222> LOCATION: (10)..(1572)

<400> SEQUENCE: 5 gtcgacaca atg aag gcc aaa aca atc aca aac ccg gag atc caa gtc tcc      51
          Met Lys Ala Lys Thr Ile Thr Asn Pro Glu Ile Gln Val Ser
            1               5                  10 acg acc atg acc acc acg acc acg acc gcc act ctc ccc aac ttc aag        99
Thr Thr Met Thr Thr Thr Thr Thr Ala Thr Leu Pro Asn Phe Lys
 15              20                  25                  30 tcc tcc atc aac tta cac cac gtc aag ctc ggc tac cac tac tta atc       147
Ser Ser Ile Asn Leu His His Val Lys Leu Gly Tyr His Tyr Leu Ile
                 35                  40                  45 tcc aat gcc ctc ttc ctc gta ttc atc ccc ctt ttg ggc ctc gct tcg       195
Ser Asn Ala Leu Phe Leu Val Phe Ile Pro Leu Leu Gly Leu Ala Ser
             50                  55                  60 gcc cac ctc tcc tcc ttc tcg gcc cat gac ttg tcc ctg ctc ttc gac       243
Ala His Leu Ser Ser Phe Ser Ala His Asp Leu Ser Leu Leu Phe Asp
         65                  70                  75 ctc ctt cgc cgc aac ctc ctc ccc gtt gtc gtt tgt tct ttc ctc ttc       291
Leu Leu Arg Arg Asn Leu Leu Pro Val Val Val Cys Ser Phe Leu Phe
     80                  85                  90 gtt tta tta gca acc cta cat ttc ttg acc cgg cct agg aat gtc tac       339
Val Leu Leu Ala Thr Leu His Phe Leu Thr Arg Pro Arg Asn Val Tyr
 95                 100                 105                 110 ttg gtg gac ttt gcc tgc tat aag cct cac ccg aac ctg ata aca tcc       387
Leu Val Asp Phe Ala Cys Tyr Lys Pro His Pro Asn Leu Ile Thr Ser
                115                 120                 125 cac gag atg ttc atg gac cgg acc tcc cgg gcc ggg tcg ttt tct aag       435
His Glu Met Phe Met Asp Arg Thr Ser Arg Ala Gly Ser Phe Ser Lys
            130                 135                 140 gag aat att gag ttt cag agg aag atc ttg gag agg gcc ggt atg ggc       483
Glu Asn Ile Glu Phe Gln Arg Lys Ile Leu Glu Arg Ala Gly Met Gly
        145                 150                 155 cgg gaa acc tac gtc ccc gaa tcc gtc act aag gtg ccg ccc gag ccg       531
Arg Glu Thr Tyr Val Pro Glu Ser Val Thr Lys Val Pro Pro Glu Pro
    160                 165                 170 agc ata gca gca gcc agg gcc gag gcg gag gag gtg atg tac ggg gcg       579
Ser Ile Ala Ala Ala Arg Ala Glu Ala Glu Glu Val Met Tyr Gly Ala
175                 180                 185                 190 atc gac gag gtg ttg gag aag acg ggg gtg aag ccg aag cag ata gga       627
Ile Asp Glu Val Leu Glu Lys Thr Gly Val Lys Pro Lys Gln Ile Gly
                195                 200                 205 ata ctg gtg gtg aac tgc agc ttg ttt aac cca acg ccg tcg ctg tca       675
Ile Leu Val Val Asn Cys Ser Leu Phe Asn Pro Thr Pro Ser Leu Ser
            210                 215                 220 tcc atg ata gtt aac cat tac aag ctt agg ggt aat ata ctt agc tat       723
Ser Met Ile Val Asn His Tyr Lys Leu Arg Gly Asn Ile Leu Ser Tyr
        225                 230                 235 aat ctt ggt ggc atg ggt tgc agt gct ggg ctc att tcc att gat ctt       771
Asn Leu Gly Gly Met Gly Cys Ser Ala Gly Leu Ile Ser Ile Asp Leu
    240                 245                 250
```

-continued

```
gcc aag gac ctc cta cag gtt tac cgt aac aca tat gtg tta gta gtg      819
Ala Lys Asp Leu Leu Gln Val Tyr Arg Asn Thr Tyr Val Leu Val Val
255                 260                 265                 270 agc aca gaa aac atg acc ctt aat tgg tac tgg ggc aat gac cgc tcc      867
Ser Thr Glu Asn Met Thr Leu Asn Trp Tyr Trp Gly Asn Asp Arg Ser
                275                 280                 285 atg ctt atc acc aac tgc cta ttt cgc atg ggt ggc gct gcc atc atc      915
Met Leu Ile Thr Asn Cys Leu Phe Arg Met Gly Gly Ala Ala Ile Ile
            290                 295                 300 ctc tca aac cgc tgg cgt gat cgt cgc cga tcc aag tac caa ctc ctt      963
Leu Ser Asn Arg Trp Arg Asp Arg Arg Arg Ser Lys Tyr Gln Leu Leu
        305                 310                 315 cac aca gta cgc acc cac aag ggc gct gac gac aag tcc tat aga tgc     1011
His Thr Val Arg Thr His Lys Gly Ala Asp Asp Lys Ser Tyr Arg Cys
    320                 325                 330 gtc tta caa caa gaa gat gaa aat aac aag gta ggt gtt gcc tta tcc     1059
Val Leu Gln Gln Glu Asp Glu Asn Asn Lys Val Gly Val Ala Leu Ser
335                 340                 345                 350 aag gat ctg atg gca gtt gcc ggt gaa gcc cta aag gcc aac atc acg     1107
Lys Asp Leu Met Ala Val Ala Gly Glu Ala Leu Lys Ala Asn Ile Thr
                355                 360                 365 acc ctt ggt ccc ctc gtg ctc ccc atg tca gaa caa ctc ctc ttc ttt     1155
Thr Leu Gly Pro Leu Val Leu Pro Met Ser Glu Gln Leu Leu Phe Phe
            370                 375                 380 gcc acc tta gtg gca cgt aag gtc ttc aag atg acg aac gtg aag cca     1203
Ala Thr Leu Val Ala Arg Lys Val Phe Lys Met Thr Asn Val Lys Pro
        385                 390                 395 tac atc cca gat ttc aag ttg gca gcg aag cac ttc tgc atc cat gca     1251
Tyr Ile Pro Asp Phe Lys Leu Ala Ala Lys His Phe Cys Ile His Ala
    400                 405                 410 gga ggc aaa gca gtg ttg gat gag ctc gag acg aac ttg gag ttg acg     1299
Gly Gly Lys Ala Val Leu Asp Glu Leu Glu Thr Asn Leu Glu Leu Thr
415                 420                 425                 430 cca tgg cac ctt gaa ccc tcg agg atg aca ctg tat agg ttt ggg aac     1347
Pro Trp His Leu Glu Pro Ser Arg Met Thr Leu Tyr Arg Phe Gly Asn
                435                 440                 445 aca tcg agt agc tca tta tgg tac gag ttg gca tac gct gaa gca aaa     1395
Thr Ser Ser Ser Ser Leu Trp Tyr Glu Leu Ala Tyr Ala Glu Ala Lys
            450                 455                 460 ggg agg atc cgt aag ggt gat cga act tgg atg att gga ttt ggt tca     1443
Gly Arg Ile Arg Lys Gly Asp Arg Thr Trp Met Ile Gly Phe Gly Ser
        465                 470                 475 ggt ttc aag tgt aac agt gtt gtg tgg agg gct ttg agg agt gtc aat     1491
Gly Phe Lys Cys Asn Ser Val Val Trp Arg Ala Leu Arg Ser Val Asn
480                 485                 490 ccg gct aga gag aag aat cct tgg atg gat gaa att gag aat ttc cct     1539
Pro Ala Arg Glu Lys Asn Pro Trp Met Asp Glu Ile Glu Asn Phe Pro
495                 500                 505                 510 gtc cat gtg cct aaa atc gca cct atc gct tcg tagaactgct aggatgtgat   1592
Val His Val Pro Lys Ile Ala Pro Ile Ala Ser
                515                 520 tagtaatgaa aatgtgtat tatgttagtg atgtagaaaa agaaacttta gttgatgggt    1652
gagaacatgt ctcattgaga ataacgtgtg catcgttgtg ttgaatttga atttgagtat   1712
tggtgaaatt ctgttagaat tgacgcatga gtcatatata tacaaattta agtaagattt   1772
tacgctttct t                                                        1783
```

<210> SEQ ID NO 6
<211> LENGTH: 521

```
<212> TYPE: PRT
<213> ORGANISM: Simmondsia chinensis

<400> SEQUENCE: 6

Met Lys Ala Lys Thr Ile Thr Asn Pro Glu Ile Gln Val Ser Thr Thr
 1               5                  10                  15

Met Thr Thr Thr Thr Thr Ala Thr Leu Pro Asn Phe Lys Ser Ser
            20                  25                  30

Ile Asn Leu His His Val Lys Leu Gly Tyr His Tyr Leu Ile Ser Asn
            35                  40                  45

Ala Leu Phe Leu Val Phe Ile Pro Leu Leu Gly Leu Ala Ser Ala His
    50                  55                  60

Leu Ser Ser Phe Ser Ala His Asp Leu Ser Leu Leu Phe Asp Leu Leu
65                  70                  75                  80

Arg Arg Asn Leu Leu Pro Val Val Cys Ser Phe Leu Phe Val Leu
                85                  90                  95

Leu Ala Thr Leu His Phe Leu Thr Arg Pro Arg Asn Val Tyr Leu Val
                100                 105                 110

Asp Phe Ala Cys Tyr Lys Pro His Pro Asn Leu Ile Thr Ser His Glu
            115                 120                 125

Met Phe Met Asp Arg Thr Ser Arg Ala Gly Ser Phe Ser Lys Glu Asn
    130                 135                 140

Ile Glu Phe Gln Arg Lys Ile Leu Glu Arg Ala Gly Met Gly Arg Glu
145                 150                 155                 160

Thr Tyr Val Pro Glu Ser Val Thr Lys Val Pro Pro Glu Pro Ser Ile
                165                 170                 175

Ala Ala Ala Arg Ala Glu Ala Glu Val Met Tyr Gly Ala Ile Asp
                180                 185                 190

Glu Val Leu Glu Lys Thr Gly Val Lys Pro Lys Gln Ile Gly Ile Leu
            195                 200                 205

Val Val Asn Cys Ser Leu Phe Asn Pro Thr Pro Ser Leu Ser Ser Met
210                 215                 220

Ile Val Asn His Tyr Lys Leu Arg Gly Asn Ile Leu Ser Tyr Asn Leu
225                 230                 235                 240

Gly Gly Met Gly Cys Ser Ala Gly Leu Ile Ser Ile Asp Leu Ala Lys
                245                 250                 255

Asp Leu Leu Gln Val Tyr Arg Asn Thr Tyr Val Leu Val Val Ser Thr
            260                 265                 270

Glu Asn Met Thr Leu Asn Trp Tyr Trp Gly Asn Asp Arg Ser Met Leu
            275                 280                 285

Ile Thr Asn Cys Leu Phe Arg Met Gly Gly Ala Ala Ile Ile Leu Ser
    290                 295                 300

Asn Arg Trp Arg Asp Arg Arg Ser Lys Tyr Gln Leu Leu His Thr
305                 310                 315                 320

Val Arg Thr His Lys Gly Ala Asp Asp Lys Ser Tyr Arg Cys Val Leu
                325                 330                 335

Gln Gln Glu Asp Glu Asn Asn Lys Val Gly Val Ala Leu Ser Lys Asp
            340                 345                 350

Leu Met Ala Val Ala Gly Glu Ala Leu Lys Ala Asn Ile Thr Thr Leu
    355                 360                 365

Gly Pro Leu Val Leu Pro Met Ser Glu Gln Leu Leu Phe Ala Thr
    370                 375                 380

Leu Val Ala Arg Lys Val Phe Lys Met Thr Asn Val Lys Pro Tyr Ile
385                 390                 395                 400
```

```
Pro Asp Phe Lys Leu Ala Ala Lys His Phe Cys Ile His Ala Gly Gly
            405                 410                 415

Lys Ala Val Leu Asp Glu Leu Glu Thr Asn Leu Glu Leu Thr Pro Trp
            420                 425                 430

His Leu Glu Pro Ser Arg Met Thr Leu Tyr Arg Phe Gly Asn Thr Ser
            435                 440                 445

Ser Ser Ser Leu Trp Tyr Glu Leu Ala Tyr Ala Glu Ala Lys Gly Arg
            450                 455                 460

Ile Arg Lys Gly Asp Arg Thr Trp Met Ile Gly Phe Gly Ser Gly Phe
465                 470                 475                 480

Lys Cys Asn Ser Val Val Trp Arg Ala Leu Arg Ser Val Asn Pro Ala
            485                 490                 495

Arg Glu Lys Asn Pro Trp Met Asp Glu Ile Glu Asn Phe Pro Val His
            500                 505                 510

Val Pro Lys Ile Ala Pro Ile Ala Ser
            515                 520

<210> SEQ ID NO 7
<211> LENGTH: 1647
<212> TYPE: DNA
<213> ORGANISM: Artificial Sequence
<220> FEATURE:
<223> OTHER INFORMATION: Description of Artificial Sequence: Oleosin
      expression cassette

<400> SEQUENCE: 7
ggcgcgccgg tacctctaga cctggcgatt caacgtggtc ggatcatgac gcttccagaa      60
aacatcgagc aagctctcaa agctgacctc tttcggatcg tactgaaccc gaacaatctc     120
gttatgtccc gtcgtctccg aacagacatc ctcgtagctc ggattatcga cgaatccatg     180
gctataccca acctccgtct tcgtcacgcc tggaaccctc tggtacgcca attccgctcc     240
ccagaagcaa ccggcgccga attgcgcgaa ttgctgacct ggagacggaa catcgtcgtc     300
gggtccttgc gcgattgcgg cggaagccgg gtcgggttgg ggacgagacc cgaatccgag     360
cctggtgaag aggttgttca tcggagattt atagacggga atggatcgag cggttttggg     420
gaaaggggaa gtgggtttgg ctcttttgga tagagagagt gcagctttgg agagagactg     480
gagaggttta gagagagacg cggcggatat taccggagga gaggcgacga gagatagcat     540
tatcgaaggg gagggagaaa gagtgacgtg agaaataag aaaccgttaa gagtcggata     600
tttatcatat taaaagccca atgggcctga acccatttaa acaagacaga taaatgggcc     660
gtgtgttaag ttaacagagt gttaacgttc ggtttcaaat gccaacgcca taggaacaaa     720
acaaacgtgt cctcaagtaa acccctgccg tttacacctc aatggctgca tggtgaagcc     780
attaacacgt ggcgtaggat gcatgacgac gccattgaca cctgactctc ttcccttctc     840
ttcatatatc tctaatcaat tcaactactc attgtcatag ctattcggaa aatacataca     900
catccttttc tcttcgatct ctctcaattc acaagaagca agtcgacgg atccctgcag     960 taaattacgc catgactatt ttcatagtcc aataaggctg atgtcgggag tccagtttat    1020
gagcaataag gtgtttagaa tttgatcaat gtttataata aaggggaa gatgatatca    1080 cagtcttttg ttctttttgg cttttgttaa atttgtgtgt ttctatttgt aaacctcctg    1140
tatatgttgt acttctttcc cttttttaagt ggtatcgtct atatggtaaa acgttatgtt    1200
tggtctttcc ttttctctgt ttaggataaa aagactgcat gttttatctt tagttatatt    1260
atgttgagta aatgaacttt catagatctg gttccgtaga gtagactagc agccgagctg    1320
```

-continued

```
agctgaactg aacagctggc aatgtgaaca ctggatgcaa gatcagatgt gaagatctct    1380
aatatggtgg tgggattgaa catatcgtgt ctatattttt gttggcatta agctcttaac    1440
atagatataa ctgatgcagt cattggttca tacacatata tagtaaggaa ttacaatggc    1500
aacccaaact tcaaaaacag taggccacct gaattgcctt atcgaataag agtttgtttc    1560
cccccacttc atgggatgta atacatggga tttgggagtt tgaatgaacg ttgagacatg    1620
gcagaacctc tagaggtacc ggcgcgc                                        1647
```

<210> SEQ ID NO 8
<211> LENGTH: 1810
<212> TYPE: DNA
<213> ORGANISM: Brassica sp.
<220> FEATURE:
<221> NAME/KEY: CDS
<222> LOCATION: (4)..(1647)

<400> SEQUENCE: 8

```
gaa atg agt agg tct agc gaa caa gat cta ctc tct acc gag att gtt      48
    Met Ser Arg Ser Ser Glu Gln Asp Leu Leu Ser Thr Glu Ile Val
    1               5                  10                  15 aac cgt ggg atc gaa cct tcc ggt cca aac gcc ggt tca cca acg ttc      96
Asn Arg Gly Ile Glu Pro Ser Gly Pro Asn Ala Gly Ser Pro Thr Phe
                20                  25                  30 tcg gtc aga gtc cgg aga cgt tta ccg gat ttt ctt caa tcc gta aac    144
Ser Val Arg Val Arg Arg Leu Pro Asp Phe Leu Gln Ser Val Asn
            35                  40                  45 ttg aag tac gtg aaa ctt ggt tat cac tac ctc ata aac cat gcg gtt    192
Leu Lys Tyr Val Lys Leu Gly Tyr His Tyr Leu Ile Asn His Ala Val
        50                  55                  60 tac ttg gcg acg ata ccg gtt ctt gtg ctt gtg ttt agt gcc gaa gtt    240
Tyr Leu Ala Thr Ile Pro Val Leu Val Leu Val Phe Ser Ala Glu Val
 65                  70                  75 ggg agt tta agc gga gaa gag att tgg aag aag ctt tgg gac tat gat    288
Gly Ser Leu Ser Gly Glu Glu Ile Trp Lys Lys Leu Trp Asp Tyr Asp
 80                  85                  90                  95 atc gca acc gtc atc gga ttc ttc ggt gtc ttt gtc ttg acc gtt tgc    336
Ile Ala Thr Val Ile Gly Phe Phe Gly Val Phe Val Leu Thr Val Cys
                100                 105                 110 gtc tac ttc atg tct cgt cca cga tct gtt tat ctc att gac ttc gct    384
Val Tyr Phe Met Ser Arg Pro Arg Ser Val Tyr Leu Ile Asp Phe Ala
            115                 120                 125 tgt ttc aag cct tcc gat gaa ctt aag gtg aca aga gaa gag ttc ata    432
Cys Phe Lys Pro Ser Asp Glu Leu Lys Val Thr Arg Glu Glu Phe Ile
        130                 135                 140 gat cta gct aga aaa tca ggc aag ttc gac gaa gag atc ctc gga ttc    480
Asp Leu Ala Arg Lys Ser Gly Lys Phe Asp Glu Glu Ile Leu Gly Phe
145                 150                 155 aag aag agg atc ctt caa gcc tca gga ata ggc gat gaa acg tac gtc    528
Lys Lys Arg Ile Leu Gln Ala Ser Gly Ile Gly Asp Glu Thr Tyr Val
160                 165                 170                 175 cca aga tca atc tct tcg tcg gaa aac aca aca acg atg aaa gaa ggt    576
Pro Arg Ser Ile Ser Ser Ser Glu Asn Thr Thr Thr Met Lys Glu Gly
                180                 185                 190 cgt gaa gaa gcc tcg atg atg ata ttc ggc gca ctc gac gaa ctc ttc    624
Arg Glu Glu Ala Ser Met Met Ile Phe Gly Ala Leu Asp Glu Leu Phe
            195                 200                 205 gag aag aca cgt gtc aaa ccg aaa gac gta ggt gtc ctc gtg gtt aac    672
Glu Lys Thr Arg Val Lys Pro Lys Asp Val Gly Val Leu Val Val Asn
        210                 215                 220
```

-continued

```
tgc agt atc ttt aac ccg act ccg tca ctc tcc gcg atg gtg att aac      720
Cys Ser Ile Phe Asn Pro Thr Pro Ser Leu Ser Ala Met Val Ile Asn
225                 230                 235 cac tac aag atg aga ggg aac ata ctt agc tac aac cta gga ggg atg      768
His Tyr Lys Met Arg Gly Asn Ile Leu Ser Tyr Asn Leu Gly Gly Met
240                 245                 250                 255 ggt tgc tca gca gga atc ata gcc gtt gat ctt gct cgt gac atg ctt      816
Gly Cys Ser Ala Gly Ile Ile Ala Val Asp Leu Ala Arg Asp Met Leu
                260                 265                 270 cag tct aac ccg aat agt tac gcg gtg gtt gtg agt acc gag atg gtt      864
Gln Ser Asn Pro Asn Ser Tyr Ala Val Val Val Ser Thr Glu Met Val
            275                 280                 285 ggg tat aat tgg tac gtg gga cgt gac aag tca atg gtt ata cct aac      912
Gly Tyr Asn Trp Tyr Val Gly Arg Asp Lys Ser Met Val Ile Pro Asn
        290                 295                 300 tgc ttc ttt agg atg ggt tgc tcc gcc gtt atg ctg tct aac cgc cgc      960
Cys Phe Phe Arg Met Gly Cys Ser Ala Val Met Leu Ser Asn Arg Arg
    305                 310                 315 cgt gac ttc cgc cat gct aag tac cgc ctt gag cac att gtc cgg act     1008
Arg Asp Phe Arg His Ala Lys Tyr Arg Leu Glu His Ile Val Arg Thr
320                 325                 330                 335 cac aag gct gcc gac gac cgt agc ttc agg agt gtg tac cag gaa gaa     1056
His Lys Ala Ala Asp Asp Arg Ser Phe Arg Ser Val Tyr Gln Glu Glu
                340                 345                 350 gat gaa caa gga ttc aag gga tta aaa ata agc aga gac cta atg gaa     1104
Asp Glu Gln Gly Phe Lys Gly Leu Lys Ile Ser Arg Asp Leu Met Glu
            355                 360                 365 gtt gga ggt gaa gct ctc aag acc aac atc acc acc tta ggc cct ctc     1152
Val Gly Gly Glu Ala Leu Lys Thr Asn Ile Thr Thr Leu Gly Pro Leu
        370                 375                 380 gtc ctt cct ttc tcc gag cag ctt ctc ttc ttt gcc gct ttg atc cgt     1200
Val Leu Pro Phe Ser Glu Gln Leu Leu Phe Phe Ala Ala Leu Ile Arg
    385                 390                 395 aga act ttc tca ccc gcc gcc aaa act acc acc acc tcc tcc tca gcc     1248
Arg Thr Phe Ser Pro Ala Ala Lys Thr Thr Thr Thr Ser Ser Ser Ala
400                 405                 410                 415 act gcg aaa atc aac gga gcc aag tcg tca tcc tcc tct gat cta tcc     1296
Thr Ala Lys Ile Asn Gly Ala Lys Ser Ser Ser Ser Ser Asp Leu Ser
                420                 425                 430 aag ccg tac atc ccg gac tac aag ctt gcc ttc gag cat ttc tgc ttc     1344
Lys Pro Tyr Ile Pro Asp Tyr Lys Leu Ala Phe Glu His Phe Cys Phe
            435                 440                 445 cac gcg gca agc aaa gcg gtg ctt gag gag ctt cag aag aat cta ggc     1392
His Ala Ala Ser Lys Ala Val Leu Glu Glu Leu Gln Lys Asn Leu Gly
        450                 455                 460 ttg agt gat gag aac atg gag gct tct aag atg act tta cac agg ttt     1440
Leu Ser Asp Glu Asn Met Glu Ala Ser Lys Met Thr Leu His Arg Phe
    465                 470                 475 gga aac act tcc agc agt gga atc tgg tac gag ctt gct tac atg gag     1488
Gly Asn Thr Ser Ser Ser Gly Ile Trp Tyr Glu Leu Ala Tyr Met Glu
480                 485                 490                 495 gcc aag gag agt gtt cgt aga ggc gat agg gtt tgg cag att gct ttt     1536
Ala Lys Glu Ser Val Arg Arg Gly Asp Arg Val Trp Gln Ile Ala Phe
                500                 505                 510 ggg tca ggt ttt aag tgt aac agt gtg gtt tgg aag gca atg agg aag     1584
Gly Ser Gly Phe Lys Cys Asn Ser Val Val Trp Lys Ala Met Arg Lys
            515                 520                 525 gtg aag aag ccg gca agg aac aat cct tgg gtt gat tgc att aac cgt     1632
Val Lys Lys Pro Ala Arg Asn Asn Pro Trp Val Asp Cys Ile Asn Arg
```

-continued

```
                530                 535                 540
tac cct gtc gct ctc tgatcattta tttttaaaat tattatttct tcttaattaa      1687
Tyr Pro Val Ala Leu
        545 atcatctatg atctctcttc cttgttgttg gatgatagac gtttgtttgc tggtcattcg    1747 tatcttaaga cttctataag aatggatggt tcaagtccaa aaaaaaaaaa aaaaaaaaa    1807 aaa                                                                  1810

<210> SEQ ID NO 9
<211> LENGTH: 548
<212> TYPE: PRT
<213> ORGANISM: Brassica sp.

<400> SEQUENCE: 9

Met Ser Arg Ser Ser Glu Gln Asp Leu Leu Ser Thr Glu Ile Val Asn
 1               5                  10                  15

Arg Gly Ile Glu Pro Ser Gly Pro Asn Ala Gly Ser Pro Thr Phe Ser
             20                  25                  30

Val Arg Val Arg Arg Leu Pro Asp Phe Leu Gln Ser Val Asn Leu
         35                  40                  45

Lys Tyr Val Lys Leu Gly Tyr His Tyr Leu Ile Asn His Ala Val Tyr
     50                  55                  60

Leu Ala Thr Ile Pro Val Leu Val Leu Val Phe Ser Ala Glu Val Gly
 65                  70                  75                  80

Ser Leu Ser Gly Glu Glu Ile Trp Lys Lys Leu Trp Asp Tyr Asp Ile
                 85                  90                  95

Ala Thr Val Ile Gly Phe Phe Gly Val Phe Val Leu Thr Val Cys Val
            100                 105                 110

Tyr Phe Met Ser Arg Pro Arg Ser Val Tyr Leu Ile Asp Phe Ala Cys
        115                 120                 125

Phe Lys Pro Ser Asp Glu Leu Lys Val Thr Arg Glu Glu Phe Ile Asp
    130                 135                 140

Leu Ala Arg Lys Ser Gly Lys Phe Asp Glu Glu Ile Leu Gly Phe Lys
145                 150                 155                 160

Lys Arg Ile Leu Gln Ala Ser Gly Ile Gly Asp Glu Thr Tyr Val Pro
                165                 170                 175

Arg Ser Ile Ser Ser Glu Asn Thr Thr Met Lys Glu Gly Arg
            180                 185                 190

Glu Glu Ala Ser Met Met Ile Phe Gly Ala Leu Asp Glu Leu Phe Glu
        195                 200                 205

Lys Thr Arg Val Lys Pro Lys Asp Val Gly Val Leu Val Asn Cys
    210                 215                 220

Ser Ile Phe Asn Pro Thr Pro Ser Leu Ser Ala Met Val Ile Asn His
225                 230                 235                 240

Tyr Lys Met Arg Gly Asn Ile Leu Ser Tyr Asn Leu Gly Gly Met Gly
                245                 250                 255

Cys Ser Ala Gly Ile Ile Ala Val Asp Leu Ala Arg Asp Met Leu Gln
            260                 265                 270

Ser Asn Pro Asn Ser Tyr Ala Val Val Ser Thr Glu Met Val Gly
        275                 280                 285

Tyr Asn Trp Tyr Val Gly Arg Asp Lys Ser Met Val Ile Pro Asn Cys
    290                 295                 300

Phe Phe Arg Met Gly Cys Ser Ala Val Met Leu Ser Asn Arg Arg Arg
305                 310                 315                 320
```

```
Asp Phe Arg His Ala Lys Tyr Arg Leu Glu His Ile Val Arg Thr His
            325                 330                 335
Lys Ala Ala Asp Asp Arg Ser Phe Arg Ser Val Tyr Gln Glu Glu Asp
            340                 345                 350
Glu Gln Gly Phe Lys Gly Leu Lys Ile Ser Arg Asp Leu Met Glu Val
            355                 360                 365
Gly Gly Glu Ala Leu Lys Thr Asn Ile Thr Thr Leu Gly Pro Leu Val
370                 375                 380
Leu Pro Phe Ser Glu Gln Leu Leu Phe Phe Ala Ala Leu Ile Arg Arg
385                 390                 395                 400
Thr Phe Ser Pro Ala Ala Lys Thr Thr Thr Thr Ser Ser Ser Ala Thr
                405                 410                 415
Ala Lys Ile Asn Gly Ala Lys Ser Ser Ser Ser Asp Leu Ser Lys
                420                 425                 430
Pro Tyr Ile Pro Asp Tyr Lys Leu Ala Phe Glu His Phe Cys Phe His
                435                 440                 445
Ala Ala Ser Lys Ala Val Leu Glu Glu Leu Gln Lys Asn Leu Gly Leu
450                 455                 460
Ser Asp Glu Asn Met Glu Ala Ser Lys Met Thr Leu His Arg Phe Gly
465                 470                 475                 480
Asn Thr Ser Ser Ser Gly Ile Trp Tyr Glu Leu Ala Tyr Met Glu Ala
                485                 490                 495
Lys Glu Ser Val Arg Arg Gly Asp Arg Val Trp Gln Ile Ala Phe Gly
                500                 505                 510
Ser Gly Phe Lys Cys Asn Ser Val Val Trp Lys Ala Met Arg Lys Val
                515                 520                 525
Lys Lys Pro Ala Arg Asn Asn Pro Trp Val Asp Cys Ile Asn Arg Tyr
530                 535                 540
Pro Val Ala Leu
545

<210> SEQ ID NO 10
<211> LENGTH: 1442
<212> TYPE: DNA
<213> ORGANISM: Brassica sp.
<220> FEATURE:
<221> NAME/KEY: CDS
<222> LOCATION: (10)..(1434)

<400> SEQUENCE: 10 gtcgacaaa atg acg tcc att aac gta aag ctc ctt tac cat tac gtc ata      51
           Met Thr Ser Ile Asn Val Lys Leu Leu Tyr His Tyr Val Ile
             1               5                  10 acc aac ctt ttc aac ctt tgt ttc ttt cca tta acg gcg atc gtc gcc      99
Thr Asn Leu Phe Asn Leu Cys Phe Phe Pro Leu Thr Ala Ile Val Ala
15                  20                  25                  30 gga aaa gcc tat cgg ctt acc ata gac gat ctt cac cac tta tac tat     147
Gly Lys Ala Tyr Arg Leu Thr Ile Asp Asp Leu His His Leu Tyr Tyr
                 35                  40                  45 tcc tat ctc caa cac aac ctc ata acc att gct cca ctc ttt gcc ttc     195
Ser Tyr Leu Gln His Asn Leu Ile Thr Ile Ala Pro Leu Phe Ala Phe
             50                  55                  60 acc gtt ttc ggt tcg gtt ctc tac atc gca acc cgg ccc aaa ccg gtt     243
Thr Val Phe Gly Ser Val Leu Tyr Ile Ala Thr Arg Pro Lys Pro Val
         65                  70                  75 tac ctc gtt gag tac tca tgc tac ctt cca cca acg cat tgt aga tca     291
Tyr Leu Val Glu Tyr Ser Cys Tyr Leu Pro Pro Thr His Cys Arg Ser
```

```
                    80                  85                  90
agt atc tcc aag gtc atg gat atc ttt tac caa gta aga aaa gct gat      339
Ser Ile Ser Lys Val Met Asp Ile Phe Tyr Gln Val Arg Lys Ala Asp
 95                 100                 105                 110 cct tct cgg aac ggc acg tgc gat gac tcg tcc tgg ctt gac ttc ttg      387
Pro Ser Arg Asn Gly Thr Cys Asp Asp Ser Ser Trp Leu Asp Phe Leu
                    115                 120                 125 agg aag att caa gaa cgt tca ggt cta ggc gat gaa acc cac ggg ccc      435
Arg Lys Ile Gln Glu Arg Ser Gly Leu Gly Asp Glu Thr His Gly Pro
                130                 135                 140 gag ggg ctg ctt cag gtc cct ccc cgg aag act ttt gcg gcg gcg cgt      483
Glu Gly Leu Leu Gln Val Pro Pro Arg Lys Thr Phe Ala Ala Ala Arg
            145                 150                 155 gaa gag acg gag caa gtt atc att ggt gcg cta gaa aat cta ttc aag      531
Glu Glu Thr Glu Gln Val Ile Ile Gly Ala Leu Glu Asn Leu Phe Lys
        160                 165                 170 aac acc aat gtt aac cct aaa gat ata ggt ata ctt gtg gtg aac tca      579
Asn Thr Asn Val Asn Pro Lys Asp Ile Gly Ile Leu Val Val Asn Ser
175                 180                 185                 190 agc atg ttt aat cca act cct tcg ctc tcc gcg atg gtc gtt aac act      627
Ser Met Phe Asn Pro Thr Pro Ser Leu Ser Ala Met Val Val Asn Thr
                    195                 200                 205 ttc aag ctc cga agc aac gta aga agc ttt aac ctt ggt ggc atg ggt      675
Phe Lys Leu Arg Ser Asn Val Arg Ser Phe Asn Leu Gly Gly Met Gly
                210                 215                 220 tgt agt gcc ggc gtt ata gcc att gat cta gca aag gac ttg ttg cat      723
Cys Ser Ala Gly Val Ile Ala Ile Asp Leu Ala Lys Asp Leu Leu His
            225                 230                 235 gtc cat aaa aat acg tat gct ctt gtg gtg agc aca gag aac atc act      771
Val His Lys Asn Thr Tyr Ala Leu Val Val Ser Thr Glu Asn Ile Thr
        240                 245                 250 tat aac att tac gct ggt gat aat agg tcc atg atg gtt tca aat tgc      819
Tyr Asn Ile Tyr Ala Gly Asp Asn Arg Ser Met Met Val Ser Asn Cys
255                 260                 265                 270 ttg ttc cgt gtt ggt ggg gcc gct att ttg ctc tcc aac aag cct aga      867
Leu Phe Arg Val Gly Gly Ala Ala Ile Leu Leu Ser Asn Lys Pro Arg
                    275                 280                 285 gat cgt aga cgg tcc aag tac gag cta gtt cac acg gtt cga acg cat      915
Asp Arg Arg Arg Ser Lys Tyr Glu Leu Val His Thr Val Arg Thr His
                290                 295                 300 acc gga gct gac gac aag tct ttt cgt tgc gtg caa caa gga gac gtt      963
Thr Gly Ala Asp Asp Lys Ser Phe Arg Cys Val Gln Gln Gly Asp Val
            305                 310                 315 gag aac ggc aaa acc gga gtg agt ttg tcc aag gac ata acc gat gtt     1011
Glu Asn Gly Lys Thr Gly Val Ser Leu Ser Lys Asp Ile Thr Asp Val
        320                 325                 330 gct ggt cga acg gtt aag aaa aac ata gca acg ctg ggt ccg ttg att     1059
Ala Gly Arg Thr Val Lys Lys Asn Ile Ala Thr Leu Gly Pro Leu Ile
335                 340                 345                 350 ctt ccg tta agc gag aaa ctt ctt ttt ttc gtt acc ttc atg ggc aag     1107
Leu Pro Leu Ser Glu Lys Leu Leu Phe Phe Val Thr Phe Met Gly Lys
                    355                 360                 365 aaa ctt ttc aaa gac aaa atc aaa cat tat tac gtc ccg gac ttc aag     1155
Lys Leu Phe Lys Asp Lys Ile Lys His Tyr Tyr Val Pro Asp Phe Lys
                370                 375                 380 ctt gct atc gac cat ttt tgt ata cat gcc gga ggc aaa gcc gtg att     1203
Leu Ala Ile Asp His Phe Cys Ile His Ala Gly Gly Lys Ala Val Ile
            385                 390                 395 gat gtg cta gag aag aac cta ggc cta gca ccg atc gat gta gag gca     1251
```

```
Asp Val Leu Glu Lys Asn Leu Gly Leu Ala Pro Ile Asp Val Glu Ala
    400                 405                 410 tca aga tca acg tta cat aga ttt gga aac act tca tct agc tca ata      1299
Ser Arg Ser Thr Leu His Arg Phe Gly Asn Thr Ser Ser Ser Ser Ile
415                 420                 425                 430 tgg tat gag ttg gca tac ata gaa gca aaa gga agg atg aag aaa ggt      1347
Trp Tyr Glu Leu Ala Tyr Ile Glu Ala Lys Gly Arg Met Lys Lys Gly
                435                 440                 445 aat aaa gtt tgg cag att gct tta ggg tca ggc ttt aag tgt aac agt      1395
Asn Lys Val Trp Gln Ile Ala Leu Gly Ser Gly Phe Lys Cys Asn Ser
        450                 455                 460 gca gtt tgg gtg gct cta aac aat gtc aaa gct tcc aaa taggatcc         1442
Ala Val Trp Val Ala Leu Asn Asn Val Lys Ala Ser Lys
            465                 470                 475

<210> SEQ ID NO 11
<211> LENGTH: 475
<212> TYPE: PRT
<213> ORGANISM: Brassica sp.

<400> SEQUENCE: 11

Met Thr Ser Ile Asn Val Lys Leu Leu Tyr His Tyr Val Ile Thr Asn
  1               5                  10                  15

Leu Phe Asn Leu Cys Phe Phe Pro Leu Thr Ala Ile Val Ala Gly Lys
             20                  25                  30

Ala Tyr Arg Leu Thr Ile Asp Asp Leu His His Leu Tyr Tyr Ser Tyr
         35                  40                  45

Leu Gln His Asn Leu Ile Thr Ile Ala Pro Leu Phe Ala Phe Thr Val
     50                  55                  60

Phe Gly Ser Val Leu Tyr Ile Ala Thr Arg Pro Lys Pro Val Tyr Leu
 65                  70                  75                  80

Val Glu Tyr Ser Cys Tyr Leu Pro Pro Thr His Cys Arg Ser Ser Ile
                 85                  90                  95

Ser Lys Val Met Asp Ile Phe Tyr Gln Val Arg Lys Ala Asp Pro Ser
            100                 105                 110

Arg Asn Gly Thr Cys Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Arg Asp Arg
```

-continued

```
                275                 280                 285
Arg Arg Ser Lys Tyr Glu Leu Val His Thr Val Arg Thr His Thr Gly
    290                 295                 300

Ala Asp Asp Lys Ser Phe Arg Cys Val Gln Gln Gly Asp Val Glu Asn
305                 310                 315                 320

Gly Lys Thr Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
370                 375                 380

Ile Asp His Phe Cys Ile His Ala Gly Gly Lys Ala Val Ile Asp Val
385                 390                 395                 400

Leu Glu Lys Asn Leu Gly Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Lys
465                 470                 475

<210> SEQ ID NO 12
<211> LENGTH: 1442
<212> TYPE: DNA
<213> ORGANISM: Brassica sp.
<220> FEATURE:
<221> NAME/KEY: CDS
<222> LOCATION: (10)..(1434)

<400> SEQUENCE: 12 gtcgacaaa atg acg tcc att aac gta aag ctc ctt tac cat tac gtc ata     51
          Met Thr Ser Ile Asn Val Lys Leu Leu Tyr His Tyr Val Ile
            1               5                   10 acc aac ctt ttc aac ctt tgc ttc ttt ccg tta acg gcg atc gtc gcc     99
Thr Asn Leu Phe Asn Leu Cys Phe Phe Pro Leu Thr Ala Ile Val Ala
 15              20                  25                  30 gga aaa gcc tat cgg ctt acc ata gac gat ctt cac cac tta tac tat    147
Gly Lys Ala Tyr Arg Leu Thr Ile Asp Asp Leu His His Leu Tyr Tyr
             35                  40                  45 tcc tat ctc caa cac aac ctc ata acc atc gct cca ctc ttt gcc ttc    195
Ser Tyr Leu Gln His Asn Leu Ile Thr Ile Ala Pro Leu Phe Ala Phe
         50                  55                  60 acc gtt ttc ggt tcg gtt ctc tac atc gca acc cgg ccc aaa ccg gtt    243
Thr Val Phe Gly Ser Val Leu Tyr Ile Ala Thr Arg Pro Lys Pro Val
     65                  70                  75 tac ctc gtt gag tac tca tgc tac ctt cca cca acg cat tgt aga tca    291
Tyr Leu Val Glu Tyr Ser Cys Tyr Leu Pro Pro Thr His Cys Arg Ser
 80                  85                  90 agt atc tcc aag gtc atg gat atc ttt tat caa gta aga aaa gct gat    339
Ser Ile Ser Lys Val Met Asp Ile Phe Tyr Gln Val Arg Lys Ala Asp
 95                 100                 105                 110 cct tct cgg aac ggc acg tgc gat gac tcg tcg tgg ctt gac ttc ttg    387
Pro Ser Arg Asn Gly Thr Cys Asp Asp Ser Ser Trp Leu Asp Phe Leu
```

-continued

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 115 |     |     |     |     | 120 |     |     |     |     | 125 |     |     |      |
| agg | aag | att | caa | gaa | cgt | tca | ggt | cta | ggc | gat | gaa | act | cac | ggg | ccc | 435  |
| Arg | Lys | Ile | Gln | Glu | Arg | Ser | Gly | Leu | Gly | Asp | Glu | Thr | His | Gly | Pro |      |
|     |     |     | 130 |     |     |     |     | 135 |     |     |     |     | 140 |     |     |      |
| gag | ggg | ctg | ctt | cag | gtc | cct | ccc | cgg | aag | act | ttt | gcg | gcg | gcg | cgt | 483  |
| Glu | Gly | Leu | Leu | Gln | Val | Pro | Pro | Arg | Lys | Thr | Phe | Ala | Ala | Ala | Arg |      |
|     |     |     | 145 |     |     |     |     | 150 |     |     |     |     | 155 |     |     |      |
| gaa | gag | acg | gag | caa | gtt | atc | att | ggt | gcg | cta | gaa | aat | cta | ttc | aag | 531  |
| Glu | Glu | Thr | Glu | Gln | Val | Ile | Ile | Gly | Ala | Leu | Glu | Asn | Leu | Phe | Lys |      |
|     | 160 |     |     |     |     | 165 |     |     |     |     | 170 |     |     |     |     |      |
| aac | acc | aac | gtt | aac | cct | aaa | gat | ata | ggt | ata | ctt | gtg | gtg | aac | tca | 579  |
| Asn | Thr | Asn | Val | Asn | Pro | Lys | Asp | Ile | Gly | Ile | Leu | Val | Val | Asn | Ser |      |
| 175 |     |     |     |     | 180 |     |     |     |     | 185 |     |     |     |     | 190 |      |
| agc | atg | ttt | aat | cca | act | cca | tcg | ctc | tcc | gcg | atg | gtc | gtt | aac | act | 627  |
| Ser | Met | Phe | Asn | Pro | Thr | Pro | Ser | Leu | Ser | Ala | Met | Val | Val | Asn | Thr |      |
|     |     |     |     | 195 |     |     |     |     | 200 |     |     |     |     | 205 |     |      |
| ttc | aag | ctc | cga | agc | aac | gta | aga | agc | ttt | aac | ctt | ggt | ggc | atg | ggt | 675  |
| Phe | Lys | Leu | Arg | Ser | Asn | Val | Arg | Ser | Phe | Asn | Leu | Gly | Gly | Met | Gly |      |
|     |     |     | 210 |     |     |     |     | 215 |     |     |     |     | 220 |     |     |      |
| tgt | agt | gcc | ggc | gtt | ata | gcc | att | gat | cta | gca | aag | gac | ttg | ttg | cat | 723  |
| Cys | Ser | Ala | Gly | Val | Ile | Ala | Ile | Asp | Leu | Ala | Lys | Asp | Leu | Leu | His |      |
|     |     | 225 |     |     |     |     | 230 |     |     |     |     | 235 |     |     |     |      |
| gtc | cat | aaa | aat | acg | tat | gct | ctt | gtg | gtg | agc | aca | gag | aac | atc | act | 771  |
| Val | His | Lys | Asn | Thr | Tyr | Ala | Leu | Val | Val | Ser | Thr | Glu | Asn | Ile | Thr |      |
|     | 240 |     |     |     |     | 245 |     |     |     |     | 250 |     |     |     |     |      |
| tat | aac | att | tac | gct | ggt | gat | aat | agg | tcc | atg | atg | gtt | tca | aat | tgc | 819  |
| Tyr | Asn | Ile | Tyr | Ala | Gly | Asp | Asn | Arg | Ser | Met | Met | Val | Ser | Asn | Cys |      |
| 255 |     |     |     |     | 260 |     |     |     |     | 265 |     |     |     |     | 270 |      |
| ttg | ttc | cgt | gtt | ggt | ggg | gcc | gct | att | ttg | ctc | tcc | aac | aag | cct | gga | 867  |
| Leu | Phe | Arg | Val | Gly | Gly | Ala | Ala | Ile | Leu | Leu | Ser | Asn | Lys | Pro | Gly |      |
|     |     |     |     | 275 |     |     |     |     | 280 |     |     |     |     | 285 |     |      |
| gat | cgt | aga | cgg | tcc | aag | tac | gag | cta | gtt | cac | acg | gtt | cga | acg | cat | 915  |
| Asp | Arg | Arg | Arg | Ser | Lys | Tyr | Glu | Leu | Val | His | Thr | Val | Arg | Thr | His |      |
|     |     |     | 290 |     |     |     |     | 295 |     |     |     |     | 300 |     |     |      |
| acc | gga | gct | gac | gac | aag | tct | ttt | cgt | tgc | gtg | caa | caa | gga | gac | gat | 963  |
| Thr | Gly | Ala | Asp | Asp | Lys | Ser | Phe | Arg | Cys | Val | Gln | Gln | Gly | Asp | Asp |      |
|     |     | 305 |     |     |     |     | 310 |     |     |     |     | 315 |     |     |     |      |
| gag | aac | ggc | aaa | atc | gga | gtg | agt | ttg | tcc | aag | gac | ata | acc | gat | gtt | 1011 |
| Glu | Asn | Gly | Lys | Ile | Gly | Val | Ser | Leu | Ser | Lys | Asp | Ile | Thr | Asp | Val |      |
|     | 320 |     |     |     |     | 325 |     |     |     |     | 330 |     |     |     |     |      |
| gct | ggt | cga | acg | gtt | aag | aaa | aac | ata | gca | acg | ttg | ggt | ccg | ttg | att | 1059 |
| Ala | Gly | Arg | Thr | Val | Lys | Lys | Asn | Ile | Ala | Thr | Leu | Gly | Pro | Leu | Ile |      |
| 335 |     |     |     |     | 340 |     |     |     |     | 345 |     |     |     |     | 350 |      |
| ctt | ccg | tta | agc | gag | aaa | ctt | ctt | ttt | ttc | gtt | acc | ttc | atg | ggc | aag | 1107 |
| Leu | Pro | Leu | Ser | Glu | Lys | Leu | Leu | Phe | Phe | Val | Thr | Phe | Met | Gly | Lys |      |
|     |     |     |     | 355 |     |     |     |     | 360 |     |     |     |     | 365 |     |      |
| aaa | ctt | ttc | aaa | gat | aaa | atc | aaa | cat | tac | tac | gtc | ccg | gat | ttc | aaa | 1155 |
| Lys | Leu | Phe | Lys | Asp | Lys | Ile | Lys | His | Tyr | Tyr | Val | Pro | Asp | Phe | Lys |      |
|     |     |     | 370 |     |     |     |     | 375 |     |     |     |     | 380 |     |     |      |
| ctt | gct | att | gac | cat | ttt | tgt | ata | cat | gcc | gga | ggc | aga | gcc | gtg | att | 1203 |
| Leu | Ala | Ile | Asp | His | Phe | Cys | Ile | His | Ala | Gly | Gly | Arg | Ala | Val | Ile |      |
|     |     | 385 |     |     |     |     | 390 |     |     |     |     | 395 |     |     |     |      |
| gat | gtg | cta | gag | aag | aac | cta | gcc | cta | gca | ccg | atc | gat | gta | gag | gca | 1251 |
| Asp | Val | Leu | Glu | Lys | Asn | Leu | Ala | Leu | Ala | Pro | Ile | Asp | Val | Glu | Ala |      |
|     | 400 |     |     |     |     | 405 |     |     |     |     | 410 |     |     |     |     |      |
| tca | aga | tca | acg | tta | cat | aga | ttt | gga | aac | act | tca | tct | agc | tca | ata | 1299 |
| Ser | Arg | Ser | Thr | Leu | His | Arg | Phe | Gly | Asn | Thr | Ser | Ser | Ser | Ser | Ile |      |
| 415 |     |     |     |     | 420 |     |     |     |     | 425 |     |     |     |     | 430 |      |
| tgg | tat | gag | ttg | gca | tac | ata | gaa | gca | aaa | gga | agg | atg | aag | aaa | ggt | 1347 |

|     |     |     |     |     |     |     |     |     |     |     |     |     | |
|---|---|---|---|---|---|---|---|---|---|---|---|---|---|
| Trp | Tyr | Glu | Leu | Ala | Tyr | Ile | Glu | Ala | Lys | Gly | Arg | Met | Lys Lys Gly |
|     |     |     |     | 435 |     |     |     | 440 |     |     |     | 445 | |

```
aat aaa gtt tgg cag att gct tta ggg tca ggc ttt aag tgt aac agt       1395
Asn Lys Val Trp Gln Ile Ala Leu Gly Ser Gly Phe Lys Cys Asn Ser
            450                 455                 460 gca gtt tgg gtg gct cta aac aat gtc aaa gct tcc aaa taggatcc          1442
Ala Val Trp Val Ala Leu Asn Asn Val Lys Ala Ser Lys
        465                 470                 475
```

<210> SEQ ID NO 13
<211> LENGTH: 475
<212> TYPE: PRT
<213> ORGANISM: Brassica sp.

<400> SEQUENCE: 13

```
Met Thr Ser Ile Asn Val Lys Leu Leu Tyr His Tyr Val Ile Thr Asn
 1               5                  10                  15

Leu Phe Asn Leu Cys Phe Phe Pro Leu Thr Ala Ile Val Ala Gly Lys
            20                  25                  30

Ala Tyr Arg Leu Thr Ile Asp Asp Leu His His Leu Tyr Tyr Ser Tyr
        35                  40                  45

Leu Gln His Asn Leu Ile Thr Ile Ala Pro Leu Phe Ala Phe Thr Val
    50                  55                  60

Phe Gly Ser Val Leu Tyr Ile Ala Thr Arg Pro Lys Pro Val Tyr Leu
65                  70                  75                  80

Val Glu Tyr Ser Cys Tyr Leu Pro Pro Thr His Cys Arg Ser Ser Ile
                85                  90                  95

Ser Lys Val Met Asp Ile Phe Tyr Gln Val Arg Lys Ala Asp Pro Ser
            100                 105                 110

Arg Asn Gly Thr Cys Asp Asp Ser Ser Trp Leu Asp Phe Leu Arg Lys
        115                 120                 125

Ile Gln Glu Arg Ser Gly Leu Gly Asp Glu Thr His Gly Pro Glu Gly
    130                 135                 140

Leu Leu Gln Val Pro Pro Arg Lys Thr Phe Ala Ala Arg Glu Glu
145                 150                 155                 160

Thr Glu Gln Val Ile Ile Gly Ala Leu Glu Asn Leu Phe Lys Asn Thr
                165                 170                 175

Asn Val Asn Pro Lys Asp Ile Gly Ile Leu Val Val Asn Ser Ser Met
            180                 185                 190

Phe Asn Pro Thr Pro Ser Leu Ser Ala Met Val Val Asn Thr Phe Lys
        195                 200                 205

Leu Arg Ser Asn Val Arg Ser Phe Asn Leu Gly Gly Met Gly Cys Ser
    210                 215                 220

Ala Gly Val Ile Ala Ile Asp Leu Ala Lys Asp Leu Leu His Val His
225                 230                 235                 240

Lys Asn Thr Tyr Ala Leu Val Val Ser Thr Glu Asn Ile Thr Tyr Asn
                245                 250                 255

Ile Tyr Ala Gly Asp Asn Arg Ser Met Met Val Ser Asn Cys Leu Phe
            260                 265                 270

Arg Val Gly Gly Ala Ala Ile Leu Leu Ser Asn Lys Pro Gly Asp Arg
        275                 280                 285

Arg Arg Ser Lys Tyr Glu Leu Val His Thr Val Arg Thr His Thr Gly
    290                 295                 300

Ala Asp Asp Lys Ser Phe Arg Cys Val Gln Gln Gly Asp Asp Glu Asn
305                 310                 315                 320
```

```
Gly Lys Ile Gly Val Ser Leu Ser Lys Asp Ile Thr Asp Val Ala Gly
                325                 330                 335

Arg Thr Val Lys Lys Asn Ile Ala Thr Leu Gly Pro Leu Ile Leu Pro
            340                 345                 350

Leu Ser Glu Lys Leu Leu Phe Phe Val Thr Phe Met Gly Lys Lys Leu
        355                 360                 365

Phe Lys Asp Lys Ile Lys His Tyr Tyr Val Pro Asp Phe Lys Leu Ala
    370                 375                 380

Ile Asp His Phe Cys Ile His Ala Gly Gly Arg Ala Val Ile Asp Val
385                 390                 395                 400

Leu Glu Lys Asn Leu Ala Leu Ala Pro Ile Asp Val Glu Ala Ser Arg
                405                 410                 415

Ser Thr Leu His Arg Phe Gly Asn Thr Ser Ser Ser Ile Trp Tyr
            420                 425                 430

Glu Leu Ala Tyr Ile Glu Ala Lys Gly Arg Met Lys Lys Gly Asn Lys
        435                 440                 445

Val Trp Gln Ile Ala Leu Gly Ser Gly Phe Lys Cys Asn Ser Ala Val
    450                 455                 460

Trp Val Ala Leu Asn Asn Val Lys Ala Ser Lys
465                 470                 475

<210> SEQ ID NO 14
<211> LENGTH: 623
<212> TYPE: DNA
<213> ORGANISM: Arabidopsis thaliana
<220> FEATURE:
<221> NAME/KEY: CDS
<222> LOCATION: (1)..(623)

<400> SEQUENCE: 14 aag ctt aaa cta gtg tat cat tac cta atc tcc aac gct ctc tac atc      48
Lys Leu Lys Leu Val Tyr His Tyr Leu Ile Ser Asn Ala Leu Tyr Ile
  1               5                  10                  15 ctc ctc ctt cct ctc ctc gcc gca aca atc gct aac ctc tct tct ttc      96
Leu Leu Leu Pro Leu Leu Ala Ala Thr Ile Ala Asn Leu Ser Ser Phe
             20                  25                  30 acc atc aac gac ctc tct ctc ctc tac aac aca ctc cgt ttc cat ttc     144
Thr Ile Asn Asp Leu Ser Leu Leu Tyr Asn Thr Leu Arg Phe His Phe
         35                  40                  45 ctc tcc gcc aca ctc gcc acc gca ctc ttg atc tct ctc tcc acc gct     192
Leu Ser Ala Thr Leu Ala Thr Ala Leu Leu Ile Ser Leu Ser Thr Ala
     50                  55                  60 tac ttc acc acc cgt cct cgc cgt gtc ttc ctc ctc gac ttc tcg tgt     240
Tyr Phe Thr Thr Arg Pro Arg Arg Val Phe Leu Leu Asp Phe Ser Cys
 65                  70                  75                  80 tac aaa cca gac cct tca ctg atc tgc act cgt gaa aca ttc atg gac     288
Tyr Lys Pro Asp Pro Ser Leu Ile Cys Thr Arg Glu Thr Phe Met Asp
                 85                  90                  95 aga tct caa cgt gta ggc atc ttc aca gaa gac aac tta gct ttc caa     336
Arg Ser Gln Arg Val Gly Ile Phe Thr Glu Asp Asn Leu Ala Phe Gln
            100                 105                 110 caa aag atc ctc gaa aga tcc ggt cta ggt cag aaa act tac ttc cct     384
Gln Lys Ile Leu Glu Arg Ser Gly Leu Gly Gln Lys Thr Tyr Phe Pro
        115                 120                 125 gaa gct ctt ctt cgt gtt cct cct aat cct tgt atg gaa gaa gcg aga     432
Glu Ala Leu Leu Arg Val Pro Pro Asn Pro Cys Met Glu Glu Ala Arg
    130                 135                 140 aaa gag gca gaa aca gtt atg ttc gga gct att gac gcg gtt ctt gag     480
Lys Glu Ala Glu Thr Val Met Phe Gly Ala Ile Asp Ala Val Leu Glu
```

-continued

```
                 145                 150                 155                 160
aag acc ggt gtg aaa cct aaa gat att gga atc ctt gtg gtg aat tgt      528
Lys Thr Gly Val Lys Pro Lys Asp Ile Gly Ile Leu Val Val Asn Cys
                165                 170                 175 agc ttg ttt aat cca aca ccg tca ctt tct gct atg att gtg aat aag      576
Ser Leu Phe Asn Pro Thr Pro Ser Leu Ser Ala Met Ile Val Asn Lys
            180                 185                 190 tat aag ctt aga ggc aac att ttg agc tat aat ttc ggc ggg atg gg       623
Tyr Lys Leu Arg Gly Asn Ile Leu Ser Tyr Asn Phe Gly Gly Met Gly
        195                 200                 205
```

<210> SEQ ID NO 15
<211> LENGTH: 208
<212> TYPE: PRT
<213> ORGANISM: Arabidopsis thaliana

<400> SEQUENCE: 15

```
Lys Leu Lys Leu Val Tyr His Tyr Leu Ile Ser Asn Ala Leu Tyr Ile
 1               5                  10                  15

Leu Leu Leu Pro Leu Leu Ala Ala Thr Ile Ala Asn Leu Ser Ser Phe
            20                  25                  30

Thr Ile Asn Asp Leu Ser Leu Leu Tyr Asn Thr Leu Arg Phe His Phe
        35                  40                  45

Leu Ser Ala Thr Leu Ala Thr Ala Leu Leu Ile Ser Leu Ser Thr Ala
    50                  55                  60

Tyr Phe Thr Thr Arg Pro Arg Arg Val Phe Leu Leu Asp Phe Ser Cys
65                  70                  75                  80

Tyr Lys Pro Asp Pro Ser Leu Ile Cys Thr Arg Glu Thr Phe Met Asp
                85                  90                  95

Arg Ser Gln Arg Val Gly Ile Phe Thr Glu Asp Asn Leu Ala Phe Gln
            100                 105                 110

Gln Lys Ile Leu Glu Arg Ser Gly Leu Gly Gln Lys Thr Tyr Phe Pro
        115                 120                 125

Glu Ala Leu Leu Arg Val Pro Pro Asn Pro Cys Met Glu Glu Ala Arg
    130                 135                 140

Lys Glu Ala Glu Thr Val Met Phe Gly Ala Ile Asp Ala Val Leu Glu
145                 150                 155                 160

Lys Thr Gly Val Lys Pro Lys Asp Ile Gly Ile Leu Val Val Asn Cys
                165                 170                 175

Ser Leu Phe Asn Pro Thr Pro Ser Leu Ser Ala Met Ile Val Asn Lys
            180                 185                 190

Tyr Lys Leu Arg Gly Asn Ile Leu Ser Tyr Asn Phe Gly Gly Met Gly
        195                 200                 205
```

<210> SEQ ID NO 16
<211> LENGTH: 607
<212> TYPE: DNA
<213> ORGANISM: Arabidopsis thaliana
<220> FEATURE:
<221> NAME/KEY: CDS
<222> LOCATION: (1)..(606)

<400> SEQUENCE: 16

```
aag ctt aag tta ggc tac cac tat ctg atc act cac ttt ttt aaa ctc      48
Lys Leu Lys Leu Gly Tyr His Tyr Leu Ile Thr His Phe Phe Lys Leu
 1               5                  10                  15 atg ttc ctc cct cta atg gct gtt ttg ttc atg aat gtc tca ttg tta      96
Met Phe Leu Pro Leu Met Ala Val Leu Phe Met Asn Val Ser Leu Leu
            20                  25                  30
```

| | | | | | | | | | | | | |
|---|---|---|---|---|---|---|---|---|---|---|---|---|
| agc | cta | aac | cat | ctt | cag | ctc | tat | tac | aat | tcc | acc | gga ttc atc ttc | 144 |
| Ser | Leu | Asn | His | Leu | Gln | Leu | Tyr | Tyr | Asn | Ser | Thr | Gly Phe Ile Phe |
| | | 35 | | | | 40 | | | | | 45 | |
| gtc | atc | act | ctc | gcc | att | gtc | gga | tcc | att | gtc | ttc | ttc atg tct cga | 192 |
| Val | Ile | Thr | Leu | Ala | Ile | Val | Gly | Ser | Ile | Val | Phe | Phe Met Ser Arg |
| | 50 | | | | | 55 | | | | | 60 | |
| cct | aga | tcc | atc | tac | ctt | cta | gat | tac | tct | tgc | tac | ctc ccg cct tcg | 240 |
| Pro | Arg | Ser | Ile | Tyr | Leu | Leu | Asp | Tyr | Ser | Cys | Tyr | Leu Pro Pro Ser |
| 65 | | | | | 70 | | | | | 75 | | 80 |
| agt | caa | aaa | gtt | agc | tac | cag | aaa | ttc | atg | aac | aac | tct agt ttg att | 288 |
| Ser | Gln | Lys | Val | Ser | Tyr | Gln | Lys | Phe | Met | Asn | Asn | Ser Ser Leu Ile |
| | | | | 85 | | | | | 90 | | | 95 |
| caa | gat | ttc | agc | gaa | act | tct | ctt | gag | ttc | cag | agg | aag atc ttg att | 336 |
| Gln | Asp | Phe | Ser | Glu | Thr | Ser | Leu | Glu | Phe | Gln | Arg | Lys Ile Leu Ile |
| | | | 100 | | | | | 105 | | | | 110 |
| cgc | tct | ggt | ctc | ggt | gaa | gag | act | tat | tta | ccg | gat | tct att cac tct | 384 |
| Arg | Ser | Gly | Leu | Gly | Glu | Glu | Thr | Tyr | Leu | Pro | Asp | Ser Ile His Ser |
| | | 115 | | | | | 120 | | | | | 125 |
| atc | cct | ccg | cgt | cct | act | atg | gct | gca | gcg | cgt | gaa | gaa gcg gag cag | 432 |
| Ile | Pro | Pro | Arg | Pro | Thr | Met | Ala | Ala | Ala | Arg | Glu | Glu Ala Glu Gln |
| | 130 | | | | | 135 | | | | | 140 | |
| gta | atc | ttc | ggt | gca | ctc | gac | aat | ctt | ttc | gag | aat | aca aaa atc aat | 480 |
| Val | Ile | Phe | Gly | Ala | Leu | Asp | Asn | Leu | Phe | Glu | Asn | Thr Lys Ile Asn |
| 145 | | | | | 150 | | | | | 155 | | 160 |
| cct | agg | gag | att | ggt | gtt | ctt | gtt | gtg | aat | tgt | agt | ttg ttt aac ccc | 528 |
| Pro | Arg | Glu | Ile | Gly | Val | Leu | Val | Val | Asn | Cys | Ser | Leu Phe Asn Pro |
| | | | | 165 | | | | | 170 | | | 175 |
| acg | cct | tct | tta | tcc | gcc | atg | att | gtt | aac | aag | tat | aag ctt aga gga | 576 |
| Thr | Pro | Ser | Leu | Ser | Ala | Met | Ile | Val | Asn | Lys | Tyr | Lys Leu Arg Gly |
| | | | 180 | | | | | 185 | | | | 190 |
| aac | att | aag | agc | ttt | aat | ctc | ggc | ggc | atg | g | | | 607 |
| Asn | Ile | Lys | Ser | Phe | Asn | Leu | Gly | Gly | Met | | | |
| | | 195 | | | | | 200 | | | | | |

<210> SEQ ID NO 17
<211> LENGTH: 202
<212> TYPE: PRT
<213> ORGANISM: Arabidopsis thaliana

<400> SEQUENCE: 17

Lys Leu Lys Leu Gly Tyr His Tyr Leu Ile Thr His Phe Phe Lys Leu
 1               5                  10                  15

Met Phe Leu Pro Leu Met Ala Val Leu Phe Met Asn Val Ser Leu Leu
             20                  25                  30

Ser Leu Asn His Leu Gln Leu Tyr Tyr Asn Ser Thr Gly Phe Ile Phe
         35                  40                  45

Val Ile Thr Leu Ala Ile Val Gly Ser Ile Val Phe Phe Met Ser Arg
     50                  55                  60

Pro Arg Ser Ile Tyr Leu Leu Asp Tyr Ser Cys Tyr Leu Pro Pro Ser
 65                  70                  75                  80

Ser Gln Lys Val Ser Tyr Gln Lys Phe Met Asn Asn Ser Ser Leu Ile
                 85                  90                  95

Gln Asp Phe Ser Glu Thr Ser Leu Glu Phe Gln Arg Lys Ile Leu Ile
            100                 105                 110

Arg Ser Gly Leu Gly Glu Glu Thr Tyr Leu Pro Asp Ser Ile His Ser
        115                 120                 125

Ile Pro Pro Arg Pro Thr Met Ala Ala Ala Arg Glu Glu Ala Glu Gln
    130                 135                 140

```
Val Ile Phe Gly Ala Leu Asp Asn Leu Phe Glu Asn Thr Lys Ile Asn
145                 150                 155                 160

Pro Arg Glu Ile Gly Val Leu Val Asn Cys Ser Leu Phe Asn Pro
                165                 170                 175

Thr Pro Ser Leu Ser Ala Met Ile Val Asn Lys Tyr Lys Leu Arg Gly
            180                 185                 190

Asn Ile Lys Ser Phe Asn Leu Gly Gly Met
            195                 200

<210> SEQ ID NO 18
<211> LENGTH: 622
<212> TYPE: DNA
<213> ORGANISM: Arabidopsis thaliana
<220> FEATURE:
<221> NAME/KEY: CDS
<222> LOCATION: (1)..(621)

<400> SEQUENCE: 18 aag ctt aaa ctg ggg tac cac tac ctc att act cat ctc ttc aag ctc      48
Lys Leu Lys Leu Gly Tyr His Tyr Leu Ile Thr His Leu Phe Lys Leu
  1               5                  10                  15 tgt ttg gtt cca tta atg gcg gtt tta gtc aca gag atc tcc cga tta      96
Cys Leu Val Pro Leu Met Ala Val Leu Val Thr Glu Ile Ser Arg Leu
             20                  25                  30 aca aca gac gat ctt tac cag att tgc ctt cat ctc caa tac aat ctc     144
Thr Thr Asp Asp Leu Tyr Gln Ile Cys Leu His Leu Gln Tyr Asn Leu
         35                  40                  45 gtt gct ttc atc ttt ctc tct gct tta gct atc ttt ggc tcc acc gtt     192
Val Ala Phe Ile Phe Leu Ser Ala Leu Ala Ile Phe Gly Ser Thr Val
     50                  55                  60 tac atc atg agt cgt ccc aga tct gtt tat ctc gtt gat tac tct tgt     240
Tyr Ile Met Ser Arg Pro Arg Ser Val Tyr Leu Val Asp Tyr Ser Cys
 65                  70                  75                  80 tat ctt cct ccg gag agt ctt cag gtt aag tat cag aag ttt atg gat     288
Tyr Leu Pro Pro Glu Ser Leu Gln Val Lys Tyr Gln Lys Phe Met Asp
                 85                  90                  95 cat tct aag ttg att gaa gat ttc aat gag tca tct tta gag ttt cag     336
His Ser Lys Leu Ile Glu Asp Phe Asn Glu Ser Ser Leu Glu Phe Gln
            100                 105                 110 agg aag att ctt gaa cgt tct ggt tta gga gaa gag act tat ctc cct     384
Arg Lys Ile Leu Glu Arg Ser Gly Leu Gly Glu Glu Thr Tyr Leu Pro
        115                 120                 125 gaa gct tta cat tgt atc cct ccg agg cct acg atg atg gcg gct cgt     432
Glu Ala Leu His Cys Ile Pro Pro Arg Pro Thr Met Met Ala Ala Arg
    130                 135                 140 gag gaa gct gag cag gta atg ttt ggt gct ctt gat aag ctt ttc gag     480
Glu Glu Ala Glu Gln Val Met Phe Gly Ala Leu Asp Lys Leu Phe Glu
145                 150                 155                 160 aat acc aag att aac cct agg gat att ggt gtg ttg gtt gtg aat tgt     528
Asn Thr Lys Ile Asn Pro Arg Asp Ile Gly Val Leu Val Val Asn Cys
                165                 170                 175 agc ttg ttt aat cct aca cct tcg ttg tca gct atg att gtt aac aag     576
Ser Leu Phe Asn Pro Thr Pro Ser Leu Ser Ala Met Ile Val Asn Lys
            180                 185                 190 tat aag ctt aga ggg aat gtt aag agt ttt aac ctg ggg ggc att g       622
Tyr Lys Leu Arg Gly Asn Val Lys Ser Phe Asn Leu Gly Gly Ile
        195                 200                 205

<210> SEQ ID NO 19
<211> LENGTH: 207
```

```
<212> TYPE: PRT
<213> ORGANISM: Arabidopsis thaliana

<400> SEQUENCE: 19

Lys Leu Lys Leu Gly Tyr His Tyr Leu Ile Thr His Leu Phe Lys Leu
 1               5                  10                  15

Cys Leu Val Pro Leu Met Ala Val Leu Val Thr Glu Ile Ser Arg Leu
             20                  25                  30

Thr Thr Asp Asp Leu Tyr Gln Ile Cys Leu His Leu Gln Tyr Asn Leu
         35                  40                  45

Val Ala Phe Ile Phe Leu Ser Ala Leu Ala Ile Phe Gly Ser Thr Val
     50                  55                  60

Tyr Ile Met Ser Arg Pro Arg Ser Val Tyr Leu Val Asp Tyr Ser Cys
 65                  70                  75                  80

Tyr Leu Pro Pro Glu Ser Leu Gln Val Lys Tyr Gln Lys Phe Met Asp
                 85                  90                  95

His Ser Lys Leu Ile Glu Asp Phe Asn Glu Ser Leu Glu Phe Gln
             100                 105                 110

Arg Lys Ile Leu Glu Arg Ser Gly Leu Gly Glu Glu Thr Tyr Leu Pro
         115                 120                 125

Glu Ala Leu His Cys Ile Pro Pro Arg Pro Thr Met Met Ala Ala Arg
130                 135                 140

Glu Glu Ala Glu Gln Val Met Phe Gly Ala Leu Asp Lys Leu Phe Glu
145                 150                 155                 160

Asn Thr Lys Ile Asn Pro Arg Asp Ile Gly Val Leu Val Asn Cys
                 165                 170                 175

Ser Leu Phe Asn Pro Thr Pro Ser Leu Ser Ala Met Ile Val Asn Lys
             180                 185                 190

Tyr Lys Leu Arg Gly Asn Val Lys Ser Phe Asn Leu Gly Gly Ile
         195                 200                 205

<210> SEQ ID NO 20
<211> LENGTH: 625
<212> TYPE: DNA
<213> ORGANISM: Lunaria annua
<220> FEATURE:
<221> NAME/KEY: CDS
<222> LOCATION: (1)..(624)

<400> SEQUENCE: 20 aag ctt aag tta tgg tat cac tac ctg att tct cac ctt ttt aag ctc      48
Lys Leu Lys Leu Trp Tyr His Tyr Leu Ile Ser His Leu Phe Lys Leu
 1               5                  10                  15 ttg ttg gtt cct tta atg gcg gtt ctg ttc acg aat gtc tcc cgg tta      96
Leu Leu Val Pro Leu Met Ala Val Leu Phe Thr Asn Val Ser Arg Leu
             20                  25                  30 agc cta aac cag ctc tgt ctc gat ctc tct ctc cag ctc cag ttc aat     144
Ser Leu Asn Gln Leu Cys Leu Asp Leu Ser Leu Gln Leu Gln Phe Asn
         35                  40                  45 ctc gtc gga ttc atc ttc ttc att acc gtc tcc att ttc gga ttc aca     192
Leu Val Gly Phe Ile Phe Phe Ile Thr Val Ser Ile Phe Gly Phe Thr
     50                  55                  60 gtt atc ttc atg tcc cga cct aga tcc gtt tac ctc ctc gac tac tca     240
Val Ile Phe Met Ser Arg Pro Arg Ser Val Tyr Leu Leu Asp Tyr Ser
 65                  70                  75                  80 tgt tac ctc ccg ccg tcg aat ctc aaa gtt agc tac cag aca ttc atg     288
Cys Tyr Leu Pro Pro Ser Asn Leu Lys Val Ser Tyr Gln Thr Phe Met
                 85                  90                  95
```

```
aat cat tct aaa ctg att gaa gat ttc gac gag tcg tcg ctt gag ttc      336
Asn His Ser Lys Leu Ile Glu Asp Phe Asp Glu Ser Ser Leu Glu Phe
        100                 105                 110 cag cgg aag atc ctg aag cga tcc ggt ctc ggc gaa gag act tac ctc      384
Gln Arg Lys Ile Leu Lys Arg Ser Gly Leu Gly Glu Glu Thr Tyr Leu
        115                 120                 125 ccg gaa tct atc cac tgc atc ccg ccg cgt ccg act atg gcg gcg gcg      432
Pro Glu Ser Ile His Cys Ile Pro Pro Arg Pro Thr Met Ala Ala Ala
130                 135                 140 cgt gag gaa tcg gag cag gta atc ttc ggt gca ctc gac aat ctc ttc      480
Arg Glu Glu Ser Glu Gln Val Ile Phe Gly Ala Leu Asp Asn Leu Phe
145                 150                 155                 160 gag aat acc aaa atc gac cct agg gag att ggt gtt gtg gtg gtg aac      528
Glu Asn Thr Lys Ile Asp Pro Arg Glu Ile Gly Val Val Val Val Asn
                165                 170                 175 tgc agc ttg ttt aac ccg acg cct tct tta tcc gcc atg att gtg aac      576
Cys Ser Leu Phe Asn Pro Thr Pro Ser Leu Ser Ala Met Ile Val Asn
                180                 185                 190 aag tat aag ctt aga gga aac gtg aag agc ttt aat ctc ggt ggc atg g   625
Lys Tyr Lys Leu Arg Gly Asn Val Lys Ser Phe Asn Leu Gly Gly Met
                195                 200                 205

<210> SEQ ID NO 21
<211> LENGTH: 208
<212> TYPE: PRT
<213> ORGANISM: Lunaria annua

<400> SEQUENCE: 21

Lys Leu Lys Leu Trp Tyr His Tyr Leu Ile Ser His Leu Phe Lys Leu
  1               5                  10                  15

Leu Leu Val Pro Leu Met Ala Val Leu Phe Thr Asn Val Ser Arg Leu
             20                  25                  30

Ser Leu Asn Gln Leu Cys Leu Asp Leu Ser Leu Gln Leu Gln Phe Asn
         35                  40                  45

Leu Val Gly Phe Ile Phe Phe Ile Thr Val Ser Ile Phe Gly Phe Thr
     50                  55                  60

Val Ile Phe Met Ser Arg Pro Arg Ser Val Tyr Leu Leu Asp Tyr Ser
 65                  70                  75                  80

Cys Tyr Leu Pro Pro Ser Asn Leu Lys Val Ser Tyr Gln Thr Phe Met
                 85                  90                  95

Asn His Ser Lys Leu Ile Glu Asp Phe Asp Glu Ser Ser Leu Glu Phe
            100                 105                 110

Gln Arg Lys Ile Leu Lys Arg Ser Gly Leu Gly Glu Glu Thr Tyr Leu
        115                 120                 125

Pro Glu Ser Ile His Cys Ile Pro Pro Arg Pro Thr Met Ala Ala Ala
    130                 135                 140

Arg Glu Glu Ser Glu Gln Val Ile Phe Gly Ala Leu Asp Asn Leu Phe
145                 150                 155                 160

Glu Asn Thr Lys Ile Asp Pro Arg Glu Ile Gly Val Val Val Val Asn
                165                 170                 175

Cys Ser Leu Phe Asn Pro Thr Pro Ser Leu Ser Ala Met Ile Val Asn
                180                 185                 190

Lys Tyr Lys Leu Arg Gly Asn Val Lys Ser Phe Asn Leu Gly Gly Met
                195                 200                 205

<210> SEQ ID NO 22
<211> LENGTH: 1704
<212> TYPE: DNA
```

```
<213> ORGANISM: Lunaria annua
<220> FEATURE:
<221> NAME/KEY: CDS
<222> LOCATION: (42)..(1535)
<220> FEATURE:
<221> NAME/KEY: modified_base
<222> LOCATION: (345)
<223> OTHER INFORMATION: a, c, t, or g

<400> SEQUENCE: 22
gttcattgat ttgtttgaga ctctgttgca gaaatctcca c atg gat gat gaa tcc          56
                                              Met Asp Asp Glu Ser
                                                1               5 gtt aat gga gga tcc gta cag atc cgg acc cga aag tac gtc aag ctg          104
Val Asn Gly Gly Ser Val Gln Ile Arg Thr Arg Lys Tyr Val Lys Leu
             10                  15                  20 ggt tat cac tac ctg att tct cac ctt ttt aag ctc ttg ttg gtt cct          152
Gly Tyr His Tyr Leu Ile Ser His Leu Phe Lys Leu Leu Leu Val Pro
         25                  30                  35 tta atg gcg gtt ctg ttc acg aat gtc tcc cgg tta agc cta aac cag          200
Leu Met Ala Val Leu Phe Thr Asn Val Ser Arg Leu Ser Leu Asn Gln
     40                  45                  50 ctc tgt ctc gat ctc tct ctc cag ctc cag ttc aat ctc gtc gga ttc          248
Leu Cys Leu Asp Leu Ser Leu Gln Leu Gln Phe Asn Leu Val Gly Phe
 55                  60                  65 atc ttc ttc att acc gcc tcc att ttc gga ttc aca gtt atc ttc atg          296
Ile Phe Phe Ile Thr Ala Ser Ile Phe Gly Phe Thr Val Ile Phe Met
 70                  75                  80                  85 tcc cga cct aga tcc gtt tac ctc ctc gac tac tca tgt tac ctc ccg          344
Ser Arg Pro Arg Ser Val Tyr Leu Leu Asp Tyr Ser Cys Tyr Leu Pro
                 90                  95                 100 ncg gcg aat ctc aaa gtt agc tac cag aca ttc atg aat cat tct aaa          392
Xaa Ala Asn Leu Lys Val Ser Tyr Gln Thr Phe Met Asn His Ser Lys
                105                 110                 115 ctg att gaa gat ttc gac gag tcg tcg ctt gag ttc cag cgg aag atc          440
Leu Ile Glu Asp Phe Asp Glu Ser Ser Leu Glu Phe Gln Arg Lys Ile
            120                 125                 130 ctg aag cga tcc ggt ctc ggc gaa gag act tac ctc ccg gaa tct atc          488
Leu Lys Arg Ser Gly Leu Gly Glu Glu Thr Tyr Leu Pro Glu Ser Ile
135                 140                 145 cac tgc atc ccg ccg cgt ccg act atg gcg gcg gcg cgt gag gaa tcg          536
His Cys Ile Pro Pro Arg Pro Thr Met Ala Ala Ala Arg Glu Glu Ser
150                 155                 160                 165 gag cag gta atc ttc ggt gca ctc gac aat ctc ttc gag aat acc aaa          584
Glu Gln Val Ile Phe Gly Ala Leu Asp Asn Leu Phe Glu Asn Thr Lys
                170                 175                 180 atc gac cct agg gag att ggt gtt gtg gtg aac tgc agc ttg ttt           632
Ile Asp Pro Arg Glu Ile Gly Val Val Val Asn Cys Ser Leu Phe
            185                 190                 195 aac ccg acg cct tct tta tcc gcc atg att gtg aac aag tat aag ctt          680
Asn Pro Thr Pro Ser Leu Ser Ala Met Ile Val Asn Lys Tyr Lys Leu
            200                 205                 210 aga gga aac gtg aag agc ttt aac ctc gga gga atg gga tgt agg gct          728
Arg Gly Asn Val Lys Ser Phe Asn Leu Gly Gly Met Gly Cys Arg Ala
215                 220                 225 ggt gtc atc gcc gtt gat ctc gct aat gac att tta cag ctc cat aga          776
Gly Val Ile Ala Val Asp Leu Ala Asn Asp Ile Leu Gln Leu His Arg
230                 235                 240                 245 aac aca tta gct ctt gtg gtt agc aca gag aac atc act cag aat tgg          824
Asn Thr Leu Ala Leu Val Val Ser Thr Glu Asn Ile Thr Gln Asn Trp
            250                 255                 260
```

-continued

```
tac ttt ggt aac aac aaa gca atg ttg att cct aat tgc ttg ttt agg          872
Tyr Phe Gly Asn Asn Lys Ala Met Leu Ile Pro Asn Cys Leu Phe Arg
            265                 270                 275 gtt ggt gga tcc gcg gtt ctg ctt tcg aac aag cct cgt gat cga aaa          920
Val Gly Gly Ser Ala Val Leu Leu Ser Asn Lys Pro Arg Asp Arg Lys
        280                 285                 290 cga tcc aag tat aaa ctt gtt cac acg gta cgg act cat aaa gga tct          968
Arg Ser Lys Tyr Lys Leu Val His Thr Val Arg Thr His Lys Gly Ser
    295                 300                 305 gat gag aaa gca ttc aac tgt gtg tac caa gaa caa gac gag gac ttg         1016
Asp Glu Lys Ala Phe Asn Cys Val Tyr Gln Glu Gln Asp Glu Asp Leu
310                 315                 320                 325 aaa acc gga gtt tct ttg tct aaa gac cta atg tct ata gct gga gaa         1064
Lys Thr Gly Val Ser Leu Ser Lys Asp Leu Met Ser Ile Ala Gly Glu
                330                 335                 340 gct cta aag aca aat atc acc act ttg ggt cct ctg gtt ctt cca ata         1112
Ala Leu Lys Thr Asn Ile Thr Thr Leu Gly Pro Leu Val Leu Pro Ile
            345                 350                 355 agc gag cag att ctg ttc att gcg act ttt gtt gca aag aga ttg ttc         1160
Ser Glu Gln Ile Leu Phe Ile Ala Thr Phe Val Ala Lys Arg Leu Phe
        360                 365                 370 agt gcc aag aag aag aag aag aag cct tac ata ccg gat ttc aag ctt         1208
Ser Ala Lys Lys Lys Lys Lys Lys Pro Tyr Ile Pro Asp Phe Lys Leu
    375                 380                 385 gcc ttt gat cat ttc tgt att cac gca gga ggt aga gcc gtg atc gat         1256
Ala Phe Asp His Phe Cys Ile His Ala Gly Gly Arg Ala Val Ile Asp
390                 395                 400                 405 gaa cta gag aag agt tta aag cta ttg cca aaa cat gtg gag gct tct         1304
Glu Leu Glu Lys Ser Leu Lys Leu Leu Pro Lys His Val Glu Ala Ser
                410                 415                 420 aga atg aca ttg cat aga ttt gga aac act tca tcg agc tct att tgg         1352
Arg Met Thr Leu His Arg Phe Gly Asn Thr Ser Ser Ser Ser Ile Trp
            425                 430                 435 tat gaa tta gct tac aca gaa gct aaa gga aga atg aga aaa ggg aat         1400
Tyr Glu Leu Ala Tyr Thr Glu Ala Lys Gly Arg Met Arg Lys Gly Asn
        440                 445                 450 cga gtt tgg cag att gct ttt gga agc ggc ttt aag tgt aac agc gcg         1448
Arg Val Trp Gln Ile Ala Phe Gly Ser Gly Phe Lys Cys Asn Ser Ala
    455                 460                 465 gtt tgg gtg gct ctt cgt gat gtc gag ccc tcg gtt aac aat cct tgg         1496
Val Trp Val Ala Leu Arg Asp Val Glu Pro Ser Val Asn Asn Pro Trp
470                 475                 480                 485 gaa cat tgc atc cat aga tat ccg gtt aag atc gat ctc tgatttcagc         1545
Glu His Cys Ile His Arg Tyr Pro Val Lys Ile Asp Leu
                490                 495 ttaaccggta aaattggtct gtacatatat ttaccactga gtaaagacat cagttaatga      1605
tttgttgtta ctcaattggg ctaagtgtat tattatatgt gttgtatata ataaaggtag      1665
aacgtaaatt tactaagaaa aaaaaaaaaa aaaaaaaa                              1704
```

<210> SEQ ID NO 23
<211> LENGTH: 498
<212> TYPE: PRT
<213> ORGANISM: Lunaria annua
<220> FEATURE:
<221> NAME/KEY: MOD_RES
<222> LOCATION: (102)
<223> OTHER INFORMATION: Variable amino acid

<400> SEQUENCE: 23

Met Asp Asp Glu Ser Val Asn Gly Gly Ser Val Gln Ile Arg Thr Arg

-continued

```
  1               5               10              15
Lys Tyr Val Lys Leu Gly Tyr His Tyr Leu Ile Ser His Leu Phe Lys
             20                  25                  30
Leu Leu Leu Val Pro Leu Met Ala Val Leu Phe Thr Asn Val Ser Arg
             35                  40                  45
Leu Ser Leu Asn Gln Leu Cys Leu Asp Leu Ser Leu Gln Leu Gln Phe
             50                  55                  60
Asn Leu Val Gly Phe Ile Phe Phe Ile Thr Ala Ser Ile Phe Gly Phe
 65                  70                  75                  80
Thr Val Ile Phe Met Ser Arg Pro Arg Ser Val Tyr Leu Leu Asp Tyr
                 85                  90                  95
Ser Cys Tyr Leu Pro Xaa Ala Asn Leu Lys Val Ser Tyr Gln Thr Phe
                100                 105                 110
Met Asn His Ser Lys Leu Ile Glu Asp Phe Asp Glu Ser Ser Leu Glu
                115                 120                 125
Phe Gln Arg Lys Ile Leu Lys Arg Ser Gly Leu Gly Glu Glu Thr Tyr
                130                 135                 140
Leu Pro Glu Ser Ile His Cys Ile Pro Pro Arg Pro Thr Met Ala Ala
145                 150                 155                 160
Ala Arg Glu Glu Ser Glu Gln Val Ile Phe Gly Ala Leu Asp Asn Leu
                165                 170                 175
Phe Glu Asn Thr Lys Ile Asp Pro Arg Glu Ile Gly Val Val Val Val
                180                 185                 190
Asn Cys Ser Leu Phe Asn Pro Thr Pro Ser Leu Ser Ala Met Ile Val
                195                 200                 205
Asn Lys Tyr Lys Leu Arg Gly Asn Val Lys Ser Phe Asn Leu Gly Gly
                210                 215                 220
Met Gly Cys Arg Ala Gly Val Ile Ala Val Asp Leu Ala Asn Asp Ile
225                 230                 235                 240
Leu Gln Leu His Arg Asn Thr Leu Ala Leu Val Val Ser Thr Glu Asn
                245                 250                 255
Ile Thr Gln Asn Trp Tyr Phe Gly Asn Asn Lys Ala Met Leu Ile Pro
                260                 265                 270
Asn Cys Leu Phe Arg Val Gly Gly Ser Ala Val Leu Leu Ser Asn Lys
                275                 280                 285
Pro Arg Asp Arg Lys Arg Ser Lys Tyr Lys Leu Val His Thr Val Arg
                290                 295                 300
Thr His Lys Gly Ser Asp Glu Lys Ala Phe Asn Cys Val Tyr Gln Glu
305                 310                 315                 320
Gln Asp Glu Asp Leu Lys Thr Gly Val Ser Leu Ser Lys Asp Leu Met
                325                 330                 335
Ser Ile Ala Gly Glu Ala Leu Lys Thr Asn Ile Thr Thr Leu Gly Pro
                340                 345                 350
Leu Val Leu Pro Ile Ser Glu Gln Ile Leu Phe Ile Ala Thr Phe Val
                355                 360                 365
Ala Lys Arg Leu Phe Ser Ala Lys Lys Lys Lys Pro Tyr Ile
                370                 375                 380
Pro Asp Phe Lys Leu Ala Phe Asp His Phe Cys Ile His Ala Gly Gly
385                 390                 395                 400
Arg Ala Val Ile Asp Glu Leu Glu Lys Ser Leu Lys Leu Leu Pro Lys
                405                 410                 415
His Val Glu Ala Ser Arg Met Thr Leu His Arg Phe Gly Asn Thr Ser
                420                 425                 430
```

```
Ser Ser Ser Ile Trp Tyr Glu Leu Ala Tyr Thr Glu Ala Lys Gly Arg
        435                 440                 445

Met Arg Lys Gly Asn Arg Val Trp Gln Ile Ala Phe Gly Ser Gly Phe
    450                 455                 460

Lys Cys Asn Ser Ala Val Trp Val Ala Leu Arg Asp Val Glu Pro Ser
465                 470                 475                 480

Val Asn Asn Pro Trp Glu His Cys Ile His Arg Tyr Pro Val Lys Ile
                485                 490                 495

Asp Leu

<210> SEQ ID NO 24
<211> LENGTH: 1664
<212> TYPE: DNA
<213> ORGANISM: Lunaria annua
<220> FEATURE:
<221> NAME/KEY: CDS
<222> LOCATION: (3)..(1517)
<220> FEATURE:
<221> NAME/KEY: modified_base
<222> LOCATION: (155)
<223> OTHER INFORMATION: a, c, t, or g
<220> FEATURE:
<221> NAME/KEY: modified_base
<222> LOCATION: (217)
<223> OTHER INFORMATION: a, c, t, or g

<400> SEQUENCE: 24 ca atg acg tct gtg aac gta aaa ctc ctt tac cat tac gtc ata acc        47
   Met Thr Ser Val Asn Val Lys Leu Leu Tyr His Tyr Val Ile Thr
     1               5                  10                  15 aac ttt ttc aac ctc tgt ttc ttc cca ctg acg ggg atc ctc gcc gga       95
Asn Phe Phe Asn Leu Cys Phe Phe Pro Leu Thr Gly Ile Leu Ala Gly
             20                  25                  30 aaa ggc tct cgt ctt acc aca aac gat ctc cac cac ttc tat tca tat     143
Lys Gly Ser Arg Leu Thr Thr Asn Asp Leu His His Phe Tyr Ser Tyr
         35                  40                  45 ctc caa cac aan ctt ata acc tta acc cta ctc ttt ggc ttc acc gtt     191
Leu Gln His Xaa Leu Ile Thr Leu Thr Leu Leu Phe Gly Phe Thr Val
     50                  55                  60 ttt ggt tcg gtt ctc tac ttc gta anc cga ccc aaa ccg gtt tac ctc     239
Phe Gly Ser Val Leu Tyr Phe Val Xaa Arg Pro Lys Pro Val Tyr Leu
 65                  70                  75 gtt gac tac tcc tgc tac ctt cca cca caa cat ctt agc gct ggt atc     287
Val Asp Tyr Ser Cys Tyr Leu Pro Pro Gln His Leu Ser Ala Gly Ile
 80                  85                  90                  95 tct aag acc atg gaa atc ttt tat caa ata aga aaa tct gat cct tta     335
Ser Lys Thr Met Glu Ile Phe Tyr Gln Ile Arg Lys Ser Asp Pro Leu
             100                 105                 110 cga aac gtg gca tta gat gat tcg tct tct ctt gat ttc ttg aga aag     383
Arg Asn Val Ala Leu Asp Asp Ser Ser Ser Leu Asp Phe Leu Arg Lys
         115                 120                 125 att caa gag cgt tca ggt cta ggc gat gaa acc tac ggc ccc gag gga     431
Ile Gln Glu Arg Ser Gly Leu Gly Asp Glu Thr Tyr Gly Pro Glu Gly
     130                 135                 140 ctg ttt gag att cct ccg agg aag aat tta gcg tcg gcg cgt gaa gag     479
Leu Phe Glu Ile Pro Pro Arg Lys Asn Leu Ala Ser Ala Arg Glu Glu
 145                 150                 155 acg gag caa gta atc aac ggt gcg cta aaa aat cta ttc gag aac aac     527
Thr Glu Gln Val Ile Asn Gly Ala Leu Lys Asn Leu Phe Glu Asn Asn
160                 165                 170                 175 aaa gtt aac cct aaa gag att ggt ata ctt gtg gtg aac tca agc atg     575
```

```
                                            -continued

Lys Val Asn Pro Lys Glu Ile Gly Ile Leu Val Val Asn Ser Ser Met
            180                 185                 190 ttt aat ccg act cct tcg tta tcc gcg atg gta gtt aat act tcc aag        623
Phe Asn Pro Thr Pro Ser Leu Ser Ala Met Val Val Asn Thr Ser Lys
            195                 200                 205 ctc cga agc aac atc aaa agc ttt aat ctt gga gga atg ggt tgc agt        671
Leu Arg Ser Asn Ile Lys Ser Phe Asn Leu Gly Gly Met Gly Cys Ser
            210                 215                 220 gct ggt gtt atc gcc att gat cta gct aaa gac ttg ttg cat gtt cat        719
Ala Gly Val Ile Ala Ile Asp Leu Ala Lys Asp Leu Leu His Val His
        225                 230                 235 aaa aac aca tat gct ctt gtg gtg agc aca gag aac atc act caa aac        767
Lys Asn Thr Tyr Ala Leu Val Val Ser Thr Glu Asn Ile Thr Gln Asn
240                 245                 250                 255 att tat acc ggt gat aac aga tcc atg atg gtt tcg aat tgc ttg ttc        815
Ile Tyr Thr Gly Asp Asn Arg Ser Met Met Val Ser Asn Cys Leu Phe
                260                 265                 270 cgt gtc ggt ggg gca gcg att ctg ctc tcc aac aag ccg ggg gat cga        863
Arg Val Gly Gly Ala Ala Ile Leu Leu Ser Asn Lys Pro Gly Asp Arg
            275                 280                 285 aga cgg tcc aag tac aag cta gct cac acg gtt cga acg cat acc gga        911
Arg Arg Ser Lys Tyr Lys Leu Ala His Thr Val Arg Thr His Thr Gly
        290                 295                 300 gct gac gac aag tct ttt gga tgt gtg cgg caa gaa gaa gat gat agc        959
Ala Asp Asp Lys Ser Phe Gly Cys Val Arg Gln Glu Glu Asp Asp Ser
305                 310                 315 ggt aaa acc gga gtt agt ttg tca aaa gac ata acc gtt gtt gcc ggg       1007
Gly Lys Thr Gly Val Ser Leu Ser Lys Asp Ile Thr Val Val Ala Gly
320                 325                 330                 335 ata acg gtt cag aaa aac ata aca aca ttg ggt ccg ttg gtt ctt cct       1055
Ile Thr Val Gln Lys Asn Ile Thr Thr Leu Gly Pro Leu Val Leu Pro
                340                 345                 350 ctg agc gaa aaa atc ctt ttt gtc gtt aca ttc gta gcc aag aaa cta       1103
Leu Ser Glu Lys Ile Leu Phe Val Val Thr Phe Val Ala Lys Lys Leu
            355                 360                 365 tta aaa gat aag atc aaa cac tat tac gtg ccg gat ttc aaa ctt gca       1151
Leu Lys Asp Lys Ile Lys His Tyr Tyr Val Pro Asp Phe Lys Leu Ala
        370                 375                 380 gta gat cat ttc tgt att cat gcg gga ggt aga gcc gtg ata gat gtg       1199
Val Asp His Phe Cys Ile His Ala Gly Gly Arg Ala Val Ile Asp Val
385                 390                 395 tta gag aag aac tta ggg cta tcg ccg ata gat gtg gag gca tca aga       1247
Leu Glu Lys Asn Leu Gly Leu Ser Pro Ile Asp Val Glu Ala Ser Arg
400                 405                 410                 415 tca aca tta cat aga ttt ggg aat aca tcg tct agt tca att tgg tat       1295
Ser Thr Leu His Arg Phe Gly Asn Thr Ser Ser Ser Ser Ile Trp Tyr
                420                 425                 430 gaa tta gca tac ata gag cca aaa gga agg atg aag aaa ggt aat aaa       1343
Glu Leu Ala Tyr Ile Glu Pro Lys Gly Arg Met Lys Lys Gly Asn Lys
            435                 440                 445 gct tgc caa ata gct ggt ggg tca ggt ttt aag tgt aat agt gcg gtt       1391
Ala Cys Gln Ile Ala Gly Gly Ser Gly Phe Lys Cys Asn Ser Ala Val
        450                 455                 460 tgg gtc gct tta cgc aat gtc gag gct tca gct aat agt cct tgg gaa       1439
Trp Val Ala Leu Arg Asn Val Glu Ala Ser Ala Asn Ser Pro Trp Glu
465                 470                 475 cat tgc att cac aaa tat ccg gtt caa atg tat tct ggt tca tca aag       1487
His Cys Ile His Lys Tyr Pro Val Gln Met Tyr Ser Gly Ser Ser Lys
480                 485                 490                 495
```

-continued

```
tca gag act cct gtc caa aac ggt cgg tcc taatttatgt atctcaaatg      1537
Ser Glu Thr Pro Val Gln Asn Gly Arg Ser
            500                 505 atgttgtcca ctttctcttt tttttttct ttttttagtt ataatttaat ggttacgatg   1597
ttttgtctag gtcgttataa ataaagaata catgggtgtt actagtataa aaaaaaaaa   1657 aaaaaaa                                                            1664
```

<210> SEQ ID NO 25
<211> LENGTH: 505
<212> TYPE: PRT
<213> ORGANISM: Lunaria annua
<220> FEATURE:
<221> NAME/KEY: MOD_RES
<222> LOCATION: (51)
<223> OTHER INFORMATION: Variable amino acid
<220> FEATURE:
<221> NAME/KEY: MOD_RES
<222> LOCATION: (72)
<223> OTHER INFORMATION: Variable amino acid

<400> SEQUENCE: 25

```
Met Thr Ser Val Asn Val Lys Leu Leu Tyr His Tyr Val Ile Thr Asn
 1               5                  10                  15

Phe Phe Asn Leu Cys Phe Phe Pro Leu Thr Gly Ile Leu Ala Gly Lys
            20                  25                  30

Gly Ser Arg Leu Thr Thr Asn Asp Leu His His Phe Tyr Ser Tyr Leu
        35                  40                  45

Gln His Xaa Leu Ile Thr Leu Thr Leu Leu Phe Gly Phe Thr Val Phe
    50                  55                  60

Gly Ser Val Leu Tyr Phe Val Xaa Arg Pro Lys Pro Val Tyr Leu Val
65                  70                  75                  80

Asp Tyr Ser Cys Tyr Leu Pro Pro Gln His Leu Ser Ala Gly Ile Ser
                85                  90                  95

Lys Thr Met Glu Ile Phe Tyr Gln Ile Arg Lys Ser Asp Pro Leu Arg
            100                 105                 110

Asn Val Ala Leu Asp Asp Ser Ser Leu Asp Phe Leu Arg Lys Ile
        115                 120                 125

Gln Glu Arg Ser Gly Leu Gly Asp Glu Thr Tyr Gly Pro Glu Gly Leu
    130                 135                 140

Phe Glu Ile Pro Pro Arg Lys Asn Leu Ala Ser Ala Arg Glu Glu Thr
145                 150                 155                 160

Glu Gln Val Ile Asn Gly Ala Leu Lys Asn Leu Phe Glu Asn Asn Lys
                165                 170                 175

Val Asn Pro Lys Glu Ile Gly Ile Leu Val Val Asn Ser Ser Met Phe
            180                 185                 190

Asn Pro Thr Pro Ser Leu Ser Ala Met Val Val Asn Thr Ser Lys Leu
        195                 200                 205

Arg Ser Asn Ile Lys Ser Phe Asn Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Asn Ile
                245                 250                 255

Tyr Thr Gly Asp Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285
```

-continued

```
Arg Ser Lys Tyr Lys Leu Ala His Thr Val Arg Thr His Thr Gly Ala
    290                 295                 300
Asp Asp Lys Ser Phe Gly Cys Val Arg Gln Glu Glu Asp Asp Ser Gly
305                 310                 315                 320
Lys Thr Gly Val Ser Leu Ser Lys Asp Ile Thr Val Val Ala Gly Ile
                325                 330                 335
Thr Val Gln Lys Asn Ile Thr Thr Leu Gly Pro Leu Val Leu Pro Leu
            340                 345                 350
Ser Glu Lys Ile Leu Phe Val Val Thr Phe Val Ala Lys Lys Leu Leu
        355                 360                 365
Lys Asp Lys Ile Lys His Tyr Tyr Val Pro Asp Phe Lys Leu Ala Val
    370                 375                 380
Asp His Phe Cys Ile His Ala Gly Gly Arg Ala Val Ile Asp Val Leu
385                 390                 395                 400
Glu Lys Asn Leu Gly Leu Ser Pro Ile Asp Val Glu Ala Ser Arg Ser
                405                 410                 415
Thr Leu His Arg Phe Gly Asn Thr Ser Ser Ser Ile Trp Tyr Glu
            420                 425                 430
Leu Ala Tyr Ile Glu Pro Lys Gly Arg Met Lys Lys Gly Asn Lys Ala
        435                 440                 445
Cys Gln Ile Ala Gly Gly Ser Gly Phe Lys Cys Asn Ser Ala Val Trp
    450                 455                 460
Val Ala Leu Arg Asn Val Glu Ala Ser Ala Asn Ser Pro Trp Glu His
465                 470                 475                 480
Cys Ile His Lys Tyr Pro Val Gln Met Tyr Ser Gly Ser Ser Lys Ser
                485                 490                 495
Glu Thr Pro Val Gln Asn Gly Arg Ser
                500                 505
```

```
<210> SEQ ID NO 26
<211> LENGTH: 1732
<212> TYPE: DNA
<213> ORGANISM: Lunaria annua
<220> FEATURE:
<221> NAME/KEY: CDS
<222> LOCATION: (19)..(1611)

<400> SEQUENCE: 26
```

```
ctttcttctt ccccaaca atg acc cat aac caa aac caa cct cac cgg gca      51
                    Met Thr His Asn Gln Asn Gln Pro His Arg Ala
                     1               5                  10 gtt ccg gtt cac gtt aca aac tcc gat caa aac caa aac caa aac caa      99
Val Pro Val His Val Thr Asn Ser Asp Gln Asn Gln Asn Gln Asn Gln
             15                  20                  25 aac aat ctc cca aat ttt ctc tta tct gtt cgg ctc aaa tat gta aaa    147
Asn Asn Leu Pro Asn Phe Leu Leu Ser Val Arg Leu Lys Tyr Val Lys
         30                  35                  40 ctt ggg tac cat tac cta atc tcc aac ggt ctc tac atc ctc ctc ctc    195
Leu Gly Tyr His Tyr Leu Ile Ser Asn Gly Leu Tyr Ile Leu Leu Leu
     45                  50                  55 cct ctc ctc ggc ggc aca atc gta aaa ctc tct tcc ttc aca ctc aac    243
Pro Leu Leu Gly Gly Thr Ile Val Lys Leu Ser Ser Phe Thr Leu Asn
 60                  65                  70                  75 gaa ctc tct ctc ctc tac aac cac ctc cgt ttt cat ttc ctc tcc gcc    291
Glu Leu Ser Leu Leu Tyr Asn His Leu Arg Phe His Phe Leu Ser Ala
                 80                  85                  90 aca ctc gct acc gga ctc tta atc tct ctc tcc acc gcc tac ttc acc    339
```

```
                Thr Leu Ala Thr Gly Leu Leu Ile Ser Leu Ser Thr Ala Tyr Phe Thr
                            95                  100                 105 acc cgt cct cgt cat gtc ttc ctc ctc gac ttc tca tgc tac aaa cct          387
Thr Arg Pro Arg His Val Phe Leu Leu Asp Phe Ser Cys Tyr Lys Pro
            110                 115                 120 gac cct tcc tta ata tgc act cgt gaa aca ttc atg gac cga tct caa          435
Asp Pro Ser Leu Ile Cys Thr Arg Glu Thr Phe Met Asp Arg Ser Gln
125                 130                 135 cgt gta ggt atc ttc aca gaa gac aac ctc gct ttt caa caa aag atc          483
Arg Val Gly Ile Phe Thr Glu Asp Asn Leu Ala Phe Gln Gln Lys Ile
140                 145                 150                 155 ctc gaa aga tcc ggt ctt ggg cag aaa act tac ttc cct gaa gct ctt          531
Leu Glu Arg Ser Gly Leu Gly Gln Lys Thr Tyr Phe Pro Glu Ala Leu
                160                 165                 170 ctt cgt gtt cct ccc aat cct tgt atg gaa gaa gcg aga aaa gaa gca          579
Leu Arg Val Pro Pro Asn Pro Cys Met Glu Glu Ala Arg Lys Glu Ala
                175                 180                 185 gag act gtt atg ttc gga gct ata gac tct gtt ctt gag aaa acc ggt          627
Glu Thr Val Met Phe Gly Ala Ile Asp Ser Val Leu Glu Lys Thr Gly
                190                 195                 200 gtg aaa cct aaa gat atc gga atc ctt gtc gtg aat tgt agt ttg ttt          675
Val Lys Pro Lys Asp Ile Gly Ile Leu Val Val Asn Cys Ser Leu Phe
205                 210                 215 aat ccg acg ccg tca ctt tcc gcc atg att gtg aat aag tat aag ctt          723
Asn Pro Thr Pro Ser Leu Ser Ala Met Ile Val Asn Lys Tyr Lys Leu
220                 225                 230                 235 aga gga aac att ttg agc tat aat ctc ggt gga atg ggt tgt agt gct          771
Arg Gly Asn Ile Leu Ser Tyr Asn Leu Gly Gly Met Gly Cys Ser Ala
                240                 245                 250 gga ctt atc tcc att gat ctc gct aaa cag ctt ctt cag gtc caa cca          819
Gly Leu Ile Ser Ile Asp Leu Ala Lys Gln Leu Leu Gln Val Gln Pro
                255                 260                 265 aac tca tac gca cta gtg gtg agc aca gag aac ata acc tta aac tgg          867
Asn Ser Tyr Ala Leu Val Val Ser Thr Glu Asn Ile Thr Leu Asn Trp
                270                 275                 280 tac tta ggc aac gac cga tca atg ctt ctc tct aac tgc atc ttc cgt          915
Tyr Leu Gly Asn Asp Arg Ser Met Leu Leu Ser Asn Cys Ile Phe Arg
285                 290                 295 atg gga gga gcc gcc gta ctt ctc tca aac cgt tcc tcc gat cgc acc          963
Met Gly Gly Ala Ala Val Leu Leu Ser Asn Arg Ser Ser Asp Arg Thr
300                 305                 310                 315 cgt tca aaa tat cag ctc atc cac ccc gtc cgt acc cac aaa gga gcc         1011
Arg Ser Lys Tyr Gln Leu Ile His Pro Val Arg Thr His Lys Gly Ala
                320                 325                 330 aac gac aac gca ttt ggc tgc gtt tac caa cga gaa gac aac aac gaa         1059
Asn Asp Asn Ala Phe Gly Cys Val Tyr Gln Arg Glu Asp Asn Asn Glu
                335                 340                 345 gaa gaa acc gcc aaa atc gga gtc tca ctc tct aaa aac cta atg gca         1107
Glu Glu Thr Ala Lys Ile Gly Val Ser Leu Ser Lys Asn Leu Met Ala
                350                 355                 360 ata gcc gga gaa gct ctc aag aca aac ata aca aca ctc gga cca cta         1155
Ile Ala Gly Glu Ala Leu Lys Thr Asn Ile Thr Thr Leu Gly Pro Leu
365                 370                 375 gtc tta cca atg tcc gaa cag att ctg ttt ttc cca aca ctc gtg gct         1203
Val Leu Pro Met Ser Glu Gln Ile Leu Phe Phe Pro Thr Leu Val Ala
380                 385                 390                 395 cga aaa atc ttc aaa gtc aag aaa ata aag cct tac ata ccc gat ttc         1251
Arg Lys Ile Phe Lys Val Lys Lys Ile Lys Pro Tyr Ile Pro Asp Phe
                400                 405                 410
```

-continued

```
aag cta gct ttc gag cat ttc tgc atc cat gcg gga ggt aga gca gtg       1299
Lys Leu Ala Phe Glu His Phe Cys Ile His Ala Gly Gly Arg Ala Val
            415                 420                 425 ctt gat gag ata gag aag aat ttg gat tta tca gag tgg cat atg gaa       1347
Leu Asp Glu Ile Glu Lys Asn Leu Asp Leu Ser Glu Trp His Met Glu
        430                 435                 440 cca tcg agg atg act tta aac cgg ttt ggt aat act tcg agt agc tca       1395
Pro Ser Arg Met Thr Leu Asn Arg Phe Gly Asn Thr Ser Ser Ser Ser
    445                 450                 455 ctt tgg tat gaa ctt gcg tat agt gaa gct aaa ggg agg att aag aga       1443
Leu Trp Tyr Glu Leu Ala Tyr Ser Glu Ala Lys Gly Arg Ile Lys Arg
460                 465                 470                 475 gga gat agg act tgc caa att gcg ttt gga tcg gga ttt aag tgt aat       1491
Gly Asp Arg Thr Cys Gln Ile Ala Phe Gly Ser Gly Phe Lys Cys Asn
                480                 485                 490 agt gcg gtt tgg aaa gct ttg aga acc att gat cct att gat gag aag       1539
Ser Ala Val Trp Lys Ala Leu Arg Thr Ile Asp Pro Ile Asp Glu Lys
            495                 500                 505 aag aat cca tgg agt gat gag att cat gag ttt cca gtt tct gtt cct       1587
Lys Asn Pro Trp Ser Asp Glu Ile His Glu Phe Pro Val Ser Val Pro
        510                 515                 520 agg atc act cca gtt act tct aac tagtgttttt tttttgggtc caactaggga      1641
Arg Ile Thr Pro Val Thr Ser Asn
    525                 530 taatatttgt tatggttttg ttcttacgta cgtactttaa gtgatttagt ctaaaaataa     1701
attggtttca taaaaaaaaa aaaaaaaaaa a                                    1732

<210> SEQ ID NO 27
<211> LENGTH: 531
<212> TYPE: PRT
<213> ORGANISM: Lunaria annua

<400> SEQUENCE: 27

Met Thr His Asn Gln Asn Gln Pro His Arg Ala Val Pro Val His Val
 1               5                  10                  15

Thr Asn Ser Asp Gln Asn Gln Asn Gln Asn Asn Leu Pro Asn
            20                  25                  30

Phe Leu Leu Ser Val Arg Leu Lys Tyr Val Lys Leu Gly Tyr His Tyr
        35                  40                  45

Leu Ile Ser Asn Gly Leu Tyr Ile Leu Leu Pro Leu Leu Gly Gly
    50                  55                  60

Thr Ile Val Lys Leu Ser Ser Phe Thr Leu Asn Glu Leu Ser Leu Leu
65                  70                  75                  80

Tyr Asn His Leu Arg Phe His Phe Leu Ser Ala Thr Leu Ala Thr Gly
                85                  90                  95

Leu Leu Ile Ser Leu Ser Thr Ala Tyr Phe Thr Thr Arg Pro Arg His
            100                 105                 110

Val Phe Leu Leu Asp Phe Ser Cys Tyr Lys Pro Asp Pro Ser Leu Ile
        115                 120                 125

Cys Thr Arg Glu Thr Phe Met Asp Arg Ser Gln Arg Val Gly Ile Phe
    130                 135                 140

Thr Glu Asp Asn Leu Ala Phe Gln Gln Lys Ile Leu Glu Arg Ser Gly
145                 150                 155                 160

Leu Gly Gln Lys Thr Tyr Phe Pro Glu Ala Leu Leu Arg Val Pro Pro
                165                 170                 175

Asn Pro Cys Met Glu Glu Ala Arg Lys Glu Ala Glu Thr Val Met Phe
            180                 185                 190
```

Gly Ala Ile Asp Ser Val Leu Glu Lys Thr Gly Val Lys Pro Lys Asp
            195                 200                 205

Ile Gly Ile Leu Val Val Asn Cys Ser Leu Phe Asn Pro Thr Pro Ser
        210                 215                 220

Leu Ser Ala Met Ile Val Asn Lys Tyr Lys Leu Arg Gly Asn Ile Leu
225                 230                 235                 240

Ser Tyr Asn Leu Gly Gly Met Gly Cys Ser Ala Gly Leu Ile Ser Ile
                245                 250                 255

Asp Leu Ala Lys Gln Leu Leu Gln Val Gln Pro Asn Ser Tyr Ala Leu
            260                 265                 270

Val Val Ser Thr Glu Asn Ile Thr Leu Asn Trp Tyr Leu Gly Asn Asp
        275                 280                 285

Arg Ser Met Leu Leu Ser Asn Cys Ile Phe Arg Met Gly Gly Ala Ala
290                 295                 300

Val Leu Leu Ser Asn Arg Ser Ser Asp Arg Thr Arg Ser Lys Tyr Gln
305                 310                 315                 320

Leu Ile His Pro Val Arg Thr His Lys Gly Ala Asn Asp Asn Ala Phe
            325                 330                 335

Gly Cys Val Tyr Gln Arg Glu Asp Asn Asn Glu Glu Thr Ala Lys
        340                 345                 350

Ile Gly Val Ser Leu Ser Lys Asn Leu Met Ala Ile Ala Gly Glu Ala
        355                 360                 365

Leu Lys Thr Asn Ile Thr Thr Leu Gly Pro Leu Val Leu Pro Met Ser
370                 375                 380

Glu Gln Ile Leu Phe Phe Pro Thr Leu Val Ala Arg Lys Ile Phe Lys
385                 390                 395                 400

Val Lys Lys Ile Lys Pro Tyr Ile Pro Asp Phe Lys Leu Ala Phe Glu
            405                 410                 415

His Phe Cys Ile His Ala Gly Gly Arg Ala Val Leu Asp Glu Ile Glu
            420                 425                 430

Lys Asn Leu Asp Leu Ser Glu Trp His Met Glu Pro Ser Arg Met Thr
        435                 440                 445

Leu Asn Arg Phe Gly Asn Thr Ser Ser Ser Ser Leu Trp Tyr Glu Leu
450                 455                 460

Ala Tyr Ser Glu Ala Lys Gly Arg Ile Lys Arg Gly Asp Arg Thr Cys
465                 470                 475                 480

Gln Ile Ala Phe Gly Ser Gly Phe Lys Cys Asn Ser Ala Val Trp Lys
            485                 490                 495

Ala Leu Arg Thr Ile Asp Pro Ile Asp Glu Lys Lys Asn Pro Trp Ser
            500                 505                 510

Asp Glu Ile His Glu Phe Pro Val Ser Val Pro Arg Ile Thr Pro Val
        515                 520                 525

Thr Ser Asn
    530

<210> SEQ ID NO 28
<211> LENGTH: 622
<212> TYPE: DNA
<213> ORGANISM: Tropaeolum majus
<220> FEATURE:
<221> NAME/KEY: CDS
<222> LOCATION: (1)..(621)

<400> SEQUENCE: 28 aag ctt aaa cta gta tac cat tac ttg atc tcc aac gcc atg tat ttg      48

-continued

```
              Lys Leu Lys Leu Val Tyr His Tyr Leu Ile Ser Asn Ala Met Tyr Leu
                1               5                  10                  15 tta atg gtg ccg ctt cta gca gta gcc ttt gct cat ctc tcc acg ttg           96
Leu Met Val Pro Leu Leu Ala Val Ala Phe Ala His Leu Ser Thr Leu
                    20                  25                  30 acg att caa gat ctg gtt cat ctt tgg gaa cag ctt aag ttc aat tta          144
Thr Ile Gln Asp Leu Val His Leu Trp Glu Gln Leu Lys Phe Asn Leu
                35                  40                  45 ctg tca gta act ctc tgc tcg agc ctt atg gtg ttt tta ggg act ctg          192
Leu Ser Val Thr Leu Cys Ser Ser Leu Met Val Phe Leu Gly Thr Leu
            50                  55                  60 tat ttc atg agc cga ccg acg aag att tac ttg gtg gat ttc tct tgt          240
Tyr Phe Met Ser Arg Pro Thr Lys Ile Tyr Leu Val Asp Phe Ser Cys
        65                  70                  75                  80 tac aag ccg gaa aaa gag cgt ata tgc acg aga gag att ttc tat gag          288
Tyr Lys Pro Glu Lys Glu Arg Ile Cys Thr Arg Glu Ile Phe Tyr Glu
                    85                  90                  95 aga tcg aaa cta act ggg aat ttt acc gat gat aat tta act ttc caa          336
Arg Ser Lys Leu Thr Gly Asn Phe Thr Asp Asp Asn Leu Thr Phe Gln
                100                 105                 110 aag aaa att atc gaa aga tct gga tta ggt cag aac acg tac tta cct          384
Lys Lys Ile Ile Glu Arg Ser Gly Leu Gly Gln Asn Thr Tyr Leu Pro
            115                 120                 125 gag gcc gtt cta cgg gtt ccg ccc aat ccg tgt atg gcg gag gct aga          432
Glu Ala Val Leu Arg Val Pro Pro Asn Pro Cys Met Ala Glu Ala Arg
        130                 135                 140 aag gag gct gag atg gtt atg ttc ggt gcg atc gat gaa ttg ttg gag          480
Lys Glu Ala Glu Met Val Met Phe Gly Ala Ile Asp Glu Leu Leu Glu
145                 150                 155                 160 aaa acc ggg gtt aaa cct aag gat atc ggt att ctt gtg gtg aat tgc          528
Lys Thr Gly Val Lys Pro Lys Asp Ile Gly Ile Leu Val Val Asn Cys
                    165                 170                 175 agc ttg ttc aat ccg acg ccg tct ctg tcc gca atg gtg gtt aat cgg          576
Ser Leu Phe Asn Pro Thr Pro Ser Leu Ser Ala Met Val Val Asn Arg
                180                 185                 190 tac aag ctt aga ggg aat atc ata agt tat aac ctt ggc ggg atg g            622
Tyr Lys Leu Arg Gly Asn Ile Ile Ser Tyr Asn Leu Gly Gly Met
            195                 200                 205
```

<210> SEQ ID NO 29
<211> LENGTH: 207
<212> TYPE: PRT
<213> ORGANISM: Tropaeolum majus

<400> SEQUENCE: 29

```
Lys Leu Lys Leu Val Tyr His Tyr Leu Ile Ser Asn Ala Met Tyr Leu
  1               5                  10                  15

Leu Met Val Pro Leu Leu Ala Val Ala Phe Ala His Leu Ser Thr Leu
                 20                  25                  30

Thr Ile Gln Asp Leu Val His Leu Trp Glu Gln Leu Lys Phe Asn Leu
             35                  40                  45

Leu Ser Val Thr Leu Cys Ser Ser Leu Met Val Phe Leu Gly Thr Leu
         50                  55                  60

Tyr Phe Met Ser Arg Pro Thr Lys Ile Tyr Leu Val Asp Phe Ser Cys
 65                  70                  75                  80

Tyr Lys Pro Glu Lys Glu Arg Ile Cys Thr Arg Glu Ile Phe Tyr Glu
                 85                  90                  95

Arg Ser Lys Leu Thr Gly Asn Phe Thr Asp Asp Asn Leu Thr Phe Gln
             100                 105                 110
```

```
Lys Lys Ile Ile Glu Arg Ser Gly Leu Gly Gln Asn Thr Tyr Leu Pro
        115                 120                 125

Glu Ala Val Leu Arg Val Pro Pro Asn Pro Cys Met Ala Glu Ala Arg
    130                 135                 140

Lys Glu Ala Glu Met Val Met Phe Gly Ala Ile Asp Glu Leu Leu Glu
145                 150                 155                 160

Lys Thr Gly Val Lys Pro Lys Asp Ile Gly Ile Leu Val Val Asn Cys
                165                 170                 175

Ser Leu Phe Asn Pro Thr Pro Ser Leu Ser Ala Met Val Val Asn Arg
            180                 185                 190

Tyr Lys Leu Arg Gly Asn Ile Ile Ser Tyr Asn Leu Gly Gly Met
        195                 200                 205

<210> SEQ ID NO 30
<211> LENGTH: 11
<212> TYPE: PRT
<213> ORGANISM: Simmondsia chinensis

<400> SEQUENCE: 30

Glu Thr Tyr Val Pro Glu Ser Val Thr Lys Lys
1               5                   10

<210> SEQ ID NO 31
<211> LENGTH: 10
<212> TYPE: PRT
<213> ORGANISM: Simmondsia chinensis
<220> FEATURE:
<221> NAME/KEY: MOD_RES
<222> LOCATION: (3)
<223> OTHER INFORMATION: Unknown
<220> FEATURE:
<221> NAME/KEY: MOD_RES
<222> LOCATION: (10)
<223> OTHER INFORMATION: Unknown

<400> SEQUENCE: 31

Val Pro Xaa Glu Pro Ser Ile Ala Ala Xaa
1               5                   10

<210> SEQ ID NO 32
<211> LENGTH: 10
<212> TYPE: PRT
<213> ORGANISM: Simmondsia chinensis

<400> SEQUENCE: 32

Glu Thr Tyr Val Pro Glu Glu Val Thr Lys
1               5                   10

<210> SEQ ID NO 33
<211> LENGTH: 11
<212> TYPE: PRT
<213> ORGANISM: Simmondsia chinensis

<400> SEQUENCE: 33

Asp Leu Met Ala Val Ala Gly Glu Ala Leu Lys
1               5                   10

<210> SEQ ID NO 34
<211> LENGTH: 11
<212> TYPE: PRT
<213> ORGANISM: Simmondsia chinensis

<400> SEQUENCE: 34
```

```
Met Thr Asn Val Lys Pro Tyr Ile Pro Asp Phe
 1               5                  10
```

<210> SEQ ID NO 35
<211> LENGTH: 11
<212> TYPE: PRT
<213> ORGANISM: Simmondsia chinensis
<220> FEATURE:
<221> NAME/KEY: MOD_RES
<222> LOCATION: (4)..(5)
<223> OTHER INFORMATION: Unknown

<400> SEQUENCE: 35

```
Phe Leu Pro Xaa Xaa Val Ala Ile Thr Gly Glu
 1               5                  10
```

<210> SEQ ID NO 36
<211> LENGTH: 17
<212> TYPE: PRT
<213> ORGANISM: Simmondsia chinensis
<220> FEATURE:
<221> NAME/KEY: MOD_RES
<222> LOCATION: (7)..(8)
<223> OTHER INFORMATION: Unknown
<220> FEATURE:
<221> NAME/KEY: MOD_RES
<222> LOCATION: (11)
<223> OTHER INFORMATION: Unknown

<400> SEQUENCE: 36

```
Phe Gly Asn Thr Ser Ser Xaa Xaa Leu Tyr Xaa Glu Leu Ala Tyr Ala
 1               5                  10                  15
Lys
```

<210> SEQ ID NO 37
<211> LENGTH: 17
<212> TYPE: PRT
<213> ORGANISM: Simmondsia chinensis

<400> SEQUENCE: 37

```
Ala Glu Ala Glu Glu Val Met Tyr Gly Ala Ile Asp Glu Val Leu Glu
 1               5                  10                  15
Lys
```

<210> SEQ ID NO 38
<211> LENGTH: 23
<212> TYPE: PRT
<213> ORGANISM: Acinetobacter sp.
<220> FEATURE:
<221> NAME/KEY: MOD_RES
<222> LOCATION: (1)
<223> OTHER INFORMATION: Unknown
<220> FEATURE:
<221> NAME/KEY: MOD_RES
<222> LOCATION: (17)
<223> OTHER INFORMATION: Unknown

<400> SEQUENCE: 38

```
Xaa Asp Ile Ala Ile Ile Gly Ser Gly Ser Ala Gly Leu Ala Gln Ala
 1               5                  10                  15
Xaa Ile Leu Lys Asp Ala Gly
                20
```

<210> SEQ ID NO 39
<211> LENGTH: 13
<212> TYPE: PRT
<213> ORGANISM: Acinetobacter sp.

```
<220> FEATURE:
<221> NAME/KEY: MOD_RES
<222> LOCATION: (7)
<223> OTHER INFORMATION: Unknown

<400> SEQUENCE: 39

Gln Gln Phe Thr Val Trp Xaa Asn Ala Ser Glu Pro Ser
 1               5                  10

<210> SEQ ID NO 40
<211> LENGTH: 6
<212> TYPE: PRT
<213> ORGANISM: Simmondsia chinensis

<400> SEQUENCE: 40

Asn Ile Thr Thr Leu Gly
 1               5

<210> SEQ ID NO 41
<211> LENGTH: 6
<212> TYPE: PRT
<213> ORGANISM: Simmondsia chinensis

<400> SEQUENCE: 41

Ser Asn Cys Lys Phe Gly
 1               5

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)
<223> OTHER INFORMATION: a, c, t, g, other or unknown
<220> FEATURE:
<221> NAME/KEY: modified_base
<222> LOCATION: (12)
<223> OTHER INFORMATION: a, c, t, g, other or unknown
<220> FEATURE:
<221> NAME/KEY: modified_base
<222> LOCATION: (15)
<223> OTHER INFORMATION: a, c, t, g, other or unknown

<400> SEQUENCE: 42
aayathacna cnytngg                                                17

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (15)
<223> OTHER INFORMATION: a, c, t, g, other or unknown

<400> SEQUENCE: 43
swrttrcayt traancc                                                17

<210> SEQ ID NO 44
<211> LENGTH: 42
<212> TYPE: DNA
<213> ORGANISM: Artificial Sequence
```

```
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer

<400> SEQUENCE: 44
caucaucauc augtcgacaa aatgacgtcc attaacgtaa ag                              42

<210> SEQ ID NO 45
<211> LENGTH: 50
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer

<400> SEQUENCE: 45
cuacuacuac uagtcgacgg atcctatttg gaagctttga cattgtttag                     50

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Leu or Gly

<400> SEQUENCE: 46

Lys Leu Xaa Tyr His Tyr
 1               5

<210> SEQ ID NO 47
<211> LENGTH: 41
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (30)
<223> OTHER INFORMATION: a, c, t, g, other or unknown
<220> FEATURE:
<221> NAME/KEY: modified_base
<222> LOCATION: (33)
<223> OTHER INFORMATION: a, c, t, g, other or unknown

<400> SEQUENCE: 47
caucaucauc augaattcaa gcttaarytn bkntaycayt a                              41

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48
```

Asn Leu Gly Gly Met Gly Cys
 1               5

<210> SEQ ID NO 49
<211> LENGTH: 41
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (30)
<223> OTHER INFORMATION: a, c, t, g, other or unknown
<220> FEATURE:
<221> NAME/KEY: modified_base
<222> LOCATION: (33)
<223> OTHER INFORMATION: a, c, t, g, other or unknown
<220> FEATURE:
<221> NAME/KEY: modified_base
<222> LOCATION: (36)
<223> OTHER INFORMATION: a, c, t, g, other or unknown

<400> SEQUENCE: 49
caucaucauc augaattcaa gcttaayytn ggnggnatgg g                    41

<210> SEQ ID NO 50
<211> LENGTH: 40
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (29)
<223> OTHER INFORMATION: a, c, t, g, other or unknown
<220> FEATURE:
<221> NAME/KEY: modified_base
<222> LOCATION: (32)
<223> OTHER INFORMATION: a, c, t, g, other or unknown
<220> FEATURE:
<221> NAME/KEY: modified_base
<222> LOCATION: (35)
<223> OTHER INFORMATION: a, c, t, g, other or unknown

<400> SEQUENCE: 50
cuacuacuac uaggatccgt cgacccatnc cnccnarrtt                      40

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Phe Lys Cys Asn Ser
 1               5

<210> SEQ ID NO 52
<211> LENGTH: 41
<212> TYPE: DNA
<213> ORGANISM: Artificial Sequence

```
-continued

<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (39)
<223> OTHER INFORMATION: a, c, t, g, other or unknown

<400> SEQUENCE: 52
cuacuacuac uaggatccgt cgacswrttr cayttraanc c                      41

<210> SEQ ID NO 53
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic primer
<220> FEATURE:
<223> OTHER INFORMATION: Description of Artificial Sequence: Synthetic
      primer
<220> FEATURE:
<221> NAME/KEY: modified_base
<222> LOCATION: (27)
<223> OTHER INFORMATION: a, c, t, g, other or unknown

<400> SEQUENCE: 53
cuacuacuac uaswrttrca yttraancc                                    29
```